US008895007B2

(12) United States Patent
Hagemann et al.

(10) Patent No.: US 8,895,007 B2
(45) Date of Patent: Nov. 25, 2014

(54) ANTIBODIES WHICH BIND TO THE HUMAN CC CHEMOKINE RECEPTOR 4 AND USES THEREOF

(75) Inventors: Urs Beat Hagemann, Oslo (NO); Remko Albert Griep, Slemmestad (NO); Herald Reiersen, Sofiemyr (NO); Sergej Michailovič Kiprijanov, Oslo (NO)

(73) Assignee: Affitech Research AS, Oslo (NO)

( * ) Notice: Subject to any disclaimer, the term of this patent is extended or adjusted under 35 U.S.C. 154(b) by 151 days.

(21) Appl. No.: 13/313,541

(22) Filed: Dec. 7, 2011

(65) Prior Publication Data

US 2012/0164161 A1    Jun. 28, 2012

Related U.S. Application Data

(60) Provisional application No. 61/420,370, filed on Dec. 7, 2010.

(51) Int. Cl.
| | | |
|---|---|---|
| C07K 16/28 | (2006.01) | |
| C07K 5/10 | (2006.01) | |
| A61K 39/395 | (2006.01) | |
| A61K 39/00 | (2006.01) | |

(52) U.S. Cl.
CPC .... *C07K 16/2866* (2013.01); *G01N 2333/7158* (2013.01); *C07K 2317/33* (2013.01); *C07K 2317/732* (2013.01); *C07K 2317/76* (2013.01); *C07K 2317/41* (2013.01); *C07K 2317/21* (2013.01); *A61K 2039/505* (2013.01)
USPC ............... 424/143.1; 530/388.1; 530/388.22; 530/388.7; 530/387.7; 530/391.3; 530/391.7; 530/350; 424/133.1; 424/135.1; 424/138.1

(58) Field of Classification Search
None
See application file for complete search history.

(56) References Cited

U.S. PATENT DOCUMENTS

| 8,461,304 | B2 * | 6/2013 | Cicortas Gunnarsson et al. |
|---|---|---|---|
| 2002/0098527 | A1 | 7/2002 | Shitara et al. |
| 2003/0175273 | A1 | 9/2003 | Shitara et al. |
| 2006/0246062 | A1 | 11/2006 | Wu et al. |
| 2007/0031896 | A1 | 2/2007 | Wu et al. |

FOREIGN PATENT DOCUMENTS

| AU | 2004201168 A1 | 4/2004 |
|---|---|---|
| EP | 1270595 A1 | 1/2003 |
| EP | 1449850 A1 | 8/2004 |
| EP | 1688436 A1 | 8/2006 |
| EP | 1992644 A1 | 11/2008 |
| WO | 0042074 A1 | 7/2000 |
| WO | 0067791 A1 | 11/2000 |
| WO | 02067771 A2 | 9/2002 |
| WO | 2009037454 A2 | 3/2009 |
| WO | 2009086514 A1 | 7/2009 |
| WO | 2010142952 A2 | 12/2010 |

OTHER PUBLICATIONS

Vajdos et al., Comprehensive functional maps of the antigen-binding site of an anti-ErbB2 antibody obtained with shotgun scanning mutagenesis, J. Mol. Biol. 320:415-428, 2002.*
Pascalis et al., Grafting of "abbreviated" complementarity-determining regions containing specificity-determining residues essential for ligand contact to engineer a less immunogenic humanized monoclonal antibody, J. Immunol. 169:3076-3084, 2002.*
Rudikoff et al., Single amino acid substitution altering antigen-binding specificity, Proc. Natl. Acad. Sci. USA, 79:1979-1983, 1982.*
Agrawal, Lokesh, et al., "Multiple determinants are involved in HIV coreceptor use as demonstraed by CCR4/CCL22 interaction in peripheral blood mononuclear cells (PBMCs)," Journal of Leukocyte Biology, 72: 1063-1074 (Nov. 2002).
Andrew, David P., et al., "C—C Chemokine Receptor 4 Expression Defines a Major Subset of Circulating Nonintestinal Memory T Cells of Both Th1 and Th2 Potential," The Journal of Immunology, 166: 103-111 (2001).
Baatar, Dolgor, et al., "Human Peripheral Blood T Regulatory Cells (Tregs), Functionally Primed CCR4+ Tregs and Unprimed CCR4- Tregs, Regulate Effector T Cells Using FasL," The Journal of Immunology, 178: 4891-4900 (2007).
Baatar, Dolgor, et al., "CCR4-Expressing T Cell Tumors Can Be Specifically Controlled via Delivery of Toxins to Chemokine Receptors," The Journal of Immunology, 179: 1996-2004 (2007).
Bayry, Jagadeesh, et al., "In silico identified CCR4 antagonists target regulatory T cells and exert adjuvant activity in vaccination," PNAS, 105(29): 10221-10226 (Jul. 22, 2008).
Burdi, Douglas F., et al., "Small molecule antagonists of the CC chemokine receptor 4 (CCR4)," Bioorganic & Medicinal Chemistry Letters, 17: 3141-3145 (2007).
Chvatchko, Yolande, et al., "A Key Role for CC Chemokine Receptor 4 in Lipopolysaccharide-induced Endotoxic Shock," J. Exp. Med., 191(10): 1755-63 (May 15, 2000).
Davies, Matthew N., et al., "Toward the Discovery of Vaccine Adjuvants: Coupling In Silico Screening and In Vitro Analysis of Antagonist Binding to Human and Mouse CCR4 Receptors," PLoS One, 4(11); e8084, 12 pages (2009).

(Continued)

*Primary Examiner* — Claire Kaufman
(74) *Attorney, Agent, or Firm* — Rothwell, Figg, Ernst & Manbeck, p.c.

(57) ABSTRACT

The present invention provides antibodies which bind to an epitope in the extracellular domain of human CC chemokine receptor 4 (CCR4) and which are capable of inhibiting the binding of macrophage-derived chemokine (MDC) and/or thymus and activation regulated chemokine (TARC) to CCR4. Also provided are inter alia immunoconjugates and compositions comprising such antibodies and methods and uses involving such antibodies, particularly in the medical and diagnostic fields.

13 Claims, 16 Drawing Sheets

(56) References Cited

OTHER PUBLICATIONS

Figure 1:
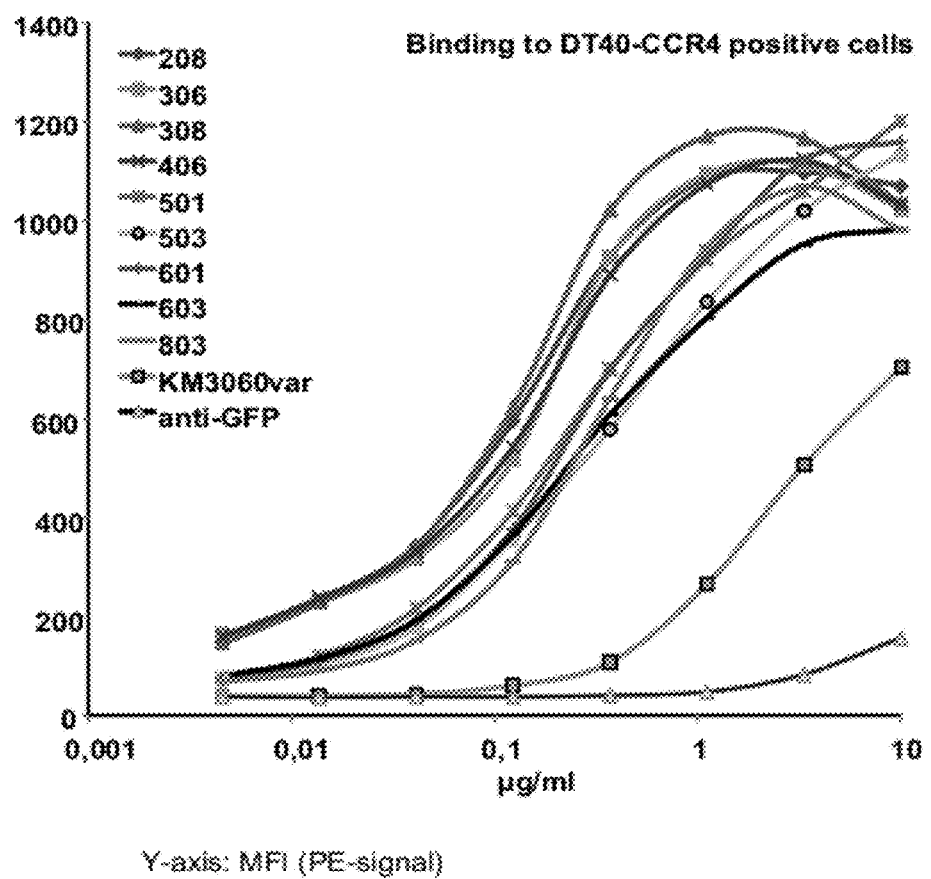
Figure 1:
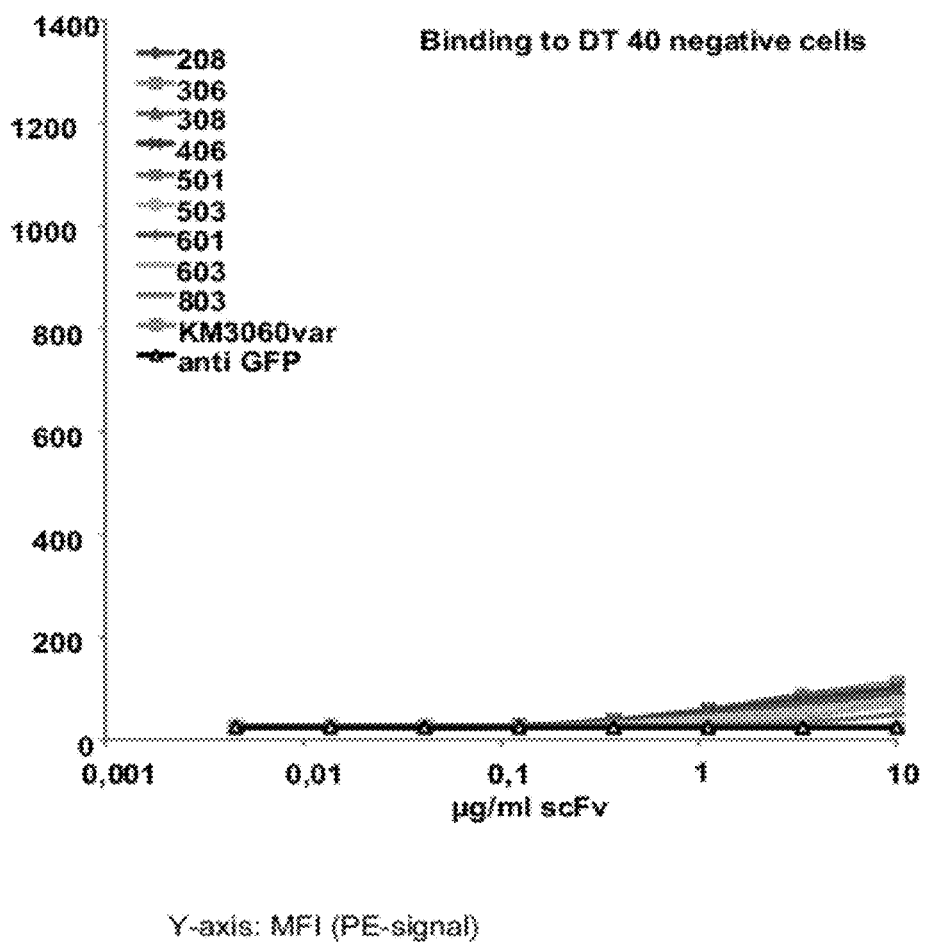

Hoogenboom, Hennie R., et al., "Selection-dominant and nonaccessible epitopes on cell-surface receptors revealed by cell-panning with a large phage antibody library," Eur. J. Biochem., 260: 774-784 (1999).

Ishida, Takashi, et al., "Specific Recruitment of CC Chemokine Receptor 4-Positive Regulatory T Cells in Hodgkin Lymphoma Fosters Immune Privilege," Cancer Research, 66(11): 5716-5722 (Jun. 1, 2006).

Ishida, T., et al., "Defucosylated Humanized Anti-CCR4 MAB KW-0761 as a Novel Immunotherapeutic Agent for Peripheral T-Cell Lymphoma," Annals of Oncology, 19(Supp. 4), No. 513 (Jun. 2008).

Ishida, Takashi, et al., "CXC Chemokine Receptor 3 and CC Chemokine Receptor 4 Expression in T-Cell and NK-Cell Lymphomas with Special Reference to Clinicopathological Significance for Peripheral T-Cell Lymphoma, Unspecified," Clinical Cancer Research, 10: 5494-5500 (Aug. 15, 2004).

Ishida, Takashi, et al., "Clinical Significance of CCR4 Expression in Adult-Cell Leukemia/Lymphoma: Its Close Association with Skin Involvement and Unfavorable Outcome," Clinical Cancer Research, 9: 3625-3634 (Sep. 1, 2003).

Ishida, Takashi, et al., "CCR4 as a novel molecular target for immunotherapy of cancer," Cancer Sci, 97(11): 1139-1146 (Nov. 2006).

Kawasaki. Shin, et al., "Intervention of Thymus and Activation-Regulated Chemokine Attenuates the Development of Allergic Airway Inflammation and Hyperresponsiveness in Mice," The Journal of Immunology, 166:2055-2062 (2001).

Niwa, Rinpei, et al., "Defucosylated Chimeric Anti-CC Chemokine Receptor 4 IgG1 with Enhanced Antibody-Dependent Cellular Cytotoxicity Shows Potent Therapeutic Activity to T-Cell Leukemia and Lymphoma," Cancer Research, 64: 2127-33 (2004).

Panina-Bordignon, Paola, et al., "The C—C chemokine receptors CCR4 and CCR8 identify airway T cells of allergen-challenged atopic asthmatics," The Journal of Clinical Investigtion, 107(11): 1357-64 (Jun. 2001).

Purandare, Ashok V., et al., "Core exploration in optimization of chemokine receptor CCR4 antagonists," Bioorganic & Medicinal Chemistry Letters, 17: 679-682 (2007).

Sui, Jianhua, et al., "Identification of CD4 and transferrin receptor antibodies by CXCR4 antibody-guided Pathfinder selection," Eur. J. Biochem., 270: 4497-4506 (2003).

Yokoyama, Kazuhiro, et al., "Potent CCR4 antagonists: Synthesis, evaluation, and docking study of 2,4-diaminoquinazolines," Bioorganic & Medicinal Chemistry, 16: 7968-7974 (2008).

Yokoyama, Kazuhiro, et al., "Potent and orally bioavailable CCR4 antagonists: Synthesis and structure-activity relationship study of 2-aminoquinazolines," Bioorganic & Medicinal Chemistry, 17: 64-73 (2009).

Jopling, Louise A., "The Identification, Characterization, and Distribution of Guinea Pig CCR4 and Epitope Mapping of a Blocking Antibody," The Journal of Biological Chemistry, 272(9): 6864-6873 (Mar. 1, 2002).

PCT International Search Report for PCT/GB2011/052421 dated Feb. 15, 2012.

Perros, F., et al., "Blockade of CCR5 in a humanized model of asthma reveals a critical role for DC-derived CCL17 and CCL22 in attracting Th2 cells and inducing airway inflammation," Allergy, 64:993-1002 (2009).

Fletcher, Liz, "PDL's mAb technology finds right timing," Nature Biotechnology, 19: 395-396 (May 2001).

Ménétrier-Caux, Christine, et al., "Differences in Tumor Regulatory T-Cell Localization and Activation Status Impact Patient Outcome," Cancer Res., 69(20): 7895-7898 (Oct. 15, 2009).

GB Combined Search and Examination Report dated Oct. 27, 2009 for GB Application No. 0909906.0.

Ishida, Takasha, et al., "The CC Chemokine Receptor 4 as a Novel Specific Molecule Target for Immunotherapy in Adult T-Cell Leukemia/Lymphoma," Clinical Cancer Research, 10: 7529-7639 (Nov. 15, 2004).

\* cited by examiner

ANTIBODIES WHICH BIND TO THE HUMAN CC CHEMOKINE RECEPTOR 4 AND USES THEREOF

This application is a non-provisional of U.S. Ser. No. 61/420,370, filed 7 Dec. 2010. This previous application is incorporated herein by reference.

FIELD OF THE INVENTION

The present invention relates generally to the fields of antibodies, CCR4 biology and related therapies. More particularly, it provides antibodies that bind to CCR4. Such anti-CCR4 antibodies have diagnostic and therapeutic uses in diseases and conditions associated with CCR4, such as in imaging tumour blood vessels, treating cancer and treating viral and other infections, and inflammatory and immune diseases. The antibody-based compositions and methods of the invention also extend to the use of immunoconjugates and other therapeutic combinations, kits and methods.

BACKGROUND

With more than 800 members, G-protein-coupled receptors (GPCRs) represent the largest family of cell surface molecules involved in signal transmission, accounting for >2% of the total genes encoded by human genome. Members of the GPCR superfamily share a common membrane topology: an extracellular N-terminus, an intracellular C-terminus and seven transmembrane (TM) helices, which are connected by three intracellular loops and three extracellular loops. On the basis of their shared topological structure, GPCRs are also referred to as seven transmembrane (7TM) receptors. These receptors control key physiological functions, including neurotransmission, hormone and enzyme release from endocrine and exocrine glands, immune responses, cardiac- and smooth-muscle contraction and blood pressure regulation. Their dysfunction contributes to some of the most prevalent human diseases. Emerging experimental and clinical data indicate that GPCRs have a crucial role in cancer progression and metastasis. Hence, there is the possibility that some GPCRs may be suitable targets for anti-cancer drugs.

Chemokines play an important role inter alia in immune and inflammatory responses in various diseases and disorders, including cancer, viral infections, asthma and allergic diseases, as well as autoimmune pathologies such as rheumatoid arthritis and atherosclerosis. These small, secreted molecules are a growing superfamily of 8-14 kDa proteins characterised by a conserved four cysteine motif.

Studies have demonstrated that the actions of chemokines are mediated by subfamilies of G protein-coupled receptors, among which is the receptor designated chemokine (C-C motif) receptor 4, or CC chemokine receptor 4 (CCR4). Specific ligands for CCR4 include the chemokines thymus and activation-regulated chemokine (TARC) (also known as CCL17) and macrophage-derived chemokine (MDC) (also known as CCL22). CCR4 may also bind to RANTES, MCP-1 and MIP-1alpha, and CCR4 signalling in response to these ligands has also been reported.

CCR4 is believed to be important inter alia in the function of T cell chemotaxis and the migration of phagocytic cells to sites of inflammation. CCR4 is preferentially expressed on T-helper cell type 2 (Th2) cells and regulatory T (Treg) cells, whereas only limited expression on other healthy cells or tissues occurs.

Tumour cells, in particular adult T cell leukaemia/lymphoma cells, may be positive for CCR4. Expression of CCR4 by tumour cells is associated with skin involvement. Certain T-cell malignancies typically are located to the skin. For example, CCR4 is found at high levels in cutaneous T cell lymphoma lesions.

More recently, CCR4 has also been found to be expressed by certain solid tumours (WO2009/037454). CCR4 expression is believed to be an early event in carcinogenesis of solid tumours, particularly cancer of the cervix, oesophagus, kidney, brain, breast, ovary, prostate, stomach and pancreas. Thus, both haematological and non-haematological cancer cells may express CCR4. Consequently, these cancers maybe diagnosed, monitored and treated using anti-CCR4 antibodies.

In addition, CCR4 has an important role in normal and tumour immunity. A significant fraction of $CD4^+$ $CD25^+$ regulatory T-cells (Tregs) are positive for CCR4 (Baatar et al, 2007b). These Tregs suppress immune responses through a variety of mechanisms, and it has been shown that they can inhibit tumour-specific immunity. Increased numbers of Tregs infiltrating the stroma, the tumour itself, or draining lymph nodes, correlate with worsened outcome in a variety of cancers. Studies in mouse model show that reducing Treg activity leads to increased endogenous anti-tumour immunity and increased efficacy of anti-tumour interventions by the immune system. Consequently, inhibiting Treg function is a promising strategy in immunotherapy of tumours. The inhibition can be achieved by killing the Tregs (depletion), interfering with their suppressor functions, changing their trafficking pattern or changing their differentiation.

In a subset of patients with CCR4+ T-cell leukaemia/lymphoma, the tumour cells themselves function as Treg cells, contributing to tumour survival in the face of host antitumour immune responses. In other types of cancers, MDC and TARC are produced by tumour cells and the tumour microenvironment and attract CCR4+ Treg cells to the tumour, where they create a favourable environment for tumour escape from the host immune responses. A higher frequency of Tregs in peripheral blood of patients with following cancers has been reported: Breast cancer, Colorectal cancer, Oesophageal cancer, Gastric cancer, Hepatocellular carcinoma, Lung cancer, Melanoma, Ovarian cancer and Pancreatic cancer. Treg cells have been reported to create a favourable environment for tumours. Hence, blocking the interaction between CCR4 and its ligands such as MDC could be useful in the treatment or prevention of cancers, especially the cancers listed above. It has been reported that in a SCID mouse model, antibody to human MDC/CCL22 was able to block infiltration of human Treg cells into transplanted human ovarian tumours. It is believed that the Treg cells present in human solid tumours prevent immune effector responses developing which could contribute to the slowing of tumour growth and metastasis. Thus, killing of Treg cells in the tumour mass, and/or prevention of migration of Treg cells to the tumour sites by using a neutralising MAb (monoclonal antibody) directed against CCR4 may result in enhanced immune responses towards solid tumours, and act as an adjunct to conventional cytotoxic or anti-hormonal therapies.

Cancer causes about 13% of all human deaths. According to the American Cancer Society, 7.6 million people died from cancer in the world during 2007, so there remains a strong and urgent need for further anti-cancer therapeutics.

CCR4 has been shown to play a role in inflammation and immune disorders. Th2 cells and basophils are key cells in the allergic response in the lung and skin. There are a number of reports which describe the presence of CCR4-expressing T cells and concomitant expression of CCR4 ligands (MDC, TARC) on airway epithelial cells in bronchial biopsies in allergen-challenged asthmatics (Panina-Bordignon et al, 2001). CCR4+ T cells are also found in increased numbers in patients with atopic dermatitis, with a marked reduction of CCR4+ T cells observed when the disease improved. Using a humanized SCID mouse model of asthma, it was shown that blockade of CCR4 with antibodies prior to allergen challenge reduced allergic airway inflammation, as well as the levels of Th2 cytokines in the lungs. Depletion of CCR4+ T cells via lung delivery of a blocking antibody may be a suitable treatment option for asthmatic patients. Targeted delivery of a CCR4 blocking antibody to the skin may also be an attractive treatment for atopic dermatitis.

In allergic asthma, the presence of high levels of allergen-specific IgE is a reflection of an aberrant Th2 cell immune response to commonly inhaled environmental allergens. Asthma is characterized by infiltration of Th2 lymphocytes and eosinophils and by the production of Th2 chemokines. Allergens are presented to T cells by dendritic cells (DCs) that continuously sample incoming foreign antigens. Upon proper activation by DCs, allergen-specific lymphocytes that are present in diseased airways produce Th2 cytokines interleukin (IL)-4, IL-5 and IL-13 that furthermore control leukocyte extravasation, goblet cell hyperplasia and bronchial hyper-reactivity (BHR). TARC and MDC produced by DCs induce the selective migration of Th2 cells but not Th1 cells through triggering CCR4 (Perros et al, 2009). It was shown in murine models of asthma, that treatment with anti-TARC antibodies reduced the number of CD4+ T cells and eosinophils in bronchoalveolar lavage (BAL) fluid, the production of Th2 cytokines and airway hyper-responsiveness after allergen challenge (Kawasaki et al, 2001). In contrast, CCR4-deficient mice showed no protection against airway inflammation and BHR (Chvatchko et al, 2000). Using a humanized SCID mouse model of asthma, it was shown that blockade of CCR4 with antibodies prior to allergen challenge reduced allergic airway inflammation as well as the levels of Th2 cytokines in the lungs (Perros et al, 2009). These data indicate that CCR4 blockade is a feasible strategy for inhibiting allergic inflammation in humans.

Treg cells may suppress dendritic cells (DCs), thereby facilitating the development and progression of diseases, particularly infectious diseases and cancer. Anti-CCR4 antibodies able to block the suppression of dendritic cells by Treg cells may therefore be useful as adjuvants in vaccines, particularly as adjuvants in tumour vaccination or vaccination against infectious disease. Thus, an anti-CCR4 antibody may enhance the therapeutic effect of a vaccine, particularly enhancing the vaccine-induced immune response.

CCR4 binding compounds have been reported to show efficacy in murine allergic inflammation (Purandare et al, 2007, Burdi et al. 2007). It has been reported that a CCR4-binding compound has reasonable potency in vivo, as CCR4 dependent recruitment of leucocytes to the peritoneum induced by TARC was inhibited by almost 90%. Yokoyama and colleagues presented a quinazoline derivative targeting CCR4 which proved in vivo to be effective in reducing hypersensitivity reactions in a mouse model (Yokoyama et al, 2008b); a derivative of this compound proved to be effective in a similar in vivo mouse model upon oral administration (Yokoyama et al, 2009). Recently, a group of scientists has identified a number CCR4 antagonists using in silico modelling approach (Bayry et al, 2008; Davies et al, 2009). By docking compounds to modelled CCR4, the authors found molecules able to bind within the transmembrane region. Sixteen compounds inhibited CCR4-mediated migration of CCRF-CEM cells. When CCR4 antagonists were tested for their adjuvant function in vivo with *Mycobacterium tuberculosis* and hepatitis B vaccines, enhanced immunogenicity was observed for both cellular and humoral immune responses. The observed effect was ascribed to inhibition of Treg activity (Bayry et al, 2008; Davies et al, 2009). The fact that a significant fraction of Treg cells are CCR4-positive is well known in the art (Baatar et al 2007b). The observed effect is believed to be useful not only in the context of vaccination against infectious diseases (caused, for example by a virus, a bacterium, a mycobacterium or a parasite such as protozoa), but also in the context of cancer vaccines.

As the cause for the efficacy of these compounds as adjuvants is based on inhibiting Tregs by blocking CCR4 mediated signaling, it is expected that antibodies binding to CCR4 in an antagonistic manner would work the same way; the pharmacological advantages of antibodies compared to small molecule drugs are well known in the art. The anti-CCR4 antibody KW-0761 by Kyowa-Hakko is known in the art. However, this antibody is effective only by ADCC; it does not prevent ligand-mediated signalling through CCR4 receptor. Therefore, the antibodies described in this invention are expected to be clearly superior in their modulation of immune reactions via Tregs.

Another application where modulating Tregs is of clinical use is cancer treatment. Tregs can inhibit tumour-specific immunity and their increased numbers correlate with unfavourable prognosis and disease progression in some cancers. Studies in mouse models demonstrate that reducing Treg activity boosts endogenous anti-tumour immunity, and increases the efficacy of active immune interventions. Consequently, inhibiting Treg function is a strategy worth considering in human cancer immunotherapy (Curiel, 2008; Ruter et al, 2009). This inhibition can be achieved both by modulating Tregs, or by directly killing them.

Examples for this approaches are described in the art by compounds targeting other surface markers of Treg like CD25. Daclizumab (Zenapax®; Roche)) and basiliximab (Simulect® Novartis) are anti-human CD25 antibodies approved for use in autoimmune diseases, transplantation and cancers including HTLV-1 induced adult T-cell lymphoma/leukaemia (Church, 2003). Denileukin diftitox (Ontak®, DAB389IL-2; Ligand Pharmaceuticals Inc.) is a recombinant protein fusing the active domain of diphtheria toxin to human IL-2. In 1998, FDA has approved it to treat cutaneous T cell leukaemia/lymphoma (Olsen et al, 2001), which usually are CD4+CD25+. Denileukin diftitox is targeted to the IL-2 receptor and is proposed to be internalized through CD25 by endocytosis. There is also evidence that Denileukin diftitox improves immunogenicity of a tumour vaccine in patients with renal cell cancer (Dannull et al, 2005). In addition, a report showed that denileukin diftitox reduces Treg numbers and function in melanoma with improved melanoma-specific immunity (Mahnke et al, 2007).

Other molecules on Tregs which are targeted for cancer treatment or improved cancer vaccine effects include GITR (glucocorticoid-induced tumour necrosis factor receptor-related gene) (Levings et al, 2002), Toll-like receptors (TLR) are expressed ubiquitously on a variety of mammalian cells, including human Tregs (Yang et al, 2004, Rutter et al, 2009) and Cytotoxic T lymphocyte antigen-4 (CTLA-4; CD152) (Sutmuller et al. 2001). Currently, Phase II and III clinical trials of anti-CTLA-4 monoclonal antibody therapy are being conducted in melanoma, and Phase I and II trials are being conducted in other tumour types. Two human monoclonal antibodies are under investigation—ipilimumab (MDX-010; Bristol-Myers Squibb/Medarex) and tremelimumab (CP-675,206; Pfizer).

CCR4 has also been implicated inter alia in the following disorders: Adult T-cell leukemia/lymphoma, Peripheral T-cell lymphoma, Cutaneous T-Cell Lymphoma (CTCL), unspecified Diffuse large B-cell lymphoma, Hodgkin's lymphoma, B-cell chronic lymphocytic leukemia, Epstein-Barr virus (EBV) infection, Mycosis fungoides (a mature T-cell lymphoma), Sezary syndrome (a variant of mycosis fungoides), allergic bronchopulmonary aspergillosis (ABPA), Asthma, LPS-induced endotoxic shock, Allergic inflammation, T-cell mediated neurodegenerative diseases such as Multiple Sclerosis (MS), Autoimmune diseases such as Psoriasis, Castleman's disease and Rheumatoid arthritis (RA).

Due to their complex structures, GPCRs are considered as "difficult targets" for raising specific antibodies. They can neither be easily purified from the membrane fraction of lysed cells, nor be recombinantly produced in different expression systems as correctly folded soluble proteins. To the inventors' knowledge, to date all known attempts of others to generate anti-GPCR antibodies using phage display have proven to be unsuccessful.

The difficulties associated with generating antibodies against GPCRs are set out in Hoogenboom et al., 1999. Furthermore, Sui et al. (2003) explain the difficulties associated with trying to obtain human antibodies against the GPCR chemokine receptor CXCR4 and report that even using the pathfinder method combined with step-back selection no specific antibodies could be identified. Thus, in the field of GPCRs, the generation of specific antibodies remains a major challenge.

A murine monoclonal antibody called 1G1 which reacts with human CCR4 is commercially available from BD Pharmingen. This antibody may be used for immunofluorescent staining, but the antibody is not a neutralising antibody.

A chimeric antibody to CCR4 designated KM2760 is disclosed in Ishida et al., 2006. The authors report that this antibody does not block the binding of CCR4 to its ligands MDC or TARC.

The inventors have recognized that the identification of additional antibodies that recognize CCR4 would be of benefit in expanding the number of therapeutic options. In particular, antibodies that block the binding of CCR4 to one or more of its ligands would offer further therapeutic avenues.

The inventors have also recognized that the development of therapeutic agents for the treatment of humans that are better tolerated from an immunological perspective would be advantageous. In this regard, human antibodies generally have at least three potential advantages for use in human therapy. First, the human immune system should not recognize the antibody as foreign. Second, the half-life in the human circulation will be similar to naturally occurring human antibodies, allowing smaller and less frequent doses to be given. Third, because the effector portion is human, it will interact better with the other parts of the human immune system.

The art therefore still lacks anti-CCR4 antibodies that can be used in the safe and effective treatment of patients having disorders in which CCR4 is involved, including in long-term administration, and poses challenges to the development of such antibodies.

In particular, there is a need for human antibodies to CCR4. Although human antibodies are generally recognized to display advantages, it is known that the development of human antibodies that have high enough affinities and appropriate functional properties to make them candidates for successful human therapy is by no means straightforward. This is even more so the case with GPCRs, due to their complex and transmembrane nature.

There also remains a strong need for anti-CCR4 antibodies which can block the binding between CCR4 and one or more of its ligands such as MDC and/or TARC.

DESCRIPTION OF THE INVENTION

The present invention overcomes certain limitations in the prior art by providing new therapeutic compositions and methods for use in the safe and effective treatment of tumors, viral infections and other diseases and conditions in which CCR4+ cells are involved such as inflammatory or immune disorders. The invention is based on antibodies that bind to CCR4, preferably to an epitope within the extracellular domain of CCR4, particularly human antibodies. Such antibodies are effective in treating tumors and viral infections and other diseases and conditions in which CCR4+ cells are involved, such as inflammatory or immune disorders. The compositions and methods of the invention also extend to the use of immunoconjugates and combinations using this particular category of antibodies.

A particular advantage of the present invention is that the antibodies provided inhibit binding of MDC and/or TARC to CCR4. This contrasts with the leading antibodies in the clinical field, which do not inhibit binding of MDC and/or TARC to CCR4.

The present inventors have prepared CCR4-specific antibodies that bind to CCR4. For example, the antibodies bind to CCR4+ cells, in particular HEK293T-cells transfected with CCR4, DT40-cells transfected with CCR4 and CCRF-CEM cells which naturally express CCR4, as well as the following cells which express CCR4: Hut78 (cutaneous T-cell lymphoma, ATCC number TIB-161), 786-O (human renal cell carcinoma, ATCC number CRL-1932), MCF-7 (human breast adenocarcinoma, ATCC number HTB-22), KatoIII (human gastric cancer, ATCC number HTB-103), L-428 cells (Non-Hodgkin Lymphoma, DSMZ number ACC 197) and A-498 (human renal cell carcinoma, DSMZ number ACC 55) (see Example 2). Importantly, the antibodies do not significantly bind to CCR4– cells, i.e. cells which do not express CCR4. Thus, the antibodies disclosed herein bind specifically to CCR4, making them suitable candidates for diagnostics and therapy of the conditions discussed herein.

Amino acid and/or DNA sequences of preferred antibody molecules of the invention which bind to an epitope in the extracellular domain of CCR4, their VH and VL domains including complementarity determining regions (CDRs), are set forth in the various SEQ ID NOs. listed herein.

Thus, the present invention provides an antibody which binds to CCR4 and which is capable of inhibiting the binding of MDC and/or TARC to CCR4. Preferably, the antibody is isolated. Also preferably, the antibody is human. Preferably, the antibody binds to an epitope in the extracellular domain of CCR4. The CCR4 is preferably human. Thus, any reference to "binding to CCR4" includes the preferred embodiment of "binding to an epitope in the extracellular domain of CCR4".

Thus, the invention preferably provides an isolated human antibody which binds to an epitope in the extracellular domain of human CCR4 and which is capable of inhibiting the binding of MDC and/or TARC to CCR4.

In one embodiment, the present invention provides an antibody that binds to CCR4 and which is capable of inhibiting the binding of MDC and/or TARC to CCR4 comprising at least a heavy chain CDR comprising one of the heavy chain CDR sequences listed in the Tables disclosed herein, and/or at least a light chain CDR comprising one of the light chain CDR sequences listed in the Tables disclosed herein. Preferably, the antibody comprises at least 2, or 3 heavy and/or light chain CDRs, each comprising a relevant sequence listed in the Tables disclosed herein.

In one embodiment, the antibody of the invention comprises one or more, e.g. at least 2, 3, 4 or 5, preferably 6 of the CDRs selected from the group consisting of SEQ ID NOs: 1, 2, 3, 4, 5 and 6; or 1, 2, 3, 17, 5 and 6; or 1, 2, 20, 22, 5 and 24; or 26, 27, 20, 22, 5, 24 or sequences substantially homologous to any one of the foregoing SEQ ID NOs.

In one embodiment, the antibody comprises a heavy chain CDR1 of SEQ ID NO: 1 or 26, a heavy chain CDR2 of SEQ ID NO: 2 or 27 and a heavy chain CDR3 of SEQ ID NO: 3 or 20, or sequences substantially homologous to any one of the foregoing SEQ ID NOs, and/or a a light chain CDR1 of SEQ ID NO: 4, 17 or 22, a light chain CDR2 of SEQ ID: 5 and/or a light chain CDR3 of SEQ ID: 6 or 24, or sequences substantially homologous to any one of the foregoing SEQ ID NOs.

Thus, in one embodiment the antibody comprises heavy chain CDR1 of SEQ ID NO: 26, a heavy chain CDR2 of SEQ ID NO: 2 and a heavy chain CDR3 of SEQ ID NO: 20. Preferably, said antibody also comprises light chain CDRs selected from the sequences set out herein.

In one embodiment, the heavy chain CDR1 of any of the of the antibodies disclosed herein has the sequence SYAXS, wherein X may be any amino acid (SEQ ID NO: 119), preferably M or I (SEQ ID NO: 120); and/or the heavy chain CDR2 of any of the of the antibodies disclosed herein has the sequence GIIPIFGTXNYAQKFQG, wherein X may be any amino acid (SEQ ID NO:121), preferably V, I or A (SEQ ID NO: 122); and/or the heavy chain CDR3 of any of the of the antibodies disclosed herein has the sequence $RX_1GX_2X_3FDY$, wherein each X may independently be any amino acid (SEQ ID NO: 123), preferably $X_1$ is R or G, and/or $X_2$ is S or A, and/or $X_3$ is Y or K, most preferably $X_1$ is R or G, and $X_2$ is S or A, and $X_3$ is Y or K (SEQ ID NO: 124); and/or the light chain CDR1 of any of the of the antibodies disclosed herein has the sequence SGSTSNIGSHYVX, wherein X is any amino acid (SEQ ID NO: 125), preferably F, S or V (SEQ ID NO:126); and or the light chain CDR2 of any of the of the antibodies disclosed herein has the sequence of SEQ ID NO: 5; and/or the light chain CDR3 of any of the of the antibodies disclosed herein has the sequence A V W D X X X X G W V, wherein each X may independently be any amino acid (SEQ ID NO:127), preferably $X_1$ is A or D, and/or $X_2$ is K or T, and/or $X_3$ is Y or L, and/or $X_4$ is R or S, more preferably $X_1$ is A or D, and $X_2$ is K or T, and $X_3$ is Y or L, and $X_4$ is R or S (SEQ ID NO:128).

This applies mutatis mutandis to the VH, VL, scFv and IgG sequences disclosed herein. Thus, any of the sequences disclosed herein which include CDR sequences preferably include one or more of SEQ ID NOs 119-128 instead of the corresponding CDR sequences listed in Tables 1-9.

In one especially preferred embodiment, the antibody comprises a heavy chain CDR1 of SEQ ID NO: 1, a heavy chain CDR2 of SEQ ID NO: 2 and a heavy chain CDR3 of SEQ ID NO: 3 or 20. Preferably, said antibody also comprises a light chain CDR1 of SEQ ID NO: 4, 17 or 22, a light chain CDR2 of SEQ ID: 5 and/or a light chain CDR3 of SEQ ID: 6 or 24, or sequences substantially homologous to any one of the foregoing SEQ ID NOs.

In one embodiment, the antibody comprises a heavy chain CDR1 of SEQ ID NO: 26, a heavy chain CDR2 of SEQ ID NO: 27 and a heavy chain CDR3 of SEQ ID NO: 20. Preferably, said antibody also comprises a light chain CDR1 of SEQ ID NO: 4, 17 or 22, a light chain CDR2 of SEQ ID: 5 and/or a light chain CDR3 of SEQ ID: 6 or 24, or sequences substantially homologous to any one of the foregoing SEQ ID NOs.

In one embodiment, the antibody comprises a light chain CDR1 of SEQ ID NO: 4, 17 or 22, a light chain CDR2 of SEQ ID: 5 and a light chain CDR3 of SEQ ID: 6 or 24. Preferably, said antibody also comprises a heavy chain CDR1 of SEQ ID NO: 1 or 26, a heavy chain CDR2 of SEQ ID NO: 2 or 27 and/or a heavy chain CDR3 of SEQ ID NO: 3 or 20, or sequences substantially homologous to any one of the foregoing SEQ ID NOs.

In one embodiment, the antibody comprises a light chain CDR1 of SEQ ID NO: 4 or 17, a light chain CDR2 of SEQ ID: 5 and a light chain CDR3 of SEQ ID: 6. Preferably, said antibody also comprises a heavy chain CDR1 of SEQ ID NO: 1 or 26, a heavy chain CDR2 of SEQ ID NO: 2 or 27 and/or a heavy chain CDR3 of SEQ ID NO: 3 or 20, or sequences substantially homologous to any one of the foregoing SEQ ID NOs.

In one embodiment, the antibody comprises a light chain CDR1 of SEQ ID NO: 22, a light chain CDR2 of SEQ ID: 5 and a light chain CDR3 of SEQ ID: 24. Preferably, said antibody also comprises a heavy chain CDR1 of SEQ ID NO: 1 or 26, a heavy chain CDR2 of SEQ ID NO: 2 or 27 and/or a heavy chain CDR3 of SEQ ID NO: 3 or 20, or sequences substantially homologous to any one of the foregoing SEQ ID NOs.

Certain especially preferred antibodies comprise a heavy chain CDR1 domain of SEQ ID NO: 1, a heavy chain CDR2 domain of SEQ ID NO: 2, and a heavy chain CDR3 domain of SEQ ID NO: 3; and comprise a light chain CDR1 domain of SEQ ID NO: 4, a light chain CDR2 domain of SEQ ID NO: 5, and a light chain CDR 3 domain of SEQ ID NO: 6.

Certain especially preferred antibodies comprise a heavy chain CDR1 domain of SEQ ID NO: 1, a heavy chain CDR2 domain of SEQ ID NO: 2, and a heavy chain CDR3 domain of SEQ ID NO: 3; and comprise a light chain CDR1 domain of SEQ ID NO: 17, a light chain CDR2 domain of SEQ ID NO: 5, and a light chain CDR 3 domain of SEQ ID NO: 6.

Certain most preferred antibodies comprise a heavy chain CDR1 domain of SEQ ID NO: 1, a heavy chain CDR2 domain of SEQ ID NO: 2, and a heavy chain CDR3 domain of SEQ ID NO: 20; and comprise a light chain CDR1 domain of SEQ ID NO: 22, a light chain CDR2 domain of SEQ ID NO: 5, and a light chain CDR 3 domain of SEQ ID NO: 24.

Certain especially preferred antibodies comprise a heavy chain CDR1 domain of SEQ ID NO: 26, a heavy chain CDR2 domain of SEQ ID NO: 27, and a heavy chain CDR3 domain of SEQ ID NO: 20; and comprise
a light chain CDR1 domain of SEQ ID NO: 22, a light chain CDR2 domain of SEQ ID NO: 5, and a light chain CDR 3 domain of SEQ ID NO: 24.

In a further embodiment, the invention provides an antibody that binds to CCR4 and which is capable of inhibiting the binding of MDC and/or TARC to CCR4 and that comprises at least one heavy chain variable region that comprises three CDRs and at least one light chain variable region that comprises three CDRs, wherein said heavy chain variable region comprises:

(i) a variable heavy (VH) CDR1 that has the amino acid sequence of SEQ ID NO: 1, (ii) a VH CDR2 that has the amino acid sequence of SEQ ID NO: 2, and (iii) a VH CDR3 that has the amino acid sequence of SEQ ID NO: 3; and/or said light chain variable region comprises:
(i) a VL CDR1 that has the amino acid sequence of SEQ ID NO: 4, 17 or 22, preferably 4 or 17
(ii) a VL CDR2 that has the amino acid sequence of SEQ ID NO: 5, and
(iii) a VL CDR3 that has the amino acid sequence of SEQ ID NO: 6 or 24, preferably 6.

In a further embodiment, the invention provides an antibody that binds to CCR4 and which is capable of inhibiting the binding of MDC to CCR4 and that comprises at least one heavy chain variable region that comprises three CDRs and at least one light chain variable region that comprises three CDRs, wherein said heavy chain variable region comprises:
(i) a variable heavy (VH) CDR1 that has the amino acid sequence of SEQ ID NO: 1,
(ii) a VH CDR2 that has the amino acid sequence of SEQ ID NO: 2, and
(iii) a VH CDR3 that has the amino acid sequence of SEQ ID NO: 20; and/or
wherein light chain variable region comprises:
(i) a VL CDR1 that has the amino acid sequence of SEQ ID NO: 4, 17 or 22, preferably 22,
(ii) a VL CDR2 that has the amino acid sequence of SEQ ID NO: 5, and
(iii) a VL CDR3 that has the amino acid sequence of SEQ ID NO: 6 or 24, preferably 24.

In a further embodiment, the invention provides an antibody that binds to CCR4 and which is capable of inhibiting the binding of MDC to CCR4 and that comprises at least one heavy chain variable region that comprises three CDRs and at least one light chain variable region that comprises three CDRs, wherein said heavy chain variable region comprises:
(i) a variable heavy (VH) CDR1 that has the amino acid sequence of SEQ ID NO: 26,
(ii) a VH CDR2 that has the amino acid sequence of SEQ ID NO: 27, and
(iii) a VH CDR3 that has the amino acid sequence of SEQ ID NO: 20; and/or wherein
said light chain variable region comprises:
(i) a VL CDR1 that has the amino acid sequence of SEQ ID NO: 4, 17 and 22, preferably 22
(ii) a VL CDR2 that has the amino acid sequence of SEQ ID NO: 5, and
(iii) a VL CDR3 that has the amino acid sequence of SEQ ID NO: 6 or 24, preferably 24.

Certain preferred embodiments of the invention provide an antibody that binds to CCR4 and which is capable of inhibiting the binding of MDC and/or TARC to CCR4 comprising a VH domain that has the amino acid sequence of SEQ ID NO: 29, 31, 33, 35, 37, 39, 41, 43 or 45 or a sequence substantially homologous thereto and/or a VL domain that has the amino acid sequence of SEQ ID NO: 30, 32, 34, 36, 38, 40, 42, 44 or 46 or a sequence substantially homologous thereto.

Preferably, said VH domain has 3 heavy chain CDRs and/or said VL domain has 3 light chain CDRs. More preferably, at least 1, at least 2, preferably 3 of the light chain CDR sequences are selected from the light chain CDR sequences disclosed herein and/or at least 1, at least 2, preferably 3 of the heavy chain CDR sequences are selected from the heavy chain CDR sequences disclosed herein.

Thus, in one embodiment, said VH domain has a sequence of SEQ ID NO: 29, 31, 33 or 35 or a sequence substantially homologous thereto and comprises a heavy chain CDR1 domain of SEQ ID NO: 1, a heavy chain CDR2 domain of SEQ ID NO: 2, and a heavy chain CDR3 domain of SEQ ID NO: 3.

In one embodiment said VH domain has a sequence of SEQ ID NO: 37, 39, 41 or 43 or a sequence substantially homologous thereto and comprises a heavy chain CDR1 domain of SEQ ID NO: 1, a heavy chain CDR2 domain of SEQ ID NO: 2, and a heavy chain CDR3 domain of SEQ ID NO: 20.

In one embodiment said VH domain has a sequence of SEQ ID NO: 45 or a sequence substantially homologous thereto and comprises a heavy chain CDR1 domain of SEQ ID NO: 26, a heavy chain CDR2 domain of SEQ ID NO: 27, and a heavy chain CDR3 domain of SEQ ID NO: 20.

In one embodiment said VL domain has a sequence of SEQ ID NO: 30 or 34 or a sequence substantially homologous thereto and comprises a light chain CDR1 domain of SEQ ID NO: 4, a light chain CDR2 domain of SEQ ID NO: 5, and a light chain CDR 3 domain of SEQ ID NO: 6.

In one embodiment said VL domain has a sequence of SEQ ID NO: 32 or 36 or a sequence substantially homologous thereto and comprises a light chain CDR1 domain of SEQ ID NO: 17, a light chain CDR2 domain of SEQ ID NO: 5, and a light chain CDR 3 domain of SEQ ID NO: 6.

In one embodiment said VL domain has a sequence of SEQ ID NO: 38, 40, 42, 44 or 46 or a sequence substantially homologous thereto and comprises a light chain CDR1 domain of SEQ ID NO: 22, a light chain CDR2 domain of SEQ ID NO: 5, and a light chain CDR 3 domain of SEQ ID NO: 24.

The antibody may have any combination of the VL and VH sequences discussed above. The following combinations are preferred:

A VH domain that has the amino acid sequence of SEQ ID NO: 29 or a sequence substantially homologous thereto and a VL domain that has the amino acid sequence of SEQ ID NO: 30 or a sequence substantially homologous thereto.

A VH domain that has the amino acid sequence of SEQ ID NO: 31 or a sequence substantially homologous thereto and a VL domain that has the amino acid sequence of SEQ ID NO: 32 or a sequence substantially homologous thereto.

A VH domain that has the amino acid sequence of SEQ ID NO: 33 or a sequence substantially homologous thereto and a VL domain that has the amino acid sequence of SEQ ID NO: 34 or a sequence substantially homologous thereto.

A VH domain that has the amino acid sequence of SEQ ID NO: 35 or a sequence substantially homologous thereto and a VL domain that has the amino acid sequence of SEQ ID NO: 36 or a sequence substantially homologous thereto.

A VH domain that has the amino acid sequence of SEQ ID NO: 37 or a sequence substantially homologous thereto and a VL domain that has the amino acid sequence of SEQ ID NO: 38 or a sequence substantially homologous thereto.

A VH domain that has the amino acid sequence of SEQ ID NO: 39 or a sequence substantially homologous thereto and a VL domain that has the amino acid sequence of SEQ ID NO: 40 or a sequence substantially homologous thereto.

A VH domain that has the amino acid sequence of SEQ ID NO: 41 or a sequence substantially homologous thereto and a VL domain that has the amino acid sequence of SEQ ID NO: 42 or a sequence substantially homologous thereto.

A VH domain that has the amino acid sequence of SEQ ID NO: 43 or a sequence substantially homologous thereto and a VL domain that has the amino acid sequence of SEQ ID NO: 44 or a sequence substantially homologous thereto.

A VH domain that has the amino acid sequence of SEQ ID NO: 45 or a sequence substantially homologous thereto and a VL domain that has the amino acid sequence of SEQ ID NO: 46 or a sequence substantially homologous thereto.

In a yet further embodiment, the present invention provides an antibody that binds CCR4 and which is capable of inhibiting the binding of MDC and/or TARC to CCR4 comprising the amino acid sequence of SEQ ID NO: 47 (said antibody also being referred to herein as 208 scFv), SEQ ID NO: 48 (said antibody also being referred to herein as 306 scFv), SEQ ID NO: 49 (said antibody also being referred to herein as 308 scFv), SEQ ID NO: 50 (said antibody also being referred to herein as 406 scFv), SEQ ID NO: 51 (said antibody also being referred to herein as 501 scFv), SEQ ID NO: 52 (said antibody also being referred to herein as 503 scFv), SEQ ID NO: 53 (said antibody also being referred to herein as 601 scFv), SEQ ID NO: 54 (said antibody also being referred to herein as 603 scFv), or SEQ ID NO: 55 (said antibody also being referred to herein as 803 scFv), or comprising a fragment of any thereof that binds CCR4 and which is capable of inhibiting the binding of MDC and/or TARC to CCR4, or a sequence substantially homologous to any of the above sequence.

The invention is exemplified by monoclonal antibodies 208, 306, 308, 406, 501, 503, 601, 603 and 803, single chain forms of which are shown in Tables 1, 2, 3, 4, 5, 6, 7, 8 and 9 (SEQ ID NOs: 47, 48, 49, 50, 51, 21, 53, 54 and 55 respectively). Full length IgG forms of antibodies 208, 306, 308, 406, 501, 503, 601, 603 and 803 have been made and their sequences are shown in Tables 10-18 respectively. The CDR domains, VH and VL domains of the 208, 306, 308, 406, 501, 503, 601, 603 and 803 antibodies are shown in Tables 1 to 9. Antibodies comprising these CDR domains and/or VH and/or VL domains (or sequences substantially homologous thereto) are preferred aspects of the invention.

A preferred embodiment of the invention is a scFv form of the 208 antibody comprising or consisting of SEQ ID NO: 47, which is preferably encoded by SEQ ID NO: 56. Another preferred embodiment of the invention is a scFv form of the 306 antibody comprising or consisting of SEQ ID NO: 48, which is preferably encoded by SEQ ID NO: 57. Another preferred embodiment of the invention is a scFv form of the 308 antibody comprising or consisting of SEQ ID NO: 49, which is preferably encoded by SEQ ID NO: 58. Another preferred embodiment of the invention is a scFv form of the 406 antibody comprising or consisting of SEQ ID NO: 50, which is preferably encoded by SEQ ID NO: 59. Another preferred embodiment of the invention is a scFv form of the 501 antibody comprising or consisting of SEQ ID NO: 51, which is preferably encoded by SEQ ID NO: 60. Another preferred embodiment of the invention is a scFv form of the 503 antibody comprising or consisting of SEQ ID NO: 52, which is preferably encoded by SEQ ID NO: 61. Another preferred embodiment of the invention is a scFv form of the 601 antibody comprising or consisting of SEQ ID NO: 53, which is preferably encoded by SEQ ID NO: 62. Another preferred embodiment of the invention is a scFv form of the 603 antibody comprising or consisting of SEQ ID NO: 54, which is preferably encoded by SEQ ID NO: 63. Another preferred embodiment of the invention is a scFv form of the 803 antibody comprising or consisting of SEQ ID NO: 55, which is preferably encoded by SEQ ID NO: 64.

Other preferred embodiments are IgG forms of the 208, 306, 308, 406, 501, 503, 601, 603 and 803 antibodies, preferably full length IgG forms. The IgG1 form of any of these antibodies is most preferred.

Thus, another preferred embodiment of the invention is a full length IgG antibody which comprises a heavy chain of SEQ ID NO: 67 (amino acid) and/or a light chain of SEQ ID NO: 68 (amino acid). Also preferred is an IgG antibody which comprises a heavy chain encoded by SEQ ID NO: 65 and/or a light chain encoded by SEQ ID NO: 66.

Another preferred embodiment of the invention is a full length IgG antibody which comprises a heavy chain of SEQ ID NO: 71 (amino acid) and/or a light chain of SEQ ID NO: 72 (amino acid). Also preferred is an IgG antibody which comprises a heavy chain encoded by SEQ ID NO: 69 and/or a light chain encoded by SEQ ID NO: 70.

Another preferred embodiment of the invention is a full length IgG antibody which comprises a heavy chain of SEQ ID NO: 75 (amino acid) and/or a light chain of SEQ ID NO: 76 (amino acid). Also preferred is an IgG antibody which comprises a heavy chain encoded by SEQ ID NO: 73 and/or a light chain encoded by SEQ ID NO: 74.

Another preferred embodiment of the invention is a full length IgG antibody which comprises a heavy chain of SEQ ID NO: 79 (amino acid) and/or a light chain of SEQ ID NO: 80 (amino acid). Also preferred is an IgG antibody which comprises a heavy chain encoded by SEQ ID NO: 77 and/or a light chain encoded by SEQ ID NO: 78.

Another preferred embodiment of the invention is a full length IgG antibody which comprises a heavy chain of SEQ ID NO: 83 (amino acid) and/or a light chain of SEQ ID NO: 84 (amino acid). Also preferred is an IgG antibody which comprises a heavy chain encoded by SEQ ID NO: 81 and/or a light chain encoded by SEQ ID NO: 82.

Another preferred embodiment of the invention is a full length IgG antibody which comprises a heavy chain of SEQ ID NO: 87 (amino acid) and/or a light chain of SEQ ID NO: 88 (amino acid). Also preferred is an IgG antibody which comprises a heavy chain encoded by SEQ ID NO: 85 and/or a light chain encoded by SEQ ID NO: 86.

Another preferred embodiment of the invention is a full length IgG antibody which comprises a heavy chain of SEQ ID NO: 91 (amino acid) and/or a light chain of SEQ ID NO: 92 (amino acid). Also preferred is an IgG antibody which comprises a heavy chain encoded by SEQ ID NO: 89 and/or a light chain encoded by SEQ ID NO: 90. substantially identical heavy chains and two substantially identical light chains.

Another preferred embodiment of the invention is a full length IgG antibody which comprises a heavy chain of SEQ ID NO: 95 (amino acid) and/or a light chain of SEQ ID NO: 96 (amino acid). Also preferred is an IgG antibody which comprises a heavy chain encoded by SEQ ID NO: 93 and/or a light chain encoded by SEQ ID NO: 94.

Another preferred embodiment of the invention is a full length IgG antibody which comprises a heavy chain of SEQ ID NO: 99 (amino acid) and/or a light chain of SEQ ID NO: 100 (amino acid). Also preferred is an IgG antibody which comprises a heavy chain encoded by SEQ ID NO: 97 and/or a light chain encoded by SEQ ID NO: 98.

It is of course understood that full IgG antibodies will comprise two substantially identical heavy chains and two substantially identical light chains.

It is believed that the antibodies of the invention may bind to a different epitope to the known anti-CCR4 antibody family which comprises KM2160, KM3060, KM2760 and KW-0761. Antibody KM2160 is a murine antibody which was raised against a peptide fragment of CCR4 and which recognises an epitope existing in a region of positions 2-29 from the N-terminal amino acid of human CCR4 (EP1270595). KM2760 is a chimeric version of the antibody having the same binding characteristics (EP1270595). Antibody KM3060 is identical to KM2760, except that it is highly fucosylated (Niwa et al. 2004, Cancer Research 64, 2127-2133). KW-0761 is a humanised version of KM2760 (Ishida et al. Annals of Oncology 2008, vol 19, supplement 4, 513).

KM2760 has been reported not to block the interaction between CCR4 and TARC or MDC (Ishida et al. 2006, Cancer Research 66 (11), pp 5716-5722), which is consistent with the applicant's findings using the equivalent antibody KM3060var (corresponding to KM3060, but potentially having a different sugar profile as it was expressed in a different host). By contrast, the antibodies of the present invention were found to block the interaction between CCR4 and MDC and the interaction between CCR4 and TARC (see Example 3). This strongly suggests that the antibodies of the invention bind to a different epitope than the prior art family which comprises KM2160, KM3060, KM2760 and KW-0761.

Moreover, antibodies 208, 306, 308, 406, 501, 503, 601, 603 and 803 were found to compete with one another for binding to CCR4, indicating that they bind to the same, similar or at least overlapping epitopes. None of these antibodies competes with KW-0761 for binding to CCR4, indicating that KW-0761 binds to a different epitope (Example 4).

It is also believed that the antibodies of the invention may bind to a different epitope to the commercially available anti-CCR4 antibody 1G1. BD Pharmingen make it clear on the technical data sheet for this antibody that this antibody is not a neutralising antibody. By contrast, the antibodies of the present invention are capable of blocking the binding of MDC and/or TARC to CCR4. This strongly suggests that the antibodies of the invention bind to a different epitope than the 1G1 antibody.

Certain examples of substantially homologous sequences are sequences that have at least 80%, 85%, 90% or 95% identity to the amino acid sequences disclosed. In certain embodiments, the antibodies of the invention that bind to CCR4 and which are capable of inhibiting the binding of MDC and/or TARC to CCR4 comprise at least one light chain variable region that includes an amino acid sequence region of at least about 70%, 75%, 80% or 85%, more preferably at least about 90%, more preferably at least about 95%, more preferably at least about 96%, 97% or 98% and most preferably at least 99% amino acid sequence identity to the amino acid sequence of SEQ ID NO: 30, 32, 34, 36, 38, 40, 42, 44 or 46; and/or at least one heavy chain variable region that includes an amino acid sequence region of SEQ ID NO: 29, 31, 33, 35, 37, 39, 41, 43 or 45.

In certain embodiments, the antibodies of the invention that bind to CCR4 and which are capable of inhibiting the binding of MDC and/or TARC to CCR4 comprise at least one heavy chain variable region that includes an amino acid sequence region of at least about 70%, 75%, 80% or 85%, more preferably at least about 90%, more preferably at least about 95%, more preferably at least about 96%, 97% or 98% and most preferably at least 99% amino acid sequence identity to the amino acid sequence of SEQ ID NO: 29, 31, 33, 35, 37, 39, 41, 43 or 45; and/or at least one light chain variable region that includes an amino acid sequence region of SEQ ID NO: 30, 32, 34, 36, 38, 40, 42, 44 or 46.

Other preferred examples of substantially homologous sequences are sequences containing conservative amino acid substitutions of the amino acid sequences disclosed. Preferably, the substantially homologous sequence contains no more than 30, 25, 20, 15, 10, 9, 8, 7, 6, 5, 4, 3, 2 or 1 altered amino acids across the whole VH domain and/or no more than 30, 25, 20, 15, 10, 9, 8, 7, 6, 5, 4, 3, 2 or 1 altered amino acids across the whole VL domain. In some embodiments, any such altered amino acids, if present, are only found in the framework regions.

In some embodiments, the substantially homologous sequence contains no more than 10, 9, 8, 7, 6, 5, 4, 3, 2 or 1 altered amino acids in one or more or each of the FR regions disclosed. Thus preferably the substantially homologous sequence contains no more than 10, 9, 8, 7, 6, 5, 4, 3, 2 or 1 altered amino acids in the heavy FR1, heavy FR2, heavy FR3, heavy FR4, light FR1, light FR2, light FR3, and/or light FR4 disclosed herein.

A preferred substantially homologous sequence of any of the sequences disclosed herein that comprise a light chain FR1 is one in which the amino acid at position 1 of the light chain FR1 (serine) is substituted with another amino acid, preferably glutamine (Q) and/or the amino acid at position 2 (tyrosine) of the light chain FR1 is substituted with another amino acid, preferably serine (S). Thus, preferred sequences that are substantially homologous to SEQ ID NOs: 12, 21 or 25 preferably have one or more preferably both of these substitutions, so they most preferably start with amino acids QS instead of SY. Any sequences which comprise SEQ ID NOs 12, 21 or 25 preferably also have one or both of these substitutions. Thus, preferred sequences that are substantially homologous to SEQ ID NOs: 30, 32, 34, 36, 38, 40, 42, 44 or 46, 47-55, 67, 71, 75, 79, 83, 87, 91, 95 or 99 have another amino acid, preferably Q, instead of S at position 1 of the FR1 and/or another amino acid, preferably S, instead or Y at position 2 of FR1.

Thus, a preferred homologe of SEQ ID NO: 12 is $X_1X_2$VLTQPPSASGTPGQSVTISC, wherein each X may be independently be any amino acid (SEQ ID NO: 129), preferably $X_1$ is Q, and/or $X_2$ is S (SEQ ID NO: 130). A preferred homologe of SEQ ID NO: 21 is $X_1X_2$VLTQQPPSASGTPGQSVTISC, wherein each X may be independently be any amino acid (SEQ ID NO: 131), preferably $X_1$ is Q, and/or $X_2$ is S (SEQ ID NO: 132). This applies mutatis mutandis to the VL, scFv and IgG sequences disclosed herein. Thus, any of the sequences disclosed herein which include FR1 sequences preferably include one or more of SEQ ID NOs 129-132 instead of the corresponding FR1 sequences listed in Tables 1-9.

Other preferred examples of substantially homologous sequences are sequences containing up to 1, 2, 3 or 4 preferably up to 1 or 2, altered amino acids in one or more of the CDR regions disclosed.

In all such embodiments, such alterations might be conservative or non-conservative amino acid substitutions, or a mixture thereof and preferred alterations are conservative amino acid substitutions. Thus, in one embodiment all altered amino acids are conservative substitutions.

A "conservative amino acid substitution", as used herein, is one in which the amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., glycine, cysteine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Homology may be assessed by any convenient method. However, for determining the degree of homology between sequences, computer programs that make multiple alignments of sequences are useful, for instance Clustal W (Thompson et al., 1994). If desired, the Clustal W algorithm can be used together with BLOSUM 62 scoring matrix (Henikoff and Henikoff, 1992) and a gap opening penalty of 10 and gap extension penalty of 0.1, so that the highest order match is obtained between two sequences wherein at least 50% of the total length of one of the sequences is involved in the alignment. Other methods that may be used to align sequences are the alignment method of Needleman and Wunsch (1970), as revised by Smith and Waterman (1981) so that the highest order match is obtained between the two sequences and the number of identical amino acids is determined between the two sequences. Other methods to calculate the percentage identity between two amino acid sequences are generally art recognized and include, for example, those described by Carillo and Lipton (1988) and those described in Computational Molecular Biology, Lesk, e.d. Oxford University Press, New York, 1988, Biocomputing: Informatics and Genomics Projects.

Generally, computer programs will be employed for such calculations. Programs that compare and align pairs of sequences, like ALIGN (Myers and Miller, 1988), FASTA (Pearson and Lipman, 1988; Pearson, 1990) and gapped BLAST (Altschul et al., 1997), BLASTP, BLASTN, or GCG (Devereux et al., 1984) are also useful for this purpose. Furthermore, the Dali server at the European Bioinformatics institute offers structure-based alignments of protein sequences (Holm, 1993; 1995; 1998).

By way of providing a reference point, sequences according to the present invention having 70%, 75%, 80%, 85%, 90%, 95%, 96%, 97%, 98% or 99% homology, sequence identity etc. may be determined using the ALIGN program with default parameters (for instance available on Internet at the GENESTREAM network server, IGH, Montpellier, France).

The term "substantially homologous" also includes modifications or chemical equivalents of the amino acid and nucleotide sequences of the present invention that perform substantially the same function as the proteins or nucleic acid molecules of the invention in substantially the same way.

Any substantially homologous antibody should retain the ability to specifically bind to CCR4, and preferably to the same epitope thereof as recognized by the antibody in question, for example, the same epitope or antigen recognised by the CDR domains of the invention or the $V_H$ and $V_L$ domains of the invention as described herein. Binding to the same epitope/antigen can be readily tested by methods well known and described in the art, e.g. using eptiope mapping or binding assays, e.g. a competition assay, ELISA assay or BIAcore assay. Thus, a person skilled in the art will appreciate that binding assays can be used to identify other antibodies and antibody fragments with the same binding specificities as the antibodies 208, 306, 308, 406, 501, 503, 601, 603 and 803 respectively. As exemplified, below, a competition binding assay can be used to identify such other antibodies. The method described below is only one example of a suitable competition assay. The skilled person will be aware of other suitable methods and variations.

Preferably, any substantially homologous antibody should retain the functional capabilities of the antibody, e.g. as defined elsewhere herein. Retention of functional properties can readily be tested by methods well known and described in the art.

In some embodiments, the substantially homologous sequence lacks one or more of the following sites compared with the sequences disclosed herein:

a sequence susceptible to a post-translational modification such as de-amidation and/or glycosylation;

a sequence susceptible to proteolytic digestion; and/or a sequence capable of binding to human MHC classII receptors, i.e. a T cell epitopes.

In silico testing may, for example, be carried out to determine the susceptibility of the antibody sequences to post-translational modifications such as de-amidation, glycosylation, to proteolytic digestion, and/or binding to human MHC classII receptors. Binding to human MHC classII receptors may cause T cell responses in humans, so it may be useful to identify potential T cell epitopes. Amino acids or peptide sequences identified as being putative sites susceptible to post-translational modifications, proteolytic digestion, or putative T cell epitopes, may then be modified to alter their susceptibility. Thus, the substantially homologous sequences may contain one or more of such modifications.

In silico testing for T cell epitopes may, for example, involve a program termed iTOPE™ (Antitope, Cambridge, UK). iTope™ is a molecular modelling technology which models the binding of peptides to 34 MHC class II alleles. The contribution of individual amino acids to peptide binding can be determined for each allele, and this provides information on the precise location of the core 9mer sequences that interact with the MHC class II binding groove.

Alternatively or in addition, sequences may be analyzed using the TCED (T-cell epitope database) program (Antitope, Cambridge, UK) which identifies T-cell epitopes in antibody variable regions and which can also be interrogated by BLAST searching to identify common motifs.

Epitope mapping can be performed using standard techniques. By way of example, the following methods for the identification and definition of epitopes are mentioned herein. The amino acid sequence of CCR4 is known, so synthetic peptides may be used for epitope mapping, e.g. using the Pepscan assay. Site directed mutagenesis is also a powerful tool in epitope mapping and can be used to evaluate the role of single amino acids in immune complex formation. Protein footprinting relies on the fact that the epitope is protected from cleavage when bound as an antibody-antigen complex. Enzyme linked immunosorbent assay (ELISA) and haemaglutination and slot-blotting may also be used in epitope mapping. Crystallisation of the antigen with the antibody may be used to map a non-linear epitope. Protocols for carrying out such methods are widely available and the skilled person will be aware of suitable alternative methods of epitope mapping.

Before a competition assay is performed using flow cytometry, some quantities of the tested antibody should be labeled, e.g. by biotinylation. The functionality (retention of the cell-binding properties) of the biotinylated product and the minimal concentration of the biotinylated antibody of the invention (Ab1) that gives sub-maximal binding against a fixed number of CCR4+ cells is determined. A total of $10^6$ cells are harvested from exponentially growing cultures and incubated with various antibody concentrations for a suitable period of time at a suitable temperature, e.g. 1 hr at 4° C. The cells are washed and incubated with a suitable detection antibody for a suitable period of time at a suitable temperature, e.g. an additional hour at 4° C. After washing, the cells are analyzed by flow cytometry. For each test antibody, a saturation curve is generated from the data by plotting median fluorescence intensity (MFI) against the antibody concentration.

For the competition assay, CCR4+ cells may be prepared as above and treated in duplicate with a mixture of fixed concentration of labeled (biotinylated) antibody (bio-Ab1) and increasing concentrations of non-labeled competitive antibody. The fixed concentration is the minimal concentration of antibody that generates reasonable fluorescence signal against a fixed number of tumor cells as determined above. Ideally, this fixed concentration in nM should be below the affinity of the treated antibody at equilibrium ($K_D$). In this case the described method can be used for estimation of affinities of competitive antibodies (Schodin and Kranz, 1993, J Biol Chem 268:25755-7). The antibody mixture is incubated with target cells for a suitable period of time at a suitable temperature, e.g. 1 hr at 4° C. The cells are washed and the cell binding of biotinylated antibody is revealed by incubation with FITC-labeled streptavidin. After subtracting the background fluorescence (PBS-5% FCS) from the median fluorescence reading for each test sample (bio-Ab1+Ab2), the percent of inhibition is calculated for each Ab2 concentration "c" according to the formula: % inhibition=(1−MFI$^{bio\text{-}Ab1+Ab2"c"}$/MFI$^{bio\text{-}Ab1}$)×100 is calculated.

In all embodiments, the antibodies containing substantially homologous sequences retain the ability to bind CCR4 and the ability to inhibit the binding of MDC and/or TARC to CCR4.

Other embodiments of the present invention provide binding proteins that bind to CCR4 and have the ability to inhibit the binding of MDC and/or TARC to CCR4 and that comprise an antibody of the invention, a VH or VL domain of the invention, or one or more of the CDRs of the invention. In a preferred embodiment, such binding proteins are antibodies.

Preferred antibodies of the invention comprise at least one heavy chain variable region that comprises three CDRs and at least one light chain variable region that comprises three CDRs. Exemplary and preferred sequences for these CDRs are described herein.

As used herein, the succinct term "CCR4", unless otherwise specifically stated or made clear from the scientific terminology, means CC chemokine receptor 4 (also known as CD194).

CCR4 may be free CCR4, e.g. recombinant or purified CCR4, but preferably it is present in a native form, e.g. on the surface of a cell.

The antibodies or binding proteins of the invention can also bind to fragments of CCR4, in particular fragments comprising or consisting of the extracellular domain, or can bind to entities comprising CCR4 or fragments of CCR4. Indeed, the epitope of the antibodies of the invention is located in the extracellular domain of CCR4.

"CCR4" may also refer to any form of CCR4, particularly as CCR4 is conserved across mammalian species. The antibodies or antibody fragments of the invention may thus bind to human, monkey (e.g. cynomolgus monkey), cow (bovine), mouse, rat, hamster, ferret, guinea pig and/or rabbit CCR4, for example. Preferably, the antibodies or antibody fragments of the invention will bind at least to human CCR4. Thus, unless stated otherwise, any reference herein to "CCR4" may be read to mean "human CCR4". In certain preferred embodiments, the antibodies or antibody fragments of the invention will bind at least to human and monkey (e.g. cynomologus monkey) CCR4. In other preferred embodiments the antibodies or antibody fragments of the invention will bind at least to human and mouse CCR4. In other preferred embodiments the antibodies or antibody fragments of the invention will bind at least to human, monkey and mouse CCR4. In other preferred embodiments the antibodies or antibody fragments of the invention will bind at least to human, monkey, guinea pig and mouse CCR4. In some preferred embodiments, the antibodies or antibody fragments of the invention will bind at least to human and monkey CCR4, but not to murine CCR4. In other preferred embodiments, the antibodies or antibody fragments of the invention will bind to human and monkey CCR4, but not to murine CCR4, e.g. only to human and monkey CCR4.

The Examples have shown that the antibodies of the invention can bind to human and monkey CCR4, and that they also have the ability to bind to murine CCR4.

As used herein, the term "that binds to CCR4" or "anti-CCR4" in the context of antibodies or antibody fragments of the present invention, means antibodies or antibody fragments that are capable of one or more of the following; preferably, of more than one of the following; and most preferably, of all of the following:

(a) bind to CCR4 expressed on the surface of a cell, e.g. as assessed by flow cytometry or immunohistochemistry;
(b) bind to a conformationally dependent (e.g. non linear) CCR4 epitope, e.g. as assessed by binding to CCR4 in a Western blot under non-reducing conditions;
(c) bind to free CCR4; e.g. recombinantly expressed CCR4, on a solid support, e.g. as assessed by ELISA assay or BIAcore assay;
(d) bind at least to human CCR4, more preferably to human and monkey CCR4 or to human and mouse CCR4, most preferably to human, monkey and mouse CCR4 or to human and monkey CCR4 but not mouse CCR4;
(e) bind to human CCR4 with a binding affinity (Kd) of 10 nM or less, preferably 5 nM or less, more preferably 3 nM or less or 2 nM or less, most preferably 1 nM or less as also discussed elsewhere herein;
(f) bind to human and monkey CCR4 or to human and mouse CCR4, preferably to human and monkey CCR4 but not mouse CCR4, with similar affinities, e.g. with a Kd of 10 nM or less, preferably 5 nM or less, more preferably 3 nM or less or 2 nM or less, for example 1 nM or less as also discussed elsewhere herein;
(g) induce ADCC of CCR4+ cells as described elsewhere herein;
(h) inhibit the binding of CCR4 to at least MDC and/or TARC, preferably MDC and TARC, or preferably at least MDC and/or TARC and one or more selected from RANTES, MCP-1 and MIP-1 alpha;
(i) induce anti tumour effects in vivo;
(j) localize to tumours upon administration to an animal with a tumour;
(k) induce CDC of CCR4+ cells;
(l) inhibit CCR4-mediated cellular responses to a CCR4 ligand, preferably inhibit the increase in intracellular calcium ion concentration in response to a CCR4 ligand;
(m) inhibit chemotaxis of CCR4+ cells towards a CCR4 ligand such as MDC and/or TARC.

In the context of binding to CCR4+ cells, it should be understood that the antibodies of the present invention bind to CCR4+ cells and do not significantly bind to CCR4− cells (as shown in Example 2).

The term "do not significantly bind to CCR4− cells" should be understood such that any binding of the antibody to CCR4− cells does not prohibit the use of said antibody for therapeutic or diagnostic purposes. Thus, by "insignificant" binding to CCR4− cells is meant that the binding of the antibody to CCR4− cells is weaker than its binding to one or more CCR4+ cells. Some cross-reaction with normal cells may thus occur, but this level of binding can be considered to be "background" binding. For therapeutic or diagnostic purposes the main consideration is that the antibody must bind more strongly to one or more types of CCR4+ cells than to any CCR4− with which the antibody may come into contact during the therapeutic or diagnostic application.

The antibody of the invention may be referred to as "CCR4-specific". The term "CCR-specific" should be interpreted such that the binding of the antibody to CCR4 expressing cells is specific enough to allow the use of said antibody for therapeutic or diagnostic purposes. The skilled person can easily determine if any given antibody is CCR4-specific by comparing the binding strength to the target CCR4+ cell with the binding strength to one or more types of CCR4− cells, e.g. wild-type (i.e. not transformed with CCR4) HEK293T-cells or DT40-cells.

The skilled person will be aware that binding to CCR4+ cells compared to CCR4− cells may be assessed, for example, using flow cytometry and a suitable example is described in Example 2.

Immunohistochemistry techniques, which are well known in the art, may be used to score the binding of antibodies to cells or samples. Such assays may be used to test the specificity of a particular antibody, or to detect CCR4 expression in tissue samples. Briefly, the antibody may tested for example on a high-density array of human tissues including a positive control (cells known to be CCR4-positive) and a negative contrail (cells known to be CCR4-negative). The membranous staining intensity may be estimated by visual inspection in a four step scale (0, 1, 2, 3). Preferred antibodies show weak or strong, preferably strong immunohistochemical scores for CCR4+ tissues.

The Examples show that binding of the anti-CCR4-antibodies to the CCR4-positive cell line CCRF-CEM is not inhibited in presence of increasing concentrations of human serum. Thus, the antibodies of the invention can preferably bind to CCR4 in the presence of serum, their binding not being significantly inhibited by serum.

The binding profile of the anti-CCR4-antibodies of the invention to the different CCR4+ cell lines tested in Example 2 shows increased binding to some of the CCR4+ cell lines compared to other CCR4+ cell lines. For instance, binding to L-428 is decreased in comparison to CCRF-CEM. Without wishing to be bound by theory, this is believed to be because L-428 secrete the CCR4-ligand TARC and the anti-CCR4 antibodies of the invention compete for the CCR4-binding site with the ligand (see Example 3). Binding to CCR4 is therefore best assayed using cells that do not secrete a CCR4 ligand.

The binding profile of the anti-CCR4-antibodies of the invention differs from that of KW0761. Without wishing to be bound by theory, this is believed to be due to different epitope binding sites of these antibodies (as outlined in Example 4). KW0761 does not block the binding of CCR4 and TARC, so it does not compete with the TARC secreted by L-428.

In addition, EC50 values were determined (data not shown) with varying values from cell line to cell line, which is believed to be due to differences in CCR4 expression on the surface of the various cell types.

Species cross-reactivity may be assayed using known methods, for example by flow cytometry using cells transfected with human CCR4 and CCR4 from another species respectively. A suitable assay is described in Example 8, which shows that the antibodies of the invention can bind to human, monkey and murine CCR4.

The antibodies 208, 306, 308, 406, 501, 503, 601, 603 and 803 have been shown to be capable of inhibiting the binding of CCR4 to its ligands TARC and MDC (Example 3). Thus, preferably the antibodies of the invention are capable of inhibiting the binding of CCR4 to one or more of its ligands. Preferably, the binding to at least MDC is inhibited. More preferably, the binding to MDC and TARC is inhibited. In some embodiments, the binding of CCR4 to TARC is inhibited. In embodiments of any of the aspects disclosed herein, the antibodies of the invention are capable of inhibiting the binding of MDC and/or TARC to CCR4.

By the "inhibition of binding" of a ligand to CCR4 is meant that binding of the ligand to CCR4 is reduced by at least 20, 30, or 40%, more preferably at least 45, 50, 55, 60, 65, 70 or 75%, even more preferably at least 80% in the presence of the antibody compared to binding in the absence of the antibody. Embodiments in which the binding of ligand to CCR4 is reduced by at least 85, 90 or 95% are also contemplated.

Alternatively viewed, when the ligand is first contacted with CCR4 and the antibody is subsequently added, the ligand can inhibit the binding of the antibody to CCR4.

Assays for determining whether an antibody can inhibit the binding of a ligand to CCR4 are well known and a suitable assay is descried in Example 3. Briefly, CCR4+ cells were incubated with or without Alexa647-labelled MDC-SNAP, then antibody was added. Pre-incubation in the presence of the MDC complex resulted in a reduction in antibody binding to CCR4. Particularly, the binding of antibody to CCRF-CEM cells (which naturally express CCR4) and pre-incubated with MDC (or an appropriate MDC complex) is inhibited.

Alternative assays for determining whether an antibody can block the binding of a ligand to CCR4 include the use of labeled ligand, e.g. radiolabelled ligand or biotinylated ligand and analysis with flow cytometry.

With regard to MDC, it should be noted that this agent is able to bind at least one GPCR receptor other than CCR4 with high affinity. For example, MDC has been reported to bind to the GPCR receptor D6 (Graham 2009; Locati et al. 2005), and this may affect the outcome of binding assays.

The antibodies of the invention are preferably capable of inhibiting CCR4-mediated cellular responses to a CCR4 ligand, in particular by inhibiting the increase in intracellular calcium ion concentration in response to a CCR4 ligand.

In particular, the antibodies are preferably capable of inhibiting MDC-induced calcium flux and/or TARC-induced calcium flux in CCRF-CEM cells (ATCC CCL-119). Suitable assay methods are known and an example is mentioned in Example 5.

Other preferred properties include the absence of significant toxicity in vivo when the antibodies of the invention are administered and the absence of significant other side effects in vivo.

In some embodiments, the antibodies may inhibit chemotaxis of CCR4+ cells towards a ligand of CCR4 such as MDC or TARC. This was demonstrated in Example 6.

In some embodiments, the antibodies may induce complement-dependent cytotoxicity (CDC) of CCR4+ cells, but in other embodiments the antibodies are not capable of inducing CDC. In some embodiments, the antibodies may induce apoptosis of CCR4+ cells, but in other embodiments the antibodies are not capable of inducing apoptosis. In some embodiments, the antibodies may be internalised by CCR4+ cells upon binding to CCR4, but in other embodiments no significant internalisation takes place.

The induction of apoptosis may be assayed using well-known standard methods, for example methods which assay Annexin V staining. Briefly, cells may be incubated with an antibody for a suitable period of time, e.g. 24 hours and the effect, after cell harvesting and Annexin V staining may be measured by FACS analysis (e.g. using EasyCyte).

The induction of CDC may be assayed using well-known standard methods, for example methods which measure the relative number of viable cells based on the uptake and metabolism of a redox dye such as Alamar blue. A suitable assay is disclosed in H Gazzano-Santoro et al. J Immunol Methods. 1997, 28; 202(2):163-71.

The skilled person will be aware of suitable ways to assay internalisation, for example using temperature-differential fluorescence labeling on flow cytometry or confocal microscopy. An example of a suitable assay involves a secondary antibody labelled with a pH-sensitive dye (such as CypHer5E), which is minimally fluorescent at a basic pH (as found outside of cells) and maximally fluorescent at an acidic pH (as found inside of cells).

The inhibition of chemotaxis may be assayed using standard methods, for example using a transwell assay. Briefly, cells capable of chemotaxis and which express CCR4 are contacted with an antibody in one chamber and a ligand of CCR4 such as MDC is placed in another chamber separated from the first chamber by a membrane of filter having a suitable pore size. The effect of the antibody on cell migration towards the ligand (chemotaxis) is determined by comparing chemotaxis in the presence of the antibody to chemotaxis in the absence of the antibody. A suitable method is described in Example 6.

The term "ligand" of CCR4 includes the natural ligands of CCR4 such as MDC, TARC, RANTES, MCP-1 and/or MIP-1alpha, which may be naturally produced, recombinantly expressed or synthesised in the laboratory.

By "CCR4+ cells" is meant cells which express CCR4 on their surface, preferably at least substantially in its wild-type conformation. CCR4+ cells may be naturally positive for CCR4, or they may be transformants which express recombinant CCR4. CCR4+ cells may inter alia include solid tumor cells, hematological tumor cells and/or Tregs. Preferred examples of CCR4+ cells, particularly for in vitro assays, are CCRF-CEM, L-428, Hut78, 786-O, A498 and KatoIII.

In light of this invention, therefore, a range of anti-CCR4 antibodies can be made and used in a variety of embodiments, including in the treatment of any of the disorders discussed elsewhere herein, particularly cancer, immune disorders, inflammatory disorders and infections.

As used throughout the entire application, the terms "a" and "an" are used in the sense that they mean "at least one", "at least a first", "one or more" or "a plurality" of the referenced components or steps, except in instances wherein an upper limit is thereafter specifically stated. Therefore, an "antibody", as used herein, means "at least a first antibody". The operable limits and parameters of combinations, as with the amounts of any single agent, will be known to those of ordinary skill in the art in light of the present disclosure.

Preferred embodiments of the invention are compositions comprising at least one anti-CCR4 antibody of the invention, or antigen binding fragment thereof.

Nucleic acid molecules comprising nucleotide sequences that encode the antibodies of the present invention as defined herein or parts or fragments thereof, or nucleic acid molecules substantially homologous thereto, form yet further aspects of the invention. The nucleic acid sequences disclosed in the Tables are preferred.

Preferred nucleic acid molecules comprise sequences which encode the amino acid sequence set out in SEQ ID NO: 47 (which is preferably encoded by SEQ ID NO: 56 or a sequence substantially homologous thereto), SEQ ID NO: 48 (which is preferably encoded by SEQ ID NO: 57 or a sequence substantially homologous thereto), SEQ ID NO: 49 (which is preferably encoded by SEQ ID NO: 58 or a sequence substantially homologous thereto), SEQ ID NO: 50 (which is preferably encoded by SEQ ID NO: 59 or a sequence substantially homologous thereto), SEQ ID NO: 51 (which is preferably encoded by SEQ ID NO: 60 or a sequence substantially homologous thereto), SEQ ID NO: 52 (which is preferably encoded by SEQ ID NO: 61 or a sequence substantially homologous thereto), SEQ ID NO: 53 (which is preferably encoded by SEQ ID NO: 62 or a sequence substantially homologous thereto), SEQ ID NO: 54 (which is preferably encoded by SEQ ID NO: 63 or a sequence substantially homologous thereto) or SEQ ID NO: 55 (which is preferably encoded by SEQ ID NO: 64 or a sequence substantially homologous thereto).

Other preferred nucleic acid molecules comprise sequences which encode a heavy chain variable region (VH) that has the amino acid sequence of SEQ ID NO: 29, 31, 33, 35, 37, 39, 41, 43 or 45 or a sequence substantially homologous thereto (which is preferably encoded by SEQ ID NO: 101, 103, 105, 107, 109, 111, 113, 115 or 117 respectively or a sequence substantially homologous thereto) and/or comprise sequences which encode a light chain variable region (VL) which has the amino acid sequence of SEQ ID NO: 30, 32, 34, 36, 38, 40, 42, 44 or 46 or a sequence substantially homologous thereto (which is preferably encoded by SEQ ID NO: 102, 104, 106, 108, 110, 112, 114, 116 or 118 respectively or a sequence substantially homologous thereto).

More preferred are nucleic acids which encode the following combinations: SEQ ID NOs: 29 and 30; or SEQ ID NOs: 31 and 32; or SEQ ID NOs: 33 and 34; or SEQ ID NOs 35 and 36; or SEQ ID NOs 37 and 38; or SEQ ID NOs 39 and 40; or SEQ ID NOs 41 and 42; or SEQ ID NOs 43 and 44; or SEQ ID NOs 45 and 46. Also preferred are nucleic acid molecules which comprise the following combinations: SEQ ID NOs: 101 and 102; or SEQ ID NOs: 103 and 104; or SEQ ID NOs: 105 and 106; or SEQ ID NOs: 107 and 108; or SEQ ID NOs: 109 and 110; or SEQ ID NOs: 111 and 112; or SEQ ID NOs: 113 and 114; or SEQ ID NOs: 115 and 116; or SEQ ID NOs: 117 and 118.

As mentioned above, the FR1 region of the light chain may have residues QS at positions 1 and 2. A preferred nucleic acid sequence is therefore one which comprises or consists of a sequence which encodes a VL substantially homologous to VL 503 (SEQ ID NO: 40) having residues QS at positions 1 and 2, preferably having the sequence set out below in which the changes compared to SEQ ID NO: 40 are underlined:

```
                                         (SEQ ID NO: 133)
CAAAGCgtgctgactcagccaccctcagcgtctgggaccccgggcaga gcgtcaccatctcttgttctggaagcacctccaacatcggaagtcatta tgtggtctggtaccagcagctcccaggaacggcccccagactcctcatc tataggaatcatcagcggccctcaggggtccctgaccgactctctggct ccaagtctggcacctcagcctccctggccatcggtgggctccggtccga ggatgaggctgattattactgtgcagtgtgggatgacaccctgagtggc tgggtgttcggcggagggaccaagctgaccgtccta.
```

Other preferred nucleic acid molecules comprise sequences that encode IgG forms of the antibodies of the invention, for example those as described in Example 1, or murine chimeric forms.

As indicated above, other nucleic acid molecules encompassed by the present invention are those encoding parts or fragments of the human antibodies of the present invention, e.g., those encoding a heavy chain variable region (VH) of an antibody or those encoding a light chain variable region (VL) of an antibody. Other preferred nucleic acid molecules are those encoding a heavy chain of an antibody of the present invention (e.g., those encoding SEQ ID NO: 67, 71, 75, 79, 83, 87, 91, 95 or 99, such as SEQ ID NOs: 65, 69, 73, 77, 81, 85, 89, 93 or 97 respectively or a sequence substantially homologous thereto) or those encoding a light chain of an antibody (e.g., those encoding SEQ ID NO: 68, 72, 76, 80, 84, 88, 92, 96 or 100 such as SEQ ID NOs: 66, 70, 74, 82, 86, 90, 94 or 98 respectively or a sequence substantially homologous thereto).

Thus, fragments of the antibodies of the invention as defined herein, or sequences substantially homologous thereto, or nucleic acid molecules comprising sequences encoding such fragments form a yet further aspect of the invention.

The term "substantially homologous" as used herein in connection with a nucleic acid sequence includes sequences having at least 70% or 75%, preferably at least 80%, and even more preferably at least 85%, 90%, 95%, 96%, 97%, 98% or 99%, sequence identity to the amino acid or nucleic acid sequence disclosed. Substantially homologous nucleic acid sequences of the invention thus include single or multiple base alterations (additions, substitutions, insertions or deletions) to the sequences of the invention.

Preferably, the antibodies of the present invention, when in IgG format, have a high binding affinity for CCR4, for example they may have a Kd in the range of $1 \times 10^{-8}$ M or $1 \times 10^{-9}$ M or less. Importantly, antibodies with such an affinity are in the established range that has been shown to be useful for therapy. Preferably, the antibodies of the invention, when in IgG format, have a binding affinity for CCR4 that corresponds to a Kd of less than 30 nM, 20 nM, 15 nM or 10 nM, more preferably of less than 10, 9.5, 9, 8.5, 8, 7.5, 7, 6.5, 6, 5.5, 5, 4.5, 4, 3.5, 3, 2.5, 2, 1.5 or 1 nM, most preferably less than 0.9, 0.8, 0.7, 0.6, 0.5, 0.4, 0.3, 0.2 or 0.1 nM.

Any appropriate method of determining Kd may be used. However, preferably the Kd is determined by testing various concentrations of the test antibody against various concentrations of antigen (CCR4) in vitro to establish a saturation curve, for example using the Lineweaver-Burk method, or by using commercially available binding model software, such as the 1:1 binding model in the BIAcore 1000 Evaluation software. Kd values may be calculated from IgG titrations on CCR+ cells using "one site-specific binding" model f the software Prism (GraphPad, San Diego, Calif.).

With regard to determinations of Kd values, the skilled person will appreciate that apparent Kd values derived from binding experiments using cells expressing a target (e.g. CCR4) cannot be considered to be an absolute indication of affinity, because the experimental conditions will affect the apparent binding affinity. For example, the levels of expression of CCR4 may vary depending on the conditions under which the cells are cultured, as well as differing between different cell types. It is consequently best to compare apparent Kd values obtained within one set of experiments and it may not always be appropriate to compare Kd values obtained in one set of experiments with Kd values obtained in a different set of experiments, particularly if the experimental conditions varied significantly.

Alternatively, the off-rate and the antibody half-life on the surface of the CCR4-positive cell can be determined by performing the cell surface retention assay Adams et al., 1998, Prolonged in vivo tumour retention of a human diabody targeting the extracellular domain of human HER2/neu. Br J Cancer 77: 1405-12; Le Gall et al., 1999, Di-, tri- and tetrameric single chain Fv antibody fragments against human CD19: effect of valency on cell binding. FEBS Lett 453: 164-8. The latter method allows more appropriate mimicking the real situation in human patient under the treatment conditions.

In some embodiments, antibodies of the invention may bind to both human CCR4 and monkey CCR4. Such cross-reactivity between species and in particular between humans and species commonly used as pre-clinical animal models may be an advantage as it allows a more effective translation from pre-clinical studies to clinical use. For example, having an antibody which cross reacts with the native CCR4 present in the particular animal model used means that the results in this model are more likely to reflect the situation in a human patient, thereby allowing a more accurate assessment of for example dosing to be made and an increased likelihood of identifying any potentially relevant or problematic side effects.

For example, the ability of an antibody of the invention to bind to both human CCR4 and monkey CCR4 means that such antibodies can be tested in preclinical toxicity studies to assess adverse side effects of the treatment and to find appropriate tolerated dosages.

In addition, the ability to bind both human CCR4 and mouse CCR4 means that the results shown by such antibodies of the invention in mouse models, e.g. mouse syngeneic models using immunocompetent mice, are more likely to be representative of the activity of the antibodies in human subjects. The reason for this is that antibodies which can bind to human CCR4 but not mouse CCR4 will bind to CCR4 expressed by the human tumor cells in the mouse model but will not be able to bind to endogenous murine CCR4. This is of course unlike the situation in a human patient, in which CCR4 expressed by the tumor and endogenous CCR4 would be present.

This is especially the case if the antibody has similar affinity to both murine and human CCR4.

The potential disadvantage with such a situation is that an antibody which binds to human CCR4 but not, or with significantly lower affinity, to mouse CCR4 might perform well in a human tumor xenograft model in immunocompromised mice (e.g. nude or SCID mice) but this might not be reflected by a similar performance in a human system where much more CCR4 was present. In other words, the anti-tumor effect seen in a mouse xenograft system with an antibody which can bind to human CCR4 but not mouse CCR4 might look better than the clinical reality. In contrast, when working with an antibody that can bind to both human and mouse CCR4 then this will bind to all forms of CCR4 present in the mouse model system and is likely to be more representative of the situation when the antibody is put into humans. This is especially the case if the antibody has similar affinity to both murine and human CCR4.

In preferred embodiments, antibodies of the invention bind to human and monkey CCR4 or to human and mouse CCR4 with similar affinities, e.g. with a Kd of 10 nM or less or 5 nM or less, more preferably 3 nM or less or 2 nM or less, most preferably 1 nM or less.

By "similar affinity" is also meant that the binding affinity of the antibody for human CCR4 and for one or more of the other species of interest (e.g. monkey or mouse) is comparable, e.g. is not more than a factor of 20 different. More preferably the difference between the binding affinities is less than a factor of 15, more preferably less than a factor of 10, most preferably less than a factor of 5, 4, 3 or 2.

However, in other embodiments the antibodies of the present invention may not bind to monkey CCR4 and/or they may not bind to mouse CCR4.

The antibodies of the invention bind to CCR4. Thus the antibodies or binding proteins of the invention can be used to detect CCR4 in vivo or in vitro, in particular to detect CCR4+ cells. For example, as CCR4 is expressed on certain tumour cells, the antibodies or binding proteins of the invention can be used to detect tumour cells in vivo or in vitro. In addition, the ability of the antibodies to localize to CCR4+ cells means that the antibodies of the invention can target body sites at which CCR4+ cells are present, whereupon the antibody can act at the target site. In particular, the ability of the antibodies to localize to CCR4+ tumour cells means that the antibodies of the invention can target body sites at which CCR4+ tumour cells are present, whereupon the antibody can act at the target site.

For example, the antibody may induce an anti-CCR4+ cell effect itself i.e. as a naked antibody, e.g. by activating or inducing ADCC. This ability to act as a naked Ab is advantageous. Alternatively, or in addition, the antibody can induce an anti-CCR4+ cell effect by virtue of being conjugated to an additional therapeutic molecule, e.g. a toxin or other anti-cancer molecule or an anti-inflammatory agent as described herein.

The antibodies of the invention preferably have the ability to induce antibody dependent cellular cytotoxicity (ADCC) of CCR4+ cells. ADCC may be assayed in vitro using methods well known in the art. Killing of the CCR4+ cell line CCRF-CEM in the presence of human PBMCs may be assayed, for example. A Chromium-51 release assay may be used, for example. Thus, the antibodies of the invention may for example cause at least 10%, 15%, 20%, 22%, 25%, 30%, 40%, 50%, 60%, 70%, 80% or 90% killing of CCR4+ cells in vitro, e.g. in the presence of human PBMCs. ADCC is advantageous for some applications, particularly some therapeutic applications. Thus, in preferred embodiments the antibody can induce ADCC of CCR4+ cells, preferably of CCR4+ tumour cells and/or CCR4+ Th2 cells. In some embodiments the antibody-mediated ADCC is in the presence of PBMCs, but embodiments in which antibody-mediated ADCC is in the absence of PBMCs are also contemplated. The ability of the antibodies of the invention to induce ADCC of CCR4+ cells was shown in Example 9. The results clearly demonstrate that the anti-CCR4 antibodies of the invention are able to induce ADCC in the presence of human PBMCs on all three target cell lines. The antibody 503 was determined to have an EC50 of 5.3 pM when tested on CCRF-CEM cells, compared to 315 pM of KW0761. In addition, the anti-CCR4 antibodies of the invention also exhibited comparable maximum killing activities when challenged for ADCC on isolated Treg cells.

The antibodies of the invention are preferably also shown to be suitably potent in terms of the concentration of antibody required to achieve such ADCC levels. Thus, the antibody concentration required for half maximal cell lysis (EC50) of CCR4+ cells, e.g. CCRF-CEM cells, in vitro is preferably less than 700 ng/ml, 650 ng/ml, 620 ng/ml, 600 ng/ml, 550 ng/ml, 500 ng/ml, 450 ng/ml, 400 ng/ml, 350 ng/ml, 300 ng/ml, 250 ng/ml, 200 ng/ml, 150 ng/ml, 100 ng/ml, 90 ng/ml, 80 ng/ml, 70 ng/ml, 60 ng/ml, 50 ng/ml, 46 ng/ml, 40 ng/ml, 35 ng/ml, 30 ng/ml, 25 ng/ml, 20 ng/ml, 15 ng/ml, 10 ng/ml, 9 ng/ml, 7 ng/ml, 5 ng/ml, 2 ng/ml, 1 ng/ml, 0.5 ng/ml or 0.25 ng/ml.

Preferably, the above described abilities are observed at a measurable or significant level and more preferably at a statistically significant level, when compared to appropriate control levels.

It should be noted that PBMC (effector cells) prepared from different donors may exhibit a significant variation of ADCC with respect to the extent of non-specific and specific tumour cell lysis, as well as EC50 values. This phenomenon has been described by Naundorf et al, 2002.

Human IgG1 is a glycoprotein bearing two N-linked oligosaccharide chains bound to the Fc region. The oligosaccharides are of the complex biantennary type, composed of a trimannosyl core structure with the presence or absence of core fucose, bisecting N-acetylglucosamine (GlcNAc), galactose, and terminal sialic acid, which gives rise to structural heterogeneity. Both human serum IgG and therapeutic antibodies are well known typically to be heavily fucosylated.

It has been reported that ADCC enhancement may in some instances be achieved by manipulating the state of oligosaccharides on human IgG1 subclass. In particular, defucosylation has been shown to cause an increase in ADCC activity of some antibodies (Niwa R et al, 2004). Thus, in preferred embodiments, antibodies according of the invention are modified during production/expression of the protein, and/or in vitro after production/expression, to generate a specific glycosylation pattern, particularly a glycosylation pattern which is beneficial for therapeutic application of the antibodies. Preferably, said specific glycosylation pattern is the reduction or absence of fucose-based glycosylation, which preferably increases the antibody's ability to induce ADCC. Thus, in preferred embodiments, the antibodies of the invention have a specific glycosylation pattern, preferably a specific glycosylation pattern which increases the ability of said antibody to induce ADCC. Preferable, the antibodies of the invention are defucosylated or non-fucosylated.

The skilled person is aware of suitable ways of preparing defucosylated or non-fucosylated antibodies. For example, this can be achieved by producing the antibody in presence of Kifunensine (for example 100 ng/ml), a selective inhibitor of class I α-mannosidases, leading to a decrease in fucosylation of the molecule during production. Suitable host cells which lack one or more proteins required for fucosylation of oligosaccharide moieties can be used to produce defucosulated antibodies, e.g. fucosyltransferase-deficient host cells. Examples of suitable host cells are cells wherein the activity of an enzyme relating to the synthesis of an intracellular sugar nucleotide, GDP-fucose and/or the activity of an enzyme relating to the modification of a sugar chain in which 1-position of fucose is bound to 6-position of N-acetylglucosamine in the reducing end through an α-bond in the complex N-glycoside-linked sugar chain is decreased or deleted. Examples of such enzymes include enzymes relating to the synthesis of GDP-fucose include GMD (GDP-mannose 4,6-dehydratase), Fx (GDP-keto-6-deoxymannose 3,5-epimerase, 4-reductase), GFPP (GDP-beta-L-fucose pyrophosphorylase).

As described in Example 2, defucosylated version of antibodies 306, 406 and 503 were produced in the presence of Kifunensine, a selective inhibitor of class I α-mannosidases, causing a stop in fucosylation of the IgG during production in cell culture.

By "defucosulated" is meant that at least 10%, preferably at least 20, 30, 40 50, 60, 75, 80, 85, 90, 91, 92, 93, 94, 95, 96, 97, 98 or at least 99% of the total complex N-glycoside-linked sugar chains bound to the Fc region are sugar chains in which fucose is not bound to N-acetylglucosamine in the reducing end in the sugar chain. By "non-fucosylated" is meant that no significant levels of fucose are present in the antibody.

Some antibodies are capable of being internalized into the cells to which they become bound. Thus, in some embodiments of the invention the antibodies are capable of being internalized. This property is particularly advantageous for use in immunoconjugates as any other agent attached to the antibody molecule should be internalized with the antibody molecule. In other embodiments no significant internalization is seen.

CCR4 is known to be expressed on platelets, and its ligands MDC and TARC are known to induce platelet aggregation. This could potentially be problematic, as IgG molecules have two ligand binding sites, so there is a possibility that an IgG capable of recognizing CCR4 may be able to cross link platelets if both arms are able to bind to CCR4 on different platelets. This might result in blot clotting in vivo. Particularly for medical applications, it is desirable that the antibody does not induce any significant platelet aggregation. Platelet aggregation may be assayed using known methods. The effect of the antibodies of the invention on platelet aggregation was assayed as described in Example 11. Essentially, the antibodies were incubated with isolated platelets alone or in combination ADP, a well-described inducer of aggregation (Varon and Spectre "Antiplatelet agents" Hematology Am Soc Hematol Educ Program. 267-72, 2009). Binding of the anti-CCR4 antibodies to platelets was observed, but the antibodies were shown to have no effect on platelet aggregation. They do not induce aggregation, nor do they inhibit e.g. ADP-induced platelet aggregation. Thus, the antibodies do not have any significant effect on platelet aggregation.

As discussed above, certain PBLs, including Tregs, express CCR4, so in some embodiments of the invention the antibodies can bind to PBLs, preferably to Tregs and/or Th2 cells. This feature is advantageous, particularly in immunotherapy, as it may allow the depletion of Treg cells.

In the following descriptions of the compositions, immunoconjugates, pharmaceuticals, combinations, cocktails, kits, first and second medical uses and all methods in accordance with this invention, the terms "antibody" and "immunoconjugate", or an antigen-binding region or fragment thereof, unless otherwise specifically stated or made clear from the scientific terminology, refer to a range of anti-CCR4 antibodies as well as to the specific 208, 306, 308, 406, 501, 503, 601, 603 and 803 antibodies.

The terms "antibody" and "immunoglobulin", as used herein, refer broadly to any immunological binding agent or molecule that comprises a human antigen binding domain, including polyclonal and monoclonal antibodies. Depending on the type of constant domain in the heavy chains, whole antibodies are assigned to one of five major classes: IgA, IgD, IgE, IgG, and IgM and the antibodies of the invention may be in any one of these classes. Several of these are further divided into subclasses or isotypes, such as IgG1, IgG2, IgG3, IgG4, and the like. The heavy-chain constant domains that correspond to the difference classes of immunoglobulins are termed α, δ, ε, γ and μ, respectively. The subunit structures and three-dimensional configurations of different classes of immunoglobulins are well known.

Generally, where whole antibodies rather than antigen binding regions are used in the invention, IgG and/or IgM are preferred because they are the most common antibodies in the physiological situation and because they are most easily made in a laboratory setting. IgG1 antibodies are particularly preferred.

The "light chains" of mammalian antibodies are assigned to one of two clearly distinct types: kappa (κ) and lambda (λ), based on the amino acid sequences of their constant domains and some amino acids in the framework regions of their variable domains. There is essentially no preference to the use of κ or λ light chain constant regions in the antibodies of the present invention.

As will be understood by those in the art, the immunological binding reagents encompassed by the term "antibody" extend to all antibodies and antigen binding fragments thereof, including whole antibodies, dimeric, trimeric and multimeric antibodies; bispecific antibodies; chimeric antibodies; recombinant and engineered antibodies, and fragments thereof.

The term "antibody" is thus used to refer to any antibody-like molecule that has an antigen binding region, and this term includes antibody fragments that comprise an antigen binding domain such as Fab', Fab, F(ab')2, single domain antibodies (DABs), TandAbs dimer, Fv, scFv (single chain Fv), dsFv, ds-scFv, Fd, linear antibodies, minibodies, diabodies, bispecific antibody fragments, bibody, tribody (scFv-Fab fusions, bispecific or trispecific, respectively); sc-diabody; kappa (lamda) bodies (scFv-CL fusions); Bispecific T-cell Engager (BiTE) (scFv-scFv tandems to attract T cells); dual variable domain (DVD)-Ig (bispecific format); small immunoprotein (SIP) (kind of minibody); SMIP ("small modular immunopharmaceutical" scFv-Fc dimer; DART (ds-stabilized diabody "Dual Affinity ReTargeting"); small antibody mimetics comprising one or more CDRs and the like.

The techniques for preparing and using various antibody-based constructs and fragments are well known in the art (see Kabat et al., 1991, specifically incorporated herein by reference). Diabodies, in particular, are further described in EP 404, 097 and WO 93/11161; whereas linear antibodies are further described in Zapata et al. (1995).

Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art. For example, each of Beckman et al., 2006; Holliger & Hudson, 2005; Le Gall et al., 2004; Reff & Heard, 2001; Reiter et al., 1996; and Young et al., 1995 further describe and enable the production of effective antibody fragments.

The antibodies or antibody fragments can be produced naturally or can be wholly or partially synthetically produced. Thus the antibody may be from any appropriate source, for example recombinant sources and/or produced in transgenic animals or transgenic plants, or in eggs using the IgY technology. Thus, the antibody molecules can be produced in vitro or in vivo.

Preferably, the antibody or antibody fragment comprises an antibody light chain variable region (VL) that comprises three CDR domains and an antibody heavy chain variable region (VH) that comprises three CDR domains. Said VL and VH generally form the antigen binding site.

An "Fv" fragment is the minimum antibody fragment that contains a complete antigen-recognition and binding site. This region has a dimer of one heavy chain and one light chain variable domain in tight, non-covalent association. It is in this configuration that the three hypervariable regions (CDRs) of each variable domain interact to define an antigen-binding site on the surface of the VH-VL dimer. Collectively, the six hypervariable regions (CDRs) confer antigen-binding specificity to the antibody.

However, it is well documented in the art that the presence of three CDRs from the light chain variable domain and three CDRs from the heavy chain variable domain of an antibody is not necessary for antigen binding. Thus, constructs smaller than the above classical antibody fragment are known to be effective.

For example, camelid antibodies (Hamers-Casterman et al., 1993; Arbabi Ghahroudi et al., 1997) have an extensive antigen binding repertoire but are devoid of light chains. Also, results with single domain antibodies comprising VH domains alone (Ward et al., 1989; Davies and Riechmann, 1995) or VL domains alone (van den Beucken et al., 2001) show that these domains can bind to antigen with acceptably high affinities. Thus, three CDRs can effectively bind antigen.

It is also known that a single CDR, or two CDRs, can effectively bind antigen. As a first example, a single CDR can be inserted into a heterologous protein and confer antigen binding ability on the heterologous protein, as exemplified by showing that a VH CDR3 region inserted into a heterologous protein, such as GFP, confers antigen binding ability on the heterologous protein (Kiss et al., 2006; Nicaise et al., 2004).

It is further known that two CDRs can effectively bind antigen, and even confer superior properties than possessed by the parent antibody. For example, it has been shown (Qiu et al., 2007) that two CDRs from a parent antibody (a VH CDR1 and a VL CDR3 region) retain the antigen recognition properties of the parent molecule but have a superior capacity to penetrate tumours. Joining these CDR domains with an appropriate linker sequence (e.g., from VH FR2) to orientate the CDRs in a manner resembling the native parent antibody produced even better antigen recognition. Therefore, it is known in the art that it is possible to construct antigen binding antibody mimetics comprising two CDR domains (preferably one from a VH domain and one from a VL domain, more preferably, with one of the two CDR domains being a CDR3 domain) orientated by means of an appropriate framework region to maintain the conformation found in the parent antibody.

Thus, although preferred antibodies of the invention might comprise six CDR regions (three from a light chain and three from a heavy chain), antibodies with fewer than six CDR regions and as few as one or two CDR regions are encompassed by the invention. In addition, antibodies with CDRs from only the heavy chain or light chain are also contemplated.

Preferred antibodies of the invention that bind to CCR4 comprise at least one heavy chain variable region that comprises three CDRs and at least one light chain variable region that comprises three CDRs, wherein said heavy chain variable region comprises heavy chain CDRs having the sequences disclosed herein.

Preferred light chain CDR regions for use in conjunction with the specified heavy chain CDR regions are described elsewhere herein. However, other light chain variable regions that comprise three CDRs for use in conjunction with the heavy chain variable regions of the invention are also contemplated. Appropriate light chain variable regions which can be used in combination with the heavy chain variable regions of the invention and which give rise to an antibody which binds CCR4 can be readily identified by a person skilled in the art.

For example, a heavy chain variable region of the invention can be combined with a single light chain variable region or a repertoire of light chain variable regions and the resulting antibodies tested for binding to CCR4. It would be expected that a reasonable number of such combinations of heavy chain variable regions of the invention with different light chain variable regions would retain the ability to bind CCR4.

Similar methods could be used to identify alternative heavy chain variable regions for use in combination with preferred light chain variable regions of the invention.

In certain embodiments, the antibody or antibody fragment comprises all or a portion of a heavy chain constant region, such as an IgG1, IgG2, IgG3, IgG4, IgA1, IgA2, IgE, IgM or IgD constant region. Preferably, the heavy chain constant region is an IgG1 heavy chain constant region, or a portion thereof. Furthermore, the antibody or antibody fragment can comprise all or a portion of a kappa light chain constant region or a lambda light chain constant region, or a portion thereof. All or part of such constant regions may be produced naturally or may be wholly or partially synthetic. Appropriate sequences for such constant regions are well known and documented in the art. When a full complement of constant regions from the heavy and light chains are included in the antibodies of the invention, such antibodies are typically referred to herein as "full length" antibodies or "whole" antibodies.

Antibodies containing an Fc region are preferred for certain uses, particularly therapeutic uses in vivo, where the Fc region mediates effector functions such as ADCC.

The substantially homologous nucleic acid sequences also include nucleotide sequences that hybridize to the nucleic acid sequences disclosed (or their complementary sequences), e.g., hybridize to nucleotide sequences encoding one or more of the light chain or heavy chain CDRs of the invention, the light or heavy chain variable regions of the invention, or the antibodies of the invention (or hybridize to their complementary sequences), under at least moderately stringent hybridization conditions, preferably highly stringent conditions.

Substantially homologous sequences of proteins of the invention also include, without limitation, alterations that do not affect the VH, VL or CDR domains of the antibodies, e.g., include scFv antibodies where a different linker sequence is used or antibodies where tag sequences or other components are added that do not contribute to the binding of antigen, or alterations to convert one type or format of antibody molecule or fragment to another type or format of antibody molecule or fragment (e.g., conversion from Fab to scFv or vice versa), or the conversion of an antibody molecule to a particular class or subclass of antibody molecule (e.g., the conversion of an antibody molecule to IgG or a subclass thereof, e.g., IgG1 or IgG3).

In other preferred embodiments, second generation antibodies are provided that have enhanced or superior properties in comparison to an original anti-CCR4 antibody, such as 208, 306, 308, 406, 501, 503, 601, 603 and 803. For example, the second generation antibodies may have a stronger binding affinity for CCR4, a superior cross reactivity profile, superior ability to target CCR4+ cells, particularly tumour cells, an improved ability to induce ADCC, an improved ability to induce CDC, an improved treatment of the disorders discussed elsewhere herein.

Comparisons to identify effective second generation antibodies are readily conducted and quantified, e.g., using one or more of the various assays described in detail herein or in the art. Second generation antibodies that have an enhanced biological property or activity of at least about 2-fold, 5-fold, 10-fold, 20-fold, and preferably, at least about 50-fold, in comparison to the anti-CCR4 antibodies of the present invention, as exemplified by the 208, 306, 308, 406, 501, 503, 601, 603 and 803 antibody, are encompassed by the present invention.

The antibody, binding protein and nucleic acid molecules of the invention are generally "isolated" or "purified" molecules insofar as they are distinguished from any such components that may be present in situ within a human or animal body or a tissue sample derived from a human or animal body. The sequences may, however, correspond to or be substantially homologous to sequences as found in a human or animal body. Thus, the term "isolated" or "purified" as used herein in reference to nucleic acid molecules or sequences and proteins or polypeptides, e.g., antibodies, refers to such molecules when isolated from, purified from, or substantially free of their natural environment, e.g., isolated from or purified from the human or animal body (if indeed they occur naturally), or refers to such molecules when produced by a technical process, i.e., includes recombinant and synthetically produced molecules.

Thus, when used in connection with a nucleic acid molecule, such terms may refer to a nucleic acid substantially free of material with which it is naturally associated such as other nucleic acids/genes or polypeptides. These terms may also refer to a nucleic acid substantially free of cellular material or culture medium when produced by recombinant DNA techniques, or substantially free of chemical precursors, or other chemicals when chemically synthesized. An isolated or purified nucleic acid may also be substantially free of sequences that naturally flank the nucleic acid (i.e., sequences located at the 5' and 3' ends of the nucleic acid) from which the nucleic acid is derived or sequences that have been made to flank the nucleic acid (e.g., tag sequences or other sequence that have no therapeutic value) by, for example, genetic engineering.

Thus, when used in connection with a protein or polypeptide molecule such as light chain CDRs 1, 2 and 3, heavy chain CDRs 1, 2 and 3, light chain variable regions, heavy chain variable regions, and binding proteins or antibodies of the invention, including full length antibodies, the term "isolated" or "purified" typically refers to a protein substantially free of cellular material or other proteins from the source from which it is derived. In some embodiments, particularly where the protein is to be administered to humans or animals, such isolated or purified proteins are substantially free of culture medium when produced by recombinant techniques, or chemical precursors or other chemicals when chemically synthesized. Such isolated or purified proteins may also be free of flanking sequences such as those described above for the isolated nucleic acid molecules.

The term "nucleic acid sequence" or "nucleic acid molecule" as used herein refers to a sequence of nucleoside or nucleotide monomers composed of naturally occurring bases, sugars and intersugar (backbone) linkages. The term also includes modified or substituted sequences comprising non-naturally occurring monomers or portions thereof. The nucleic acid sequences of the present invention may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. The nucleic acid molecules may be double stranded or single stranded. The nucleic acid molecules may be wholly or partially synthetic or recombinant.

In preferred embodiments the antibodies of the invention are human antibodies, more preferably fully human antibodies. In this regard, human antibodies generally have at least three potential advantages for use in human therapy. First, the human immune system should not recognize the antibody as foreign. Second, the half-life in the human circulation will be similar to naturally occurring human antibodies, allowing smaller and less frequent doses to be given. Third, because the effector portion is human, it will interact better with the other parts of the human immune system, e.g., to destroy target cells more efficiently by complement-dependent cytotoxicity (CDC) or antibody-dependent cellular cytotoxicity (ADCC).

However, although human antibodies are generally recognized to display these advantages, it is known that the development of human antibodies that have high enough affinities and appropriate functional properties to make them candidates for successful human therapy is by no means straightforward. The art therefore still lacks anti-CCR4 for the safe and effective treatment of humans, and poses challenges to the development of such agents.

The term "human" as used herein in connection with antibody molecules and binding proteins first refers to antibodies and binding proteins having variable regions (e.g., VH, VL, CDR or FR regions) and, optionally, constant antibody regions, isolated or derived from a human repertoire or derived from or corresponding to sequences found in humans, e.g., in the human germline or somatic cells.

The 208, 306, 308, 406, 501, 503, 601, 603 and 803 antibodies are examples of such a human antibody molecules wherein the variable regions have been isolated from a human repertoire.

The "human" antibodies and binding proteins of the invention further include amino acid residues not encoded by human sequences, e.g., mutations introduced by random or site directed mutations in vitro, for example mutations introduced by in vitro cloning or PCR. Particular examples of such mutations are mutations that involve conservative substitutions or other mutations in a small number of residues of the antibody or binding protein, e.g., in up to 5, 4, 3, 2 or 1 of the residues of the antibody or binding protein, preferably e.g., in up to 5, 4, 3, 2 or 1 of the residues making up one or more of the CDRs of the antibody or binding protein. Certain examples of such "human" antibodies include antibodies and variable regions that have been subjected to standard modification techniques to reduce the amount of potentially immunogenic sites.

Thus, the "human" antibodies of the invention include sequences derived from and related to sequences found in humans, but which may not naturally exist within the human antibody germline repertoire in vivo. In addition, the human antibodies and binding proteins of the present invention include proteins comprising human consensus sequences identified from human sequences, or sequences substantially homologous to human sequences.

In addition, the human antibodies and binding proteins of the present invention are not limited to combinations of VH, VL, CDR or FR regions that are themselves found in combination in human antibody molecules. Thus, the human antibodies and binding proteins of the invention can include or correspond to combinations of such regions that do not necessarily exist naturally in humans.

In preferred embodiments, the human antibodies will be fully human antibodies. "Fully human" antibodies, as used herein, are antibodies comprising "human" variable region domains and/or CDRs, as defined above, without substantial non-human antibody sequences or without any non-human antibody sequences. For example, antibodies comprising human variable region domains and/or CDRs "without substantial non-human antibody sequences" are antibodies, domains and/or CDRs in which only up to 5, 4, 3, 2 or 1 amino acids are amino acids that are not encoded by human antibody sequences. Thus, "fully human" antibodies are distinguished from "humanized" antibodies, which are based on substantially non-human variable region domains, e.g., mouse variable region domains, in which certain amino acids have been changed to better correspond with the amino acids typically present in human antibodies.

The "fully human" antibodies of the invention may be human variable region domains and/or CDRs without any other substantial antibody sequences, such as being single chain antibodies. Alternatively, the "fully human" antibodies of the invention may be human variable region domains and/or CDRs integral with or operatively attached to one or more human antibody constant regions. Certain preferred fully human antibodies are IgG antibodies with the full complement of IgG constant regions.

In other embodiments, "human" antibodies of the invention will be part-human chimeric antibodies. "Part-human chimeric" antibodies, as used herein, are antibodies comprising "human" variable region domains and/or CDRs operatively attached to, or grafted onto, a constant region of a non-human species, such as rat or mouse. Such part-human chimeric antibodies may be used, for example, in pre-clinical studies, wherein the constant region will preferably be of the same species of animal used in the pre-clinical testing. These part-human chimeric antibodies may also be used, for example, in ex vivo diagnostics, wherein the constant region of the non-human species may provide additional options for antibody detection.

The term "fragment" as used herein refers to fragments of biological relevance, e.g., fragments that contribute to antigen binding, e.g., form part of the antigen binding site, and/or contribute to the inhibition or reduction in function of the CCR4 antigen. Certain preferred fragments comprise a heavy chain variable region (VH domain) and/or a light chain variable region (VL domain) of the antibodies of the invention. Other preferred fragments comprise one or more of the heavy chain CDRs of the antibodies of the invention (or of the VH domains of the invention), or one or more of the light chain CDRs of the antibodies of the invention (or of the VL domains of the invention). Certain preferred fragments are at least 5 amino acids in length and comprise at least one CDR region, preferably a CDR3 region, more preferably a heavy chain CDR3 region.

In embodiments where the antibodies of the invention comprise a fragment of any of the defined sequences disclosed herein, e.g., are antibodies comprising VH and/or VL domains of the invention, or are antibodies or binding proteins comprising one or more CDRs of the invention, then these regions/domains are generally separated within the antibody or binding protein so that each region/domain can perform its biological function and so that the contribution to antigen binding is retained. Thus, the VH and VL domains are preferably separated by appropriate scaffold sequences/linker sequences and the CDRs are preferably separated by appropriate framework regions such as those found in naturally occurring antibodies and/or effective engineered antibodies. Thus, the VH, VL and individual CDR sequences of the invention are preferably provided within or incorporated into an appropriate framework or scaffold to enable antigen binding. Such framework sequences or regions may correspond to naturally occurring framework regions, FR1, FR2, FR3 and/or FR4, as appropriate to form an appropriate scaffold, or may correspond to consensus framework regions, for example identified by comparing various naturally occurring framework regions. Alternatively, non-antibody scaffolds or frameworks, e.g., T cell receptor frameworks can be used.

Appropriate sequences that can be used for framework regions are well known and documented in the art and any of these may be used. Preferred sequences for framework regions are one or more (i.e. one, two, three or four) of the framework regions making up the $V_H$ and/or $V_L$ domains of the invention, i.e., one or more of the framework regions disclosed in Tables 1, 2, 3 or 4, or framework regions substantially homologous thereto, and in particular framework regions that allow the maintenance of antigen specificity, for example framework regions that result in substantially the same or the same 3D structure of the antibody.

In certain preferred embodiments, all four of the variable light chain (SEQ ID NOs: 12, 13, 14 and 15) and/or variable heavy chain (SEQ ID NOs: 7, 8, 9, 10), as appropriate, FR regions of SEQ ID NO: 47 (also shown in Table 1), or FR regions substantially homologous thereto, are found in the antibodies of the invention.

In certain preferred embodiments, all four of the variable light chain (SEQ ID NOs: 12, 13, 14 and 15) and/or variable heavy chain (SEQ ID NOs: 7, 8, 16 and 10), as appropriate, FR regions of SEQ ID NO: 48 (also shown in Table 2), or FR regions substantially homologous thereto, are found in the antibodies of the invention.

In certain preferred embodiments, all four of the variable light chain (SEQ ID NOs: 12, 13, 14, 15) and/or variable heavy chain (SEQ ID NOs: 7, 8, 18 and 10), as appropriate, FR regions of SEQ ID NO: 49 (also shown in Table 3), or FR regions substantially homologous thereto, are found in the antibodies of the invention.

In certain preferred embodiments, all four of the variable light chain (SEQ ID NOs: 12, 13, 14 and 15) and/or variable heavy chain (SEQ ID NOs: 19, 8, 9 and 10), as appropriate, FR regions of SEQ ID NO: 50 (also shown in Table 4), or FR regions substantially homologous thereto, are found in the antibodies of the invention.

In certain preferred embodiments, all four of the variable light chain (SEQ ID NOs: 21, 13, 23 and 15) and/or variable heavy chain (SEQ ID NOs: 19, 8, 9 and 10), as appropriate, FR regions of SEQ ID NO: 51 (also shown in Table 5), or FR regions substantially homologous thereto, are found in the antibodies of the invention.

In certain preferred embodiments, all four of the variable light chain (SEQ ID NOs: 12, 13, 23 and 15) and/or variable heavy chain (SEQ ID NOs: 19, 8, 9 and 10), as appropriate, FR regions of SEQ ID NO: 52 (also shown in Table 6), or FR regions substantially homologous thereto, are found in the antibodies of the invention.

In certain preferred embodiments, all four of the variable light chain (SEQ ID NOs: 21, 13, 23 and 15) and/or variable heavy chain (SEQ ID NOs: 7, 8, 9 and 10), as appropriate, FR regions of SEQ ID NO: 53 (also shown in Table 7), or FR regions substantially homologous thereto, are found in the antibodies of the invention.

In certain preferred embodiments, all four of the variable light chain (SEQ ID NOs: 25, 13, 23 and 15) and/or variable heavy chain (SEQ ID NOs: 7, 8, 9 and 10), as appropriate, FR regions of SEQ ID NO: 54 (also shown in Table 8), or FR regions substantially homologous thereto, are found in the antibodies of the invention.

In certain preferred embodiments, all four of the variable light chain (SEQ ID NOs: 12, 13, 23 and 15) and/or variable heavy chain (SEQ ID NOs: 7, 8, 28 and 10), as appropriate, FR regions of SEQ ID NO: 55 (also shown in Table 9), or FR regions substantially homologous thereto, are found in the antibodies of the invention.

Thus, in the heavy chain FR1 position 26 is preferably E in some embodiments, but G in other embodiments. In the heavy chain FR3 position 22 is preferably P in some embodiments, but S in other embodiments and position 23 is preferably E in some embodiments, but D in other embodiments. In the light chain FR1 position 7 is preferably P in some embodiments, but Q in other embodiments. In the light chain FR3 position 20 is preferably S in some embodiments, but G in other embodiments.

As mentioned above, a preferred homologue of SEQ ID NO: 12 is SEQ ID NO: 129 or 130 and a preferred homolog of SEQ ID NO:21 is SEQ ID NO: 131 or 132, so all of the statements above should be understood to include a reference to SEQ ID NOs 129-132.

In addition, although preferred antibodies of the invention are made up of VH, VL or CDRs of the invention, it should be noted that the antibodies of the invention also encompass one or more VH, VL or CDRs of the invention in combination with other VH, VL or CDRs not of the invention, provided that the CCR4 binding properties or anti-CCR4 properties of the antibodies of the invention as outlined herein are still present.

The term "heavy chain complementarity determining region" ("heavy chain CDR") as used herein refers to regions of hypervariability within the heavy chain variable region (VH domain) of an antibody molecule. The heavy chain variable region has three CDRs termed heavy chain CDR1, heavy chain CDR2 and heavy chain CDR3 from the amino terminus to carboxy terminus. The heavy chain variable region also has four framework regions (FR1, FR2, FR3 and FR4 from the amino terminus to carboxy terminus). These framework regions separate the CDRs.

The term "heavy chain variable region" (VH domain) as used herein refers to the variable region of a heavy chain of an antibody molecule.

The term "light chain complementarity determining region" ("light chain CDR") as used herein refers to regions of hypervariability within the light chain variable region (VL domain) of an antibody molecule. Light chain variable regions have three CDRs termed light chain CDR1, light chain CDR2 and light chain CDR3 from the amino terminus to the carboxy terminus. The light chain variable region also has four framework regions (FR1, FR2, FR3 and FR4 from the amino terminus to carboxy terminus). These framework regions separate the CDRs.

The term "light chain variable region" (VL domain) as used herein refers to the variable region of a light chain of an antibody molecule.

It should be noted that the Kabat nomenclature is followed herein, where necessary, in order to define the positioning of the CDRs (Kabat et al., 1991, specifically incorporated herein by reference).

A person skilled in the art will appreciate that the proteins and polypeptides of the invention, such as the light and heavy CDRs, the light and heavy chain variable regions, antibodies, antibody fragments, and immunoconjugates, may be prepared in any of several ways well known and described in the art, but are most preferably prepared using recombinant methods.

Nucleic acid fragments encoding the light and heavy chain variable regions of the antibodies of the invention can be derived or produced by any appropriate method, e.g., by cloning or synthesis. Such sequences could, for example, be prepared by cloning appropriate sequences from e.g., human germ line genes and then making any necessary modifications to the germ line sequences to obtain the sequences of the invention using methods well known and described in the art. An alternative and more efficient method would be to synthesize the appropriate light or heavy chain variable region sequence as overlapping primers, and use primer extension to obtain the full sequence. This full sequence could then be amplified via PCR with primers containing appropriate restriction sites for further cloning and manipulation, e.g., for cloning into an appropriate expression vector. Five to seven overlapping primers per variable region are normally be sufficient, thereby making this technique very efficient and precise.

Once nucleic acid fragments encoding the light and heavy chain variable regions of the antibodies of the invention have been obtained, these fragments can be further manipulated by standard recombinant DNA techniques, for example to convert the variable region fragments into full length antibody molecules with appropriate constant region domains, or into particular formats of antibody fragment discussed elsewhere herein, e.g., Fab fragments, scFv fragments, etc. Typically, or as part of this further manipulation procedure, the nucleic acid fragments encoding the antibody molecules of the invention are generally incorporated into an appropriate expression vector in order to facilitate production of the antibodies of the invention.

Possible expression vectors include but are not limited to cosmids, plasmids, or modified viruses (e.g., replication defective retroviruses, adenoviruses and adeno-associated viruses), so long as the vector is compatible with the host cell used. The expression vectors are "suitable for transformation of a host cell", which means that the expression vectors contain a nucleic acid molecule of the invention and regulatory sequences selected on the basis of the host cells to be used for expression, which are operatively linked to the nucleic acid molecule. Operatively linked is intended to mean that the nucleic acid is linked to regulatory sequences in a manner that allows expression of the nucleic acid.

The invention therefore contemplates a recombinant expression vector containing a nucleic acid molecule of the invention, or a fragment thereof, and the necessary regulatory sequences for the transcription and translation of the protein sequence encoded by the nucleic acid molecule of the invention.

Suitable regulatory sequences may be derived from a variety of sources, including bacterial, fungal, viral, mammalian, or insect genes (for example, see the regulatory sequences described in Goeddel, 1990). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors of the invention may also contain a selectable marker gene that facilitates the selection of host cells transformed or transfected with a recombinant molecule of the invention. Examples of selectable marker genes are genes encoding a protein such as neomycin and hygromycin that confer resistance to certain drugs, β-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes that encode a fusion moiety that provides increased expression of the recombinant protein; increased solubility of the recombinant protein; and aid in the purification of the target recombinant protein by acting as a ligand in affinity purification (for example appropriate "tags" to enable purification and/or identification may be present, e.g., His tags or myc tags). For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMal (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Recombinant expression vectors can be introduced into host cells to produce a transformed host cell. The terms "transformed with", "transfected with", "transformation" and "transfection" are intended to encompass introduction of nucleic acid (e.g., a vector) into a cell by one of many possible techniques known in the art. The term "transformed host cell" as used herein is intended to also include cells capable of glycosylation that have been transformed with a recombinant expression vector of the invention. Prokaryotic cells can be transformed with nucleic acid by, for example, electroporation or calcium-chloride mediated transformation. For example, nucleic acid can be introduced into mammalian cells via conventional techniques such as calcium phosphate or calcium chloride co-precipitation, DEAE-dextran mediated transfection, lipofection, electroporation or microinjection. Suitable methods for transforming and transfecting host cells can be found in Sambrook et al., 1989, and other laboratory textbooks.

Suitable host cells include a wide variety of eukaryotic host cells and prokaryotic cells. For example, the proteins of the invention may be expressed in yeast cells or mammalian cells. Other suitable host cells can be found in Goeddel, 1990. In addition, the proteins of the invention may be expressed in prokaryotic cells, such as *Escherichia coli* (Zhang et al., 2004).

Yeast and fungi host cells suitable for carrying out the present invention include, but are not limited to *Saccharomyces cerevisiae*, the genera *Pichia* or *Kluyveromyces* and various species of the genus *Aspergillus*. Examples of vectors for expression in yeast *S. cerevisiae* include pYepSec1 (Baldari. et al., 1987), pMFa (Kurjan and Herskowitz, 1982), pJRY88 (Schultz et al., 1987), and pYES2 (Invitrogen Corporation, San Diego, Calif.). Protocols for the transformation of yeast and fungi are well known to those of ordinary skill in the art (see Hinnen et al., 1978; Ito et al., 1983, and Cullen et al. 1987).

Mammalian cells suitable for carrying out the present invention include, among others: COS (e.g., ATCC No. CRL 1650 or 1651), BHK (e.g., ATCC No. CRL 6281), CHO (ATCC No. CCL 61), HeLa (e.g., ATCC No. CCL 2), 293 (ATCC No. 1573), NS-1 cells, NS0 (ATCC CRL-11177), and Per.C6® (Crucell, Leiden, Netherlands). Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., 1987) and pMT2PC (Kaufman et al., 1987).

Given the teachings provided herein, promoters, terminators, and methods for introducing expression vectors of an appropriate type into plant, avian, and insect cells may also be readily accomplished. For example, within one embodiment, the proteins of the invention may be expressed from plant cells (see Sinkar et al., 1987, which reviews the use of *Agrobacterium rhizogenes* vectors; see also Zambryski et al., 1984, which describes the use of expression vectors for plant cells, including, among others, PAPS2022, PAPS2023, and PAPS2034).

Insect cells suitable for carrying out the present invention include cells and cell lines from *Bombyx, Trichoplusia* or *Spodotera* species. Baculovirus vectors available for expression of proteins in cultured insect cells (SF 9 cells) include the pAc series (Smith et al., 1983) and the pVL series (Luckow and Summers 1989). Some baculovirus-insect cell expression systems suitable for expression of the recombinant proteins of the invention are described in PCT/US/02442.

Alternatively, the proteins of the invention may also be expressed in non-human transgenic animals such as, rats, rabbits, sheep and pigs (Hammer et al. 1985; Palmiter et al. 1983; Brinster et al. 1985; Palmiter and Brinster 1985, and U.S. Pat. No. 4,736,866).

The proteins of the invention may also be prepared by chemical synthesis using techniques well known in the chemistry of proteins such as solid phase synthesis (Merrifield (1964); Frische et al., 1996) or synthesis in homogenous solution.

N-terminal or C-terminal fusion proteins comprising the antibodies and proteins of the invention conjugated to other molecules, such as proteins, may be prepared by fusing through recombinant techniques. The resultant fusion proteins contain an antibody or protein of the invention fused to the selected protein or marker protein, or tag protein as described herein. The antibodies and proteins of the invention may also be conjugated to other proteins by known techniques. For example, the proteins may be coupled using heterobifunctional thiol-containing linkers as described in WO 90/10457, N-succinimidyl-3-(2-pyridyldithio-proprionate) or N-succinimidyl-5 thioacetate. Examples of proteins that may be used to prepare fusion proteins or conjugates include cell binding proteins such as immunoglobulins, hormones, growth factors, lectins, insulin, low density lipoprotein, glucagon, endorphins, transferrin, bombesin, asialoglycoprotein glutathione-S-transferase (GST), hemagglutinin (HA), and truncated myc.

Irrespective of the manner of preparation of a first anti-CCR4 antibody nucleic acid segment, further suitable antibody nucleic acid segments may be readily prepared by standard molecular biological techniques. In order to confirm that any variant, mutant or second generation anti-CCR4 antibody nucleic acid segment is suitable for use in the present invention, the nucleic acid segment will be tested to confirm expression of an anti-CCR4 antibody in accordance with the present invention. Preferably, the variant, mutant or second generation nucleic acid segment will also be tested to confirm hybridization under standard, more preferably, standard stringent hybridization conditions. Exemplary suitable hybridization conditions include hybridization in about 7% sodium dodecyl sulfate (SDS), about 0.5 M NaPO4, about 1 mM EDTA at about 50° C.; and washing with about 1% SDS at about 42° C.

As a variety of antibodies may be readily prepared, the treatment methods of the invention may be executed by providing to the animal or patient at least a first nucleic acid segment or molecule that expresses a biologically effective amount of at least a first anti-CCR4 antibody of the invention in the patient. The "nucleic acid segment or molecule that expresses an anti-CCR4 antibody" will generally be in the form of at least an expression construct or vector, and may be in the form of an expression construct or vector comprised within a virus or within a recombinant host cell. Preferred gene therapy vectors of the present invention will generally be viral vectors, such as comprised within a recombinant retrovirus, herpes simplex virus (HSV), adenovirus, adeno-associated virus (AAV), cytomegalovirus (CMV), and the like.

A yet further aspect provides an expression construct or expression vector comprising one or more of the nucleic acid segments or molecules of the invention. Preferably the expression constructs or vectors are recombinant. Preferably said constructs or vectors further comprise the necessary regulatory sequences for the transcription and translation of the protein sequence encoded by the nucleic acid molecule of the invention.

A yet further aspect provides a host cell or virus comprising one or more expression constructs or expression vectors of the invention. Also provided are host cells or viruses comprising one or more of the nucleic acid molecules of the invention. A host cell or virus expressing an antibody of the invention forms a yet further aspect.

A yet further aspect of the invention provides a method of producing an antibody of the present invention comprising a step of culturing the host cells of the invention. Preferred methods comprise the steps of (i) culturing a host cell comprising one or more of the recombinant expression vectors or one or more of the nucleic acid sequences of the invention under conditions suitable for the expression of the encoded antibody or protein; and optionally (ii) isolating or obtaining the antibody or protein from the host cell or from the growth medium/supernatant. Such methods of production may also comprise a step of purification of the antibody or protein product and/or formulating the antibody or product into a composition including at least one additional component, such as a pharmaceutically acceptable carrier or excipient.

In embodiments when the antibody or protein of the invention is made up of more than one polypeptide chain (e.g., certain fragments such as Fab fragments), then all the polypeptides are preferably expressed in the host cell, either from the same or a different expression vector, so that the complete proteins, e.g., binding proteins of the invention, can assemble in the host cell and be isolated or purified therefrom.

The antibodies of the invention may also be used to produce further antibodies that bind to CCR4. Such uses involve for example the addition, deletion, substitution or insertion of one or more amino acids in the amino acid sequence of a parent antibody to form a new antibody, wherein said parent antibody is one of the antibodies of the invention as defined elsewhere herein, and testing the resulting new antibody to identify antibodies that bind to CCR4. Such methods can be used to form multiple new antibodies that can all be tested for their ability to bind CCR4. Preferably said addition, deletion, substitution or insertion of one or more amino acids takes place in one or more of the CDR domains.

Such modification or mutation to a parent antibody can be carried out in any appropriate manner using techniques well known and documented in the art, for example by carrying out methods of random or directed mutagenesis. If directed mutagenesis is to be used then one strategy to identify appropriate residues for mutagenesis utilizes the resolution of the crystal structure of the binding protein-antigen complex, e.g., the Ab-Ag complex, to identify the key residues involved in the antigen binding (Davies and Cohen, 1996). Subsequently, those residues can be mutated to enhance the interaction. Alternatively, one or more amino acid residues can simply be targeted for directed mutagenesis and the effect on binding to CCR4 assessed.

Random mutagenesis can be carried out in any appropriate way, e.g., by error-prone PCR, chain shuffling or mutator *E. coli* strains.

Thus, one or more of the VH domains of the invention can be combined with a single VL domain or a repertoire of VL domains from any appropriate source and the resulting new antibodies tested to identify antibodies specific for CCR4. Conversely, one or more of the VL domains of the invention can be combined with a single VH domain or repertoire of VH domains from any appropriate source and the resulting new antibodies tested to identify antibodies that bind to CCR4.

Similarly, one or more, or preferably all three CDRs of the VH and/or VL domains of the invention can be grafted into a single VH and/or VL domain or a repertoire of VH and/or VL domains, as appropriate, and the resulting new antibodies tested to identify antibodies that bind to CCR4.

The targeted mutations of the CDRs, especially CDR3 of the light and/or heavy chains, have been shown to be an effective technique for increasing antibody affinity and are preferred. Preferably, blocks of 3 to 4 amino acids of the CDR3 or specific regions called "hot-spots" are targeted for mutagenesis.

"Hot spots" are the sequences where somatic hypermutation takes place in vivo (and below Neuberger and Milstein, 1995). The hotspot sequences can be defined as consensus nucleotide sequences in certain codons. The consensus sequence is the tetranucleotide, RGYW, in which R can be either A or G, Y can be C or T and W can be either A or T (Neuberger and Milstein, 1995). In addition, the serine residues encoded by the nucleotides AGY are predominantly present in the CDRs regions of the variable domain over those encoded by TCN corresponding to a potential hot-spot sequences (Wagner et al., 1995).

Thus, the nucleotide sequence of the CDRs of the heavy and light chains of each antibody of the invention can be scanned for the presence of the hot-spot sequences and AGY codons. The identified hot-spots of the CDR regions of the light and heavy chain can then optionally be compared to the germinal sequences of the heavy and light chains using the International ImMunoGen Tics database (IMGT, http://imgt-.cines.fr/textes/vquest/) (Davies et al., 1990). A sequence, identical to the germ line, suggest that somatic mutation has not occurred; therefore random mutations can be introduced mimicking the somatic events occurring in vivo or alternatively, site directed mutagenesis can be carried out, e.g., at the hot spots and/or AGY codons. In contrast, a different sequence shows that some somatic mutations have already occurred. It will remain to be determined if the in vivo somatic mutation was optimal.

Preferred hot-spots for mutation are those that code for exposed amino acids and preferably those that encode amino acids that form part of the antigen binding sites. Other preferred hot-spots for mutation are those that code for non-conserved amino acids. The hot-spots that code for buried or conserved amino acids within the CDRs are preferably not mutagenized. These residues are usually critical for the overall structure and are unlikely to interact with the antigen since they are buried.

Methods of carrying out the above described manipulation of amino acids and protein domains are well known to a person skilled in the art. For example, said manipulations could conveniently be carried out by genetic engineering at the nucleic acid level wherein nucleic acid molecules encoding appropriate binding proteins and domains thereof are modified such that the amino acid sequence of the resulting expressed protein is in turn modified in the appropriate way.

Testing the ability of one or more antibodies to specifically bind to CCR4 can be carried out by any appropriate method, which are well known and described in the art. CCR4+ cell lines may be obtained from culture collections, or they may be prepared by transforming CCR4-negative cells with a construct that allows expression of recombinant CCR4. Such cells, or immobilised CCR4 can readily be used to assay binding, for example by conventional methods such as ELISA, BiaCon, etc.

The new antibodies produced by these methods will preferably have improved functional properties, e.g. a higher or enhanced affinity (or at least an equivalent affinity) for CCR4 as the parent antibodies, and can be treated and used in the same way as the antibodies of the invention as described elsewhere herein (e.g., for therapy, diagnosis, in compositions etc). Alternatively, or additionally, the new antibodies will have one or more other improved functional properties as described elsewhere herein.

New antibodies produced, obtained or obtainable by these methods form a yet further aspect of the invention.

This invention further provides compositions comprising at least one human antibody or antibody fragment of the invention, optionally including a diluent. Such compositions may be pharmaceutically acceptable compositions or compositions for use in laboratory studies. In terms of the pharmaceutical compositions, they may preferably be formulated for parenteral, intravenous or even subcutaneous administration.

The present invention provides a number of methods and uses of the human antibodies and antibody fragments of the invention. Concerning all methods, the terms "a" and "an" are used to mean "at least one", "at least a first", "one or more" or "a plurality" of steps in the recited methods, except where specifically stated. This is particularly relevant to the administration steps in the treatment methods. Thus, not only may different doses be employed with the present invention, but different numbers of doses, e.g., injections, may be used, up to and including multiple injections. Combined therapeutics may be used, administered before, after or during administration of the anti-CCR4 therapeutic antibody.

Various useful in vitro methods and uses of the antibodies or immunoconjugates of the invention are provided that have important biological implications. First provided are methods of, and uses in, binding CCR4, which generally comprise effectively contacting a composition comprising CCR4 with at least a first anti-CCR4 antibody of the invention, or antigen-binding fragment thereof. The antibodies of the invention, or immunoconjugates thereof, can thus be used in binding assays. Suitably useful binding assays include those commonly employed in the art, such as in immunoblots, Western blots, dot blots, RIAs, ELISAs, immunohistochemistry, fluorescent activated cell sorting (FACS), immunoprecipitation, affinity chromatography, and the like.

Methods of, and uses in, detecting CCR4 are provided, which generally comprise contacting a composition suspected of containing CCR4 or known to contain CCR4 with at least a first antibody or immunoconjugate of the invention, or antigen-binding fragment thereof, under conditions effective to allow the formation of CCR4/antibody complexes and detecting the complexes so formed. The detection methods and uses may be used in connection with biological samples, e.g., in diagnostics for tumours, and diagnostic kits based thereon are also provided.

The antibody of the invention may also be used to determine whether a subject may benefit from anti-CCR4 therapy. Thus, there is provided the use of an antibody of the invention for detecting the presence or measuring the amount of CCR4 expressed by a cell, target site, tissue or organ of a subject suffering from a CCR4-related disorder, wherein an increased presence or amount of CCR4 detected or measured compared to a healthy control indicates that said subject may benefit from anti-CCR4 therapy. Alternatively viewed, there is provided a method of determining whether a subject may benefit from anti-CCR4 therapy, comprising administering an effective amount of an antibody of the invention to a subject and detecting the presence or measuring the amount of CCR4 expressed by a cell, target site, tissue or organ of said subject, wherein an increased presence or amount of CCR4 detected or measured compared to a healthy control indicates that said subject may benefit from anti-CCR4 therapy.

Said cell or target site may preferably be a solid tumour or a haematological tumour. Preferably, the presence or amount of CCR4 detected or measured is used to predict whether the CCR4-related disorder will be susceptible treatment with an anti-CCR4 agent, preferably the anti-CCR4 antibody of the invention. Preferably, the presence or amount of CCR4 detected or measured is used to decide to administer an anti-CCR4 agent, preferably the anti-CCR4 antibody of the invention.

The methods and uses of the present invention are particularly intended for use in animals and patients that have, or are at risk for developing, any disease or condition associated with CCR4 expression or activity or in which CCR4 plays a biological role. Such diseases and disorders include diseases which are mediated by CCR4 positive cells, typically CCR4+ Th2 or Th17 cells, which, upon binding of a ligand to CCR4, may take part in a signaling pathway which will cause or contribute to a disorder or disease. They also include diseases caused by aberrant proliferation of cells expressing CCR4. Such aberrantly proliferating cells may naturally be CCR4+, or they may have mutated/been transformed to express CCR4 As mentioned above, expression of CCR4 may help cancer cells expressing this antigen to evade the immune system. Thus, there is provided a method of treating a disease or disorder mediated by CCR4 and/or characterised by aberrant proliferation of CCR4-positive cells.

Alternatively viewed, there is provided the treatment of a condition which can benefit from one or more of the following
(i) the selective elimination of CCR4+ cells
(ii) the inhibition of CCR4 binding to one or more of its ligands
(iii) the inhibition of CCR4-mediated cellular responses to a CCR4 ligand, particularly the inhibition of chemotaxis or increased intracellular calcium ion concentration (cell activation).

Preferably, the CCR4 ligand is MDC and/or TARC.

It is well known to those of ordinary skill in the art that as CCR4 is involved in a wide range of diseases and disorders, a given anti-CCR4 therapy, once shown to be effective in any acceptable model system, can be used to treat the entire range of diseases and disorders connected with CCR4 expression.

In one embodiment, the CCR4-mediated condition is a T-helper cell type 2-mediated immune disease. By "T-helper cell type 2-mediated immune disease" is meant a disease involving immunoglobulin E (IgE) and mast cells due to the development and activation of allergen-specific Th2 cells.

The CCR4-mediated disease or disorder may be a disease or condition associated with inflammation, infection and/or cancer, including hematological and non-hematological cancers. Such diseases or disorders can be treated or prevented with the present antibodies and compositions. Preferred diseases or conditions include: (1) allergic diseases such as systemic anaphylaxis or hypersensitivity responses, drug allergies, allergic bronchopulmonary aspergillosis (ABPA), insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, (5) vasculitis, (6) spondyloarthropathies, (7) scleroderma, (8) asthma and respiratory allergic diseases such as allergic asthma, allergic rhinitis, chronic obstructive pulmonary disease, hypersensitivity lung diseases and the like, (9) autoimmune diseases, such as arthritis (including rheumatoid and psoriatic), multiple sclerosis, systemic lupus erythematosus, type I diabetes, glomerulonephritis, and the like, (10) graft rejection (including allograft rejection and graft-v-host disease), and (11) other diseases in which undesired inflammatory responses are to be inhibited, such as atherosclerosis, myositis, T-cell mediated neurodegenerative diseases, multiple sclerosis, encephalitis, meningitis, hepatitis, nephritis, sepsis, sarcoidosis, allergic conjunctivitis, otitis, Castleman's disease, sinusitis, LPS-induced endotoxic shock, Behcet's syndrome and gout, (12) cancers, both hematological and non-hematological cancers, preferably Breast cancer, Colorectal cancer, Esophageal cancer, Gastric cancer, Hepatocellular carcinoma, Lung cancer, Melanoma, Ovarian cancer, Pancreatic cancer, Adult T-cell leukemia/lymphoma (ATL), Peripheral T-cell lymphoma, unspecified Diffuse large B-cell lymphoma, Hodgkin's lymphoma, B-cell chronic lymphocytic leukemia, CTCL, particularly Mycosis fungoides, Sézary syndrome, cervical cancer, kidney cancer, brain cancer, prostate cancer, stomach cancer (13) infections such as Epstein-Barr virus (EBV) infection, HIV infection and other viral infections.

The binding of the antibody of the present invention to CCR4 may also impair the ability of CCR4-positive aberrant cells such as cancer cells to evade the host immune system. The antibodies of the present invention may be used to block the suppression of DCs by Treg cells, so there is provided the use of an anti-CCR4 antibody of the present invention as an adjuvant in a vaccine. The vaccine is preferably a vaccine for cancer or an infectious disease. The vaccine may be a preventative vaccine or a curative vaccine. By "adjuvant" is meant an agent which enhances the immune response of a host to an antigen. When used as vaccine adjuvants, the antibodies of the present invention are therefore typically administered in conjunction or combined with an antigen against which it is desired to elicit an immune response.

As used herein, the term "aberrant proliferation" means cell proliferation that deviates from the normal, proper, or expected course. For example, aberrant cell proliferation may include inappropriate proliferation of cells whose DNA or other cellular components have become damaged or defective. Aberrant cell proliferation may include cell proliferation whose characteristics are associated with an indication caused by, mediated by, or resulting in inappropriately high levels of cell division, inappropriately low levels of apoptosis, or both. Such indications may be characterized, for example, by single or multiple local abnormal proliferations of cells, groups of cells, or tissue (s), cancerous or non-cancerous, benign or malignant.

Any reference to "tumour(s)" herein also refers to "cancer(s)" or "carcinoma(s)". Metastatic cancers can also be treated, as can the reduction of metastases from a primary tumour. So-called minimal residual disease (MRD), which is left in post-surgery patients, may be amenable for immunotherapy with anti-CCR4 antibodies.

The present invention thus further provides methods of, and uses in, treating a disease as defined above, comprising administering to an animal or patient with such a disease, a therapeutically effective amount of an anti-CCR4 antibody of the invention, or an antigen-binding fragment or immunoconjugate of such an anti-CCR4 antibody.

A yet further aspect of the invention provides the use of the antibodies of the invention or an antigen-binding fragment or immunoconjugate of such an antibody in the manufacture of a composition or medicament for use in therapy, imaging or diagnosis.

A yet further aspect provides the antibodies of the invention or an antigen-binding fragment or immunoconjugate of such an antibody for use in therapy, diagnosis or imaging.

In addition, the invention provides compositions comprising the antibodies of the invention or an antigen-binding fragment or immunoconjugate of such an antibody with one or more pharmaceutically acceptable excipient, carrier, diluent, buffer or stabilizer.

The in vivo methods as described herein are generally carried out in a mammal. Any mammal may be treated, for example humans and any livestock, domestic or laboratory animal. Specific examples include mice, rats, pigs, cats, dogs, sheep, rabbits, cows and monkey. Preferably, however, the mammal is a human.

Thus, the term "animal" or "patient" as used herein includes any mammal, for example humans and any livestock, domestic or laboratory animal. Specific examples include mice, rats, pigs, cats, dogs, sheep, rabbits, cows and monkey. Preferably, however, the animal or patient is a human subject.

This invention links both methods of treating disorders as defined above using unconjugated or naked antibodies and fragments thereof, and CCR4+ cell, preferably CCR4+ tumour cell, targeting methods using immunoconjugates in which an antibody of the invention or antigen-binding fragment thereof, is operatively attached to a therapeutic agent. Unless otherwise specifically stated or made clear in scientific terms, the terms "antibody and fragment thereof", as used herein, therefore mean an "unconjugated or naked" antibody or fragment, which is not attached to another agent, particularly a therapeutic or diagnostic agent. These definitions do not exclude modifications of the antibody, such as, by way of example only, modifications to improve the biological half life, affinity, avidity or other properties of the antibody, or combinations of the antibody with other effectors.

The treatment methods and uses of the invention also encompass the use of both unconjugated or naked antibodies and immunoconjugates. In the immunoconjugate-based treatment methods, an antibody of the invention, or antigen-binding fragment thereof, is preferably operatively attached to a second therapeutic agent (the anti-CCR4 antibody itself, being the first therapeutic agent). The therapeutic agent may for example be an anti-cancer agent or an anti-inflammatory agent, including corticosteroids and non-steroidal anti-inflammatory drugs (NSAIDs).

The foregoing treatment methods and uses will generally involve the administration of the pharmaceutically effective composition to the animal or patient systemically, such as by transdermal, intramuscular, intravenous injection and the like. However, any route of administration that allows the therapeutic agent to localize to the tumour site or sites, will be acceptable. Therefore, other suitable routes of delivery include oral, nasal or respiratory and topical.

"Administration", as used herein, means provision or delivery of anti-CCR4 antibody therapeutics in an amount(s) and for a period of time(s) effective to exert therapeutic, e.g. anti-tumour effects. The passive administration of proteinaceous therapeutics is generally preferred, in part, for its simplicity and reproducibility.

However, the term "administration" is herein used to refer to any and all means by which anti-CCR4 antibodies of the invention are delivered or otherwise provided to the target site. "Administration" therefore includes the provision of cells that produce the anti-CCR4 antibody of the invention in a manner effective to result in delivery to the target site. In such embodiments, it may be desirable to formulate or package the cells in a selectively permeable membrane, structure or implantable device, generally one that can be removed to cease therapy. Exogenous anti-CCR4 antibody of the invention will still generally be preferred, as this represents a non-invasive method that allows the dose to be closely monitored and controlled.

The therapeutic methods and uses of the invention also extend to the provision of nucleic acids that encode an anti-CCR4 antibody of the invention in a manner effective to result in their expression in the vicinity of the tumour or their localization to the target site. Any gene therapy technique may be employed, such as naked DNA delivery, recombinant genes and vectors, cell-based delivery, including ex vivo manipulation of patients' cells, and the like.

The anti-CCR4 antibodies of the invention can also be used to deliver other therapeutic or diagnostic agents to the target site In such embodiments, the other therapeutic or diagnostic agents are generally operatively attached to the anti-CCR4 antibodies of the invention.

The "therapeutically effective amounts" for use in the invention are amounts of anti-CCR4 antibody of the invention, or immunoconjugates thereof, effective to specifically kill at least a portion of target CCR4+ cells; to specifically induce apoptosis in at least a portion of target CCR4+ cells; to specifically induce necrosis in at least a portion of target CCR4+ cells; to inhibit the binding of a CCR4 ligand to CCR4; to inhibit CCR4-mediated cellular responses to a CCR4 ligand, preferably inhibit the increase in intracellular calcium ion concentration in response to a CCR4 ligand; to reduce inflammation; and/or to induce tumour regression or remission upon administration to animals or patients having a CCR4+ tumour. Such effects are preferably achieved while exhibiting little or no binding to, or little or no killing of cells in normal, healthy tissues; and exerting negligible or manageable adverse side effects on normal, healthy tissues of the animal or patient.

By "target site" is meant the location of CCR4+ cells which mediate a disorder or which proliferate in an aberrant manner causing or exacerbating a disorder. The target site may thus for example be a tumour or the site of CCR4-mediated inflammation. "Target cells" are CCR4+ cells which mediate a disorder or which proliferate in an aberrant manner causing or exacerbating a disorder. Thus, target cells may for example include CCR4+ tumour cells, CCR4+ Treg cells and/or CCR4+ Th2 cells.

The terms "preferentially" and "specifically", as used herein in the context of killing or inducing apoptosis or of inducing necrosis of CCR4+ cells such as CCR4+ tumour cells or of reducing inflammation or of inducing tumour regression or remission, thus mean that the anti-CCR4 antibody of the invention or immunoconjugates thereof, function to achieve CCR4+ target cell destruction, e.g. tumour cell destruction and/or tumour necrosis, that is substantially confined to the target site, and does not substantially extend to causing destruction and/or tissue necrosis in normal, healthy tissues of the animal or subject.

Anti-CCR4 antibodies of the invention or therapeutic conjugates are preferably linked to one or more radiotherapeutic agents, chemotherapeutic agents, anti-angiogenic agents, apoptosis-inducing agents, anti-tubulin drugs, anti-cellular or cytotoxic agents, cytokine or chemokine antagonists, inhibitors of cytokine or chemokine expression, ATPase inhibitors, anti-inflammatory agents, other antibodies (e.g. as bispecific antibodies) or coagulants (coagulation factors) or anti-inflammatory agents such as corticosteroids, preferably glucocorticoids, or non-steroidal anti-inflammatory drugs (NSAIDs).

The invention thus provides a range of conjugated antibodies and fragments thereof in which the anti-CCR4 antibody is operatively attached to at least one other therapeutic or diagnostic agent. The term "immunoconjugate" is broadly used to define the operative association of the antibody with another effective agent and is not intended to refer solely to any type of operative association, and is particularly not limited to chemical "conjugation". Recombinant fusion proteins are particularly contemplated. So long as the delivery or targeting agent is able to bind to the target and the therapeutic or diagnostic agent is sufficiently functional upon delivery, the mode of attachment will be suitable.

Attachment of agents via the carbohydrate moieties on antibodies is also contemplated. Glycosylation, both O-linked and N-linked, naturally occurs in antibodies. Recombinant antibodies can be modified to recreate or create additional glycosylation sites if desired, which is simply achieved by engineering the appropriate amino acid sequences (such as Asn-X-Ser, Asn-X-Thr, Ser, or Thr where X is any amino acid except Pro) into the primary sequence of the antibody.

Currently preferred agents for use in anti-CCR4 antibody or therapeutic conjugates of the invention and related methods and uses are those that complement or enhance the effects of the antibody and/or those selected for a particular type of disorder (e.g. tumour type) or patient.

"Therapeutic agents that complement or enhance the effects of the antibody" include radiotherapeutic agents, chemotherapeutic agents, anti-angiogenic agents, apoptosis-inducing agents, anti-tubulin drugs, anti-cellular or cytotoxic agents, coagulants, cytokine or chemokine antagonists, inhibitors of cytokine or chemokine expression, ATPase inhibitors, anti-inflammatory agents such as corticosteroids, preferably glucocorticoids, or non-steroidal anti-inflammatory drugs (NSAIDs), other antibodies, (e.g. as bispecific antibodies), any one or more of which are preferred for use herewith.

Currently preferred anti-cancer, particularly anti-leukaemia agents include Anthracycline drugs such as daunorubicin, Doxorubicin, Cytarabine, 6-thioguanine, Mitoxantrone, busulfan (Myleran®), dasatinib (Sprycel™), prednisone, vincristine sulfate (Oncovin®), Chlorambucil, Fludarabine, Pentostatin and Cladribine.

Currently preferred agents for the treatment of ATL include zidovudine (azidothymidine) and the CHOP regimen. CHOP stands for Cyclophosphamide, Hydroxydaunorubicin (Adriamycin), Oncovin (Vincristine), Prednisone/Prednisolone.

Currently preferred anti-angiogenic agents include angiostatin, endostatin, any one of the angiopoietins, vasculostatin, canstatin and maspin.

"Anti-tubulin drug(s)", as used herein, means any agent, drug, prodrug or combination thereof that inhibits cell mitosis, preferably by directly or indirectly inhibiting tubulin activities necessary for cell mitosis, preferably tubulin polymerization or depolymerization. Currently preferred anti-tubulin drugs include colchicine, taxol, vinblastine, vincristine, vindesine and one or more of the combretastatins.

Currently preferred NSAIDs include COX-2 inhibitors, sulphonanilides, licofelone and omega-3 fatty acids The attachment or association of the preferred agents with anti-CCR4 antibodies of the invention gives "immunoconjugates", wherein such immunoconjugates often have enhanced and even synergistic therapeutic properties, e.g. anti-tumour or anti-inflammatory properties.

The use of anti-cellular and cytotoxic agents results in anti-CCR4 antibody "immunotoxins" of the invention, whereas the use of coagulation factors results in anti-CCR4 antibody "coaguligands" of the invention.

The use of at least two therapeutic agents is also contemplated, such as combinations of one or more radiotherapeutic agents, chemotherapeutic agents, anti-angiogenic agents, apoptosis-inducing agents, anti-tubulin drugs, anti-cellular and cytotoxic agents, cytokine or chemokine antagonists, inhibitors of cytokine or chemokine expression, ATPase inhibitors, anti-inflammatory agents such as corticosteroids, preferably glucocorticoids, or non-steroidal anti-inflammatory drugs (NSAIDs), other antibodies, (e.g. as bispecific antibodies) and coagulation factors.

In certain applications, the anti-CCR4 antibody therapeutics of the invention will be operatively attached to cytotoxic, cytostatic or otherwise anti-cellular agents that have the ability to kill or suppress the growth or cell division of cells. Suitable anti-cellular agents include chemotherapeutic agents, as well as cytotoxins and cytostatic agents. Cytostatic agents are generally those that disturb the natural cell cycle of a target cell, preferably so that the cell is taken out of the cell cycle.

Exemplary chemotherapeutic agents include: hormones, such as steroids; anti-metabolites, such as cytosine arabinoside, fluorouracil, methotrexate or aminopterin; anthracyclines; mitomycin C; vinca alkaloids; antibiotics; demecolcine; etoposide; mithramycin; and anti-tumor alkylating agents, such as chlorambucil or melphalan. Certain preferred anti-cellular agents are DNA synthesis inhibitors, such as daunorubicin, doxorubicin/adriamycin, and the like. Overall, taxol/paclitaxel, docetaxel, cisplatin, gemcitabine, a combretastatin and doxorubicin/adriamycin are currently preferred anti-cancer agents.

V-type ATPase inhibitors are also currently preferred, such as salicylihalamide, concanamycin or bafilomycin, as are protein synthesis inhibitors, such as psymberin, pederin, irciniastatin A.

In certain therapeutic applications, toxin moieties will be preferred, due to the much greater ability of most toxins to deliver a cell killing effect, as compared to other potential agents. Therefore, certain preferred anti-cellular agents for anti-CCR4 antibody constructs of the invention are plant-, fungus- or bacteria-derived toxins. Exemplary toxins include epipodophyllotoxins; bacterial endotoxin or the lipid A moiety of bacterial endotoxin; ribosome inactivating proteins, such as saporin or gelonin; a-sarcin; aspergillin; restrictocin; ribonucleases, such as placental ribonuclease; diphtheria toxin and pseudomonas exotoxin. Currently preferred examples are ricin, gelonin, abrin, diphtheria, pseudomonas and pertussis toxins.

Certain preferred toxins are the A chain toxins, such as ricin A chain. The most preferred toxin moiety is often ricin A chain that has been treated to modify or remove carbohydrate residues, so called "deglycosylated A chain" (dgA). Deglycosylated ricin A chain is preferred because of its extreme potency, longer half-life, and because it is economically feasible to manufacture it a clinical grade and scale. Recombinant and/or truncated ricin A chain may also be used.

The anti-CCR4 antibody therapeutics of the invention may comprise a component that is capable of promoting coagulation, i.e., a coagulant. Here, the targeting antibody may be directly or indirectly, e.g., via another antibody, linked to a factor that directly or indirectly stimulates coagulation.

Preferred coagulation factors for such uses are Tissue Factor (TF) and TF derivatives, such as truncated TF (tTF), dimeric, trimeric, polymeric/multimeric TF, and mutant TF deficient in the ability to activate Factor VII. Other suitable coagulation factors include vitamin K-dependent coagulants, such as Factor II/IIa, Factor VII/VIIa, Factor IX/IXa and Factor X/Xa; vitamin K-dependent coagulation factors that lack the GIa modification; Russell's viper venom Factor X activator; platelet-activating compounds, such as thromboxane A2 and thromboxane A2 synthase; and inhibitors of fibrinolysis, such as α2-antiplasmin. Overall, truncated Tissue Factor (tTF) is currently preferred.

The preparation of immunoconjugates and immunotoxins is generally well known in the art (see, e.g., U.S. Pat. No. 4,340,535). Each of the following patents are further incorporated herein by reference for the purposes of even further supplementing the present teachings regarding immunotoxin generation, purification and use: U.S. Pat. Nos. 6,004,554; 5,855,866; 5,965,132; 5,776,427; 5,863,538; 5,660,827 and 6,051,230.

A variety of chemotherapeutic and other pharmacological agents can also be successfully conjugated to anti-CCR4 antibody therapeutics of the invention. Exemplary antineoplastic agents that have been conjugated to antibodies include doxorubicin, daunomycin, methotrexate and vinblastine. Moreover, the attachment of other agents such as neocarzinostatin, macromycin, trenimon and α-amanitin has been described (see U.S. Pat. Nos. 5,660,827; 5,855,866; and 5,965,132; each incorporated herein.)

The preparation of coaguligands is also easily practiced. The operable association of one or more coagulation factors with an anti-CCR4 antibody of the invention may be a direct linkage, such as those described above for the immunotoxins. Alternatively, the operative association may be an indirect attachment, such as where the antibody is operatively attached to a second binding region, preferably an antibody or antigen binding region of an antibody, which binds to the coagulation factor. The coagulation factor should be attached to the anti-CCR4 antibody of the invention at a site distinct from its functional coagulating site, particularly where a covalent linkage is used to join the molecules.

Bispecific or trispecific antibodies may also be employed in the methods of the invention. In such antibodies one arm binds to CCR4 and is an antibody of the present invention. Methods for preparing bispecific antibodies are well known and described in the art.

In the preparation of immunoconjugates, immunotoxins and coaguligands, recombinant expression may be employed. The nucleic acid sequences encoding the chosen anti-CCR4 antibody of the invention, and therapeutic agent, toxin or coagulant, are attached in-frame in an expression vector. Recombinant expression thus results in translation of the nucleic acid to yield the desired immunoconjugate. Chemical cross-linkers and avidin:biotin bridges may also join the therapeutic agents to the anti-CCR4 antibody of the invention.

The compositions and methods of the present invention may be used in combination with other therapeutics and diagnostics. In terms of biological agents, preferably diagnostic or therapeutic agents, for use "in combination" with an anti-CCR4 antibody in accordance with the present invention, the term "in combination" is succinctly used to cover a range of embodiments. The "in combination" terminology, unless otherwise specifically stated or made clear from the scientific terminology, thus applies to various formats of combined compositions, pharmaceuticals, cocktails, kits, methods, and first and second medical uses.

The "combined" embodiments of the invention thus include, for example, where the anti-CCR4 of the invention is a naked antibody and is used in combination with an agent or therapeutic agent that is not operatively attached thereto. In such cases, the agent or therapeutic agent may be used in a non-targeted or targeted form. In "non-targeted form", the agent, particularly therapeutic agents, will generally be used according to their standard use in the art. In "targeted form", the agent will generally be operatively attached to a distinct antibody or targeting region that delivers the agent or therapeutic agent to the target disease site. The use of such targeted forms of biological agents, both diagnostics and therapeutics, is also quite standard in the art.

In other "combined" embodiments of the invention, the anti-CCR4 antibody of the invention is an immunoconjugate wherein the antibody is itself operatively associated or combined with the agent or therapeutic agent. The operative attachment includes all forms of direct and indirect attachment as described herein and known in the art.

The "combined" uses, particularly in terms of an anti-CCR4 antibody of the invention in combination with therapeutic agents, also include combined compositions, pharmaceuticals, cocktails, kits, methods, and first and second medical uses wherein the therapeutic agent is in the form of a prodrug. In such embodiments, the activating component able to convert the prodrug to the functional form of the drug may again be operatively associated with the anti-CCR4 antibodies of the present invention.

In certain preferred embodiments, the therapeutic compositions, combinations, pharmaceuticals, cocktails, kits, methods, and first and second medical uses will be "prodrug combinations". As will be understood by those of ordinary skill in the art, the term "prodrug combination", unless otherwise stated, means that the antibody of the invention is operatively attached to a component capable of converting the prodrug to the active drug, not that the antibody is attached to the prodrug itself. However, there is no requirement that the prodrug embodiments of the invention need to be used as prodrug combinations. Accordingly, prodrugs may be used in any manner that they are used in the art, including in ADEPT and other forms.

Thus, where combined compositions, pharmaceuticals, cocktails, kits, methods, and first and second medical uses are described, preferably in terms of diagnostic agents, and more preferably therapeutic agents, the combinations include anti-CCR4 antibodies that are naked antibodies and immunoconjugates, and wherein practice of the in vivo embodiments of the invention involves the prior, simultaneous or subsequent administration of the naked antibodies or immunoconjugate and the biological, diagnostic or therapeutic agent; so long as, in some conjugated or unconjugated form, the overall provision of some form of the antibody and some form of the biological, diagnostic or therapeutic agent is achieved.

The foregoing and other explanations of the effects of the present invention on tumors are made for simplicity to explain the combined mode of operation, type of attached agent(s) and such like. This descriptive approach should not be interpreted as either an understatement or an oversimplification of the beneficial properties of the anti-CCR4 antibodies of the invention. It will therefore be understood that such antibodies themselves have anti-CCR4 properties and that immunoconjugates of such antibodies will maintain these properties and combine them with the properties of the attached agent; and further, that the combined effect of the antibody and any attached agent will typically be enhanced and/or magnified.

The invention therefore provides compositions, pharmaceutical compositions, therapeutic kits and medicinal cocktails comprising, optionally in at least a first composition or container, a biologically effective amount of at least a first anti-CCR4 antibody of the invention, or an antigen-binding fragment or immunoconjugate of such an anti-CCR4 antibody; and a biologically effective amount of at least a second biological agent, component or system.

The "at least a second biological agent, component or system" will often be a therapeutic or diagnostic agent, component or system, but it need not be. For example, the at least a second biological agent, component or system may comprise components for modification of the antibody and/or for attaching other agents to the antibody. Certain preferred second biological agents, components or systems are prodrugs or components for making and using prodrugs, including components for making the prodrug itself and components for adapting the antibodies of the invention to function in such prodrug or ADEPT embodiments.

Where therapeutic or diagnostic agents are included as the at least a second biological agent, component or system, such therapeutics and/or diagnostics will typically be those for use in connection with the treatment or diagnosis of one or more of the disorders defined above.

Thus, in certain embodiments "at least a second therapeutic agent" will be included in the therapeutic kit or cocktail. The term "at least a second therapeutic agent" is chosen in reference to the anti-CCR4 antibody of the invention being the first therapeutic agent. The antibodies of the invention may thus be combined with chemotherapeutic agents, radiotherapeutic agents, cytokine or chemokine antagonists, inhibitors of cytokine or chemokine expression, anti-angiogenic agents, apoptosis-inducing agents or anti-cancer immunotoxins or coaguligands, or anti-inflammatory agents including corticosteroids and NSAIDs, some examples of which are discussed elsewhere herein.

Other exemplary anti-cancer agent include, e.g., neomycin, podophyllotoxin(s), TNF-α, αvβ3 antagonists, calcium ionophores, calcium-flux inducing agents, and any derivative or prodrug thereof. Currently preferred anti-tubulin drugs include colchicine, taxol, vinblastine, vincristine, vindescine, a combretastatin or a derivative or prodrug thereof.

In terms of compositions, kits and/or medicaments of the invention, the combined effective amounts of the therapeutic agents may be comprised within a single container or container means, or comprised within distinct containers or container means. The cocktails will generally be admixed together for combined use. Agents formulated for intravenous administration will often be preferred. Imaging components may also be included. The kits may also comprise instructions for using the at least a first antibody and the one or more other biological agents included.

Speaking generally, the at least a second therapeutic agent may be administered to the animal or patient substantially simultaneously with the anti-CCR4 antibody of the invention; such as from a single pharmaceutical composition or from two pharmaceutical compositions administered closely together.

Alternatively, the at least a second therapeutic agent may be administered to the animal or patient at a time sequential to the administration of the anti-CCR4 antibody of the invention. "At a time sequential", as used herein, means "staggered", such that the at least a second anti-cancer agent is administered to the animal or patient at a time distinct to the administration of the anti-CCR4 antibody of the invention. Generally, the two agents are administered at times effectively spaced apart to allow the two agents to exert their respective therapeutic effects, i.e., they are administered at "biologically effective time intervals". The at least a second therapeutic agent may be administered to the animal or patient at a biologically effective time prior to the anti-CCR4 antibody of the invention, or at a biologically effective time subsequent to that therapeutic.

Accordingly, the present invention provides methods for treating an animal or patient with a tumor, comprising:

(a) subjecting the animal or patient to a first treatment that substantially reduces the tumor burden; and (b) subsequently administering at least a first anti-CCR4 antibody of the invention, or antigen-binding fragment thereof; optionally wherein the antibody or fragment is operatively associated with a second therapeutic agent.

Preferred first treatments include surgical resection and chemotherapeutic intervention.

In other embodiments, the present invention provides methods for treating an animal or patient with a CCR4-mediated disorder, comprising:

(a) subjecting the animal or patient to a first treatment that substantially reduces the CCR4-mediated burden such as inflammation; and (b) subsequently administering at least a first anti-CCR4 antibody of the invention, or antigen-binding fragment thereof; optionally wherein the antibody or fragment is operatively associated with a second therapeutic agent.

In certain other embodiments, the antibodies and immunoconjugates of the invention may be combined with one or more diagnostic agents, typically diagnostic agents for use in connection with the diagnosis of a disorder as defined above. A range of diagnostic compositions, kits and methods are thus included within the invention.

Yet further aspects are methods of diagnosis or imaging of a subject comprising the administration of an appropriate amount of an antibody or other protein of the invention as defined herein to the subject and detecting the presence and/or amount and/or the location of the antibody or other protein of the invention in the subject.

In one embodiment, the invention provides a method of reducing immunosuppression associated with CCR4 expression in an animal, comprising administering to said animal the antibody of the invention, or an immunoconjugate thereof, in an amount effective to form complexes between said antibody and CCR4 in said animal, thereby reducing immunosuppression associated with CCR4 expression in an animal.

Appropriate diseases to be imaged or diagnosed in accordance with the above described uses and methods include any disease and preferably any cancer as described elsewhere herein.

In one embodiment, the invention provides a method of diagnosing disease or monitoring the progress of disease in an animal comprising the step of:

(a) contacting a test sample taken from said animal with an antibody of the invention or an immunoconjugate thereof.

In a further embodiment, the invention provides a method of diagnosing disease or monitoring the progress of disease in an animal comprising the steps of:

(a) contacting a test sample taken from said animal with an antibody of the invention or an immunoconjugate thereof;

(b) measuring or detecting the presence and/or amount and/or location of antibody-antigen complex in the test sample; and, optionally (c) comparing the presence and/or amount of antibody-antigen complex in the test sample to a control.

In the above methods, said contacting step is carried out under conditions that permit the formation of an antibody-antigen complex. Appropriate conditions can readily be determined by a person skilled in the art.

In the above methods any appropriate test sample may be used, for example biopsy cells, tissues or organs suspected of being affected by disease or histological sections.

In certain of the above methods, the presence of any amount of antibody-antigen complex in the test sample would be indicative of the presence of disease. Preferably, for a positive diagnosis to be made, the amount of antibody-antigen complex in the test sample is greater than, preferably significantly greater than, the amount found in an appropriate control sample. More preferably, the significantly greater levels are statistically significant, preferably with a probability value of <0.05. Appropriate methods of determining statistical significance are well known and documented in the art and any of these may be used.

Monitoring the progress of a disease may also involve monitoring the presence and/or amount of antibody-antigen complex in test samples over time. Thus, monitoring may involve (d) comparing the presence and/or amount of antibody-antigen complex in a first test sample to the presence and/or amount of antibody-antigen complex in a second test sample taken from said animal. By "first test sample" is meant a sample that was taken prior to taking the "second test sample", for example 1, 2, 3, 4, 5, 6, 7, 8, 9, 10, 11 or 12 days, weeks, months or years prior to taking the second test sample. A decrease in the amount of antibody-antigen complex in the second test sample compared to the first test sample is indicative of the disease regressing, whereas an increase is indicative of the disease progressing.

Appropriate control samples could be readily chosen by a person skilled in the art, for example, in the case of diagnosis of a particular disease, an appropriate control would be a sample from a subject that did not have that disease. Appropriate control "values" could also be readily determined without running a control "sample" in every test, e.g., by reference to the range for normal subjects known in the art.

For use in the diagnostic or imaging applications, the antibodies of the invention may be labeled with a detectable marker such as a radio-opaque or radioisotope, such as 3H, 14C, 32P, 35S, 123I, 125I, 131I; a radioactive emitter (e.g., α, β or γ emitters); a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion; or a chemical moiety such as biotin which may be detected by binding to a specific cognate detectable moiety, e.g., labelled avidin/streptavidin. Methods of attaching a label to a binding protein, such as an antibody or antibody fragment, are known in the art. Such detectable markers allow the presence, amount or location of binding protein-antigen complexes in the test sample to be examined.

Preferred detectable markers for in vivo use include an X-ray detectable compound, such as bismuth (III), gold (III), lanthanum (III) or lead (II); a radioactive ion, such as copper67, gallium67, gallium68, indium111, indium113, iodine-123, iodine-125, iodine-131, mercury197, mercury203, rhenium186, rhenium188, rubidium97, rubidium103, technetium99m or yttrium90; a nuclear magnetic spin-resonance isotope, such as cobalt (II), copper (II), chromium (III), dysprosium (III), erbium (III), gadolinium (III), holmium (III), iron (II), iron (III), manganese (II), neodymium (III), nickel (II), samarium (III), terbium (III), vanadium (II) or ytterbium (III); or rhodamine or fluorescein.

The invention also includes diagnostic or imaging agents comprising the antibodies of the invention attached to a label that produces a detectable signal, directly or indirectly. Appropriate labels are described elsewhere herein.

The invention further includes kits comprising one or more of the antibodies, immunoconjugates or compositions of the invention or one or more of the nucleic acid molecules encoding the antibodies of the invention, or one or more recombinant expression vectors comprising the nucleic acid sequences of the invention, or one or more host cells or viruses comprising the recombinant expression vectors or nucleic acid sequences of the invention. Preferably said kits are for use in the methods and uses as described herein, e.g., the therapeutic, diagnostic or imaging methods as described herein, or are for use in the in vitro assays or methods as described herein. The antibody in such kits may preferably be an antibody conjugate as described elsewhere herein, e.g., may be conjugated to a detectable moiety or may be an immumoconjugate. Preferably said kits comprise instructions for use of the kit components, for example in diagnosis. Preferably said kits are for diagnosing or treating diseases as described elsewhere herein and optionally comprise instructions for use of the kit components to diagnose or treat such diseases.

The antibodies of the invention as defined herein may also be used as molecular tools for in vitro or in vivo applications and assays. As the antibodies have an antigen binding site, these can function as members of specific binding pairs and these molecules can be used in any assay where the particular binding pair member is required.

Thus, yet further aspects of the invention provide a reagent that comprises an antibody of the invention as defined herein and the use of such antibodies as molecular tools, for example in in vitro or in vivo assays.

Cancer treatment may also be carried out by:

(a) forming an image of a tumor by administering to an animal or patient having a tumor a diagnostic amount of at least a first detectably-labeled anti-CCR4 antibody of the invention, comprising a diagnostic agent operatively attached to the anti-CCR4 antibody of the invention, thereby forming a detectable image of the tumor; and (b) subsequently administering to the same animal or patient a therapeutically optimized amount of at least a first naked anti-CCR4 antibody of the invention or therapeutic agent-antibody construct using such an antibody, thereby causing an anti-tumor effect.

SEQ ID NOs: 16 and 18 are identical, so in any of the embodiments disclosed herein, a reference to SEQ ID NO:16 should be understood to include a reference to SEQ ID NO: 18 and vice versa.

The invention will now be described in more detail in the following non-limited examples with reference to the Tables and Figures in which:

Table 1 lists some of the sequences disclosed herein relating to antibody 208.

Table 2 lists some of the sequences disclosed herein relating to antibody 306.

Table 3 lists some of the sequences disclosed herein relating to antibody 308.

Table 4 lists some of the sequences disclosed herein relating to antibody 406.

Table 5 lists some of the sequences disclosed herein relating to antibody 501.

Table 6 lists some of the sequences disclosed herein relating to antibody 503.

Table 7 lists some of the sequences disclosed herein relating to antibody 601.

Table 8 lists some of the sequences disclosed herein relating to antibody 603.

Table 9 lists some of the sequences disclosed herein relating to antibody 803.

Table 10 lists some of the sequences disclosed herein relating to the IgG form of antibody 208. The variable regions are underlined.

Table 11 lists some of the sequences disclosed herein relating to IgG form of antibody 306. The variable regions are underlined.

Table 12 lists some of the sequences disclosed herein relating to IgG form of antibody 308. The variable regions are underlined.

Table 13 lists some of the sequences disclosed herein relating to IgG form of antibody 406. The variable regions are underlined.

Table 14 lists some of the sequences disclosed herein relating to IgG form of antibody 501. The variable regions are underlined.

Table 15 lists some of the sequences disclosed herein relating to IgG form of antibody 503. The variable regions are underlined.

Table 16 lists some of the sequences disclosed herein relating to IgG form of antibody 601. The variable regions are underlined.

Table 17 lists some of the sequences disclosed herein relating to IgG form of antibody 603. The variable regions are underlined.

Table 18 lists some of the sequences disclosed herein relating to IgG form of antibody 803. The variable regions are underlined.

Table 19 shows calculated IC50 values, derived from TARC-mediated Ca-Flux inhibition.

Table 20 shows determined IC50 values from ligand-interfering binding experiments of anti-CCR4 IgGs using labelled ligands (Example 3). No values were determined for KW0761. The quality of the fits is judged by least-square (R2) values.

Table 21 is an overview of antagonistic properties of anti-CCR4 antibodies in ligand mediated Ca-Flux experiments (Example 5). In case of TARC-induced Ca-Flux, IC50 values were determined and quality of the fits is judged by least-square (R2). The inhibitory effect on MDC-induced signaling is presented as maximum inhibition of anti-CCR4 antibodies at 10 µg/ml, expressed in %. No values were determined for KW0761.

Table 22 is an overview of determined IC50 values and remaining migration in % from inhibition of ligand-induced migration (TARC and MDC) by anti-CCR4 antibodies. IC50 values were derived from titration curves in presence of ligands as described in Example 6. The quality of the fits is judged by least-square (R2). In case of inhibition of MDC, maximum inhibition at an IgG concentration of 10 µg/ml is presented.

Table 23 is an overview of determined IC50 values from inhibition of TARC-induced invasion by anti-CCR4 antibody 503 on 786-O cells. IC50 values were derived from titration curves in presence of TARC (25 and 125 nM) as described in Example 6. The quality of the fits is judged by least-square (R2).

Table 24 is an overview of determined EC50 values from ADCC experiments as described in Example 9 on haematological tumor cell lines CCRF-CEM and L-428. The determined EC50 values were derived by fitting data to a "log (agonist) vs response model" using GraphPad (Prism). Maximum cyotoxicity values are presented at the given concentration.

Table 25 Scoring table from IHC experiments for renal cell cancer tumor microarrays (TMA) and relevant control tissues (placenta and normal kidney). Number of cores staining positive are given out of a total number of cores stained on one TMA. The number of cores stained differs for each staining since damaged cores were not scored. Zero refers to no staining, 1 refers to intermediate staining and 2 refers to strong staining.

FIG. 1. Results of Example 2: Binding of anti-CCR4 scFvs to target cells, expressing CCR4. ScFvs were cross-linked using anti-Myc-antibody (mouse) to simulate a dimeric situation and diluted 3-fold, starting at 10 μg/ml. Bound scFvs were detected using RPE-conjugated anti-mouse IgG. a.) Binding to CCR4-positive DT40 cells. b.) Binding to CCR4-negative DT40 cells.

Figure 2:
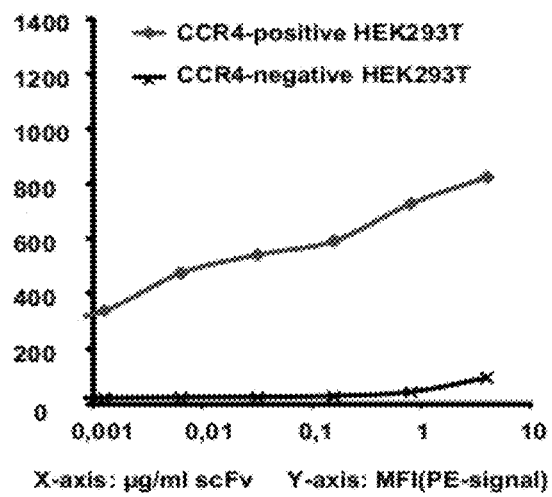

FIG. 2. Results of Example 2: Binding of anti-CCR4 scFv 208 to Hek293T cells, expressing CCR4 in comparison to a CCR4-negative Hek293T cells. ScFv was cross-linked using anti-Myc-antibody (mouse) to simulate a dimeric situation and diluted 3-fold, starting at 10 μg/ml. Bound scFvs were detected using RPE-conjugated anti-mouse IgG.

Figure 3:
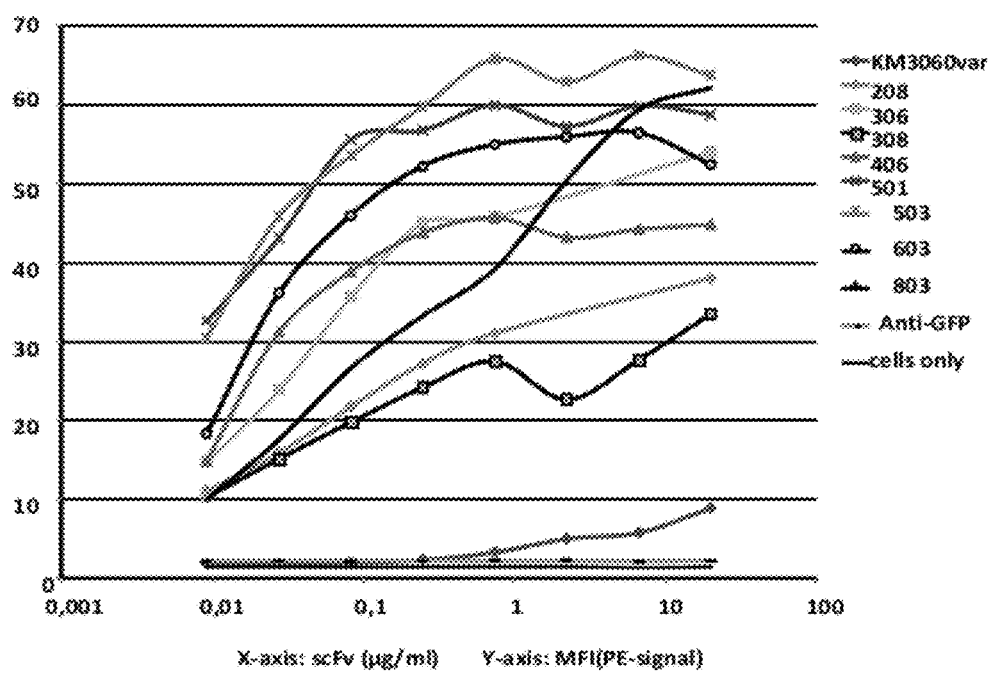

FIG. 3. Results of Example 2: Binding of anti-CCR4 scFvs to natural target cell (CCRF-CEM), expressing CCR4. ScFvs were cross-linked using anti-Myc-antibody (mouse) to simulate a dimeric situation and diluted 3-fold, starting at 20 μg/ml. Bound scFvs were detected using RPE-conjugated anti-mouse IgG.

Figure 4:
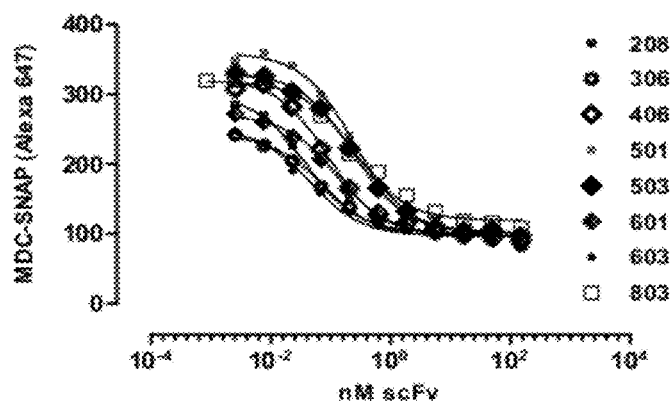

FIG. 4. Results of Example 3: Ligand-interfering binding experiments of anti-CCR4 scFvs using Alexa647-labeled MDC-SNAP. ScFvs were incubated at a concentration of 5 μg/ml (150 nM) and diluted 3-fold over twelve dilution points in the presence of a fixed concentration of MDC-SNAP (50 nM).

Figure 5:
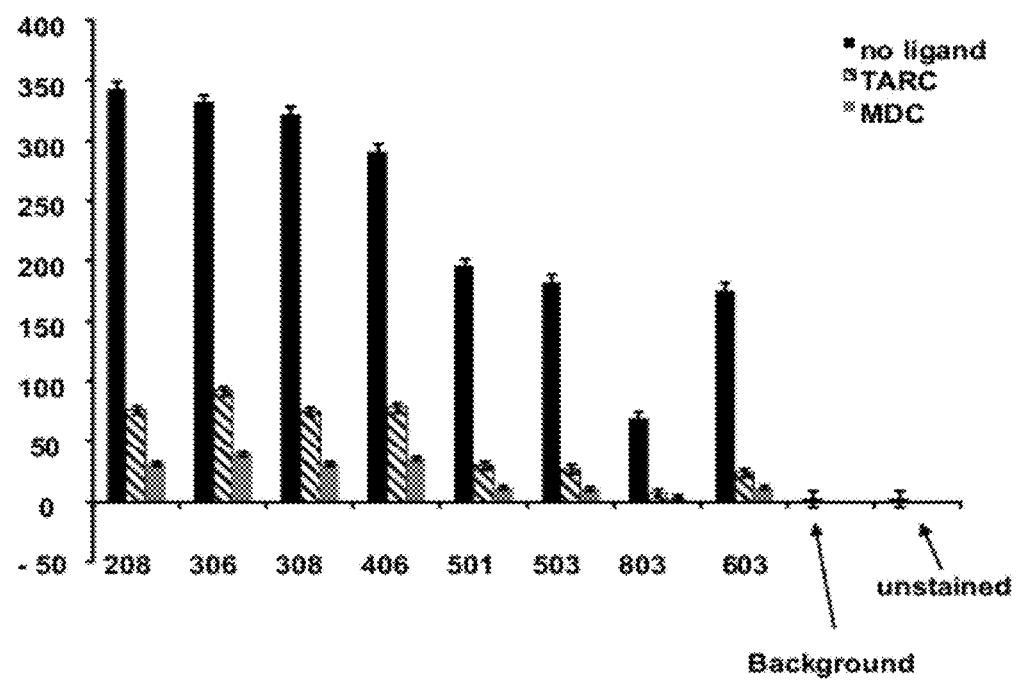

FIG. 5. Results of Example 3: Ligand-interfering binding experiments of anti-CCR4 scFvs in presence of TARC and MDC. ScFvs were incubated at a concentration of 0.5 μg/ml in presence of 2.5 μg/ml mouse anti-Myc-antibody (mouse) in presence of a fixed concentration of ligands (1 μg/ml) and stained using an anti-mouse-RPE conjugated antibody. ScFvs as described in Example 1 (candidate 601 not presented). Signals were compared to cells, stained only with antibody-controls (background) as well as to unstained cells (unstained).

Figure 6:
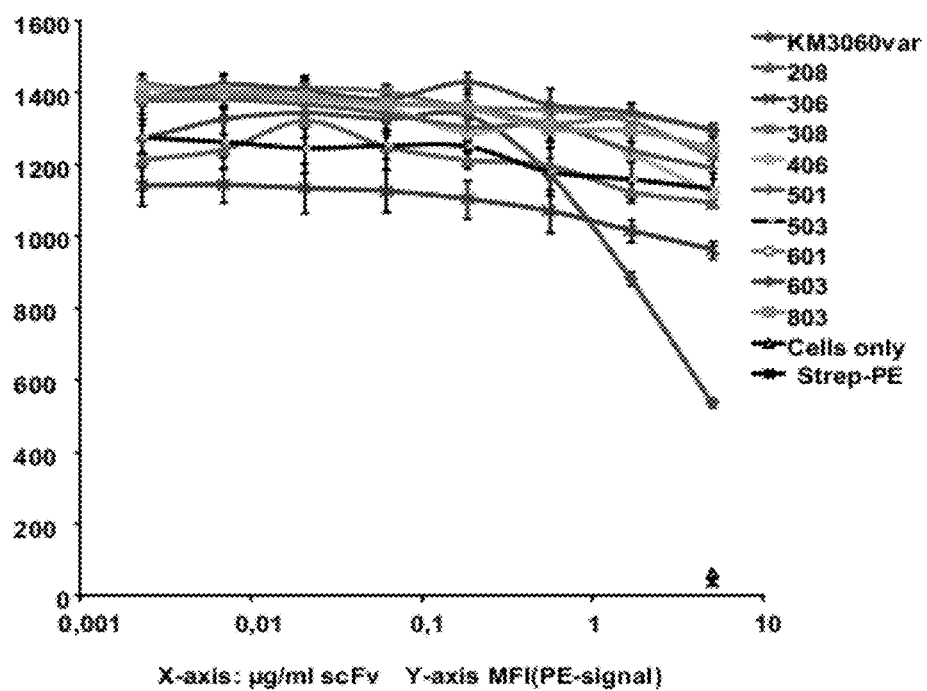

FIG. 6. Results of Example 4: Competition experiment between anti-CCR4 antibodies 208, 306, 308, 406, 501, 503, 601, 60, 803 and KM3060var in presence of biotinylated KW0761-IgG. The biotinylated KW0761-IgG was detected using PE-conjugated Streptavidin FIG. 7. Results of Example 5: Inhibition of TARC-mediated Ca-Flux by anti-CCR4 scFv antibodies in comparison to KM3060var. TARC was incubated at a final concentration of 28.6 ng/μl (3.6 nM) in presence of increasing scFv-concentrations, titrated over six dilution points, starting at 0.5 μg/ml. The signals were expressed in % where 100% signaling refers to recorded signals in presence of TARC-ligand, but no scFv antibody.

Figure 8:
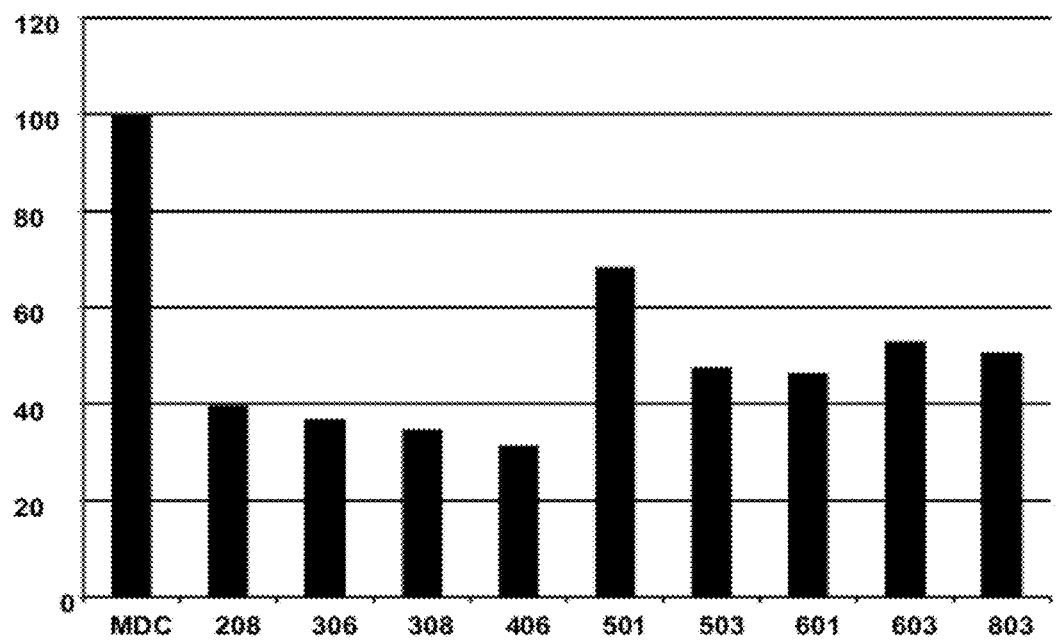

FIG. 8. Results of Example 5: Inhibition of MDC-mediated Ca-Flux by anti-CCR4 scFv antibodies. MDC was incubated at a final concentration of 5 ng/μl (6.25 nM) in presence of a fixed scFv concentration of 10 μg/ml. The signals were expressed in % where 100% signaling refers to recorded signals in presence of MDC-ligand, but no scFv antibody.

Figure 9:
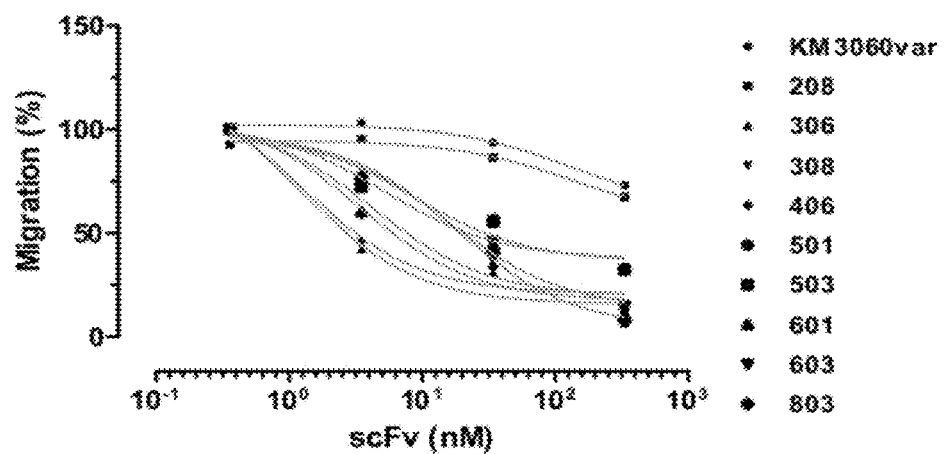

FIG. 9. Results of Example 6. Inhibition of TARC-mediated chemotaxis on CCR4+CCRF-CEM cells in presence of increasing concentrations of anti-CCR4 scFv antibodies (0.36 to 333 nM). TARC had a fixed concentration of 3.5 nM. The signals were expressed in % where 100% refers to migration of cells in presence of TARC-ligand, but no scFv antibody. The graphs were fitted.

Figure 10:
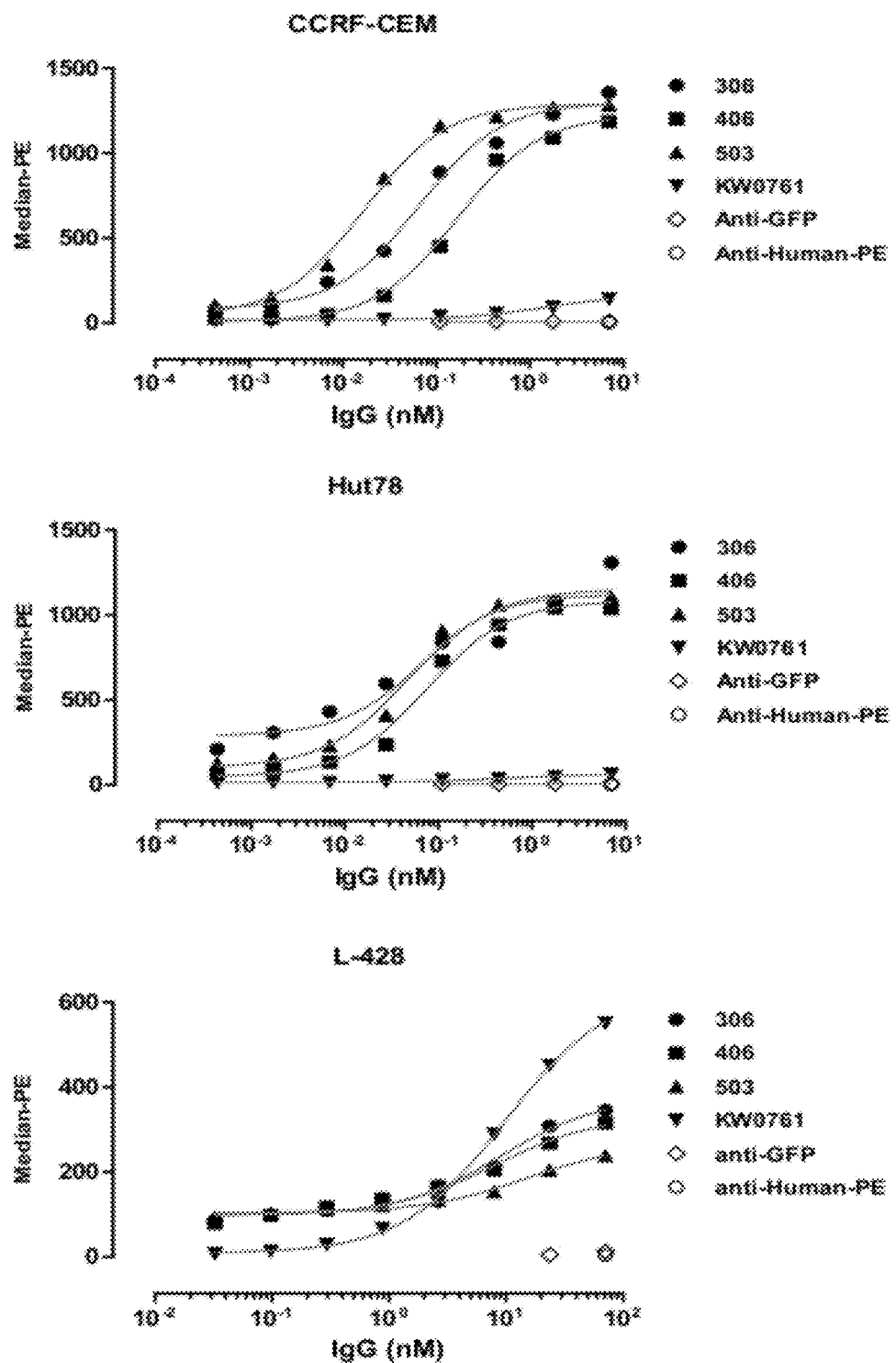

FIG. 10. Results of Example 2, binding of anti-CCR4 IgGs to target cells expressing CCR4. IgGs were incubated at defined concentrations and bound IgGs were detected using RPE-conjugated anti-Human IgG. a.) Binding to CCR4-positive CCRF-CEM cells. IgGs were diluted four-fold over eight points starting at 1 μg/ml. b.) Binding to CCR4-positive Hut78 cells. IgGs were diluted four-fold over eight points starting at 1 μg/ml. c.) Binding to CCR4-positive L-428 cells. IgGs were diluted three-fold over eight points starting at 10 μg/ml.

Figure 11:
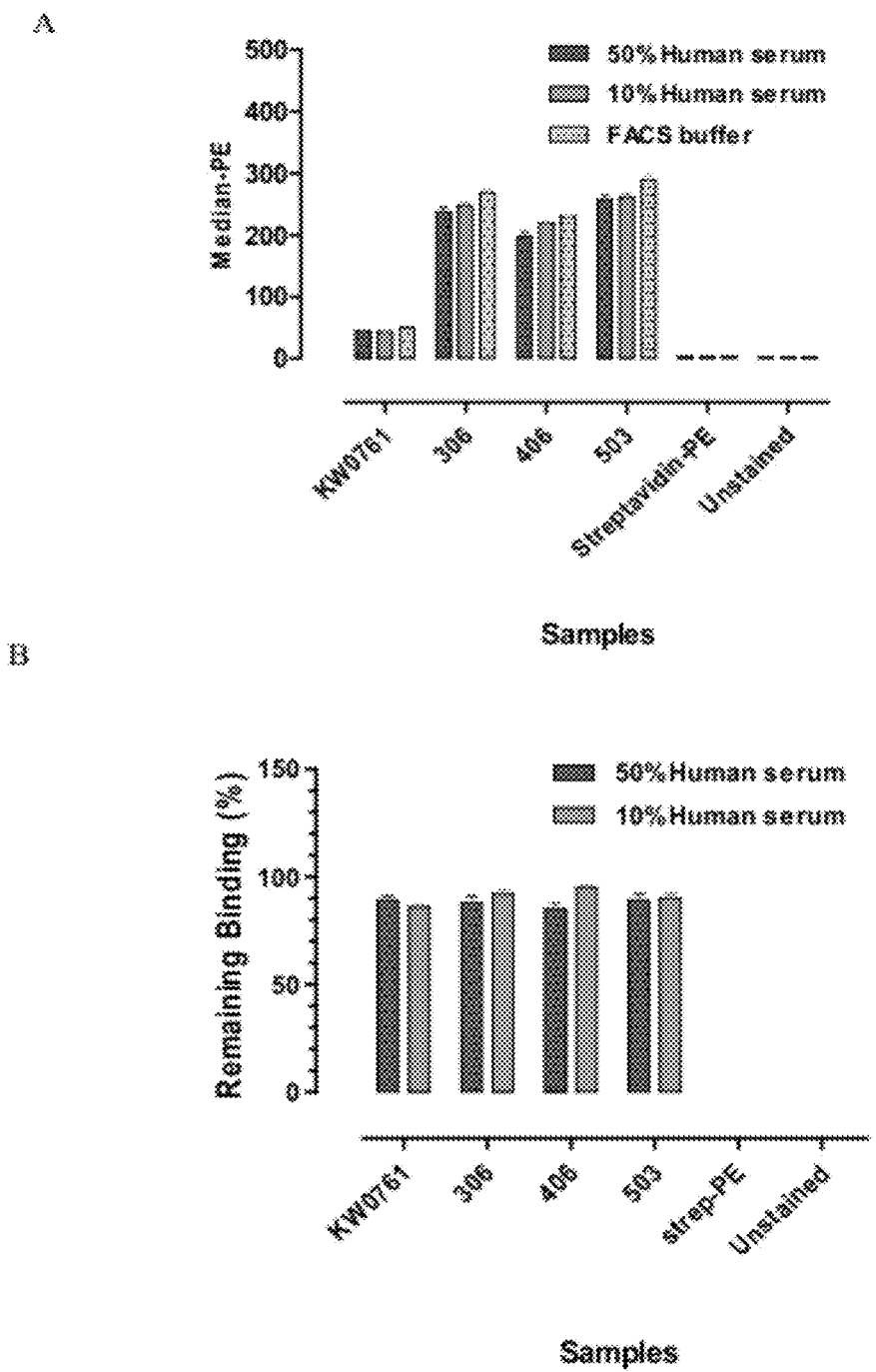

FIG. 11. Results of Example 2, binding to CCR4-expressing target cells (CCRF-CEM) in presence of human serum. Biotinylated samples were incubated at 10 μg/ml in either 0% human serum (FACS-buffer) or in 10 and 50% human serum. Samples were detected via PE-conjugated-Streptavidin. a.) Comparison of recorded binding signals. b.) Remaining binding signals converted into %.

Figure 12:
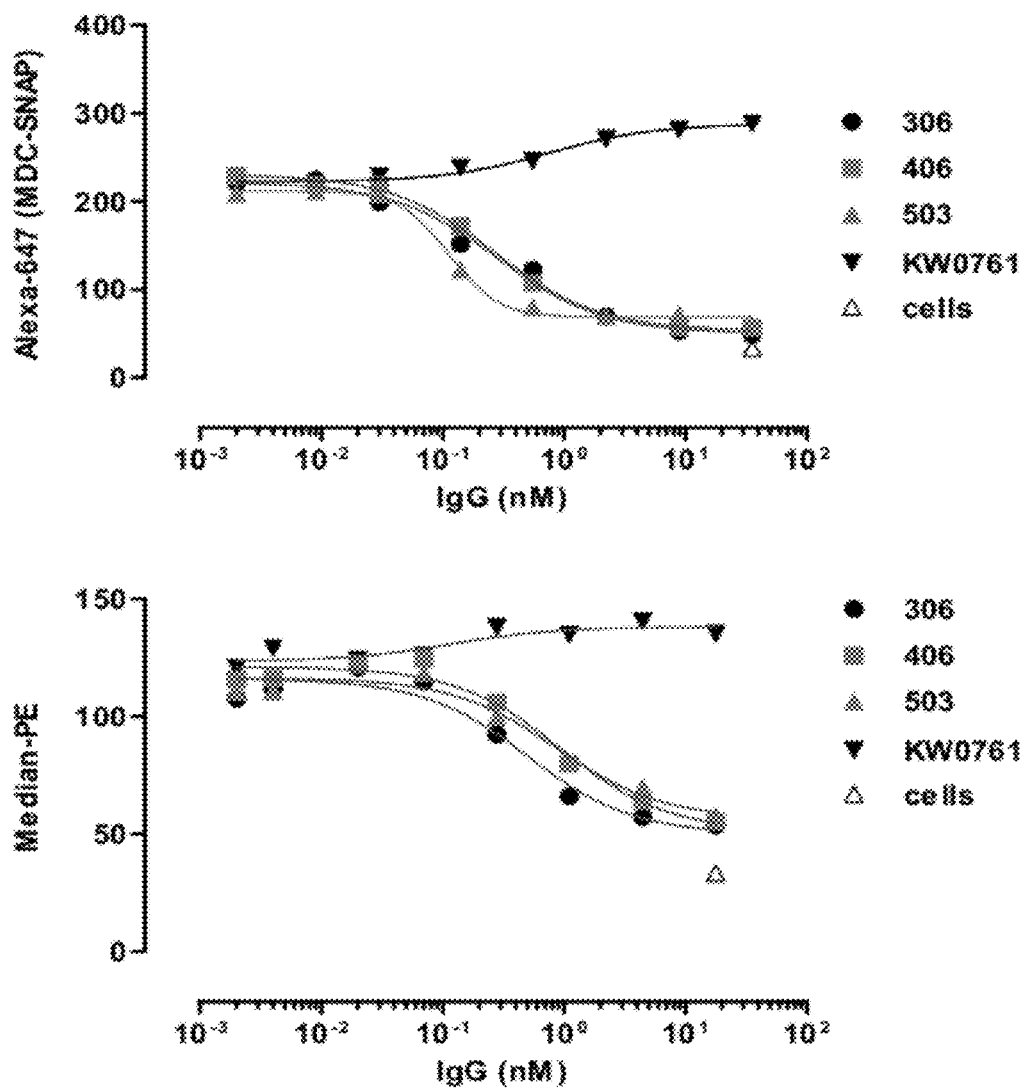

FIG. 12. Results of Example 3, Ligand-interfering binding experiments of anti-CCR4 IgGs using labelled ligands. a.) IgGs were incubated at a concentration of 5 μg/ml (35 nM) and diluted 4-fold over eight dilution points in the presence of a fixed concentration of Alexa647 labeled MDC-SNAP (50 nM). b.) IgGs were incubated at a concentration of 2.5 μg/ml (17.5 nM) and diluted 4-fold over eight dilution points in the presence of a fixed concentration of biotinylated TARC (3.12 μM). Remaining bound biotinylated TARC was detected using PE-conjugated Streptavidin.

Figure 13:
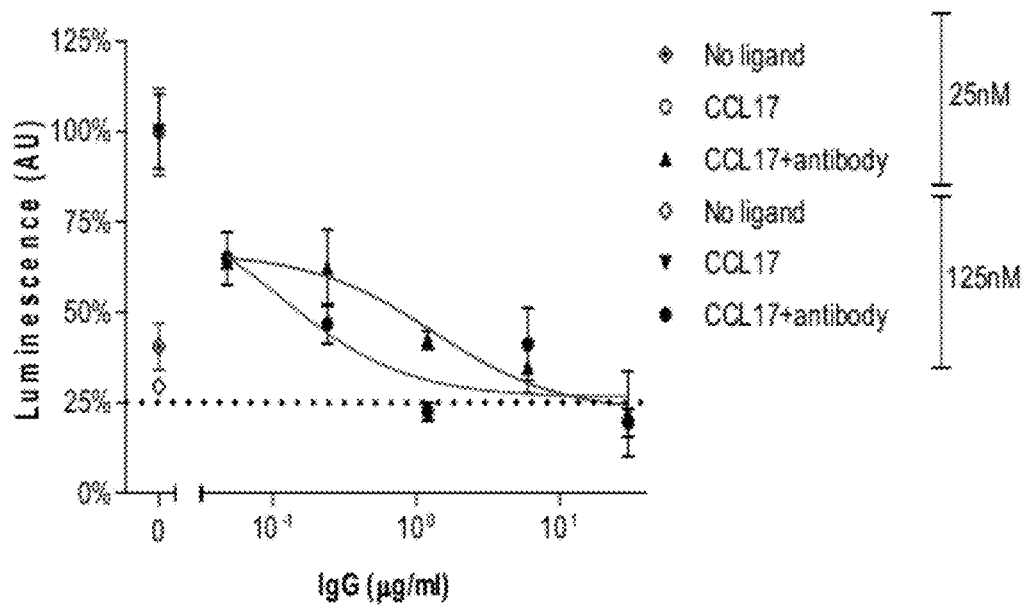

FIG. 13 Results of Example 6: Inhibition of CCL17/TARC-mediated invasion of 786-O cells. Cells were incubated at two different concentrations of CCL17/TARC (25 and 125 nM) in presence of increasing concentrations of anti-CCR4 antibody 503 (μg/ml). Migrated cells were stained and analyzed as outlined in Example 6 and converted in %. The dotted line (y=25%) indicates the basal invasive potency of the 786-O cells during the assay.

Figure 14:
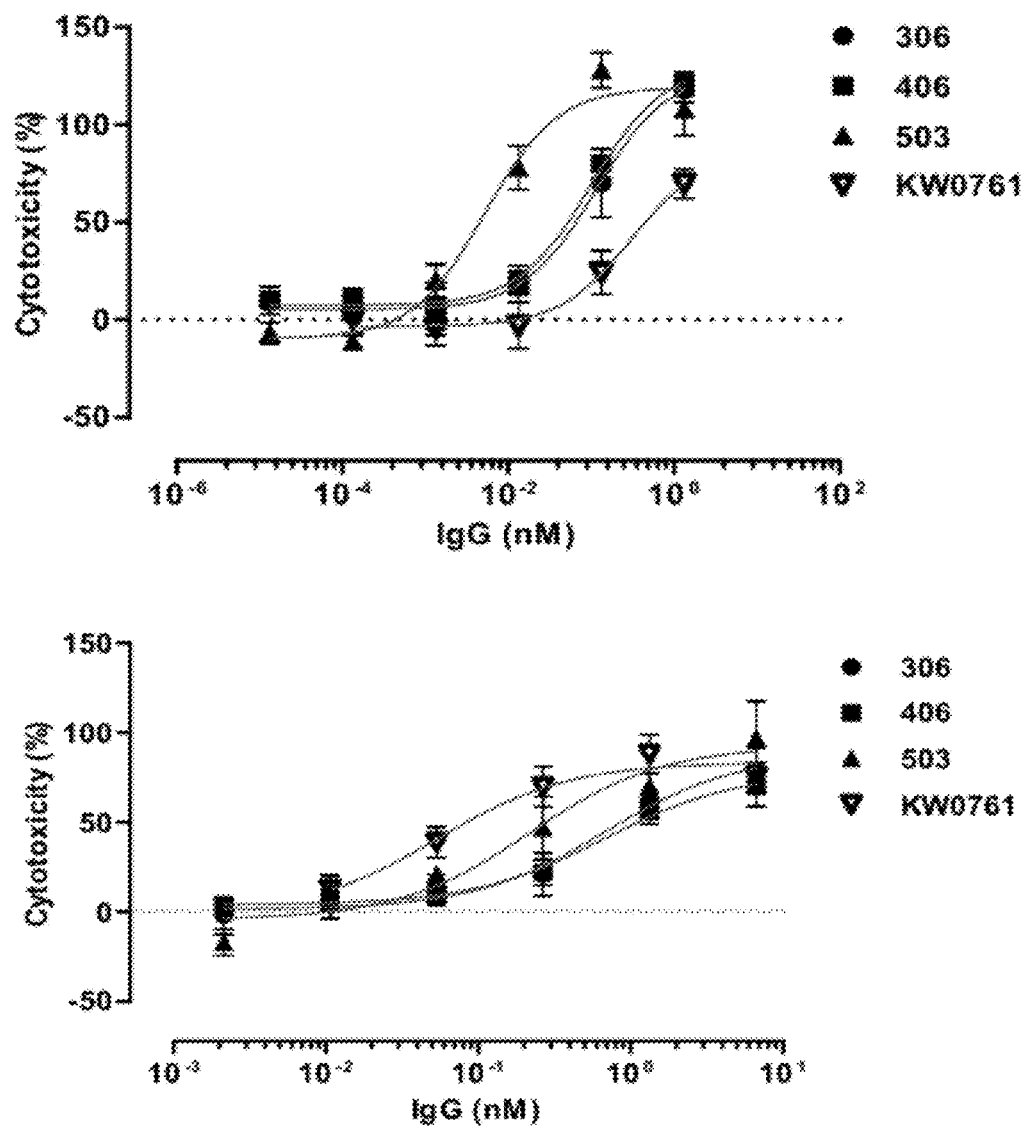

FIG. 14 Results of Example 9: Induction of ADCC on CCR4-expressing cell lines CCRF-CEM (a) and L-428 (b). Calcein-labeled target cells were incubated at different concentrations of anti-CCR4-antibodies as described in Example 1 in presence of human PBMCs. KW0761 was included as control. Induction of ADCC was converted into % based on fluorescence intensity of the samples with 100% cell lysis after treatment with TritonX-100. The dose-response curves were computed by nonlinear regression analysis.

Figure 15:
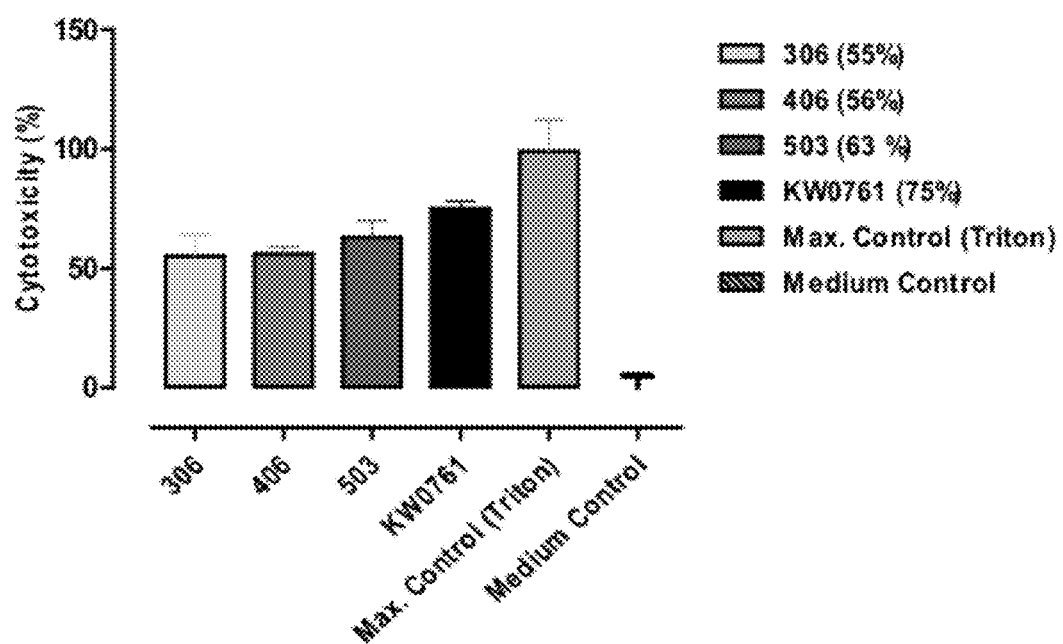

FIG. 15 Results of Example 9: Induction of ADCC on CCR4-expressing isolated Treg-cells. Treg cells were isolated as described in Example 9, calcein-labeled and incubated with a single concentration of anti-CCR4 antibodies at 4.5 μg/ml in presence of autologous PBMCs. Cytotoxicity was converted into % by normalizing to maximum release of calcein from cells in presence of Triton. The percentage of killing is indicated.

Figure 16:
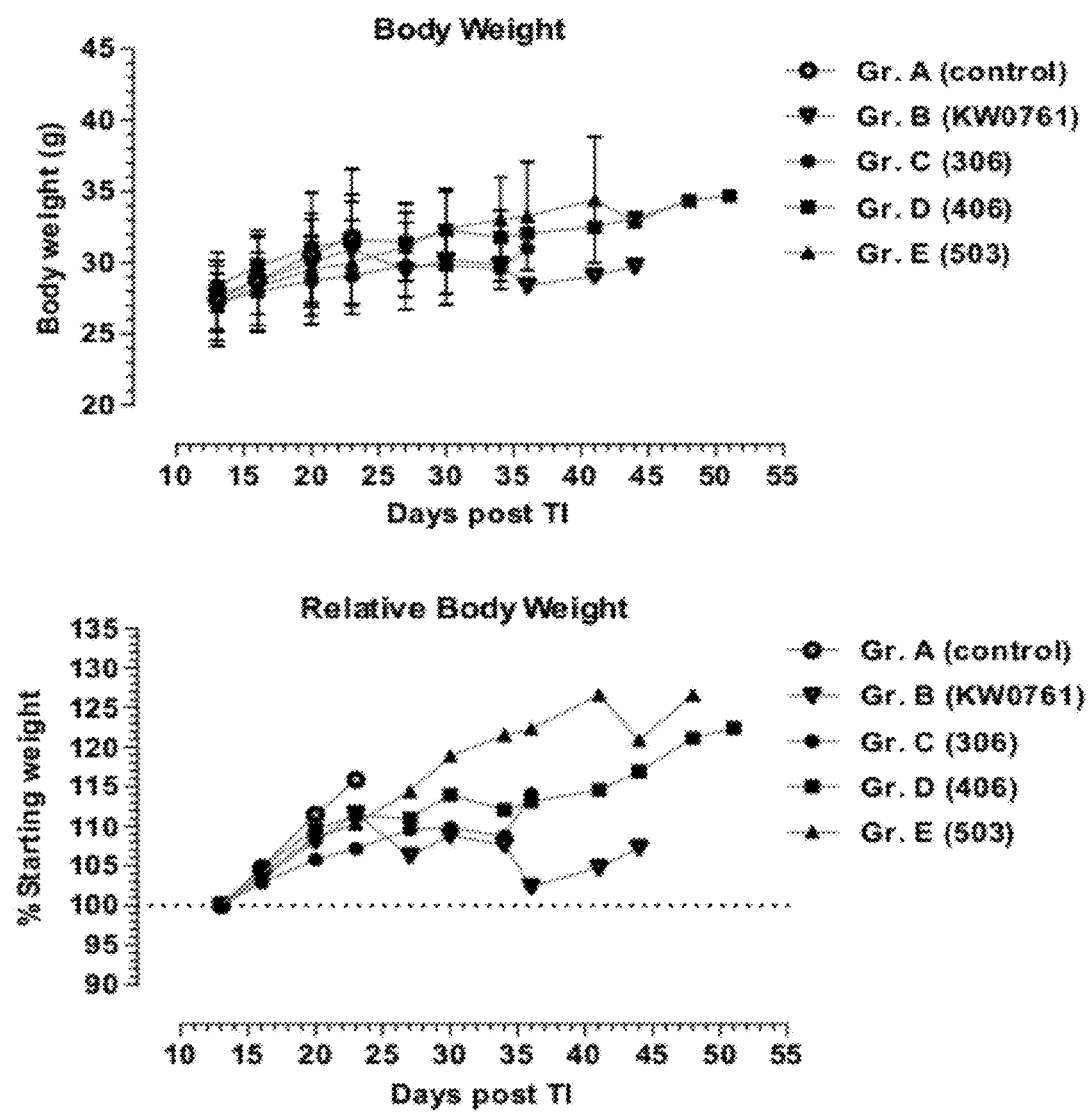

FIG. 16 Results of Example 10: In vivo efficacy of anti-CCR4 antibodies in a human xenograft model of adult T-cell lymphoma leukemia (ATLL). Presented are the measured body weights of the different groups during the study after tumor implantation (TI). Group A (control group) was sacrificed after 23 days due to large tumor volumes. a.) Mean body weight (in g) over time of treatment. b.) Relative body weight (in %) over time of treatment.

Figure 17:
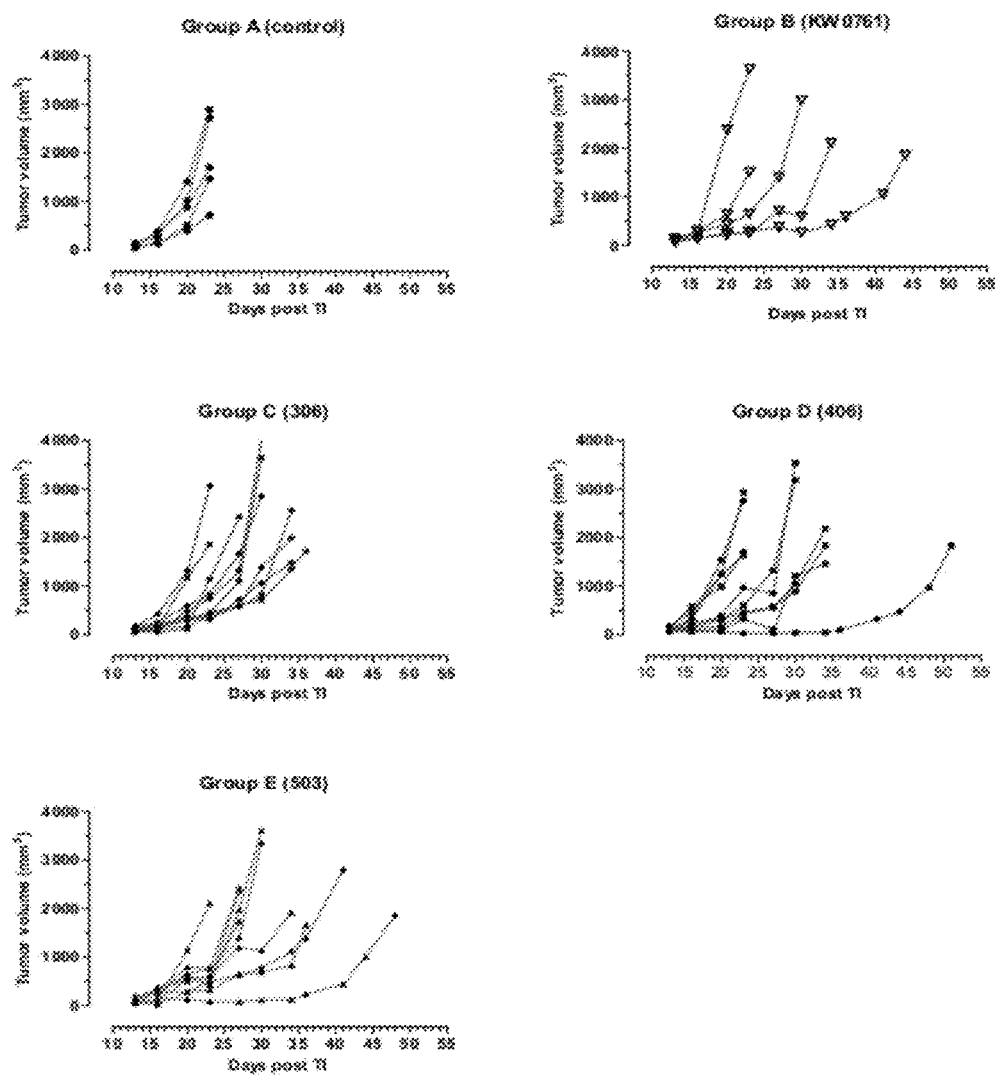

FIG. 17 Results of Example 10: In vivo efficacy of anti-CCR4 antibodies in a human xenograft model of adult T-cell lymphoma leukemia (ATLL). Comparison of measured tumor volumes of the different groups (a-e) during the study after tumor implantation (TI). Individual tumor volumes (measured in mm3) are plotted against time post tumor implantation (TI). The control group (Group A) had to be sacrificed at day 23 due to large tumor volumes.

Figure 18:
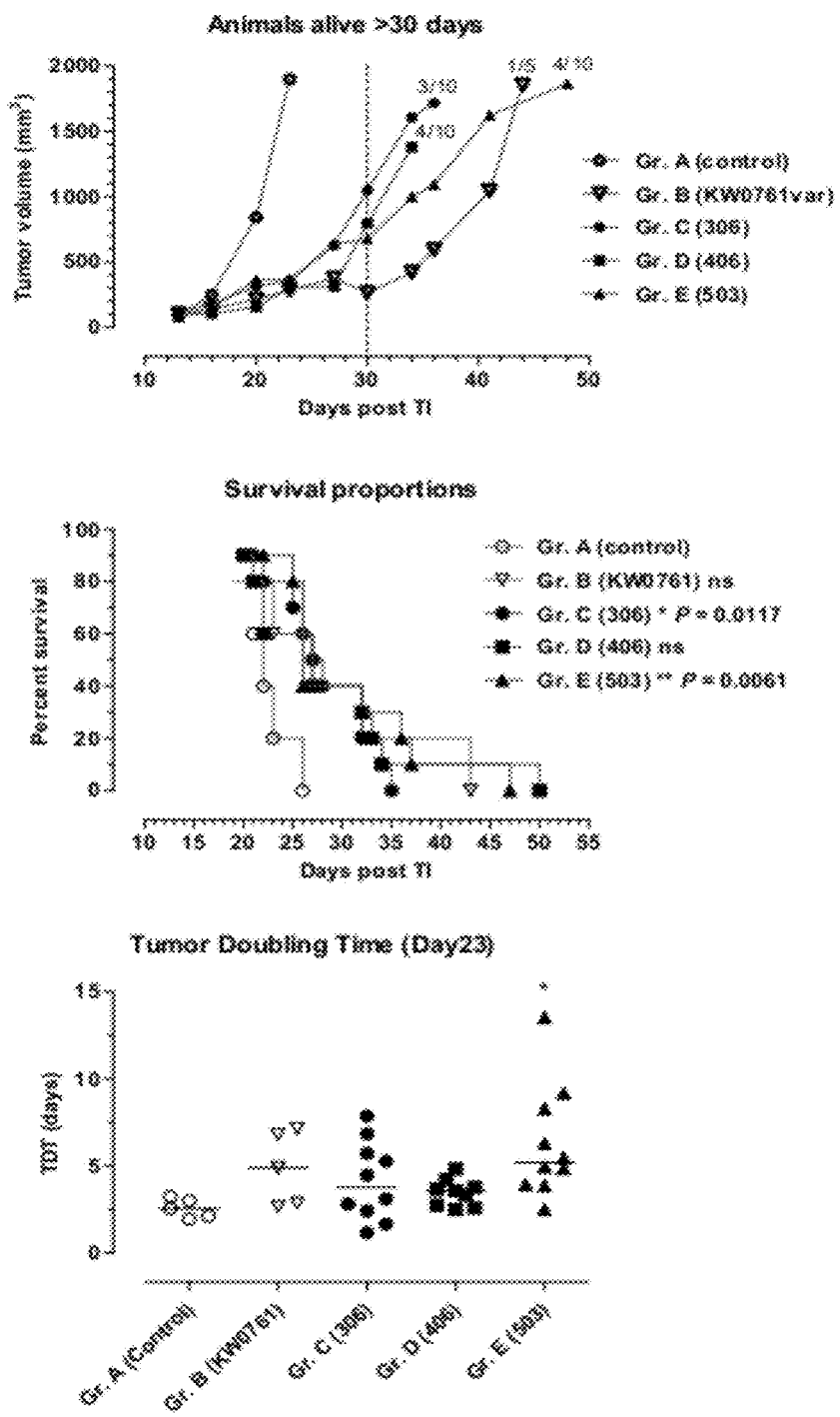

FIG. 18 Results of Example 10: In vivo efficacy of anti-CCR4 antibodies in a human xenograft model of adult T-cell lymphoma leukemia (ATLL). a.) Tumor mean values between the different experimental groups. The number of alive animals within each group is indicated. b.) Survival proportions, calculated by comparison of individual treated group (antibody) vs untreated (control) group. Statistical significant values were identified for anti-CCR4 antibody 306 and 503. c.) Calculated tumor doubling times at day 23. Statistical significant difference was identified for anti-CCR4 antibody 503 (marked with an *).

Figure 19:
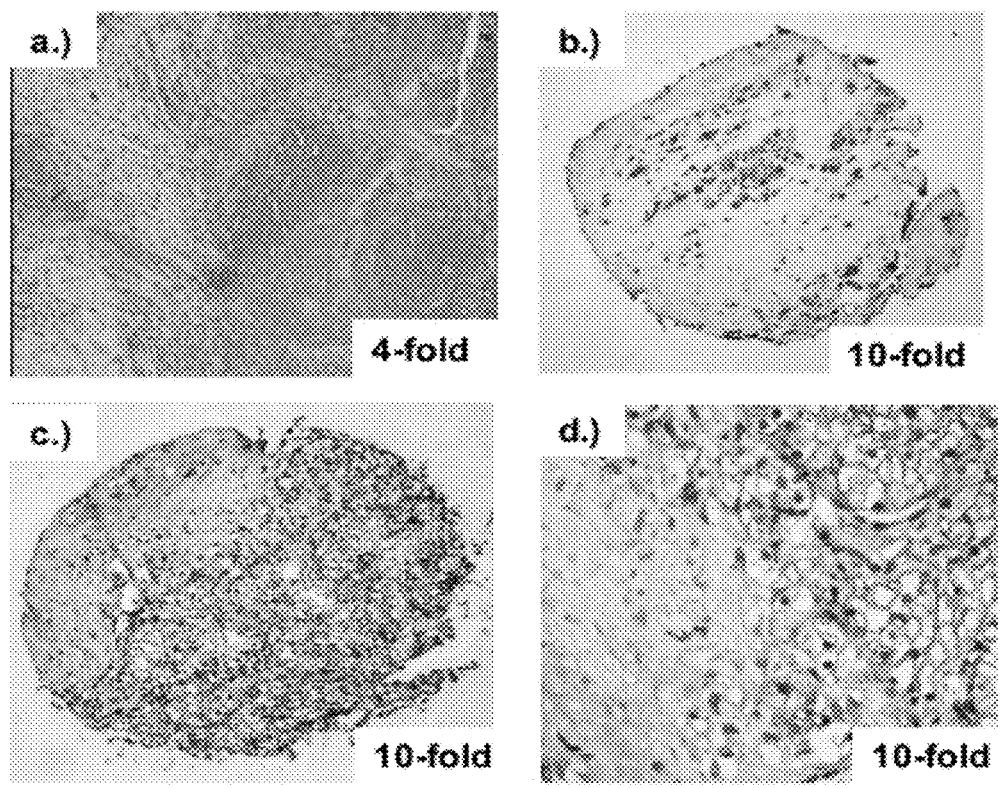

FIG. 19 Results of Example 12: Binding of anti-CCR4 antibody 503 to tumor microarray from renal cell cancer (RCC) patients. Binding of IgG 503 was assessed on paraffin-embedded tissue sections. Antibody was incubated at a concentration of 3 µg/ml and visualized upon incubation with goat biotin-conjugated anti-human antibody (1:500) and visualized using the vectastain elite ABC kit with 3,3 diaminobenzidine as substrate. The magnification of the microscope is given in x-fold. The staining was optimized on positive control tissue from spleen (a.) and confirmed for specificity on normal human placenta tissue (b.). Binding to tissue from RCC patients is presented in c.) and d.).

EXAMPLES

Comparative Information

As discussed above, a known anti-CCR4 antibody family comprises KM2160, KM3060, KM2760 and KW-0761, which recognise an epitope existing in a region of positions 2-29 from the N-terminal amino acid of human CCR4 (EP1270595).

In some of the experiments reported herein, the present inventors have used KM3060var (also referred to herein as "KM3060v"), which corresponds to KM3060, but potentially has a different sugar profile because it was expressed in a different host. This antibody was used in the scFv format.

In some of the experiments reported herein, the present inventors have used KW0761 in the IgG format.

KM2760 has been reported not to block the interaction between CCR4 and TARC or MDC (Ishida et al. 2006, Cancer Research 66 (11), pp 5716-5722). The applicant's findings using KM3060var *are* consistent with this report.

KM2760 has also been reported not to inhibit CCR4 signaling. The applicant has found that KM3060var *does not* inhibit MDC or TARC-induced calcium flux. The applicant has also found no significant inhibition of MDC or TARC-mediated chemotaxis by KM3060var.

Example 1

Novel Antibodies

Nine human antibodies have been identified which can specifically bind to CCR4. Single chain forms of the antibodies were cloned in the pHOG21 plasmid which contains a c-myc and 6×His tag epitopes. TG1 bacteria were transformed, and the scFv was expressed upon IPTG induction. The binding of the purified scFv was confirmed by EasyCyte (see Example 2).

The nucleotide sequences of the heavy and light chain of the antibody producing clones were sequenced. The antibodies are designated as 208, 306, 308, 406, 501, 503, 601, 603 and 803. The sequences of inter alia the CDR regions of the light and heavy chains of 208, 306, 308, 406, 501, 503, 601, 603 and 803 are shown in Tables 1 to 9 respectively.

The IgG form of antibodies 208, 306, 308, 406, 501, 503, 601, 603 and 803 has also been made. IgGs were prepared using standard protocols. Briefly, the genes encoding the corresponding variable domains were cloned into the mammalian expression vector pLNO comprising the genes for human constant domains (Norderhaug et al, 1997). The antibodies were expressed in a cell factory, and the first harvest was purified on a protein A column and fractionated into monomer by size exclusion chromatography. The IgGs retained their ability to specifically bind to CCR4.

The IgG form of these antibodies is of the IgG1 isotype and it comprises two heavy chains and two light chains. Each heavy chain comprises a VH domain (sequences shown in the relevant Tables), and a human IgG1 constant region. Each light chain comprises a VL domain (sequences shown in the relevant Tables), and a human lambda light constant region. As explained in Example 7, defucosylated forms of the IgG antibodies were made. Any assays described herein which use IgG form of the antibodies of the invention use the defucolysated form.

Example 2

Binding of Anti-CCR4 Antibodies to Target Expressing Cells

To demonstrate the CCR4-specificity of the antibodies disclosed in Example 1, in-house CCR4 transfected and untransfected HEK293T-cells, DT40-cells and the natural CCR4+ CCRF-CEM cell line were used in flow cytometry for staining with scFvs 208, 306, 308, 406, 501, 503, 601, 603 and 803. As a positive control, in-house cloned and expressed KM3060var scFv was used. An anti-GFP scFv-antibody (raised against the green fluorescent protein) was used as negative control.

CCRF-CEM (acute lymphoblastic leukemia, ATCC number CCL-119), HEK293T/17 (human kidney, ATCC number CRL-11268), and DT40 (chicken lymphoma, ATCC number CRL-2111) cell lines were obtained from the American Type Culture Collection (ATCC, Rockville, Md.).

For transient transfection with human CCR4, Hek293T/17 cells were seeded as 2×106 cells in a T75 (NUNC) flask. 48 h after seeding, the cells were transfected with pcDNA3.1 plasmid encoding human CCR4 using Fugene (ROCHE) as transfecting agent. 40 µl Fugene and 16 µg DNA are used per T75. The cells were used for assays 48 h after transfection.

The CCRF-CEM and DT40 cells were maintained in RPMI-1640 culture medium and the HEK293T cells were maintained in Dulbecco's Modified Eagle Medium (DMEM) culture medium. All cells were maintained with fetal calf serum, the concentration was 10% for DT40 and HEK293T cells and 20% for CCRF-CEM cells. All media were supplemented with Penicillin and Streptomycin.

For the flow cytometry experiments, the cells were harvested from the culture flasks, washed 2 times with PBS, re-suspended in PBS with 0.2% BSA and 0.09% NaN3 and finally aliquoted 1×105 cells per well into V-shaped 96-well plates (Greiner Bio-One, Frickenhausen, Germany). Cells were centrifuged at 400×g for 5 min and then incubated at 4° C. for 60 min with different scFv dilutions.

All scFv preparations were pre-incubated with a mouse anti-myc-antibody (9E10.2, Diatec, Oslo, Norway) to cross-link scFvs prior adding to the cells and diluted 3-fold, starting at a concentration of 10 µg/ml.

After washing with PBS with 0.2% BSA and 0.09% NaN3, the cells were stained with 1 µg/ml of RPE-conjugated goat anti-mouse IgG (AbD Serotec, Duesseldorf, Germany) for 30 minutes at 4° C. The stained cells were washed, re-suspended in 200 µl PBS with 0.2% BSA and 0.09% NaN3 and transferred to a U-shaped 96-well plate (Corning, Schiphol-Rijk, The Netherlands) for acquisition on EasyCyte flow cytometer (Guava Technologies, Hayward, Calif., USA).

The results obtained clearly indicate that the scFvs 208, 306, 308, 406, 501, 503, 601, 603 and 803 are specific for CCR4. Binding of scFvs 208, 306, 308, 406, 501, 503, 601, 603 and 803 to CCR4-positive DT40 cells compared to CCR4-negative DT40 cells is illustrated in FIG. 1. Selective binding of scFvs 208, 306, 308, 406, 501, 503, 601, 603 and 803 to CCR4+ HEK293T cells compared to CCR-HEK293T cells was also shown (FIG. 2; data only shown for antibody 208). Binding of scFvs 208, 306, 308, 406, 501, 503, 601, 603 and 803 to CCR4-expressing CCRF-CEM cells is illustrated in FIG. 3.

CCR4 specificity was also confirmed for antibodies 306, 406 and 503 in the defucosylated IgG1 format (see Example 7) by comparing binding to HEK293T/17 cells and HEK293T/17 transformed to express human CCR4. These antibodies were also tested for binding to the CCR4-positive cell lines CCRF-CEM, L-428, Hut78, 786-O, A498, KatoIII and MCF-7 using flow cytometry.

As positive controls, either anti-CCR4 antibody 1G1 (BD Pharmingen, Franklin Lakes, N.J., USA.), anti-CCR4 antibody Ab1669 (Abcam, Cambridge, UK) as well as in house produced KW0761 IgG (see above) were used. Isotype control antibodies 6-MAM which binds the opioid drug heroin and an anti-GFP-antibody (raised against the green fluorescent protein) were used as negative controls. Both antibodies were produced in house as IgG1-molecules.

To demonstrate binding to target expressing cells in presence of human serum, anti-CCR4 antibodies 306, 406, 503 and KW0761 were biotinylated via Cysteines following the manual of the EZ-link maleimide-PEG solid phase biotinylation kit (Thermo Fisher, Rockford, Ill. USA).

The CCR4-positive cell lines CCRF-CEM, Hut78 (cutaneous T-cell lymphoma, ATCC number TIB-161), 786-O (human renal cell carcinoma, ATCC number CRL-1932), MCF-7 (human breast adenocarcinoma, ATCC number HTB-22), KatoIII (human gastric cancer, ATCC number HTB-103) and HEK293T/17 cell lines were obtained from the American Type Culture Collection (ATCC, Rockville, Md., USA). L-428 cells (Non-Hodgkin Lymphoma, DSMZ number ACC 197) and A-498 (human renal cell carcinoma, DSMZ number ACC 55) were obtained from the "Deutsche Sammlung von Mikroorganismen and Zellkulturen" (DSMZ, Braunschweig, Germany). The CCRF-CEM, L-428, Hut78, 786-O and KatoIII cells were maintained in RPMI-1640 culture medium. HEK293T/17 and MCF-7 cells were maintained in Dulbecco's Modified Eagle Medium (DMEM; from PAA, cat# E15-810)) culture medium. A-498 cells were cultured in EMEM-medium. All cells were maintained with 10% of fetal calf serum (from PAA cat# A15-252), except for CCRF-CEM, L-428, Hut78 and KatoIII which were maintained in presence of 20% fetal calf serum. All media were supplemented with Penicillin and Streptomycin (from PAA cat#P11-010).

For the flow cytometry experiments, the suspension cell lines CCRF-CEM, Hut78 and L-428 were harvested directly from the culture flasks. Adherent cell lines Hek293T/17, 786-O, A-498, KatoIII and MCF-7 were washed 2 times with PBS and detached from the culture flasks by incubating with Accutase (PAA laboratories, Linz, Austria) for 3 minutes at room temperature according to the manufacturer's protocol. All cells were re-suspended in PBS with 0.2% BSA and 0.09% NaN3 and finally aliquoted 1×105 cells per well into V-shaped 96-well plates (Greiner Bio-One, Frickenhausen, Germany). Cells were centrifuged at 400×g for 5 min and then incubated at 4° C. for 60 min with different IgG dilutions. For binding in presence of human serum, CCRF-CEM cells were incubated with different IgG-solutions at either 10% or 50% of human serum (Sigma Aldrich, St Louis, Mo., USA) at 37° C. for 60 min.

After washing with PBS with 0.2% BSA and 0.09% NaN3, the cells were stained with 1 μg/ml of RPE-conjugated goat anti-Human IgG (AbD Serotec, Duesseldorf, Germany) for 30 minutes at 4° C. The stained cells were washed, re-suspended in 200 μl PBS with 0.2% BSA and 0.09% NaN3 and transferred to a U-shaped 96-well plate (Corning, Schiphol-Rijk, The Netherlands) for acquisition on EasyCyte (Guava Technologies, Hayward, Calif., USA).

The results obtained clearly confirm that the IgG antibodies 306, 406 and 503 are specific for CCR4. Binding of IgGs 306, 406 and 503 to CCR4-positive Hek293T/17 cells was significantly higher than binding to CCR4-negative Hek293T/17 cells. Control antibody 1G1 also bound to CCR4-positive Hek293T/17 cells, but gave a weaker signal.

Binding of IgG antibodies 306, 406 and 503 to haematological CCR4-expressing L428 cells and Hut78 cells, as well as a CCRF-CEM cells, is illustrated in FIG. 10. Binding of 306, 406 and 503 to 786-O, A498, KatoIII and MCF-7 was also confirmed, whereas the negative control antibodies did not bind to these cell lines (data not shown).

Reassuringly, binding of the anti-CCR4-antibodies to CCR4-positive cells is not inhibited in presence of increasing concentrations of human serum, as illustrated in FIG. 11 in relation to the cell line CCRF-CEM.

FIG. 11 also shows that binding of antibodies 306, 406 and 503 is superior to binding of the antibody KW0761. Similar observations were made when biding to the cell lines KatoIII, MCF-7 and A498 was assayed (data not shown).

The binding profile of the anti-CCR4-antibodies 306, 406 and 503 to the different CCR4+ cell lines shows increased binding to some of the CCR4+ cell lines compared to other CCR4+ cell lines. For instance, binding to L-428 is decreased in comparison to CCRF-CEM. L-428 are known to secrete the CCR4-ligand TARC (see Ishida T et al, Leukemia Vol 20, 2006) and the anti-CCR4 antibodies 306, 406 and 503 compete for the CCR4-binding site with TARC (see Example 3).

The binding profile of the anti-CCR4-antibodies 306, 406 and 503 differs from that of KW0761. For example, KW0761 shows increased binding to L-428. Without wishing to be bound by theory, this is believed to be due to different epitope binding sites of these antibodies (as outlined in Example 4). KW0761 does not block the binding of CCR4 and TARC, so it does not compete with the TARC secreted by L-428.

In addition, EC50 values were determined (data not shown) with varying values from cell line to cell line, which is believed to be due to differences in CCR4 expression on the surface of the various cell types.

Example 3

Anti-CCR4 Antibodies Interference with Ligand Binding

To determine whether the anti-CCR4 antibodies from Example 1 interfere with the binding of CCR4 ligands to the receptor, competition experiments were performed. To this end, CCR4-positive CCRF-CEM target cells were incubated at a fixed concentration of MDC-SNAP in presence of increasing concentrations of scFvs. MDC was genetically fused to the N-Terminus of the SNAP-tag such that the SNAP tag is fused to the C-terminus of MDC. The SNAP-tag is derived from the 20 kDa DNA repair protein 06-alkylguanine-DNA alkyltransferase. The gene was ordered at Geneart (Regensburg, Germany) and HEK293/T cells were transiently transfected with the gene, encoding for the MDC-SNAP-fusion protein. After 5-6 days, the fusion-protein was purified via a Ni-NTA-affinity column followed by size exclusion to isolate the monomeric MDC-SNAP fraction. MDC-SNAP was labeled with Alexa647, following the procedures in the manual of the Alexa Fluor 647 Molecular Probe labelling kit (Invitrogen Corporation, San Diego, Calif.). The functionality of the MDC-SNAP to bind CCR4 was confirmed in a chemotactic assay on CCRF-CEM cells (data not shown).

The CCR4+ CCRF-CEM-cells were harvested from culture flasks, washed 2 times with RPMI-1640 culture medium and aliquot 1×105 cells per well into V-shaped 96-well plates (Greiner Bio-One, Frickenhausen, Germany). Cells were centrifuged at 500×g for 5 minutes and the supernatant was aspirated. ScFvs 208, 306, 406, 501, 503, 601, 603 and 803 (sample 308 was not included) were diluted 3-fold starting at 5 µg/ml (150 nM) over eight dilution points and incubated for 60 minutes at 4° C. in presence of a fixed concentration of 140 ng/ml of MDC-SNAP (50 nM) in PBS containing 0.2% BSA and 0.09% NaN3 on the cells. After washing three times with PBS containing 0.2% BSA and 0.09% NaN3, the cells were re-suspended in 200 µl PBS with 0.2% BSA and 0.09% NaN3 and transferred to a U-shaped 96-well plate (Corning, Schiphol-Rijk, The Netherlands) for flow cytometry using a FACS Canto II flow cytometer (BD Biosciences, Heidelberg, Germany) to record the signal of the Alexa647 labeled MDC-SNAP fusion protein. The results showed a clear decrease in staining signals with increasing scFv concentrations (FIG. 4). This indicates that the antibodies interfere with the ligand binding and thus have a CCR4-blocking activity.

A similar experiment was performed to test whether the scFvs described in Example 1 interfere with TARC- and MDC-ligand binding to CCR4. Therefore, the CCR4+DT40-cells were harvested from culture flasks, washed 2 times with RPMI-1640 culture medium and aliquoted 1×105 cells per well into V-shaped 96-well plates (Greiner Bio-One, Frickenhausen, Germany). Cells were centrifuged at 500×g for 5 minutes and the supernatant was aspirated and then incubated for 30 minutes at 37° C. with 0 or 1 µg/ml of TARC or MDC (PeproTech EC, London, UK) in RPMI-1640 culture medium. The supernatants were aspirated after a centrifugation step at 500×g for 5 minutes and cells were incubated for 1 hour at 4° C. with 0.5 µg/ml of scFvs 208, 306, 308, 406, 501, 503, 601, 603 and 803 and 2.5 µg/ml of a mouse anti-cMyc (9E10.2; DIATEC Monoclonals, Oslo, Norway). Cells were centrifuged at 500×g for 5 minutes and then incubated for 45 minutes at 4° C. with 1 µg/ml of RPE-conjugated goat anti-mouse IgG (BD Pharmingen, San Diego, USA, CA). Cells were washed, re-suspended in 200 µl PBS with 0.2% BSA and 0.09% NaN3 and transferred to a U-shaped 96-well plate (Corning, Schiphol-Rijk, The Netherlands) for flow cytometry using an EasyCyte device (Guava Technologies, Hayward, Calif., USA). The results showed a clear decrease in staining signals when scFvs were incubated in presence of TARC and MDC (FIG. 5). This indicates that the scFvs described in Example 1 interfere with the ligand binding and thus have a CCR4-blocking activity.

Substantially similar protocols were used to test the effect of the IgG1 forms of 306, 406 and 503 on ligand binding. KW0761 was used for comparison. The experimental data were fitted by non-linear regression curve fit using a model "log(inhibitor) vs. response" of software Prism (GraphPad) and are summarized in Table 20.

The results showed a clear decrease in staining signals of both labelled ligands MDC and TARC with increasing concentrations of IgGs, except for KW0761 (FIG. 12). This indicates that the IgG1 forms of 306, 406 and 503 interfere with the ligand binding and thus have a CCR4-blocking activity.

Example 4

Competition Between Anti-CCR4 Antibodies

To analyze the epitope recognized by the anti-CCR4 antibodies 208, 306, 308, 406, 501, 503, 601, 603 and 803 in comparison to KM3060var, competition experiments were performed using flow cytometry. The binding of biotinylated KW0761IgG antibody to CCR4+CCRF-CEM cells was challenged in the presence of different concentrations of non-biotinylated anti-CCR4 antibodies (208, 306, 308, 406, 501, 503, 601, 603, 803 and KM3060var) in single chain format The CCR4+ CCRF-CEM-cells were harvested from culture flasks, washed 2 times with RPMI-1640 culture medium and aliquot 1×105 cells per well into V-shaped 96-well plates (Greiner Bio-One, Frickenhausen, Germany). Cells were centrifuged at 500×g for 5 minutes and the supernatant was aspirated. Antibody KW0761-IgG was biotinylated using standard methods. The biotinylated KW0761-IgG was incubated on CCRF-CEM cells for 1 hour at 4° C. at a fixed concentration of 1 µg/ml in presence of anti-CCR4 scFvs 208, 306, 308, 406, 501, 503, 601, 603, 803 and KM3060var which were three-fold diluted over eight titration points, starting at 5 µg/ml. After washing with PBS with 0.2% BSA and 0.09% NaN3, the cells were stained with 2.5 µg/ml of Streptavidin-RPE (BD Pharmingen, San Diego, Calif., USA) for 30 minutes at 4° C. for detection of biotinylated KW0761-IgG. The stained cells were washed, re-suspended in 250 µl PBS with 0.2% BSA and 0.09% NaN3 and transferred to a U-shaped 96-well plate (Corning, Schiphol-Rijk, The Netherlands) for acquisition using an FACS Canto II flow cytometer (BD Biosciences, Heidelberg, Germany).

The results shown in FIG. 6 illustrate that none of the anti-CCR4 antibodies described in Example 1 compete with KW0761 for binding to the cells and only a competition between antibodies KW0761-IgG and KM3060var scFv is observed. This indicates that the antibodies 208, 306, 308, 406, 501, 503, 601, 603 and 803 do not bind to the same epitope as KM3060var or KW0761.

A substantially similar protocol was used to assay competition of the IgG1 forms of 306, 406 and 503 with KW0761 and with one another. This experiment confirmed that antibodies 306, 406 and 503 compete with one another, but not with KW0761 (data not shown).

Example 5

Antagonistic Activity

The ability of the antibodies 208, 306, 308, 406, 501, 503, 601, 603 and 803 to reduce ligand induced calcium flux in the natural CCR4+ CCRF-CEM cell line was assessed. The CCRF-CEM target cells, cultivated under regular conditions, were sedimented by centrifugation and resuspended twice in RPMI-1640 culture medium. One ml with 2.5×106 cells was mixed with Fluo-4-AM (Invitrogen, Carlsbad, Calif.), Pluronic F-127 (Invitrogen, Carlsbad, Calif.) and Probenecid to final concentrations of 1 µM, 0.02% and 1 mM respectively. The cells were incubated at 37° C. for 30 min on a vertical rotating wheel (7 rpm). All subsequent steps were done in the presence of 1 mM Probenecid. The cells were washed twice in RPMI-1640 with 10% FCS, once in assay buffer (145 mM NaCl, 4 mM KCl, 1 mM NaH2PO4, 0.8 mM MgCl2, 25 mM Hepes, 22 mM glucose). The inhibition of TARC and MDC-mediated Ca-Flux was divided into two assays.

The inhibition of TARC-mediated Ca-Flux in presence of scFvs 208, 306, 308, 406, 501, 503, 601, 603 and 803 was evaluated using the PheraStarFS high-through put reader (BMG Labtech, Offenburg, Germany). The antibody KM3060var was used as a negative control. The cells were diluted to a final concentration of $1.6 \times 10^6$ cells/ml. A volume of 25 µl of cells was transferred to a black 96-well plate (Nunc, Thermo Fisher Scientific, Rochester, N.Y., USA) and incubated for 15 min at room temperature in presence of 25 µl of scFv antibodies in the dark. ScFvs were titrated ten-fold over six titration points, starting at 0.5 µg/ml. All scFvs were applied in triplicates, sample KM3060var was included for comparison. The plate was transferred to the PheraStarFS reader and the ligand was automatically injected to each well separately at a final concentration of 28.6 ng/µl (3.6 nM). The changes in fluorescence were measured over a total of 16 points using the 485-520 nm band pass filter (5 points before ligand injection (range 1); 1 point during the ligand injection (start of range 2); 10 points after the injection of the ligand (range 2)). The % of activation was calculated using following equation:

$$\frac{[\text{Sum of range 2 raw data} - (11 \times \text{start of range 2})]IgG - [\text{Sum of range 2 raw data} - (11 \times \text{start of range 2})]\text{buffer}}{[\text{Sum of range 2 raw data} - (11 \times \text{start of range 2})]\text{Ligand}}$$

The inhibition of MDC-mediated Ca-Flux in presence of scFvs 208, 306, 308, 406, 501, 503, 601, 603 and 803 was evaluated using a FACSCanto II flow cytometer (BD Biosciences, Heidelberg, Germany). Cells were stained as described above and diluted to a final concentration of $1.2 \times 10^6$ cells/ml. Equal volumes of cells, assay buffer with or without scFv antibodies and ligand (MDC) were mixed. The first two components (cells and antibodies) were pre-incubated for 15 min prior to addition of the ligand. The final concentrations of the scFvs were 10 µg/ml whereas MDC was 5 ng/ml. The samples were immediately analyzed using the 515-545 nm band pass filter on a FACSCanto II flow cytometer (BD Biosciences, Heidelberg, Germany). For evaluation, the average signals of stained cells, but otherwise untreated, was subtracted from all samples. The signal recorded from stained cells in presence of MDC, but no scFv antibody, was set as basis for 100% signaling and cells in presence of MDC and scFv antibodies were converted into %.

Figure 7:
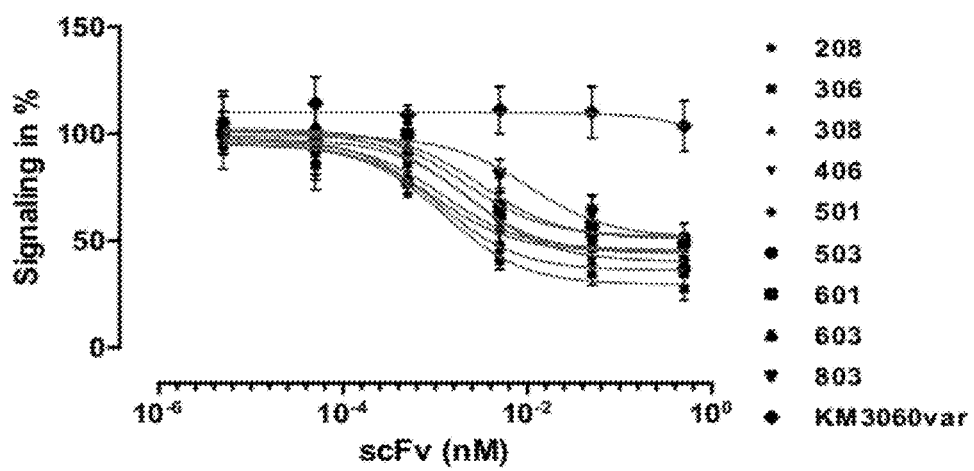

The results shown in FIGS. 7 and 8 clearly demonstrated that all scFvs described in Example 1 act as inhibitors of TARC and MDC. The IC50 values derived from the TARC inhibition are presented in Table 19.

A substantially similar protocol was used to assay the effect on ligand-induced calcium flux by the IgG1 forms of 306, 406 and 503 compared with KW0761. This experiment confirmed that antibodies 306, 406 and 503, but not KW0761, reduce ligand-induced calcium flux. The experimental data were fitted by non-linear regression curve fit using a model "log (inhibitor) vs. response" of software Prism (Graph Pad).

The results clearly demonstrate that the antibodies of the invention act as inhibitors of TARC and MDC induced Ca-Flux. The IC50 values derived from the TARC inhibition are presented in Table 21. It should be understood that a compari-son of these deduced values with values deduced under different experimental conditions would not necessarily be appropriate.

Example 6

Inhibition of Chemotaxis

The inhibition of chemotaxis by the scFv antibodies in Example 1 was assayed by contacting CCR4+ cells capable of chemotaxis with scFv antibodies in one chamber, whereas a ligand of CCR4 (MDC or TARC) was placed in another chamber separated from the first chamber by a membrane or filter having a suitable pore size. The effect of the antibodies on cell migration towards the ligand (chemotaxis) was determined by comparing chemotaxis in the presence of the antibody to chemotaxis in the absence of the antibodies. All scFv antibodies as described in Example 1 were found to inhibit chemotaxis of CCR4-positive cells towards MDC and TARC.

CCR4+CCRF-CEM target cells, cultivated as described in Example 2, were sedimented by centrifugation and re-suspended twice in RPMI-1640 culture medium without FCS. In a third centrifugation step, cells were re-suspended in RPMI-1640 culture medium supplemented with 1% FCS and adjusted to a final density of $1.6 \times 10^7$ cells/ml. In parallel, 150 µl of RPMI supplemented with 1% FCS containing TARC or MDC at 3.5 nM was added into each of the lower chamber of a Multiscreen-MIC plate 96 well (8 µm pores, Millipore, Billerica, Mass., USA, MAMIC5S10). ScFv antibodies were serial diluted from 333 nM down to 0.36 nM in presence of a mouse anti-myc-antibody (9E10.2, Diatec, Oslo, Norway) to cross-link scFvs and simulate a dimeric IgG format. 50 µl of the scFv antibodies were mixed with 50 µl of cells (final concentration of $3.9 \times 10^5$ cells/ml) and added to the upper compartment of the Multiscreen-MIC 96 chamber plate and incubated at 37° C. for 3 hr. The filter was removed and 100 µl of cells (from the lower chamber) were transferred after re-suspending into a 96-well COASTAR plate (Greiner Bio-One, Frikenhausen, Germany); an additional volume of 100 µl of PBS (supplemented with 0.2% BSA and 0.09% NaN3) was added to the samples. Migration was evaluated by counting of gated cells using a FACSCanto II flow cytometer (BD Biosciences, Heidelberg, Germany).

The number of migrated cells in presence of TARC or MDC, but no scFv antibody, was set as basis for 100% migration and the number of migrated cells in presence of ligands and scFv antibodies were converted into %.

The data presented in FIG. 9 demonstrate that all scFv antibodies described in Example 1 inhibited TARC induced chemotaxis of CCRF-CEM cells. In addition, the same scFv antibodies inhibited MDC-mediated chemotaxis (data not shown).

A substantially similar experiment was carried out with the IgG1 forms of 306, 406 and 503, confirming that the IgG1 forms also inhibited TARC induced chemotaxis of CCRF-CEM cells, as well as MDC induced chemotaxis of CCRF-CEM cells. The results were analyzed by fitting the data using a log (inhibitor) vs. response function using GraphPad Prism to extract IC50 values. Determined IC50 values are summarized in Table 22.

In a further experiment, the effect of anti-CCR4 antibody 503 (IgG1 form) on the migration of the solid tumor cell line 786-O in response to TARC was assayed using a transwell plate assay.

A multiscreen-MIC 96 well plate (8 µm pores, Millipore, Billerica, Mass., USA, MAMIC8S10) was prepared by aliquoting 50 µl of a 1 µg/ml of a matrigel solution (BD Matrigel, Cat. No. 356230, BD Biosciences, Heidelberg, Germany) on top of the pores for coating. The matrigel was allowed to polymerize for 1 h at 37° C. Non-reacted matrigel was removed by washing the pores with PBS. The 786-O cell were cultivated as outlined above. Cells were harvested from flasks after washing 2 times with PBS and detached from the culture flasks by incubating with Accutase (PAA laboratories, Linz, Austria) for 3 minutes at room temperature. Cells were aliquoted to a final cell density of 8.0×105 cells/ml in RPMI-1640, supplemented with 0.1% fetal calf serum. In parallel, IgG antibody 503 was diluted to a concentration of 60 µg/ml and serial diluted five-fold over 5 points in RPMI-1640 supplemented with 0.1% FCS. The amount of salt present in the formulation buffer of the antibody was kept constant. The ligand TARC was diluted to two final concentrations, 1000 ng/ml and 200 ng/ml in RPMI-1640 supplemented with 0.1% FCS. The amount of salt present in the formulation buffer of the antibody was kept constant. A volume of 150 µl of the ligand was aliquoted in the bottom chamber of a transwell Multiscreen-MIC plate 96 well plate (8 µm pores, Millipore, Billerica, Mass., USA, MAMIC8S10). An equal volume of 50 µl of cells were mixed with a volume of 50 µl of the antibody dilutions. The mixture was placed on top of matrigel coated membrane and incubated for 3 h at 37° C. Not-migrated cells on top of the matrigel coated membrane were mechanically removed by scraping, whereas cells migrated through the matrigel coated membrane were stained according to the manual of the cell titer glo luminescent cell viability assay kit (Promega, Madison, Wis., USA). The stained samples were transferred to a 96-well plate (NUNC, flat bottom, black) and the luminescence was analyzed on a Tecan Infinite M200 reader (Tecan, Maennerdorf, Switzerland). The number of migrated cells in presence of TARC, but without antibody, was set as basis for 100% migration and the number of migrated cells in presence of ligand and antibody were converted into %. The results were analyzed by fitting the data using a log (inhibitor) vs. response function using GraphPad Prism to extract IC50 values. The results show that antibody 503 inhibits TARC-induced migration of the solid tumor cell line 786-O (FIG. 13). Determined IC50 values are summarized in Table 23.

Similar findings were made on the murine renal cell cancer cell line RENCA where anti-CCR4-antibody 503 was able to block murine TARC induced migration of the target cells (data not shown).

Example 7

Generation of Defucoylated Anti-CCR4 IgG1 Molecules

It has been reported that ADCC enhancement can be achieved by manipulating the state of oligosaccharides on human IgG1 subclass (Niwa R et al, CanRes, Vol. 64, 2004). Modifying the amount of fucose was demonstrated to have a beneficial effect on ADCC. Therefore, antibodies 306, 406 and 503 were produced in the presence of Kifunensine, a selective inhibitor of class I α-mannosidases, causing a stop in fucosylation of the IgG during production in cell culture. Antibody KW0761 was produced under the same conditions.

IgGs were produced in the presence of Kifunensine (100 ng/ml; Sigma Aldrich, St Louis, Mo., USA). After harvesting the cell medium, IgGs were isolated first upon affinity purification using a ProteinA column (HiTrap, 5 ml, ProteinA; GE). IgGs were eluted using citrate buffer (pH 3) and transferred into 1M Tris-buffer (pH 9). Prior a second purification, IgG samples were up-concentrated and loaded on to a size exclusion chromatography (HiLoad Sephadex 200, GE; running buffer 20 mM Na-Phosphate/145 mM NaCl, pH7.2). Monomeric fractions were collected and IgGs were up-concentrated a second time.

Example 8

Species Cross-Reactivity

Antibodies 306, 406 and 503 were tested for their ability to cross-react with CCR4 from species other than human.

For transient transfection, Hek293T/17 cells were seeded as 2×106 cells in a T75 (NUNC) flask. 48 h after seeding, the cells were transfected with Fugene (ROCHE). 40 µl Fugene and 16 µg DNA are used per T75. The cells were used for assays 48 h after transfection.

HEK-293T/17 cells were transiently transfected either with pcDNA3.1 plasmid encoding human CCR4 or with pLNO plasmids (Norderhaug et al, 1997) encoding either mouse CCR4 (GeneBank CAA62372) or monkey (*Macaca mulatta*) CCR4 (PubMed access number XP_001098807) using Fugene (Roche) as a transfection reagent. Non-transfected (CCR4 negative) cells served as a negative control. The cells were cultivated further for 48 hours under regular conditions and harvested form flasks as described above. One times 105 cells per well were aliquoted into V-shaped 96-well plates (Greiner Bio-One, Frikenhausen, Germany). Cells were centrifuged (400×g, 5 min, 4° C.), re-suspended in 50 µl of antibodies (306, 406, 503 and isotype control 6-MAM) at a concentration of 1 µg/ml in PBS containing 0.2% BSA and 0.09% NaN3 and incubated at 4° C. for 60 min. Expression of human and murine CCR4 was confirmed by incubating according cells in presence of either PE-conjugated mouse anti-Human-CCR4 antibody 1G1 or with PE-conjugated hamster anti-Mouse-CCR4 antibody 2G12 (Biolgend; San Diego, Calif., USA). The samples were then washed twice by centrifugation and re-suspension in 150 µl FACS buffer. The cell pellets were finally re-suspended in 50 µl with 3 µg/ml goat anti-human-IgG-PE (AbDSerotec, Düsseldorf, Germany) for detection of antibodies 306, 406, 503 and isotype control IgG 6-MAM and incubated at 4° C. for 45 min. The samples were washed twice as described above and re-suspended in 250 µl FACS buffer followed by transfer into a U-shaped 96-well plate (Corning, Schiphol-Rijk, Netherlands) for flow cytometry on FACSCantoII (BD Biosciences, San Jose, Calif.).

Antibodies 306, 406 and 503 were found to bind to both human and monkey CCR4 and a reduced affinity to murine CCR4 was detected (data not shown).

Example 9

Antibody-Dependent Cell-Mediated Cytotoxicity (ADCC)

The ability of the anti-CCR4 antibodies 306, 406 and 503 to induce ADCC was assessed and compared to KW0761 on the natural CCR4+ cell lines CCRF-CEM, L-428 and Hut78. In addition, induction of ADCC was tested on isolated regulatory T-cells (Treg-cells) using anti-CCR4 antibodies 306, 406 and 503 in comparison to KW0761. It is well established that Treg-cells play a key role in the immune-escape of solid tumor during the cancer disease progression (see Wolf A M et al, Clin Cancer Res Vol 9, 2003). Importantly, CCR4 has been described to be expressed on CD4+CD25+ T cells which home to the stromal region of the tumor where they inhibit the immune response towards the tumor. Either inhibition of migration (induced by MDC) or direct killing (via ADCC) of these Treg-cells via CCR4 could be a promising way to block metastasis or to reduce the growth of solid tumors.

For ADCC on the suspension cells CCRF-CEM, L-428 and Hut78, cells were cultivated under regular conditions as described in Example 2. Cells were sedimented by centrifugation and re-suspended in RPMI-1640 culture medium. This step was repeated once. One ml with 2.5×106 cells was mixed with calcein-AM (Invitrogen, Carlsbad, Calif.) to a final concentration of 10 μM and then incubated at 37° C. for 30 min on a vertical rotating wheel (7 rpm). The cells were washed three times in RPMI-1640 with 10% FCS and the cell density was adjusted to 3×105/ml. Separately, peripheral blood mononuclear cells (PBMC) were prepared following conventional procedures (enriched by Ficoll-Hypaque gradient centrifugation), washed in RPMI-1640 with 10% FCS and re-suspended at 6×106 per milliliter. Fifty μl of each target and effector cells were added to the same wells in a 96-well microtiter plate giving a ratio of effector to target cells (E:T) of 20:1. The antibodies were added in quadruplicate samples to the same wells in a volume of 100 μl resulting in a concentration range as follows: 0.2 μg/ml down to 0.002 ng/ml in case of CCRF-CEM; 1 μg/ml down to 0.32 ng/ml in case of L-428; 1 μg/ml down to 0.1 ng/ml in case of Hut78. The microtiter plate was then incubated for four hours at 37° C., and 20 μl 0.9% Triton-X100 was added to some of the wells after 3 hrs and 45 minutes to achieve complete lysis of the target cells. One hundred μl supernatant of each sample was then transferred to a black microtiter plate and the fluorescence (excitation: 488 nm, emission: 518 nm) was analyzed in a TECAN Infinite M200 plate reader (Tecan, Maennerdorf, Switzerland). The fluorescence intensity in the samples with no antibodies was subtracted from the intensity of all other samples. The percentage of lysis in samples with antibodies was estimated based on fluorescence intensity of the samples with 100% cell lysis after treatment with TritonX-100. The dose-response curves were computed by nonlinear regression analysis and a three-parameter fit model using software Prism (Graph Pad, San Diego, Calif., USA).

To test induction of ADCC on Treg-cells, the following protocol was established and the setup was established using the anti-CCR4 antibody (1G1, Cat. No. #551266, BD Biosciences, Heidelberg, Germany).

The percentage of Treg cells in healthy donor blood is reported to be between 5 and 10% (see Wolf A M et al, Clin Cancer Res Vol 9, 2003). This is why the Treg cells had to be enriched from healthy donor PBMCs in order to get a decent amount of isolated Treg-cells. Isolation was performed according to the protocol from Dynabeads Regulatory CD4+ CD25+ T Cell Kit (Cat. No. #113-63D, Invitrogen Corporation, San Diego, Calif., USA), resulting in three different populations (PBMC, CD4+ and T-reg). At particular stages of the purification some cells were kept and appropriately stained as quality control. The PBMCs, the CD4+ and the Treg cells were sedimented by centrifugation and re-suspended to 1×106 cells/ml in PBS, supplemented with 0.2% BSA and 0.09% NaN3. For each experiment two hundred μl of non-separated 2×105 PBMCs and isolated CD4+ cells and 100 μl with 1×105 isolated Treg were transferred in a 96 well v-shaped plate and spun down at 400×g for 5 min at 4° C. The supernatants were discarded using a pipette, the cell pellets were re-suspended in either 50 μl of PBS supplemented with 0.2% BSA and 0.09% NaN3, in 50 μl of biotinylated anti-CD127 (Cat. No. #558633BD Biosciences, Heidelberg, Germany), which served for identification of Treg cells (see Simonetta F et al, Eur J Immunol Vol 9, 2010) or 50 μl of biotinylated anti-CCR4 antibody (1G1, Cat. No. #551266, BD Biosciences, Heidelberg, Germany) and incubated at 4° C. for 1 h. The samples were washed 3 times with PBS (supplemented with 0.2% BSA and 0.09% NaN3), spun down at 400×g for 5 min at 4° C. The supernatants were discarded using a pipette, the cell pellets were re-suspended in either 50 μl of PBS (supplemented with 0.2% BSA and 0.09% NaN3) or in a mixture of 50 μl of anti-CD4-FITC and anti-CD25-APC (Cat. No. #11-0049-42 and #17-0259-42 eBiosciences San Diego, Calif., USA) and Streptavidin-PerCP (Cat. No. #554064, BD Biosciences, Heidelberg, Germany) with or without biotinylated anti-CCR4 (1G1, Cat. No. #551266, BD Biosciences, Heidelberg, Germany) and incubated at 4° C. for 1 h. The samples were washed 3 times with PBS (supplemented with 0.2% BSA and 0.09% NaN3), spun down at 400×g for 5 min at 4° C. The supernatants were discarded using a pipette, the cell pellets with anti-CCR4-PE and unstained were re-suspended either 200 μl of PBS (supplemented with 0.2% BSA and 0.09% NaN3) and transferred to a 96 well u-shaped plate. Compensation using the different fluorochromes was performed on the FACSCanto II (BD Biosciences, Heidelberg, Germany) and the samples were analyzed. The remaining samples were stained with anti-FoxP3-antibody (Cat. No. #560046, BD Biosciences, Heidelberg, Germany) according to the protocol described in the FoxP3 staining buffer kit (Cat. No. #00-5523-00, eBiosciences San Diego, Calif., USA). Cells were re-suspended in 200 μl of PBS (supplemented with 0.2% BSA and 0.09% NaN3) and transferred to a 96 well u-shaped plate for analysis in flow cytometry using the FACSCantoII (BD Biosciences, Heidelberg, Germany). Isolated Treg cells were judged as pure Treg cells by double positive signals on anti-CD4-FITC/anti-CD25-APC as well as by double positive signals on anti-FoxP3-PE/anti-CCR4 (detection of biotinylated 1G1 using Streptavidin-PerCp). It was found that approximately 95% of isolated cells were CD4+CD25+ cells and 66% of these were FoxP3-CCR4-positive.

The ADCC experiment to evaluate the effect of the anti CCR4 antibodies described in example 1 on isolated Treg cells was performed as described, except that the E:T (effector cells in this case isolated from autologous PBMCs; target cells=Treg cells) ratio was lowered to 15, because of low isolation yields of mononuclear cells from autologous PBMCs. Antibodies 306, 406, 503 and KW0761 were incubated at a single concentration of 3.3 nM in triplicates. To confirm that the isolated autologous PBMCs were functional, the ADCC was performed in parallel on CCR4+CCRF-CEM target cells (data not shown).

The results shown in FIG. 14 and the summarized calculated EC50 values (see Table 24) clearly demonstrate that the anti-CCR4 antibodies of the invention were able to induce ADCC in the presence of human PBMCs on all three target cell lines (Hut78 not shown). The most effective anti-CCR4 antibody 503 was determined to have an EC50 of 5.3 μM when tested on CCRF-CEM cells, compared to 315 pM of KW0761. Decreased killing activity was observed for all anti-CCR4 antibodies as described in Example 1 when tested on L-428 cells in comparison to KW0761. This can be explained by the fact that this cell line was shown to secrete the CCR4-ligand CCL17/TARC, thereby competing with the antibodies binding to CCR4.

In addition, the anti-CCR4 antibodies also exhibited comparable maximum killing activities when challenged for ADCC on isolated Treg cells (see FIG. 15).

Example 10

In Vivo Model of Adult T-Cell Lymphoma Leukemia (ATLL)

The anti-CCR4 antibodies described in Example 1 306, 406 and 503 were tested for their ability to reduce tumor growth in a human T-cell lymphoma xenograft model using defucosylated IgG1 molecules. Antibody KW0761, which is based on an antibody previously demonstrated to have in vivo efficacy in ATLL (Niwa R et al, CanRes, Vol 65, 2004), was included as positive control. All experiments described were performed at EPO (Berlin, Germany).

Tumor pieces (3×3×3 mm in size) of the CCR4+ hematological adult T-cell lymphoma cell line CCRF-CEM were subcutaneously transplanted into NMRI nu/nu mice (Taconic, Hudson, N.Y., USA). In total, 5 different groups were treated in parallel with the different samples as follows: Group A=control group (vehicle formulation buffer as described in Example 2), consisting of 5 animals; Group B=KW0761-IgG, consisting of 5 animals; Group C=306-IgG, consisting of 10 animals; Group D=406-IgG, consisting of 10 animals; Group E=503-IgG, consisting of 10 animals. Antibody samples were applied intravenously (i.v.) when tumors reached a palpable size of approximate 100 mm3. The tumor volume was calculated using following equation:

Tumor volume (mm3)=0.5×(major diameter)×(minor diameter)2.

Mice were treated twice a week over 4 weeks (8 treatments in total) at a dosage of 20 mg/kg (500 µg of IgG per mouse assuming an average weight of 25 g/mouse). Animals were monitored over a total of 6 weeks after the beginning of treatment, measuring the tumor volume and body weight twice a week. Animals were sacrificed when tumor sizes exceeded a size of >1.5 cm3. The control group had to be sacrificed after 23 days due to large tumor volumes. Statistical significance of obtained data between the experimental groups were analyzed using software Prism (GraphPad, San Diego, Calif., USA). Survival proportions were analyzed using Mantel-Cox test by comparing treated (antibody) versus untreated (control) group. Tumor doubling times were analyzed via analysis of variance (ANOVA) and unpaired t-test analysis.

The results of the study are presented and summarized in FIGS. 16, 17 and 18 Treatment of the mice with the antibodies was well tolerated as could be assessed by the absence of the body weight losses (FIG. 16). Comparison of the individual tumor volumes from the different groups is shown in FIG. 17. It can be seen that the tumor volume within a group shows high variation, probably due to the fact the tumor model was inoculated from tumor pieces, which can result in a fast tumor growth after a lag-phase. The control group A had to be sacrificed after 23 days of tumor implantation, due to large tumor sizes. A clear reduction in tumor volume can be seen for all tested anti-CCR4 antibodies. The lowest mean tumor volume, measured at day 23, in comparison with the control group (treated vs. control in %; T/C) was determined for anti-CCR4 antibody 503 with a value of 35%, 67% in case of KW0761, 50% for 306 and 62% in case of 406, respectively. Statistical significant difference in the tumor doubling time was also determined for anti-CCR4 antibody 503 in comparison with the control group (6.28±1.03 vs. 2.58±0.25 days; P=0.0273, unpaired t test). This difference in tumor volume and tumor doubling time is reflected in the survival curve of animals from the same group E (anti-CCR4 antibody 503) for which a median survival time of 26 days was determined in comparison to 22 days for the control group A.

Thus, all three anti-CCR4 antibodies described in Example 1 were demonstrated to have in vivo tumor eradication efficacy. Statistical significant data were obtained for antibody 503.

Example 11

Aggregation Measurements on Platelets

CCR4 is known to be expressed on platelets, and its ligands MDC and TARC are known to induce platelet aggregation. This could potentially be problematic, because IgG molecules have two ligand binding sites, so there is a possibility that an IgG capable of recognizing CCR4 may be able to cross link platelets if both arms are able to bind to CCR4 on different platelets. This might result in blot clotting in vivo. Therefore, the effect of the anti-CCR4 antibodies as described in Example 1 on platelet aggregation were examined. The antibodies were incubated with isolated platelets alone or in combination ADP, a well-described inducer of aggregation (Varon and Spectre "Antiplatelet agents" Hematology Am Soc Hematol Educ Program. 267-72, 2009).

A total of 50 ml of fresh donor blood was collected into sodium citrate containing tubes. Platelet rich plasma was obtained by centrifuging at room temperature (RT) for 15 min at 185 g. The platelet containing plasma was transferred into a fresh tube. To define the baseline, platelet depleted plasma was prepared by centrifugation of 1 ml of the platelet rich plasma for 5 min at 1200 g at RT. The supernatant was transferred into a new tube and treated in the following the same way as the platelet rich sample. Aggregation measurements were performed at 37° C. under stirring using an AggRam-aggregometer (Helena Laboratories, Beaumont, Tex., USA). IgGs (503, 406, 306 and anti-GFP as negative control) were incubated with platelets at a concentration of 10 µg/ml in FACS buffer (PBS, pH 7.4, 0.2% BSA, 0.09% NaN3). ADP served as a positive control for aggregation and was used at a final concentration of 5 µM. The signal obtained with ADP was set as 100%, the baseline 0 was defined by the platelet depleted serum, which was measured in parallel in all experimental settings Binding of the anti-CCR4 antibodies described in Example 1 to platelets was observed (data not shown). No induction of aggregation was observed and in addition no inhibition of aggregation in presence of ADP was observed (data not shown). From these results it can be concluded that although the anti-CCR4 antibodies described in Example 1 bind to platelets, they have no effect on platelet aggregation. They do not induce aggregation, nor do they inhibit e.g. ADP-induced platelet aggregation.

Example 12

Binding to Human Renal Cell Carcinoma

CCR4 is known to be involved and to be expressed by solid tumor cell lines of clear cell renal cancer cells (CCRC; see patent application WO2009/037454). With the aim of demonstrating specific binding to CCR4 present in tissues prepared from patients suffering from renal cell cancer (RCC), immune-histochemistry experiments were performed. All experiments described were performed at the Centre for Translational Oncology Institute of Cancer (Barts and the London school of Medicine and Dentistry, Queen Mary University London, Charterhouse Square). Staining was performed using anti-CCR4 antibody 503 and compared to a positive anti-CCR4 antibody.

The RCC tumor microarrays (TMA) from patients with stage 1V diagnosis were provided by the Barts and the London school of Medicine and Dentistry (Queen Mary University London, Charterhouse Square, London, UK) and comprised a set of three different cohorts (TMA1, 2 and 3).

Paraffin-embedded sections were cut at a thickness of 4 μm, de-waxed and hydrated through alcohol gradient. Antigen retrieval was performed by microwaving to boiling point in antigen unmasking solution for 9 minutes (Vectorlaboratories, Burlingame, Calif., USA). Sections were next blocked in either 5% goat- or 20% rabbit serum (Sigma Aldrich, St Louis, Mo., USA) diluted in PBS for 1 h at RT. For the detection of CCR4, TMAs were stained using the following antibodies: CCR4 was detected using anti-CCR4 antibody 503 at a concentration of 3 μg/ml and compared to goat anti-CCR4 antibody Ab1669 (3 μg/ml; Abcam, Cambridge, UK). A human isotype control antibody (Cat. No 1-001-A, used at 3 μg/ml; RnD systems, Minneapolis, Minn. USA) was included to demonstrate binding specificity of anti-CCR4 antibody 503. Antibodies were incubated at 4° C. overnight in corresponding blocking agent (human antibodies in 5% goat serum diluted in PBS; Ab1669 in 20% rabbit serum in PBS). Slides were washed three times the following day with PBS in a volume of 30 to 50 ml per wash. Human antibodies 503 and isotype control antibody from RnD were detected using biotin-conjugated goat anti-human secondary antibody (Cat. No. AP112B, Chemicon International, a division of Millipore, Billerica, Mass., USA) at a dilution of 1:500. Anti-CCR4 antibody Ab1669 was detected following incubation with biotin-conjugated rabbit-anti-goat antibody (BA-1000; Vectorlaboratories, Burlingame, Calif., USA) at a dilution of 1:200 for 45 min at RT. Slides were washed twice using PBS in a volume of 30 to 50 ml per wash. Endogenous peroxidase was blocked by mixing methanol (Sigma Aldrich, St Louis, Mo., USA) in mixture with 30% H2O2 for 20 min at RT. The slides were washed 3 times using PBS with 30 to 50 ml per wash. Antigen was visualized using the vectastain elite ABC kit (Vectorlaboratories, Burlingame, Calif., USA) and developed using 3,3'-diaminobenzidine (DAB; Sigma Aldrich, St Louis, Mo., USA). Similar staining procedures were performed for anti-CCR4 antibodies 306, 406 and 503 on spleen tissues reported to have high expression of CCR4 and thus serving as positive control for the anti-CCR4 antibodies (data not shown). In parallel, detection of CCR4-ligands TARC and MDC were performed. The staining procedure was as outlined above, however following antibodies were used. TARC was detected using rabbit anti-human-TARC antibody (ab9816, Abcam, Cambridge, UK). The antibody was used at a dilution of 1:50 and detected using biotin-conjugated goat anti-rabbit antibody at a dilution of 0.1:200 (Vectorlaboratories, Burlingame, Calif., USA). MDC was detected using rabbit anti-human-MDC antibody (500-P107, Peprotech, Princeton, N.J., USA) at a dilution of 1:20 and detected using biotin conjugated anti-rabbit antibody. All binding patterns were analyzed using a Nikon Eclipse 80i microscope (Nikon, Tokyo, Japan).

Additionally, binding to negative control tissues was assessed for all tested antibodies described above on normal human placenta and kidney tissue.

The results of the staining of tumor microarrays from patients suffering from RCC demonstrate that anti-CCR4 antibody 503 binds to CCR4, expressed in RCC patient tissues in IHC (FIG. 19). Moreover, anti-CCR4 antibody 503 was shown to bind to areas of clear cell renal cell carcinoma, but not papillary renal cell carcinoma (data not shown). Convincingly, the binding pattern overlaps with the anti-CCR4 positive control antibody Ab1669. A slight binding to normal human tissue from placenta was observed. However, as the placenta is highly vascularised organ, these binding patterns can be referred to blood vessels where CCR4 is known to be expressed. The expression of CCR4 matched with the expression pattern of CCR4-ligands TARC and MDC. A summary of the binding results from the IHC-experiments is presented in Table 25. These data suggest that the anti-CCR4 antibody 503 could serve as therapeutic or diagnostic in RCC.

TABLE 1

| SEQ ID NO: | | scFv 208 |
|---|---|---|
| 7 | Heavy chain FR1: | QVQLVQSGAEVKKPGSSVKVSCKASGGTFS |
| 1 | CDR1: | SYAMS |
| 8 | FR2 | WVRQAPGQGLEWMG |
| 2 | CDR2: | GIIPIFGTVNYAQKFQG |
| 9 | FR3: | RVTMTRDTSTSTVYMELSSLRSDDTAVYYCAR |
| 3 | CDR3: | RGGSYFDY |
| 10 | FR4: | WGQGTLVTVSS |
| 11 | Linker: | KLSGSASAPKLEEGEFSEARV |
| 12 | Light chainFR1: | SYVLTQPPSASGTPGQSVTISC |
| 4 | CDR1: | SGSTSNIGSHYVF |
| 13 | FR2 | WYQQLPGTAPRLLIY |
| 5 | CDR2: | RNHQRPS |
| 14 | FR3: | GVPDRLSGSKSGTSASLAISGLRSEDEADYYC |
| 6 | CDR3: | AVWDAKYRGWV |

TABLE 1-continued

| SEQ ID NO: | | scFv 208 |
|---|---|---|
| 15 | FR4: | FGGGTKLTVL |
| 56 | scFv 208 | CAGGTCCAGCTTGTACAGTCTGGGGCTGAGGTGAAGAAGCCTGGGTC<br>CTCGGTGAAGGTCTCCTGCAAGGCTTCTGGAGGCACCTTCAGCAGCT<br>ATGCTATGAGCTGGGTGCGACAGGCCCCTGGGCAAGGGCTTGAGTGG<br>ATGGGAGGGATCATCCCTATCTTTGGTACAGTAAACTACGCACAGAA<br>GTTCCAGGGCAGAGTCACCATGACCAGGGACACGTCCACGAGCACAG<br>TCTACATGGAGCTGAGCAGCCTGAGATCTGATGACACGGCCGTGTAT<br>TACTGTGCGAGACGCGGTGGGAGCTACTTTGACTACTGGGGCCAAGG<br>GACCCTGGTCACCGTCTCCTCAAAGCTTTCAGGGAGTGCATCCGCCC<br>CAAAACTTGAAGAAGGTGAATTTTCAGAAGCACGCGTATCCTATGTG<br>CTGACTCAGCCACCCTCAGCGTCTGGGACCCCCGGGCAGAGCGTCAC<br>CATCTCTTGTTCTGGAAGCACCTCCAACATCGGAAGTCATTATGTGT<br>TCTGGTACCAGCAGCTCCCAGGAACGGCCCCCAGACTCCTCATCTAT<br>AGGAATCATCAGCGGCCCTCAGGGGTCCCTGACCGACTCTCTGGCTC<br>CAAGTCTGGCACCTCAGCCTCCCTGGCCATCAGTGGGCTCCGGTCCG<br>AGGATGAGGCTGATTATTACTGTGCAGTGTGGGATGCGAAATACAGG<br>GGTTGGGTGTTCGGCGAGGGACCAAGCTGACCGTCCTA |
| 47 | scFv 208 a.a. | QVQLVQSGAEVKKPGSSVKVSCKASGGTFSSYAMSWVRQAPGQGLEW<br>MGGIIPIFGTVNYAQKFQGRVTMTRDTSTSTVYMELSSLRSDDTAVY<br>YCARRGGSYFDYWGQGTLVTVSSKLSGSASAPKLEEGEFSEARVSYV<br>LTQPPSASGTPGQSVTISCSGSTSNIGSHYVFWYQQLPGTAPRLLIY<br>RNHQRPSGVPDRLSGSKSGTSASLAISGLRSEDEADYYCAVWDAKYR<br>GWVFGGGTKLTVL |
| 29 | V<sub>H(aa)</sub> | QVQLVQSGAEVKKPGSSVKVSCKASGGTFSSYAMSWVRQAPGQGLEW<br>MGGIIPIFGTVNYAQKFQGRVTMTRDTSTSTVYMELSSLRSDDTAVY<br>YCARRGGSYFDYWGQGTLVTVSS |
| 30 | V<sub>L(aa)</sub> | SYVLTQPPSASGTPGQSVTISCSGSTSNIGSHYVFWYQQLPGTAPRL<br>LIYRNHQRPSGVPDRLSGSKSGTSASLAISGLRSEDEADYYCAVWDA<br>KYRGWVFGGGTKLTVL |
| 101 | V<sub>H</sub> domain (nt) | CAGGTCCAGCTTGTACAGTCTGGGGCTGAGGTGAAGAAGCCTGGGTC<br>CTCGGTGAAGGTCTCCTGCAAGGCTTCTGGAGGCACCTTCAGCAGCT<br>ATGCTATGAGCTGGGTGCGACAGGCCCCTGGGCAAGGGCTTGAGTGG<br>ATGGGAGGGATCATCCCTATCTTTGGTACAGTAAACTACGCACAGAA<br>GTTCCAGGGCAGAGTCACCATGACCAGGGACACGTCCACGAGCACAG<br>TCTACATGGAGCTGAGCAGCCTGAGATCTGATGACACGGCCGTGTAT<br>TACTGTGCGAGACGCGGTGGGAGCTACTTTGACTACTGGGGCCAAGG<br>GACCCTGGTCACCGTCTCCTCA |
| 102 | V<sub>L</sub> domain (nt) | TCCTATGTGCTGACTCAGCCACCCTCAGCGTCTGGGACCCCCGGGCA<br>GAGCGTCACCATCTCTTGTTCTGGAAGCACCTCCAACATCGGAAGTC<br>ATTATGTGTTCTGGTACCAGCAGCTCCCAGGAACGGCCCCCAGACTC<br>CTCATCTATAGGAATCATCAGCGGCCCTCAGGGGTCCCTGACCGACT<br>CTCTGGCTCCAAGTCTGGCACCTCAGCCTCCCTGGCCATCAGTGGGC<br>TCCGGTCCGAGGATGAGGCTGATTATTACTGTGCAGTGTGGGATGCG<br>AAATACAGGGGTTGGGTGTTCGGCGGAGGGACCAAGCTGACCGTCCT<br>A |

TABLE 2

| SEQ ID NO: | | scFv 306 |
|---|---|---|
| 7 | Heavy chain FR1: | QVQLVQSGAEVKKPGSSVKVSCKASGGTFS |
| 1 | CDR1: | SYAMS |
| 8 | FR2: | WVRQAPGQGLEWMG |
| 2 | CDR2: | GIIPIFGTVNYAQKFQG |
| 16 | FR3: | RVTMTRDTSTSTVYMELSSLRPDDTAVYYCAR |
| 3 | CDR3: | RGGSYFDY |
| 10 | FR4: | WGQGTLVTVSS |

TABLE 2-continued

| SEQ ID NO: | | scFv 306 |
|---|---|---|
| 11 | Linker: | KLSGSASAPKLEEGEFSEARV |
| 12 | Light chainFR1: | SYVLTQPPSASGTPGQSVTISC |
| 17 | CDR1: | SGSTSNIGSHYVS |
| 13 | FR2 | WYQQLPGTAPRLLIY |
| 5 | CDR2: | RNHQRPS |
| 14 | FR3: | GVPDRLSGSKSGTSASLAISGLRSEDEADYYC |
| 6 | CDR3: | AVWDAKYRGWV |
| 15 | FR4: | FGGGTKLTVL |
| 57 | scFv 306 | CAGGTCCAGCTTGTACAGTCTGGGGCTGAGGTGAAGAAGCCTGGGTC CTCGGTGAAGGTCTCCTGCAAGGCTTCTGGAGGCACCTTCAGCAGCT ATGCTATGAGCTGGGTGCGACAGGCCCCTGGGCAAGGGCTTGAGTGG ATGGGAGGGATCATCCCTATCTTTGGTACAGTAAACTACGCACAGAA GTTCCAGGGCAGAGTCACCATGACCAGGGACACGTCCACGAGCACAG TCTACATGGAGCTGAGCAGCCTGAGACCTGATGACACGGCCGTGTAT TACTGTGCGAGACGCGGTGGGAGCTACTTTGACTACTGGGGCCAAGG GACCCTGGTCACCGTCTCCTCAAAGCTTTCAGGGAGTGCATCCGCCC CAAAACTTGAAGAAGGTGAATTTTCAGAAGCACGCGTATCCTATGTG CTGACTCAGCCACCCTCAGCGTCTGGGACCCCCGGGCAGAGCGTCAC CATCTCTTGTTCTGGAAGCACCTCCAACATCGGAAGTCATTATGTGT CCTGGTACCAGCAGCTCCCAGGAACGGCCCCCAGACTCCTCATCTAT AGGAATCATCAGCGGCCCTCAGGGGTCCCTGACCGACTCTCTGGCTC CAAGTCTGGCACCTCAGCCTCCCTGGCCATCAGTGGGCTCCGGTCCG AGGATGAGGCTGATTATTACTGTGCAGTGTGGGATGCGAAATACAGG GGTTGGGTGTTCGGCGGAGGGACCAAGCTGACCGTCCTA |
| 48 | scFv 306 a.a. | QVQLVQSGAEVKKPGSSVKVSCKASGGTFSSYAMSWVRQAPGQGLEW MGGIIPIFGTVNYAQKFQGRVTMTRDTSTSTVYMELSSLRPDDTAVY YCARRGGSYFDYWGQGTLVTVSSKLSGSASAPKLEEGEFSEARVSYV LTQPPSASGTPGQSVTISCSGSTSNIGSHYVSWYQQLPGTAPRLLIY RNHQRPSGVPDRLSGSKSGTSASLAISGLRSEDEADYYCAVWDAKYR GWVFGGGTKLTVL |
| 31 | $V_{H(aa)}$ | QVQLVQSGAEVKKPGSSVKVSCKASGGTFSSYAMSWVRQAPGQGLEW MGGIIPIFGTVNYAQKFQGRVTMTRDTSTSTVYMELSSLRPDDTAVY YCARRGGSYFDYWGQGTLVTVSS |
| 32 | $V_{L(aa)}$ | SYVLTQPPSASGTPGQSVTISCSGSTSNIGSHYVSWYQQLPGTAPRL LIYRNHQRPSGVPDRLSGSKSGTSASLAISGLRSEDEADYYCAVWDA KYRGWVFGGGTKLTVL |
| 103 | $V_H$ domain (nt) | CAGGTCCAGCTTGTACAGTCTGGGGCTGAGGTGAAGAAGCCTGGGTC CTCGGTGAAGGTCTCCTGCAAGGCTTCTGGAGGCACCTTCAGCAGCT ATGCTATGAGCTGGGTGCGACAGGCCCCTGGGCAAGGGCTTGAGTGG ATGGGAGGGATCATCCCTATCTTTGGTACAGTAAACTACGCACAGAA GTTCCAGGGCAGAGTCACCATGACCAGGGACACGTCCACGAGCACAG TCTACATGGAGCTGAGCAGCCTGAGACCTGATGACACGGCCGTGTAT TACTGTGCGAGACGCGGTGGGAGCTACTTTGACTACTGGGGCCAAGG GACCCTGGTCACCGTCTCCTCA |
| 104 | $V_L$ domain (nt) | TCCTATGTGCTGACTCAGCCACCCTCAGCGTCTGGGACCCCCGGGCA GAGCGTCACCATCTCTTGTTCTGGAAGCACCTCCAACATCGGAAGTC ATTATGTGTCCTGGTACCAGCAGCTCCCAGGAACGGCCCCCAGACTC CTCATCTATAGGAATCATCAGCGGCCCTCAGGGGTCCCTGACCGACT CTCTGGCTCCAAGTCTGGCACCTCAGCCTCCCTGGCCATCAGTGGGC TCCGGTCCGAGGATGAGGCTGATTATTACTGTGCAGTGTGGGATGCG AAATACAGGGGTTGGGTGTTCGGCGGAGGGACCAAGCTGACCGTCCT A |

TABLE 3

| SEQ ID NO: | | scFv 308 |
|---|---|---|
| 7 | Heavy chain FR1: | QVQLVQSGAEVKKPGSSVKVSCKASGGTFS |
| 1 | CDR1: | SYAMS |
| 8 | FR2 | WVRQAPGQGLEWMG |
| 2 | CDR2: | GIIPIFGTVNYAQKFQG |
| 18 | FR3: | RVTMTRDTSTSTVYMELSSLRPDDTAVYYCAR |
| 3 | CDR3: | RGGSYFDY |
| 10 | FR4: | WGQGTLVTVSS |
| 11 | Linker: | KLSGSASAPKLEEGEFSEARV |
| 12 | Light chainFR1: | SYVLTQPPSASGTPGQSVTISC |
| 4 | CDR1: | SGSTSNIGSHYVF |
| 13 | FR2 | WYQQLPGTAPRLLIY |
| 5 | CDR2: | RNHQRPS |
| 14 | FR3: | GVPDRLSGSKSGTSASLAISGLRSEDEADYYC |
| 6 | CDR3: | AVWDAKYRGWV |
| 15 | FR4: | FGGGTKLTVL |
| 58 | scFv 308 | CAGGTCCAGCTTGTACAGTCTGGGGCTGAGGTGAAGAAGCCTGGGTC<br>CTCGGTGAAGGTCTCCTGCAAGGCTTCTGGAGGCACCTTCAGCAGCT<br>ATGCTATGAGCTGGGTGCGACAGGCCCCTGGGCAAGGGCTTGAGTGG<br>ATGGGAGGGATCATCCCTATCTTTGGTACAGTAAACTACGCACAGAA<br>GTTCCAGGGCAGAGTCACCATGACCAGGGACACGTCCACGAGCACAG<br>TCTACATGGAGCTGAGCAGCCTGAGACCTGATGACACGGCCGTGTAT<br>TACTGTGCGAGACGCGGTGGGAGCTACTTTGACTACTGGGGCCAAGG<br>GACCCTGGTCACCGTCTCCTCAAAGCTTTCAGGGAGTGCATCCGCCC<br>CAAAACTTGAAGAAGGTGAATTTTCAGAAGCACGCGTATCCTATGTG<br>CTGACTCAGCCACCCTCAGCGTCTGGGACCCCCGGGCAGAGCGTCAC<br>CATCTCTTGTTCTGGAAGCACCTCCAACATCGGAAGTCATTATGTGT<br>TCTGGTACCAGCAGCTCCCAGGAACGGCCCCCAGACTCCTCATCTAT<br>AGGAATCATCAGCGGCCCTCAGGGGTCCCTGACCGACTCTCTGGCTC<br>CAAGTCTGGCACCTCAGCCTCCCTGGCCATCAGTGGGCTCCGGTCCG<br>AGGATGAGGCTGATTATTACTGTGCAGTGTGGGATGCGAAATACAGG<br>GGTTGGGTGTTCGGCGGAGGGACCAAGCTGACCGTCCTA |
| 49 | scFv 308 a.a. | QVQLVQSGAEVKKPGSSVKVSCKASGGTFSSYAMSWVRQAPGQGLEW<br>MGGIIPIFGTVNYAQKFQGRVTMTRDTSTSTVYMELSSLRPDDTAVY<br>YCARRGGSYFDYWGQGTLVTVSSKLSGSASAPKLEEGEFSEARVSYV<br>LTQPPSASGTPGQSVTISCSGSTSNIGSHYVFWYQQLPGTAPRLLIY<br>RNHQRPSGVPDRLSGSKSGTSASLAISGLRSEDEADYYCAVWDAKYR<br>GWVFGGGTKLTVL |
| 33 | V$_{H(aa)}$ | QVQLVQSGAEVKKPGSSVKVSCKASGGTFSSYAMSWVRQAPGQGLEW<br>MGGIIPIFGTVNYAQKFQGRVTMTRDTSTSTVYMELSSLRPDDTAVY<br>YCARRGGSYFDYWGQGTLVTVSS |
| 34 | V$_{L(aa)}$ | SYVLTQPPSASGTPGQSVTISCSGSTSNIGSHYVFWYQQLPGTAPRL<br>LIYRNHQRPSGVPDRLSGSKSGTSASLAISGLRSEDEADYYCAVWDA<br>KYRGWVFGGGTKLTVL |
| 105 | V$_H$domain (nt) | CAGGTCCAGCTTGTACAGTCTGGGGCTGAGGTGAAGAAGCCTGGGTC<br>CTCGGTGAAGGTCTCCTGCAAGGCTTCTGGAGGCACCTTCAGCAGCT<br>ATGCTATGAGCTGGGTGCGACAGGCCCCTGGGCAAGGGCTTGAGTGG<br>ATGGGAGGGATCATCCCTATCTTTGGTACAGTAAACTACGCACAGAA<br>GTTCCAGGGCAGAGTCACCATGACCAGGGACACGTCCACGAGCACAG<br>TCTACATGGAGCTGAGCAGCCTGAGACCTGATGACACGGCCGTGTAT<br>TACTGTGCGAGACGCGGTGGGAGCTACTTTGACTACTGGGGCCAAGG<br>GACCCTGGTCACCGTCTCCTCA |

TABLE 3-continued

| SEQ ID NO: | | scFv 308 |
|---|---|---|
| 106 | V_L domain (nt) | TCCTATGTGCTGACTCAGCCACCCTCAGCGTCTGGGACCCCCGGGCA GAGCGTCACCATCTCTTGTTCTGGAAGCACCTCCAACATCGGAAGTC ATTATGTGTTCTGGTACCAGCAGCTCCCAGGAACGGCCCCCAGACTC CTCATCTATAGGAATCATCAGCGGCCCTCAGGGGTCCCTGACCGACT CTCTGGCTCCAAGTCTGGCACCTCAGCCTCCCTGGCCATCAGTGGGC TCCGGTCCGAGGATGAGGCTGATTATTACTGTGCAGTGTGGGATGCG AAATACAGGGGTTGGGTGTTCGGCGGAGGGACCAAGCTGACCGTCCT A |

TABLE 4

| SEQ ID NO: | | scFv 406 |
|---|---|---|
| 19 | Heavy chain FR1: | QVQLVQSGAEVKKPGSSVKVSCKASEGTFS |
| 1 | CDR1: | SYAMS |
| 8 | FR2 | WVRQAPGQGLEWMG |
| 2 | CDR2: | GIIPIFGTVNYAQKFQG |
| 9 | FR3: | RVTMTRDTSTSTVYMELSSLRSDDTAVYYCAR |
| 3 | CDR3: | RGGSYFDY |
| 10 | FR4: | WGQGTLVTVSS |
| 11 | Linker: | KLSGSASAPKLEEGEFSEARV |
| 12 | Light chainFR1: | SYVLTQPPSASGTPGQSVTISC |
| 17 | CDR1: | SGSTSNIGSHYVS |
| 13 | FR2 | WYQQLPGTAPRLLIY |
| 5 | CDR2: | RNHQRPS |
| 14 | FR3: | GVPDRLSGSKSGTSASLAISGLRSEDEADYYC |
| 6 | CDR3: | AVWDAKYRGWV |
| 15 | FR4: | FGGGTKLTVL |
| 59 | scFv 406 | CAGGTCCAGCTTGTACAGTCTGGGGCTGAGGTGAAGAAGCCTGGGTC CTCGGTGAAGGTCTCCTGCAAGGCTTCTGAAGGCACCTTCAGCAGCT ATGCTATGAGCTGGGTGCGACAGGCCCCTGGGCAAGGGCTTGAGTGG ATGGGAGGGATCATCCCTATCTTTGGTACAGTAAACTACGCACAGAA GTTCCAGGGCAGAGTCACCATGACCAGGGACACGTCCACGAGCACAG TCTACATGGAGCTGAGCAGCCTGAGATCTGATGACACGGCCGTGTAT TACTGTGCGAGACGCGGTGGGAGCTACTTTGACTACTGGGGCCAAGG GACCCTGGTCACCGTCTCCTCAAAGCTTTCAGGGAGTGCATCCGCCC CAAAACTTGAAGAAGGTGAATTTTCAGAAGCACGCGTATCCTATGTG CTGACTCAGCCACCCTCAGCGTCTGGGACCCCCGGGCAGAGCGTCAC CATCTCTTGTTCTGGAAGCACCTCCAACATCGGAAGTCATTATGTGT CCTGGTACCAGCAGCTCCCAGGAACGGCCCCCAGACTCCTCATCTAT AGGAATCATCAGCGGCCCTCAGGGGTCCCTGACCGACTCTCTGGCTC CAAGTCTGGCACCTCAGCCTCCCTGGCCATCAGTGGGCTCCGGTCCG AGGATGAGGCTGATTATTACTGTGCAGTGTGGGATGCGAAATACAGG GGTTGGGTGTTCGGCGGAGGGACCAAGCTGACCGTCCTA |
| 50 | scFv 406 a.a. | QVQLVQSGAEVKKPGSSVKVSCKASEGTFSSYAMSWVRQAPGQGLEW MGGIIPIFGTVNYAQKFQGRVTMTRDTSTSTVYMELSSLRSDDTAVY YCARRGGSYFDYWGQGTLVTVSSKLSGSASAPKLEEGEFSEARVSYV LTQPPSASGTPGQSVTISCSGSTSNIGSHYVSWYQQLPGTAPRLLIY RNHQRPSGVPDRLSGSKSGTSASLAISGLRSEDEADYYCAVWDAKYR GWVFGGGTKLTVL |

TABLE 4-continued

| SEQ ID NO: | | scFv 406 |
|---|---|---|
| 35 | V$_{H(aa)}$ | QVQLVQSGAEVKKPGSSVKVSCKASEGTFSSYAMSWVRQAPGQGLEW MGGIIPIFGTVNYAQKFQGRVTMTRDTSTSTVYMELSSLRSDDTAVY YCARRGGSYFDYWGQGTLVTVSS |
| 36 | V$_{L(aa)}$ | SYVLTQPPSASGTPGQSVTISCSGSTSNIGSHYVSWYQQLPGTAPRL LIYRNHQRPSGVPDRLSGSKSGTSASLAISGLRSEDEADYYCAVWDA KYRGWVFGGGTKLTVL |
| 107 | V$_H$ domain (nt) | CAGGTCCAGCTTGTACAGTCTGGGGCTGAGGTGAAGAAGCCTGGGTC CTCGGTGAAGGTCTCCTGCAAGGCTTCTGAAGGCACCTTCAGCAGCT ATGCTATGAGCTGGGTGCGACAGGCCCCTGGGCAAGGGCTTGAGTGG ATGGGAGGGATCATCCCTATCTTTGGTACAGTAAACTACGCACAGAA GTTCCAGGGCAGAGTCACCATGACCAGGGACACGTCCACGAGCACAG TCTACATGGAGCTGAGCAGCCTGAGATCTGATGACACGGCCGTGTAT TACTGTGCGAGACGCGTGGGAGCTACTTTGACTACTGGGGCCAAGG GACCCTGGTCACCGTCTCCTCA |
| 108 | V$_L$ domain (nt) | TCCTATGTGCTGACTCAGCCACCCTCAGCGTCTGGGACCCCCGGGCA GAGCGTCACCATCTCTTGTTCTGGAAGCACCTCCAACATCGGAAGTC ATTATGTGTCCTGGTACCAGCAGCTCCCAGGAACGGCCCCCAGACTC CTCATCTATAGGAATCATCAGCGGCCCTCAGGGGTCCCTGACCGACT CTCTGGCTCCAAGTCTGGCACCTCAGCCTCCCTGGCCATCAGTGGGC TCCGGTCCGAGGATGAGGCTGATTATTACTGTGCAGTGTGGGATGCG AAATACAGGGGTTGGGTGTTCGGCGGAGGGACCAAGCTGACCGTCCT A |

TABLE 5

| SEQ ID NO: | | scFv 501 |
|---|---|---|
| 19 | Heavy chain FR1: | QVQLVQSGAEVKKPGSSVKVSCKASEGTFS |
| 1 | CDR1: | SYAMS |
| 8 | FR2 | WVRQAPGQGLEWMG |
| 2 | CDR2: | GIIPIFGTVNYAQKFQG |
| 9 | FR3: | RVTMTRDTSTSTVYMELSSLRSDDTAVYYCAR |
| 20 | CDR3: | RRGAKFDY |
| 10 | FR4: | WGQGTLVTVSS |
| 11 | Linker: | KLSGSASAPKLEEGEFSEARV |
| 21 | Light chainFR1: | SYVLTQQPSASGTPGQSVTISC |
| 22 | CDR1: | SGSTSNIGSHYVV |
| 13 | FR2 | WYQQLPGTAPRLLIY |
| 5 | CDR2: | RNHQRPS |
| 23 | FR3: | GVPDRLSGSKSGTSASLAIGGLRSEDEADYYC |
| 24 | CDR3: | AVWDDTLSGWV |
| 15 | FR4: | FGGGTKLTVL |
| 60 | scFv 501 | CAGGTCCAGCTTGTACAGTCTGGGGCTGAGGTGAAGAAGCCTGGGTC CTCGGTGAAGGTCTCCTGCAAGGCTTCTGAAGGCACCTTCAGCAGCT ATGCTATGAGCTGGGTGCGACAGGCCCCTGGGCAAGGGCTTGAGTGG ATGGGAGGGATCATCCCTATCTTTGGTACAGTAAACTACGCACAGAA GTTCCAGGGCAGAGTCACCATGACCAGGGACACGTCCACGAGCACAG TCTACATGGAGCTGAGCAGCCTGAGATCTGATGACACGGCCGTGTAT TACTGTGCGAGACGGCGCGGCGCTAAATTTGACTACTGGGGCCAAGG GACCCTGGTCACCGTCTCCTCAAAGCTTTCAGGGAGTGCATCCGCCC |

TABLE 5-continued

| SEQ ID NO: | | scFv 501 |
|---|---|---|
| | | CAAAACTTGAAGAAGGTGAATTTTCAGAAGCACGCGTATCCTATGTG CTGACTCAGCAACCCTCAGCGTCTGGGACCCCCGGGCAGAGCGTCAC CATCTCTTGTTCTGGAAGCACCTCCAACATCGGAAGTCATTATGTGG TCTGGTACCAGCAGCTCCCAGGAACGGCCCCCAGACTCCTCATCTAT AGGAATCATCAGCGGCCCTCAGGGGTCCCTGACCGACTCTCTGGCTC CAAGTCTGGCACCTCAGCCTCCTGGCCATCGGTGGGCTCCGGTCCG AGGATGAGGCTGATTATTACTGTGCAGTGTGGGATGACACCCTGAGT GGCTGGGTGTTCGGCGGAGGGACCAAGCTGACCGTCCTA |
| 51 | scFv 501 a.a. | QVQLVQSGAEVKKPGSSVKVSCKASEGTFSSYAMSWVRQAPGQGLEW MGGIIPIFGTVNYAQKFQGRVTMTRDTSTSTVYMELSSLRSDDTAVY YCARRRGAKFDYWGQGTLVTVSSKLSGSASAPKLEEGEFSEARVSYV LTQQPSASGTPGQSVTISCSGSTSNIGSHYVVWYQQLPGTAPRLLIY RNHQRPSGVPDRLSGSKSGTSASLAIGGLRSEDEADYYCAVWDDTLS GWVFGGGTKLTVL |
| 37 | $V_{H(aa)}$ | QVQLVQSGAEVKKPGSSVKVSCKASEGTFSSYAMSWVRQAPGQGLEW MGGIIPIFGTVNYAQKFQGRVTMTRDTSTSTVYMELSSLRSDDTAVY YCARRRGAKFDYWGQGTLVTVSS |
| 38 | $V_{L(aa)}$ | SYVLTQQPSASGTPGQSVTISCSGSTSNIGSHYVVWYQQLPGTAPRL LIYRNHQRPSGVPDRLSGSKSGTSASLAIGGLRSEDEADYYCAVWDD TLSGWVFGGGTKLTVL |
| 109 | $V_H$ domain (nt) | CAGGTCCAGCTTGTACAGTCTGGGGCTGAGGTGAAGAAGCCTGGGTC CTCGGTGAAGGTCTCCTGCAAGGCTTCTGAAGGCACCTTCAGCAGCT ATGCTATGAGCTGGGTGCGACAGGCCCCTGGGCAAGGGCTTGAGTGG ATGGGAGGGATCATCCCTATCTTTGGTACAGTAAACTACGCACAGAA GTTCCAGGGCAGAGTCACCATGACCAGGGACACGTCCACGAGCACAG TCTACATGGAGCTGAGCAGCCTGAGATCTGATGACACGGCCGTGTAT TACTGTGCGAGACGGCGCGGCGCTAAATTTGACTACTGGGGCCAAGG GACCCTGGTCACCGTCTCCTCA |
| 110 | $V_L$ domain (nt) | TCCTATGTGCTGACTCAGCAACCCTCAGCGTCTGGGACCCCCGGGCA GAGCGTCACCATCTCTTGTTCTGGAAGCACCTCCAACATCGGAAGTC ATTATGTGGTCTGGTACCAGCAGCTCCCAGGAACGGCCCCCAGACTC CTCATCTATAGGAATCATCAGCGGCCCTCAGGGGTCCCTGACCGACT CTCTGGCTCCAAGTCTGGCACCTCAGCCTCCTGGCCATCGGTGGGC TCCGGTCCGAGGATGAGGCTGATTATTACTGTGCAGTGTGGGATGAC ACCCTGAGTGGCTGGGTGTTCGGCGGAGGGACCAAGCTGACCGTCCT A |

TABLE 6

| SEQ ID NO: | | scFv 503 |
|---|---|---|
| 19 | Heavy chain FR1: | QVQLVQSGAEVKKPGSSVKVSCKASEGTFS |
| 1 | CDR1: | SYAMS |
| 8 | FR2 | WVRQAPGQGLEWMG |
| 2 | CDR2: | GIIPIFGTVNYAQKFQG |
| 9 | FR3: | RVTMTRDTSTSTVYMELSSLRSDDTAVYYCAR |
| 20 | CDR3: | RRGAKFDY |
| 10 | FR4: | WGQGTLVTSS |
| 11 | Linker: | KLSGSASAPKLEEGEFSEARV |
| 12 | Light chainFR1: | SYVLTQPPSASGTPGQSVTISC |
| 22 | CDR1: | SGSTSNIGSHYVV |
| 13 | FR2 | WYQQLPGTAPRLLIY |

TABLE 6-continued

| SEQ ID NO: | | scFv 503 |
|---|---|---|
| 5 | CDR2: | RNHQRPS |
| 23 | FR3: | GVPDRLSGSKSGTSASLAIGGLRSEDEADYYC |
| 24 | CDR3: | AVWDDTLSGWV |
| 15 | FR4: | FGGGTKLTVL |
| 61 | scFv 503 | CAGGTCCAGCTTGTACAGTCTGGGGCTGAGGTGAAGAAGCCTGGGTC CTCGGTGAAGGTCTCCTGCAAGGCTTCTGAAGGCACCTTCAGCAGCT ATGCTATGAGCTGGGTGCGACAGGCCCCTGGGCAAGGGCTTGAGTGG ATGGGAGGGATCATCCCTATCTTTGGTACAGTAAACTACGCACAGAA GTTCCAGGGCAGAGTCACCATGACCAGGGACACGTCCACGAGCACAG TCTACATGGAGCTGAGCAGCCTGAGATCTGATGACACGGCCGTGTAT TACTGTGCGAGACGGCGCGGCGCTAAATTTGACTACTGGGGCCAAGG GACCCTGGTCACCGTCTCCTCAAAGCTTTCAGGGAGTGCATCCGCCC CAAAACTTGAAGAAGGTGAATTTTCAGAAGCACGCGTATCCTATGTG CTGACTCAGCCACCCTCAGCGTCTGGGACCCCCGGGCAGAGCGTCAC CATCTCTTGTTCTGGAAGCACCTCCAACATCGGAAGTCATTATGTGG TCTGGTACCAGCAGCTCCCAGGAACGGCCCCCAGACTCCTCATCTAT AGGAATCATCAGCGGCCCTCAGGGGTCCCTGACCGACTCTCTGGCTC CAAGTCTGGCACCTCAGCCTCCCTGGCCATCGGTGGGCTCCGGTCCG AGGATGAGGCTGATTATTACTGTGCAGTGTGGGATGACACCCTGAGT GGCTGGGTGTTCGGCGGAGGGACCAAGCTGACCGTCCTA |
| 52 | scFv 503 a.a. | QVQLVQSGAEVKKPGSSVKVSCKASEGTFSSYAMSWVRQAPGQGLEW MGGIIPIFGTVNYAQKFQGRVTMTRDTSTSTVYMELSSLRSDDTAVY YCARRRGAKFDYWGQGTLVTVSSKLSGSASAPKLEEGEFSEARVSYV LTQPPSASGTPGQSVTISCSGSTSNIGSHYVVWYQQLPGTAPRLLIY RNHQRPSGVPDRLSGSKSGTSASLAIGGLRSEDEADYYCAVWDDTLS GWVFGGGTKLTVL |
| 39 | V<sub>H(aa)</sub> | QVQLVQSGAEVKKPGSSVKVSCKASEGTFSSYAMSWVRQAPGQGLEW MGGIIPIFGTVNYAQKFQGRVTMTRDTSTSTVYMELSSLRSDDTAVY YCARRRGAKFDYWGQGTLVTVSS |
| 40 | V<sub>L(aa)</sub> | SYVLTQPPSASGTPGQSVTISCSGSTSNIGSHYVVWYQQLPGTAPRL LIYRNHQRPSGVPDRLSGSKSGTSASLAIGGLRSEDEADYYCAVWDD TLSGWVFGGGTKLTVL |
| 111 | V<sub>H</sub>domain (nt) | CAGGTCCAGCTTGTACAGTCTGGGGCTGAGGTGAAGAAGCCTGGGTC CTCGGTGAAGGTCTCCTGCAAGGCTTCTGAAGGCACCTTCAGCAGCT ATGCTATGAGCTGGGTGCGACAGGCCCCTGGGCAAGGGCTTGAGTGG ATGGGAGGGATCATCCCTATCTTTGGTACAGTAAACTACGCACAGAA GTTCCAGGGCAGAGTCACCATGACCAGGGACACGTCCACGAGCACAG TCTACATGGAGCTGAGCAGCCTGAGATCTGATGACACGGCCGTGTAT TACTGTGCGAGACGGCGCGGCGCTAAATTTGACTACTGGGGCCAAGG GACCCTGGTCACCGTCTCCTCA |
| 112 | V<sub>L</sub>domain (nt) | TCCTATGTGCTGACTCAGCCACCCTCAGCGTCTGGGACCCCCGGGCA GAGCGTCACCATCTCTTGTTCTGGAAGCACCTCCAACATCGGAAGTC ATTATGTGGTCTGGTACCAGCAGCTCCCAGGAACGGCCCCCAGACTC CTCATCTATAGGAATCATCAGCGGCCCTCAGGGGTCCCTGACCGACT CTCTGGCTCCAAGTCTGGCACCTCAGCCTCCCTGGCCATCGGTGGGC TCCGGTCCGAGGATGAGGCTGATTATTACTGTGCAGTGTGGGATGAC ACCCTGAGTGGCTGGGTGTTCGGCGGAGGGACCAAGCTGACCGTCCT A |

TABLE 7

| SEQ ID NO: | | scFv 601 |
|---|---|---|
| 7 | Heavy chain FR1: | QVQLVQSGAEVKKPGSSVKVSCKASGGTFS |
| 1 | CDR1: | SYAMS |
| 8 | FR2 | WVRQAPGQGLEWMG |
| 2 | CDR2: | GIIPIFGTVNYAQKFQG |

TABLE 7-continued

| SEQ ID NO: | | scFv 601 |
|---|---|---|
| 9 | FR3: | RVTMTRDTSTSTVYMELSSLRSDDTAVYYCAR |
| 20 | CDR3: | RRGAKFDY |
| 10 | FR4: | WGQGTLVTVSS |
| 11 | Linker: | KLSGSASAPKLEEGEFSEARV |
| 21 | Light chainFR1: | SYVLTQQPSASGTPGQSVTISC |
| 22 | CDR1: | SGSTSNIGSHYVV |
| 13 | FR2 | WYQQLPGTAPRLLIY |
| 5 | CDR2: | RNHQRPS |
| 23 | FR3: | GVPDRLSGSKSGTSASLAIGGLRSEDEADYYC |
| 24 | CDR3: | AVWDDTLSGWV |
| 15 | FR4: | FGGGTKLTVL |
| 62 | scFv 601 | CAGGTCCAGCTTGTACAGTCTGGGGCTGAGGTGAAGAAGCCTGGGTC<br>CTCGGTGAAGGTCTCCTGCAAGGCTTCTGGAGGCACCTTCAGCAGCT<br>ATGCTATGAGCTGGGTGCGACAGGCCCCTGGGCAAGGGCTTGAGTGG<br>ATGGGAGGGATCATCCCTATCTTTGGTACAGTAAACTACGCACAGAA<br>GTTCCAGGGCAGAGTCACCATGACCAGGGACACGTCCACGAGCACAG<br>TCTACATGGAGCTGAGCAGCCTGAGATCTGATGACACGGCCGTGTAT<br>TACTGTGCGAGACGGCGCGGCGCTAAATTTGACTACTGGGGCCAAGG<br>GACCCTGGTCACCGTCTCCTCAAAGCTTTCAGGGAGTGCATCCGCCC<br>CAAAACTTGAAGAAGGTGAATTTTCAGAAGCACGCGTATCCTATGTG<br>CTGACTCAGCAACCCTCAGCGTCTGGGACCCCCGGGCAGAGCGTCAC<br>CATCTCTTGTTCTGGAAGCACCTCCAACATCGGAAGTCATTATGTGG<br>TCTGGTACCAGCAGCTCCCAGGAACGGCCCCCAGACTCCTCATCTAT<br>AGGAATCATCAGCGGCCCTCAGGGGTCCCTGACCGACTCTCTGGCTC<br>CAAGTCTGGCACCTCAGCCTCCCTGGCCATCGGTGGGCTCCGGTCCG<br>AGGATGAGGCTGATTATTACTGTGCAGTGTGGGATGACACCCTGAGT<br>GGCTGGGTGTTCGGCGGAGGGACCAAGCTGACCGTCCTA |
| 53 | scFv 601 a.a. | QVQLVQSGAEVKKPGSSVKVSCKASGGTFSSYAMSWVRQAPGQGLEW<br>MGGIIPIFGTVNYAQKFQGRVTMTRDTSTSTVYMELSSLRSDDTAVY<br>YCARRRGAKFDYWGQGTLVTVSSKLSGSASAPKLEEGEFSEARVSYV<br>LTQQPSASGTPGQSVTISCSGSTSNIGSHYVVWTQQLPGTAPRLLIY<br>RNHQRPSGVPDRLSGSKSGTSASLAIGGLRSEDEADYYCAVWDDTLS<br>GWVFGGGTKLTV |
| 41 | $V_{H(aa)}$ | QVQLVQSGAEVKKPGSSVKVSCKASGGTFSSYAMSWVRQAPGQGLEW<br>MGGIIPIFGTVNYAQKFQGRVTMTRDTSTSTVYMELSSLRSDDTAVY<br>YCARRRGAKFDYWGQGTLVTVSS |
| 42 | $V_{L(aa)}$ | SYVLTQQPSASGTPGQSVTISCSGSTSNIGSHYVVWYQQLPGTAPRL<br>LIYRNHQRPSGVPDRLSGSKSGTSASLAIGGLRSEDEADYYCAVWDD<br>TLSGWVFGGGTKLTV |
| 113 | $V_H$ domain (nt) | CAGGTCCAGCTTGTACAGTCTGGGGCTGAGGTGAAGAAGCCTGGGTC<br>CTCGGTGAAGGTCTCCTGCAAGGCTTCTGGAGGCACCTTCAGCAGCT<br>ATGCTATGAGCTGGGTGCGACAGGCCCCTGGGCAAGGGCTTGAGTGG<br>ATGGGAGGGATCATCCCTATCTTTGGTACAGTAAACTACGCACAGAA<br>GTTCCAGGGCAGAGTCACCATGACCAGGGACACGTCCACGAGCACAG<br>TCTACATGGAGCTGAGCAGCCTGAGATCTGATGACACGGCCGTGTAT<br>TACTGTGCGAGACGGCGCGGCGCTAAATTTGACTACTGGGGCCAAGG<br>GACCCTGGTCACCGTCTCCTCA |
| 114 | $V_L$ domain (nt) | TCCTATGTGCTGACTCAGCAACCCTCAGCGTCTGGGACCCCCGGGCA<br>GAGCGTCACCATCTCTTGTTCTGGAAGCACCTCCAACATCGGAAGTC<br>ATTATGTGGTCTGGTACCAGCAGCTCCCAGGAACGGCCCCCAGACTC<br>CTCATCTATAGGAATCATCAGCGGCCCTCAGGGGTCCCTGACCGACT<br>CTCTGGCTCCAAGTCTGGCACCTCAGCCTCCCTGGCCATCGGTGGGC<br>TCCGGTCCGAGGATGAGGCTGATTATTACTGTGCAGTGTGGGATGAC<br>ACCCTGAGTGGCTGGGTGTTCGGCGGAGGGACCAAGCTGACCGTCCT<br>A |

TABLE 8

| SEQ ID NO: | | scFv 603 |
|---|---|---|
| 7 | Heavy chain FR1: | QVQLVQSGAEVKKPGSSVKVSCKASGGTFS |
| 1 | CDR1: | SYAMS |
| 8 | FR2 | WVRQAPGQGLEWMG |
| 2 | CDR2: | GIIPIFGTVNYAQKFQG |
| 9 | FR3: | RVTMTRDTSTSTVYMELSSLRSDDTAVYYCAR |
| 20 | CDR3: | RRGAKFDY |
| 10 | FR4: | WGQGTLVTVSS |
| 11 | Linker: | KLSGSASAPKLEEGEFSEARV |
| 25 | Light chainFR1: | SYVLTQPPSASGTPGQSVTISC |
| 22 | CDR1: | SGSTSNIGSHYVV |
| 13 | FR2 | WYQQLPGTAPRLLIY |
| 5 | CDR2: | RNHQRPS |
| 23 | FR3: | GVPDRLSGSKSGTSASLAIGGLRSEDEADYYC |
| 24 | CDR3: | AVWDDTLSGWV |
| 15 | FR4: | FGGGTKLTVL |
| 63 | scFv 603 | CAGGTCCAGCTTGTACAGTCTGGGGCTGAGGTGAAGAAGCCTGGGTC<br>CTCGGTGAAGGTCTCCTGCAAGGCTTCTGGAGGCACCTTCAGCAGCT<br>ATGCTATGAGCTGGGTGCGACAGGCCCCTGGGCAAGGGCTTGAGTGG<br>ATGGGAGGGATCATCCCTATCTTTGGTACAGTAAACTACGCACAGAA<br>GTTCCAGGGCAGAGTCACCATGACCAGGGACACGTCCACGAGCACAG<br>TCTACATGGAGCTGAGCAGCCTGAGATCTGATGACACGGCCGTGTAT<br>TACTGTGCGAGACGGCGCGGCGCTAAATTTGACTACTGGGGCCAAGG<br>GACCCTGGTCACCGTCTCCTCAAAGCTTTCAGGGAGTGCATCCGCCC<br>CAAAACTTGAAGAAGGTGAATTTTCAGAAGCACGCGTATCCTATGTG<br>CTGACTCAGCCACCCTCAGCGTCTGGGACCCCCGGGCAGAGCGTCAC<br>CATCTCTTGTTCTGGAAGCACCTCCAACATCGGAAGTCATTATGTGG<br>TCTGGTACCAGCAGCTCCCAGGAACGGCCCCCAGACTCCTCATCTAT<br>AGGAATCATCAGCGGCCCTCAGGGGTCCCTGACCGACTCTCTGGCTC<br>CAAGTCTGGCACCTCAGCCTCCCTGGCCATCGGTGGGCTCCGGTCCG<br>AGGATGAGGCTGATTATTACTGTGCAGTGTGGGATGACACCCTGAGT<br>GGCTGGGTGTTCGGCGGAGGGACCAAGCTGACCGTCCTA |
| 54 | scFv 603 a.a. | QVQLVQSGAEVKKPGSSVKVSCKASGGTFSSYAMSWVRQAPGQGLEW<br>MGGIIPIFGTVNYAQKFQGRVTMTRDTSTSTVYMELSSLRSDDTAVY<br>YCARRRGAKFDYWGQGTLVTVSSKLSGSASAPKLEEGEFSEARVSYV<br>LTQPPSASGTPGQSVTISCSGSTSNIGSHYVVWYQQLPGTAPRLLIY<br>RNHQRPSGVPDRLSGSKSGTSASLAIGGLRSEDEADYYCAVWDDTLS<br>GWVFGGGTKLTVL |
| 43 | $V_{H(aa)}$ | QVQLVQSGAEVKKPGSSVKVSCKASGGTFSSYAMSWVRQAPGQGLEW<br>MGGIIPIFGTVNYAQKFQGRVTMTRDTSTSTVYMELSSLRSDDTAVY<br>YCARRRGAKFDYWGQGTLVTVSS |
| 44 | $V_{L(aa)}$ | SYVLTQPPSASGTPGQSVTISCSGSTSNIGSHYVVWYQQLPGTAPRL<br>LIYRNHQRPSGVPDRLSGSKSGTSASLAIGGLRSEDEADYYCAVWDD<br>TLSGWVFGGGTKLTVL |
| 115 | $V_H$domain (nt) | CAGGTCCAGCTTGTACAGTCTGGGGCTGAGGTGAAGAAGCCTGGGTC<br>CTCGGTGAAGGTCTCCTGCAAGGCTTCTGGAGGCACCTTCAGCAGCT<br>ATGCTATGAGCTGGGTGCGACAGGCCCCTGGGCAAGGGCTTGAGTGG<br>ATGGGAGGGATCATCCCTATCTTTGGTACAGTAAACTACGCACAGAA<br>GTTCCAGGGCAGAGTCACCATGACCAGGGACACGTCCACGAGCACAG<br>TCTACATGGAGCTGAGCAGCCTGAGATCTGATGACACGGCCGTGTAT<br>TACTGTGCGAGACGGCGCGGCGCTAAATTTGACTACTGGGGCCAAGG<br>GACCCTGGTCACCGTCTCCTCA |

TABLE 8-continued

| SEQ ID NO: | | scFv 603 |
|---|---|---|
| 116 | $V_L$ domain (nt) | TCCTATGTGCTGACTCAGCCACCCTCAGCGTCTGGGACCCCCGGGCAGAGCGTCACCATCTCTTGTTCTGGAAGCACCTCCAACATCGGAAGTCATTATGTGGTCTGGTACCAGCAGCTCCCAGGAACGGCCCCCAGACTCCTCATCTATAGGAATCATCAGCGGCCCTCAGGGGTCCCTGACCGACTCTCTGGCTCCAAGTCTGGCACCTCAGCCTCCCTGGCCATCGGTGGGCTCCGGTCCGAGGATGAGGCTGATTATTACTGTGCAGTGTGGGATGACACCCTGAGTGGCTGGGTGTTCGGCGGAGGGACCAAGCTGACCGTCCTA |

TABLE 9

| SEQ ID NO: | | scFv 803 |
|---|---|---|
| 7 | Heavy chain FR1: | QVQLVQSGAEVKKPGSSVKVSCKASGGTFS |
| 26 | CDR1: | SYAIS |
| 8 | FR2 | WVRQAPGQGLEWMG |
| 27 | CDR2: | GIIPIFGTANYAQKFQG |
| 28 | FR3: | RVTMTRDTSTSTVYMELSSLRSEDTAVYYCAR |
| 20 | CDR3: | RRGAKFDY |
| 10 | FR4: | WGQGTLVTVSS |
| 11 | Linker: | KLSGSASAPKLEEGEFSEARV |
| 12 | Light chain FR1: | SYVLTQPPSASGTPGQSVTISC |
| 22 | CDR1: | SGSTSNIGSHYVV |
| 13 | FR2 | WYQQLPGTAPRLLIY |
| 5 | CDR2: | RNHQRPS |
| 23 | FR3: | GVPDRLSGSKSGTSASLAIGGLRSEDEADYYC |
| 24 | CDR3: | AVWDDTLSGWV |
| 15 | FR4: | FGGGTKLTVL |
| 64 | scFv 803 | CAGGTCCAGCTTGTACAGTCTGGGGCTGAGGTGAAGAAGCCTGGGTCCTCGGTGAAGGTCTCCTGCAAGGCTTCTGGAGGCACCTTCAGCAGCTATGCTATCAGCTGGGTGCGACAGGCCCCTGGACAAGGGCTTGAGTGGATGGGAGGGATCATCCCTATCTTTGGTACAGCAAACTACGCACAGAAGTTCCAGGGCAGAGTCACCATGACCAGGGACACGTCCACGAGCACAGTCTACATGGAGCTGAGCAGCCTGAGATCTGAGGACACGGCCGTGTATTACTGTGCGAGACGGCGCGGCGCTAAATTTGACTACTGGGGCCAAGGGACCCTGGTCACCGTCTCCTCAAAGCTTTCAGGGAGTGCATCCGCCCCAAAACTTGAAGAAGGTGAATTTTCAGAAGCACGCGTATCCTATGTGCTGACTCAGCCACCCTCAGCGTCTGGGACCCCCGGGCAGAGCGTCACCATCTCTTGTTCTGGAAGCACCTCCAACATCGGAAGTCATTATGTGGTCTGGTACCAGCAGCTCCCAGGAACGGCCCCCAGACTCCTCATCTATAGGAATCATCAGCGGCCCTCAGGGGTCCCTGACCGACTCTCTGGCTCCAAGTCTGGCACCTCAGCCTCCCTGGCCATCGGTGGGCTCCGGTCCGAGGATGAGGCTGATTATTACTGTGCAGTGTGGGATGACACCCTGAGTGGCTGGGTGTTCGGCGGAGGGACCAAGCTGACCGTCCTA |
| 55 | scFv 803 a.a. | QVQLVQSGAEVKKPGSSVKVSCKASGGTFSSYAISWVRQAPGQGLEWMGGIIPIFGTANYAQKFQGRVTMTRDTSTSTVYMELSSLRSEDTAVYYCARRRGAKFDYWGQGTLVTVSSKLSGSASAPKLEEGEFSEARVSYVLTQPPSASGTPGQSVTISCSGSTSNIGSHYVVWYQQLPGTAPRLLIYRNHQRPSGVPDRLSGSKSGTSASLAIGGLRSEDEADYYCAVWDDTLSGWVFGGGTKLTVL |

TABLE 9-continued

| SEQ ID NO: | | scFv 803 |
|---|---|---|
| 45 | V$_{H(aa)}$ | QVQLVQSGAEVKKPGSSVKVSCKASGGTFSSYAISWVRQAPGQGLEW MGGIIPIFGTANYAQKFQGRVTMTRDTSTSTVYMELSSLRSEDTAVY YCARRRGAKFDYWGQGTLVTVSS |
| 46 | V$_{L(aa)}$ | SYVLTQPPSASGTPGQSVTISCSGSTSNIGSHYVVWYQQLPGTAPRL LIYRNHQRPSGVPDRLSGSKSGTSASLAIGGLRSEDEADYYCAVWDD TLSGWVFGGGTKLTVL |
| 117 | V$_H$ domain (nt) | CAGGTCCAGCTTGTACAGTCTGGGGCTGAGGTGAAGAAGCCTGGGTC CTCGGTGAAGGTCTCCTGCAAGGCTTCTGGAGGCACCTTCAGCAGCT ATGCTATCAGCTGGGTGCGACAGGCCCCTGGACAAGGGCTTGAGTGG ATGGGAGGGATCATCCCTATCTTTGGTACAGCAAACTACGCACAGAA GTTCCAGGGCAGAGTCACCATGACCAGGGACACGTCCACGAGCACAG TCTACATGGAGCTGAGCAGCCTGAGATCTGAGGACACGGCCGTGTAT TACTGTGCGAGACGGCGCGGCGCTAAATTTGACTACTGGGGCCAAGG GACCCTGGTCACCGTCTCCTCA |
| 118 | V$_L$ domain (nt) | TCCTATGTGCTGACTCAGCCACCCTCAGCGTCTGGGACCCCCGGGCA GAGCGTCACCATCTCTTGTTCTGGAAGCACCTCCAACATCGGAAGTC ATTATGTGGTCTGGTACCAGCAGCTCCCAGGAACGGCCCCCAGACTC CTCATCTATAGGAATCATCAGCGGCCCTCAGGGGTCCCTGACCGACT CTCTGGCTCCAAGTCTGGCACCTCAGCCTCCCTGGCCATCGGTGGGC TCCGGTCCGAGGATGAGGCTGATTATTACTGTGCAGTGTGGGATGAC ACCCTGAGTGGCTGGGTGTTCGGCGGAGGGACCAAGCTGACCGTCCT A |

TABLE 10

| SEQ. ID NO: 65 | 208 IgG1 heavy chain (nt) | CAGGTCCAGCTTGTACAGTCTGGGGCTGAGGTGAAGAAGCCTGGGTCCT CGGTGAAGGTCTCCTGCAAGGCTTCTGGAGGCACCTTCAGCAGCTATGC TATGAGCTGGGTGCGACAGGCCCCTGGGCAAGGGCTTGAGTGGATGGGA GGGATCATCCCTATCTTTGGTACAGTAAACTACGCACAGAAGTTCCAGG GCAGAGTCACCATGACCAGGGACACGTCCACGAGCACAGTCTACATGGA GCTGAGCAGCCTGAGATCTGATGACACGGCCGTGTATTACTGTGCGAGA CGCGGTGGGAGCTACTTTGACTACTGGGGCCAAGGGACCCTGGTCACCG TCTCCTCAGCCTCCACCAAGGGCCCATCGGTCTTCCCCCTGGCACCCTC CTCCAAGAGCACCTCTGGGGGCACAGCGGCCCTGGGCTGCCTGGTCAAG GACTACTTCCCCGAACCGGTGACGGTGTCGTGGAACTCAGGCGCCCTGA CCAGCGGCGTGCACACCTTCCCGGCTGTCCTACAGTCCTCAGGACTCTA CTCCCTCAGCAGCGTGGTGACCGTGCCCTCCAGCAGCTTGGGCACCCAG ACCTACATCTGCAACGTGAATCACAAGCCCAGCAACACCAAGGTGGACA AGAAAGTTGAGCCCAAATCTTGTGACAAAACTCACACATGCCCACCGTG CCCAGCACCTGAACTCCTGGGGGGACCGTCAGTCTTCCTCTTCCCCCCA AAACCCAAGGACACCCTCATGATCTCCCGGACCCCTGAGGTCACATGCG TGGTGGTGGACGTGAGCCACGAAGACCCTGAGGTCAAGTTCAACTGGTA CGTGGACGGCGTGGAGGTGCATAATGCCAAGACAAAGCCGCGGGAGGAG CAGTACAACAGCACGTACCGTGTGGTCAGCGTCCTCACCGTCCTGCACC AGGACTGGCTGAATGGCAAGGAGTACAAGTGCAAGGTCTCCAACAAAGC CCTCCCAGCCCCCATCGAGAAAACCATCTCCAAAGCCAAAGGGCAGCCC CGAGAACCACAGGTGTACACCCTGCCCCCATCCCGGGATGAGCTGACCA AGAACCAGGTCAGCCTGACCTGCCTGGTCAAAGGCTTCTATCCCAGCGA CATCGCCGTGGAGTGGGAGAGCAATGGGCAGCCGGAGAACAACTACAAG ACCACGCCTCCCGTGCTGGACTCCGACGGCTCCTTCTTCCTCTACAGCA AGCTCACCGTGGACAAGAGCAGGTGGCAGCAGGGGAACGTCTTCTCATG CTCCGTGATGCATGAGGCTCTGCACAACCACTACACGCAGAAGAGCCTC TCCCTGTCTCCGGGTAAA |
| SEQ. ID NO: 66 | 208 Lambda Light chain (nt) | TCCTATGTGCTGACTCAGCCACCCTCAGCGTCTGGGACCCCCGGGCAGA GCGTCACCATCTCTTGTTCTGGAAGCACCTCCAACATCGGAAGTCATTA TGTGTTCTGGTACCAGCAGCTCCCAGGAACGGCCCCCAGACTCCTCATC TATAGGAATCATCAGCGGCCCTCAGGGGTCCCTGACCGACTCTCTGGCT CCAAGTCTGGCACCTCAGCCTCCCTGGCCATCAGTGGGCTCCGGTCCGA GGATGAGGCTGATTATTACTGTGCAGTGTGGGATGCGAAATACAGGGGT TGGGTGTTCGGCGGAGGGACCAAGCTGACCGTCCTAGGTCAGCCCAAGG CTGCCCCCTCGGTCACTCTGTTCCCGCCCTCCTCTGAGGAGCTTCAAGC CAACAAGGCCACACTGGTGTGTCTCATAAGTGACTTCTACCCGGGAGCC GTGACAGTGGCCTGGAAGGCAGATAGCAGCCCCGTCAAGGCGGGAGTGG AGACCACCACACCCTCCAAACAAAGCAACAACAAGTACGCGGCCAGCAG CTATCTGAGCCTGACGCCTGAGCAGTGGAAGTCCCACAGAAGCTACAGC TGCCAGGTCACGCATGAAGGGAGCACCGTGGAGAAGACAGTGGCCCCTA CAGAATGTTCA |

TABLE 10-continued

| SEQ. ID NO: 67 | 208 IgG-heavy chain (aa) | QVQLVQSGAEVKKPGSSVKVSCKASGGTFSSYAMSWVRQAPGQGLEWMG GIIPIFGTVNYAQKFQGRVTMTRDTSTSTVYMELSSLRSDDTAVYYCAR RGGSYFDYWGQGTLVTVSSASTKGPSVFPLAPSSKSTSGGTAALGCLVK DYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPP KPKDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQP REPQVYTLPPSRDELTKNQVSLTCLVKGFYPSDIAVEWESNGQPENNYK TTPPVLDSDGSFFLYSKLTVDKSRWQQGNVFSCSVMHEALHNHYTQKSL SLSPGK |
| --- | --- | --- |
| SEQ. ID NO: 68 | 208 Lambda Light-chain (aa) | SYVLTQPPSASGTPGQSVTISCSGSTSNIGSHYVFWYQQLPGTAPRLLI YRNHQRPSGVPDRLSGSKSGTSASLAISGLRSEDEADYYCAVWDAKYRG WVFGGGTKLTVLGQPKAAPSVTLFPPSSEELQANKATLVCLISDFYPGA VTVAWKADSSPVKAGVETTTPSKQSNNKYAASSYLSLTPEQWKSHRSYS CQVTHEGSTVEKTVAPTECS |

TABLE 11

| SEQ. ID NO: 69 | 306 IgG1 heavy chain (nt) | CAGGTCCAGCTTGTACAGTCTGGGGCTGAGGTGAAGAAGCCTGGGTCCT CGGTGAAGGTCTCCTGCAAGGCTTCTGGAGGCACCTTCAGCAGCTATGC TATGAGCTGGGTGCGACAGGCCCCTGGGCAAGGGCTTGAGTGGATGGGA GGGATCATCCCTATCTTTGGTACAGTAAACTACGCACAGAAGTTCCAGG GCAGAGTCACCATGACCAGGGACACGTCCACGAGCACAGTCTACATGGA GCTGAGCAGCCTGAGACCTGATGACACGGCCGTGTATTACTGTGCGAGA CGCGGTGGGAGCTACTTTGACTACTGGGGCCAAGGGACCCTGGTCACCG TCTCCTCAGCCTCCACCAAGGGCCCATCGGTCTTCCCCCTGGCACCCTC CTCCAAGAGCACCTCTGGGGGCACAGCGGCCCTGGGCTGCCTGGTCAAG GACTACTTCCCCGAACCGGTGACGGTGTCGTGGAACTCAGGCGCCCTGA CCAGCGGCGTGCACACCTTCCCGGCTGTCCTACAGTCCTCAGGACTCTA CTCCCTCAGCAGCGTGGTGACCGTGCCCTCCAGCAGCTTGGGCACCCAG ACCTACATCTGCAACGTGAATCACAAGCCCAGCAACACCAAGGTGGACA AGAAAGTTGAGCCCAAATCTTGTGACAAAACTCACACATGCCCACCGTG CCCAGCACCTGAACTCCTGGGGGGACCGTCAGTCTTCCTCTTCCCCCCA AAACCCAAGGACACCCTCATGATCTCCCGGACCCCTGAGGTCACATGCG TGGTGGTGGACGTGAGCCACGAAGACCCTGAGGTCAAGTTCAACTGGTA CGTGGACGGCGTGGAGGTGCATAATGCCAAGACAAAGCCGCGGGAGGAG CAGTACAACAGCACGTACCGTGTGGTCAGCGTCCTCACCGTCCTGCACC AGGACTGGCTGAATGGCAAGGAGTACAAGTGCAAGGTCTCCAACAAAGC CCTCCCAGCCCCCATCGAGAAAACCATCTCCAAAGCCAAAGGGCAGCCC CGAGAACCACAGGTGTACACCCTGCCCCCATCCCGGGATGAGCTGACCA AGAACCAGGTCAGCCTGACCTGCCTGGTCAAAGGCTTCTATCCCAGCGA CATCGCCGTGGAGTGGGAGAGCAATGGGCAGCCGGAGAACAACTACAAG ACCACGCCTCCCGTGCTGGACTCCGACGGCTCCTTCTTCCTCTACAGCA AGCTCACCGTGGACAAGAGCAGGTGGCAGCAGGGGAACGTCTTCTCATG CTCCGTGATGCATGAGGCTCTGCACAACCACTACACGCAGAAGAGCCTC TCCCTGTCTCCGGGTAAA |
| --- | --- | --- |
| SEQ. ID NO: 70 | 306 Lambda Light chain (nt) | TCCTATGTGCTGACTCAGCCACCCTCAGCGTCTGGGACCCCCGGGCAGA GCGTCACCATCTCTTGTTCTGGAAGCACCTCCAACATCGGAAGTCATTA TGTGTCCTGGTACCAGCAGCTCCCAGGAACGGCCCCCAGACTCCTCATC TATAGGAATCATCAGCGGCCCTCAGGGGTCCCTGACCGACTCTCTGGCT CCAAGTCTGGCACCTCAGCCTCCCTGGCCATCAGTGGGCTCCGGTCCGA GGATGAGGCTGATTATTACTGCAGTGTGGGATGCAAATACAGGGGT TGGGTGTTCGGCGGAGGGACCAAGCTGACCGTCCTAGGTCAGCCCAAGG CTGCCCCCTCGGTCACTCTGTTCCCGCCCTCCTCTGAGGAGCTTCAAGC CAACAAGGCCACACTGGTGTGTCTCATAAGTGACTTCTACCCGGGAGCC GTGACAGTGGCCTGGAAGGCAGATAGCAGCCCCGTCAAGGCGGGAGTGG AGACCACCACACCCTCCAAACAAAGCAACAACAAGTACGCGGCCAGCAG CTATCTGAGCCTGACGCCTGAGCAGTGGAAGTCCCACAGAAGCTACAGC TGCCAGGTCACGCATGAAGGGAGCACCGTGGAGAAGACAGTGGCCCCTA CAGAATGTTCA |
| SEQ. ID NO: 71 | 306 IgG-heavy chain (aa) | QVQLVQSGAEVKKPGSSVKVSCKASGGTFSSYAMSWVRQAPGQGLEWMG GIIPIFGTVNYAQKFQGRVTMTRDTSTSTVYMELSSLRPDDTAVYYCAR RGGSYFDYWGQGTLVTVSSASTKGPSVFPLAPSSKSTSGGTAALGCLVK DYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPP KPKDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQP REPQVYTLPPSRDELTKNQVSLTCLVKGFYPSDIAVEWESNGQPENNYK TTPPVLDSDGSFFLYSKLTVDKSRWQQGNVFSCSVMHEALHNHYTQKSL SLSPGK |

TABLE 11-continued

| SEQ. ID NO: 72 | 306 Lambda Light-chain (aa) | SYVLTQPPSASGTPGQSVTISCSGSTSNIGSHYVSWYQQLPGTAPRLLI YRNHQRPSGVPDRLSGSKSGTSASLAISGLRSEDEADYYCAVWDAKYRG WVFGGGTKLTVLGQPKAAPSVTLFPPSSEELQANKATLVCLISDFYPGA VTVAWKADSSPVKAGVETTTPSKQSNNKYAASSYLSLTPEQWKSHRSYS CQVTHEGSTVEKTVAPTECS |

TABLE 12

| SEQ. ID NO: 73 | 308 IgG1 heavy chain (nt) | CAGGTCCAGCTTGTACAGTCTGGGGCTGAGGTGAAGAAGCCTGGGTCCT CGGTGAAGGTCTCCTGCAAGGCTTCTGGAGGCACCTTCAGCAGCTATGC TATGAGCTGGGTGCGACAGGCCCCTGGGCAAGGGCTTGAGTGGATGGGA GGGATCATCCCTATCTTTGGTACAGTAAACTACGCACAGAAGTTCCAGG GCAGAGTCACCATGACCAGGGACACGTCCACGAGCACAGTCTACATGGA GCTGAGCAGCCTGAGACCTGATGACACGGCCGTGTATTACTGTGCGAGA CGCGGTGGGAGCTACTTTGACTACTGGGGCCAAGGGACCCTGGTCACCG TCTCCTCAGCCTCCACCAAGGGCCCATCGGTCTTCCCCCTGGCACCCTC CTCCAAGAGCACCTCTGGGGGCACAGCGGCCCTGGGCTGCCTGGTCAAG GACTACTTCCCCGAACCGGTGACGGTGTCGTGGAACTCAGGCGCCCTGA CCAGCGGCGTGCACACCTTCCCGGCTGTCCTACAGTCCTCAGGACTCTA CTCCCTCAGCAGCGTGGTGACCGTGCCCTCCAGCAGCTTGGGCACCCAG ACCTACATCTGCAACGTGAATCACAAGCCCAGCAACACCAAGGTGGACA AGAAAGTTGAGCCCAAATCTTGTGACAAAACTCACACATGCCCACCGTG CCCAGCACCTGAACTCCTGGGGGGACCGTCAGTCTTCCTCTTCCCCCCA AAACCCAAGGACACCCTCATGATCTCCCGGACCCCTGAGGTCACATGCG TGGTGGTGGACGTGAGCCACGAAGACCCTGAGGTCAAGTTCAACTGGTA CGTGGACGGCGTGGAGGTGCATAATGCCAAGACAAAGCCGCGGGAGGAG CAGTACAACAGCACGTACCGTGTGGTCAGCGTCCTCACCGTCCTGCACC AGGACTGGCTGAATGGCAAGGAGTACAAGTGCAAGGTCTCCAACAAAGC CCTCCCAGCCCCCATCGAGAAAACCATCTCCAAAGCCAAAGGGCAGCCC CGAGAACCACAGGTGTACACCCTGCCCCCATCCCGGGATGAGCTGACCA AGAACCAGGTCAGCCTGACCTGCCTGGTCAAAGGCTTCTATCCCAGCGA CATCGCCGTGGAGTGGGAGAGCAATGGGCAGCCGGAGAACAACTACAAG ACCACGCCTCCCGTGCTGGACTCCGACGGCTCCTTCTTCCTCTACAGCA AGCTCACCGTGGACAAGAGCAGGTGGCAGCAGGGGAACGTCTTCTCATG CTCCGTGATGCATGAGGCTCTGCACAACCACTACACGCAGAAGAGCCTC TCCCTGTCTCCGGGTAAA |
| SEQ. ID NO: 74 | 308 Lambda Light chain (nt) | TCCTATGTGCTGACTCAGCCACCCTCAGCGTCTGGGACCCCCGGGCAGA GCGTCACCATCTCTTGTTCTGGAAGCACCTCCAACATCGGAAGTCATTA TGTGTTCTGGTACCAGCAGCTCCCAGGAACGGCCCCCAGACTCCTCATC TATAGGAATCATCAGCGGCCCTCAGGGGTCCCTGACCGACTCTCTGGCT CCAAGTCTGGCACCTCAGCCTCCCTGGCCATCAGTGGGCTCCGGTCCGA GGATGAGGCTGATTATTACTGTGCAGTGTGGGATGCGAAATACAGGGGT TGGGTGTTCGGCGGAGGGACCAAGCTGACCGTCCTAGGTCAGCCCAAGG CTGCCCCCTCGGTCACTCTGTTCCCGCCCTCCTCTGAGGAGCTTCAAGC CAACAAGGCCACACTGGTGTGTCTCATAAGTGACTTCTACCCGGGAGCC GTGACAGTGGCCTGGAAGGCAGATAGCAGCCCCGTCAAGGCGGGAGTGG AGACCACCACACCCTCCAAACAAAGCAACAACAAGTACGCGGCCAGCAG CTATCTGAGCCTGACGCCTGAGCAGTGGAAGTCCCACAGAAGCTACAGC TGCCAGGTCACGCATGAAGGGAGCACCGTGGAGAAGACAGTGGCCCCTA CAGAATGTTCA |
| SEQ. ID NO: 75 | 308 IgG- heavy chain (aa) | QVQLVQSGAEVKKPGSSVKVSCKASGGTFSSYAMSWVRQAPGQGLEWMG GIIPIFGTVNYAQKFQGRVTMTRDTSTSTVYMELSSLRPDDTAVYYCAR RGGSYFDYWGQGTLVTVSSASTKGPSVFPLAPSSKSTSGGTAALGCLVK DYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPP KPKDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQP REPQVYTLPPSRDELTKNQVSLTCLVKGFYPSDIAVEWESNGQPENNYK TTPPVLDSDGSFFLYSKLTVDKSRWQQGNVFSCSVMHEALHNHYTQKSL SLSPGK |
| SEQ. ID NO: 76 | 308 Lambda Light- chain (aa) | SYVLTQPPSASGTPGQSVTISCSGSTSNIGSHYVFWYQQLPGTAPRLLI YRNHQRPSGVPDRLSGSKSGTSASLAISGLRSEDEADYYCAVWDAKYRG WVFGGGTKLTVLGQPKAAPSVTLFPPSSEELQANKATLVCLISDFYPGA VTVAWKADSSPVKAGVETTTPSKQSNNKYAASSYLSLTPEQWKSHRSYS CQVTHEGSTVEKTVAPTECS |

TABLE 13

| SEQ. ID NO: | 406 IgG1 heavy | CAGGTCCAGCTTGTACAGTCTGGGGCTGAGGTGAAGAAGCCTGGGTCCT CGGTGAAGGTCTCCTGCAAGGCTTCTGAAGGCACCTTCAGCAGCTATGC TATGAGCTGGGTGCGACAGGCCCCTGGGCAAGGGCTTGAGTGGATGGGA |

TABLE 13-continued

| 77 | chain (nt) | GGGATCATCCCTATCTTTGGTACAGTAAACTACGCACAGAAGTTCCAGG<br>GCAGAGTCACCATGACCAGGGACACGTCCACGAGCACAGTCTACATGGA<br>GCTGAGCAGCCTGAGATCTGATGACACGGCCGTGTATTACTGTGCGAGA<br>CGCGGTGGGAGCTACTTTGACTACTGGGGCCAAGGGACCCTGGTCACCG<br>TCTCCTCAGCCTCCACCAAGGGCCCATCGGTCTTCCCCCTGGCACCCTC<br>CTCCAAGAGCACCTCTGGGGGCACAGCGGCCCTGGGCTGCCTGGTCAAG<br>GACTACTTCCCCGAACCGGTGACGGTGTCGTGGAACTCAGGCGCCCTGA<br>CCAGCGGCGTGCACACCTTCCCGGCTGTCCTACAGTCCTCAGGACTCTA<br>CTCCCTCAGCAGCGTGGTGACCGTGCCCTCCAGCAGCTTGGGCACCCAG<br>ACCTACATCTGCAACGTGAATCACAAGCCCAGCAACACCAAGGTGGACA<br>AGAAAGTTGAGCCCAAATCTTGTGACAAAACTCACACATGCCCACCGTG<br>CCCAGCACCTGAACTCCTGGGGGACCGTCAGTCTTCCTCTTCCCCCCA<br>AAACCCAAGGACACCCTCATGATCTCCCGGACCCCTGAGGTCACATGCG<br>TGGTGGTGGACGTGAGCCACGAAGACCCTGAGGTCAAGTTCAACTGGTA<br>CGTGGACGGCGTGGAGGTGCATAATGCCAAGACAAAGCCGCGGGAGGAG<br>CAGTACAACAGCACGTACCGTGTGGTCAGCGTCCTCACCGTCCTGCACC<br>AGGACTGGCTGAATGGCAAGGAGTACAAGTGCAAGGTCTCCAACAAAGC<br>CCTCCCAGCCCCCATCGAGAAAACCATCTCCAAAGCCAAAGGGCAGCCC<br>CGAGAACCACAGGTGTACACCCTGCCCCCATCCCGGGATGAGCTGACCA<br>AGAACCAGGTCAGCCTGACCTGCCTGGTCAAAGGCTTCTATCCCAGCGA<br>CATCGCCGTGGAGTGGGAGAGCAATGGGCAGCCGGAGAACAACTACAAG<br>ACCACGCCTCCCGTGCTGGACTCCGACGGCTCCTTCTTCCTCTACAGCA<br>AGCTCACCGTGGACAAGAGCAGGTGGCAGCAGGGGAACGTCTTCTCATG<br>CTCCGTGATGCATGAGGCTCTGCACAACCACTACACGCAGAAGAGCCTC<br>TCCCTGTCTCCGGGTAAA |
| --- | --- | --- |
| SEQ. ID NO: 78 | 406 Lambda Light chain (nt) | TCCTATGTGCTGACTCAGCCACCCTCAGCGTCTGGGACCCCCGGGCAGA<br>GCGTCACCATCTCTTGTTCTGGAAGCACCTCCAACATCGGAAGTCATTA<br>TGTGTCCTGGTACCAGCAGCTCCCAGGAACGGCCCCCAGACTCCTCATC<br>TATAGGAATCATCAGCGGCCCTCAGGGGTCCCTGACCGACTCTCTGGCT<br>CCAAGTCTGGCACCTCAGCCTCCTGGCCATCAGTGGGCTCCGGTCCGA<br>GGATGAGGCTGATTATTACTGTGCAGTGTGGGATGCAAATACAGGGGT<br>TGGGTGTTCGGCGGAGGGACCAAGCTGACCGTCCTAGGTCAGCCCAAGG<br>CTGCCCCCTCGGTCACTCTGTTCCCGCCCTCCTCTGAGGAGCTTCAAGC<br>CAACAAGGCCACACTGGTGTGTCTCATAAGTGACTTCTACCCGGGAGCC<br>GTGACAGTGGCCTGGAAGGCAGATAGCAGCCCCGTCAAGGCGGGAGTGG<br>AGACCACCACACCCTCCAAACAAAGCAACAACAAGTACGCGGCCAGCAG<br>CTATCTGAGCCTGACGCCTGAGCAGTGGAAGTCCCACAGAAGCTACAGC<br>TGCCAGGTCACGCATGAAGGGAGCACCGTGGAGAAGACAGTGGCCCCTA<br>CAGAATGTTCA |
| SEQ. ID NO: 79 | 406 IgG-heavy chain (aa) | QVQLVQSGAEVKKPGSSVKVSCKASEGTFSSYAMSWVRQAPGQGLEWMG<br>GIIPIFGTVNYAQKFQGRVTMTRDTSTSTVYMELSSLRSDDTAVYYCAR<br>RGGSYFDYWGQGTLVTVSSASTKGPSVFPLAPSSKSTSGGTAALGCLVK<br>DYFPEPVTVSWNSGALTSGVHTFPAVLQSSGLYSLSSVVTVPSSSLGTQ<br>TYICNVNHKPSNTKVDKKVEPKSCDKTHTCPPCPAPELLGGPSVFLFPP<br>KPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQP<br>REPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSL<br>SLSPGK |
| SEQ. ID NO: 80 | 406 Lambda Light-chain (aa) | SYVLTQPPSASGTPGQSVTISCSGSTSNIGSHYVSWYQQLPGTAPRLLI<br>YRNHQRPSGVPDRLSGSKSGTSASLAISGLRSEDEADYYCAVWDAKYRG<br>WVFGGGTKLTVLGQPKAAPSVTLFPPSSEELQANKATLVCLISDFYPGA<br>VTVAWKADSSPVKAGVETTTPSKQSNNKYAASSYLSLTPEQWKSHRSYS<br>CQVTHEGSTVEKTVAPTECS |

TABLE 14

| SEQ. ID NO: 81 | 501 IgG1 heavy chain (nt) | CAGGTCCAGCTTGTACAGTCTGGGGCTGAGGTGAAGAAGCCTGGGTCCT<br>CGGTGAAGGTCTCCTGCAAGGCTTCTGAAGGCACCTTCAGCAGCTATGC<br>TATGAGCTGGGTGCGACAGGCCCCTGGGCAAGGGCTTGAGTGGATGGGA<br>GGGATCATCCCTATCTTTGGTACAGTAAACTACGCACAGAAGTTCCAGG<br>GCAGAGTCACCATGACCAGGGACACGTCCACGAGCACAGTCTACATGGA<br>GCTGAGCAGCCTGAGATCTGATGACACGGCCGTGTATTACTGTGCGAGA<br>CGGCGCGGCGCTAAATTTGACTACTGGGGCCAAGGGACCCTGGTCACCG<br>TCTCCTCAGCCTCCACCAAGGGCCCATCGGTCTTCCCCCTGGCACCCTC<br>CTCCAAGAGCACCTCTGGGGGCACAGCGGCCCTGGGCTGCCTGGTCAAG<br>GACTACTTCCCCGAACCGGTGACGGTGTCGTGGAACTCAGGCGCCCTGA<br>CCAGCGGCGTGCACACCTTCCCGGCTGTCCTACAGTCCTCAGGACTCTA<br>CTCCCTCAGCAGCGTGGTGACCGTGCCCTCCAGCAGCTTGGGCACCCAG<br>ACCTACATCTGCAACGTGAATCACAAGCCCAGCAACACCAAGGTGGACA<br>AGAAAGTTGAGCCCAAATCTTGTGACAAAACTCACACATGCCCACCGTG<br>CCCAGCACCTGAACTCCTGGGGGACCGTCAGTCTTCCTCTTCCCCCCA<br>AAACCCAAGGACACCCTCATGATCTCCCGGACCCCTGAGGTCACATGCG<br>TGGTGGTGGACGTGAGCCACGAAGACCCTGAGGTCAAGTTCAACTGGTA |
| --- | --- | --- |

TABLE 14-continued

| | | |
|---|---|---|
| | | CGTGGACGGCGTGGAGGTGCATAATGCCAAGACAAAGCCGCGGGAGGAG<br>CAGTACAACAGCACGTACCGTGTGGTCAGCGTCCTCACCGTCCTGCACC<br>AGGACTGGCTGAATGGCAAGGAGTACAAGTGCAAGGTCTCCAACAAAGC<br>CCTCCCAGCCCCCATCGAGAAAACCATCTCCAAAGCCAAAGGGCAGCCC<br>CGAGAACCACAGGTGTACACCCTGCCCCCATCCCGGGATGAGCTGACCA<br>AGAACCAGGTCAGCCTGACCTGCCTGGTCAAAGGCTTCTATCCCAGCGA<br>CATCGCCGTGGAGTGGGAGAGCAATGGGCAGCCGGAGAACAACTACAAG<br>ACCACGCCTCCCGTGCTGGACTCCGACGGCTCCTTCTTCCTCTACAGCA<br>AGCTCACCGTGGACAAGAGCAGGTGGCAGCAGGGGAACGTCTTCTCATG<br>CTCCGTGATGCATGAGGCTCTGCACAACCACTACACGCAGAAGAGCCTC<br>TCCCTGTCTCCGGGTAAA |
| SEQ.<br>ID<br>NO:<br>82 | 501<br>Lambda<br>Light<br>chain<br>(nt) | <u>TCCTATGTGCTGACTCAGCAACCCTCAGCGTCTGGGACCCCCGGGCAGA</u><br><u>GCGTCACCATCTCTTGTTCTGGAAGCACCTCCAACATCGGAAGTCATTA</u><br><u>TGTGGTCTGGTACCAGCAGCTCCCAGGAACGGCCCCCAGACTCCTCATC</u><br><u>TATAGGAATCATCAGCGGCCCTCAGGGGTCCCTGACCGACTCTCTGGCT</u><br><u>CCAAGTCTGGCACCTCAGCCTCCCTGGCCATCGGTGGGCTCCGGTCCGA</u><br><u>GGATGAGGCTGATTATTACTGTGCAGTGTGGGATGACACCCTGAGTGGC</u><br><u>TGGGTGTTCGGCGGAGGGACCAAGCTGACCGTCCTAGGT</u>CAGCCCAAGG<br>CTGCCCCCTCGGTCACTCTGTTCCCGCCCTCCTCTGAGGAGCTTCAAGC<br>CAACAAGGCCACACTGGTGTGTCTCATAAGTGACTTCTACCCGGGAGCC<br>GTGACAGTGGCCTGGAAGGCAGATAGCAGCCCCGTCAAGGCGGGAGTGG<br>AGACCACCACACCCTCCAAACAAAGCAACAACAAGTACGCGGCCAGCAG<br>CTATCTGAGCCTGACGCCTGAGCAGTGGAAGTCCCACAGAAGCTACAGC<br>TGCCAGGTCACGCATGAAGGGAGCACCGTGGAGAAGACAGTGGCCCCTA<br>CAGAATGTTCA |
| SEQ.<br>ID<br>NO:<br>83 | 501<br>IgG-<br>heavy<br>chain<br>(aa) | <u>QVQLVQSGAEVKKPGSSVKVSCKASEGTFSSYAMSWVRQAPGQGLEWMG</u><br><u>GIIPIFGTVNYAQKFQGRVTMTRDTSTSTVYMELSSLRSDDTAVYYCAR</u><br><u>RRGAKFDYWGQGTLVTVSS</u>ASTKGPSVFPLAPSSKSTSGGTAALGCLVK<br>DYFPEPVTVSWNSGALTSGVHTFPAVLQSSGLYSLSSVVTVPSSSLGTQ<br>TYICNVNHKPSNTKVDKKVEPKSCDKTHTCPPCPAPELLGGPSVFLFPP<br>KPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQP<br>REPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSL<br>SLSPGK |
| SEQ.<br>ID<br>NO:<br>84 | 501<br>Lambda<br>Light-<br>chain<br>(aa) | <u>SYVLTQQPSASGTPGQSVTISCSGSTSNIGSHYVVWYQQLPGTAPRLLI</u><br><u>YRNHQRPSGVPDRLSGSKSGTSASLAIGGLRSEDEADYYCAVWDDTLSG</u><br><u>WVFGGGTKLTVLG</u>QPKAAPSVTLFPPSSEELQANKATLVCLISDFYPGA<br>VTVAWKADSSPVKAGVETTTPSKQSNNKYAASSYLSLTPEQWKSHRSYS<br>CQVTHEGSTVEKTVAPTECS |

TABLE 15

| SEQ.<br>ID<br>NO:<br>85 | 503<br>IgG1<br>heavy<br>chain<br>(nt) | <u>CAGGTCCAGCTTGTACAGTCTGGGGCTGAGGTGAAGAAGCCTGGGTCCT</u><br><u>CGGTGAAGGTCTCCTGCAAGGCTTCTGAAGGCACCTTCAGCAGCTATGC</u><br><u>TATGAGCTGGGTGCGACAGGCCCCTGGGCAAGGCCTTGAGTGGATGGGA</u><br><u>GGGATCATCCCTATCTTTGGTACAGTAAACTACGCACAGAAGTTCCAGG</u><br><u>GCAGAGTCACCATGACCAGGGACACGTCCACGAGCACAGTCTACATGGA</u><br><u>GCTGAGCAGCCTGAGATCTGATGACACGGCCGTGTATTACTGTGCGAGA</u><br><u>CGGCGCGGCGCTAAATTTGACTACTGGGGCCAAGGGACCCTGGTCACCG</u><br><u>TCTCCTCAG</u>CCTCCACCAAGGGCCCATCGGTCTTCCCCCTGGCACCCTC<br>CTCCAAGAGCACCTCTGGGGGCACAGCGGCCCTGGGCTGCCTGGTCAAG<br>GACTACTTCCCCGAACCGGTGACGGTGTCGTGGAACTCAGGCGCCCTGA<br>CCAGCGGCGTGCACACCTTCCCGGCTGTCCTACAGTCCTCAGGACTCTA<br>CTCCCTCAGCAGCGTGGTGACCGTGCCCTCCAGCAGCTTGGGCACCCAG<br>ACCTACATCTGCAACGTGAATCACAAGCCCAGCAACACCAAGGTGGACA<br>AGAAAGTTGAGCCCAAATCTTGTGACAAAACTCACACATGCCCACCGTG<br>CCCAGCACCTGAACTCCTGGGGGGACCGTCAGTCTTCCTCTTCCCCCCA<br>AAACCCAAGGACACCCTCATGATCTCCCGGACCCCTGAGGTCACATGCG<br>TGGTGGTGGACGTGAGCCACGAAGACCCTGAGGTCAAGTTCAACTGGTA<br>CGTGGACGGCGTGGAGGTGCATAATGCCAAGACAAAGCCGCGGGAGGAG<br>CAGTACAACAGCACGTACCGTGTGGTCAGCGTCCTCACCGTCCTGCACC<br>AGGACTGGCTGAATGGCAAGGAGTACAAGTGCAAGGTCTCCAACAAAGC<br>CCTCCCAGCCCCCATCGAGAAAACCATCTCCAAAGCCAAAGGGCAGCCC<br>CGAGAACCACAGGTGTACACCCTGCCCCCATCCCGGGATGAGCTGACCA<br>AGAACCAGGTCAGCCTGACCTGCCTGGTCAAAGGCTTCTATCCCAGCGA<br>CATCGCCGTGGAGTGGGAGAGCAATGGGCAGCCGGAGAACAACTACAAG<br>ACCACGCCTCCCGTGCTGGACTCCGACGGCTCCTTCTTCCTCTACAGCA<br>AGCTCACCGTGGACAAGAGCAGGTGGCAGCAGGGGAACGTCTTCTCATG<br>CTCCGTGATGCATGAGGCTCTGCACAACCACTACACGCAGAAGAGCCTC<br>TCCCTGTCTCCGGGTAAA |

TABLE 15-continued

| SEQ. ID NO: 86 | 503 Lambda Light chain (nt) | TCCTATGTGCTGACTCAGCCACCCTCAGCGTCTGGGACCCCCGGGCAGA GCGTCACCATCTCTTGTTCTGGAAGCACCTCCAACATCGGAAGTCATTA TGTGGTCTGGTACCAGCAGCTCCCAGGAACGGCCCCCAGACTCCTCATC TATAGGAATCATCAGCGGCCCTCAGGGGTCCCTGACCGACTCTCTGGCT CCAAGTCTGGCACCTCAGCCTCCTGGCCATCGGTGGGCTCCGGTCCGA GGATGAGGCTGATTATTACTGTGCAGTGTGGGATGACACCCTGAGTGGC TGGGTGTTCGGCGGAGGGACCAAGCTGACCGTCCTAGGTCAGCCCAAGG CTGCCCCCTCGGTCACTCTGTTCCCGCCCTCCTCTGAGGAGCTTCAAGC CAACAAGGCCACACTGGTGTGTCTCATAAGTGACTTCTACCCGGGAGCC GTGACAGTGGCCTGGAAGGCAGATAGCAGCCCCGTCAAGGCGGGAGTGG AGACCACCACACCCTCCAAACAAAGCAACAACAAGTACGCGGCCAGCAG CTATCTGAGCCTGACGCCTGAGCAGTGGAAGTCCCACAGAAGCTACAGC TGCCAGGTCACGCATGAAGGGAGCACCGTGGAGAAGACAGTGGCCCCTA CAGAATGTTCA |
| --- | --- | --- |
| SEQ. ID NO: 87 | 503 IgG-heavy chain (aa) | QVQLVQSGAEVKKPGSSVKVSCKASEGTFSSYAMSWVRQAPGQGLEWMG GIIPIFGTVNYAQKFQGRVTMTRDTSTSTVYMELSSLRSDDTAVYYCAR RRGAKFDYWGQGTLVTVSSASTKGPSVFPLAPSSKSTSGGTAALGCLVK DYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPP KPKDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQP REPQVYTLPPSRDELTKNQVSLTCLVKGFYPSDIAVEWESNGQPENNYK TTPPVLDSDGSFFLYSKLTVDKSRWQQGNVFSCSVMHEALHNHYTQKSL SLSPGK |
| SEQ. ID NO: 88 | 503 Lambda Light-chain (aa) | SYVLTQPPSASGTPGQSVTISCSGSTSNIGSHYVVWYQQLPGTAPRLLI YRNHQRPSGVPDRLSGSKSGTSASLAIGGLRSEDEADYYCAVWDDTLSG WVFGGGTKLTVLGQPKAAPSVTLFPPSSEELQANKATLVCLISDFYPGA VTVAWKADSSPVKAGVETTTPSKQSNNKYAASSYLSLTPEQWKSHRSYS CQVTHEGSTVEKTVAPTECS |

TABLE 16

| SEQ. ID NO: 89 | 601 IgG1 heavy chain (nt) | CAGGTCCAGCTTGTACAGTCTGGGGCTGAGGTGAAGAAGCCTGGGTCCT CGGTGAAGGTCTCCTGCAAGGCTTCTGGAGGCACCTTCAGCAGCTATGC TATGAGCTGGGTGCGACAGGCCCCTGGGCAAGGGCTTGAGTGGATGGGA GGGATCATCCCTATCTTTGGTACAGTAAACTACGCACAGAAGTTCCAGG GCAGAGTCACCATGACCAGGGACACGTCCACGAGCACAGTCTACATGGA GCTGAGCAGCCTGAGATCTGATGACACGGCCGTGTATTACTGTGCGAGA CGGCGCGGCGCTAAATTTGACTACTGGGGCCAAGGGACCCTGGTCACCG TCTCCTCAGCCTCCACCAAGGGCCCATCGGTCTTCCCCCTGGCACCCTC CTCCAAGAGCACCTCTGGGGGCACAGCGGCCCTGGGCTGCCTGGTCAAG GACTACTTCCCCGAACCGGTGACGGTGTCGTGGAACTCAGGCGCCCTGA CCAGCGGCGTGCACACCTTCCCGGCTGTCCTACAGTCCTCAGGACTCTA CTCCCTCAGCAGCGTGGTGACCGTGCCCTCCAGCAGCTTGGGCACCCAG ACCTACATCTGCAACGTGAATCACAAGCCCAGCAACACCAAGGTGGACA AGAAAGTTGAGCCCAAATCTTGTGACAAAACTCACACATGCCCACCGTG CCCAGCACCTGAACTCCTGGGGGGACCGTCAGTCTTCCTCTTCCCCCCA AAACCCAAGGACACCCTCATGATCTCCCGGACCCCTGAGGTCACATGCG TGGTGGTGGACGTGAGCCACGAAGACCCTGAGGTCAAGTTCAACTGGTA CGTGGACGGCGTGGAGGTGCATAATGCCAAGACAAAGCCGCGGGAGGAG CAGTACAACAGCACGTACCGTGTGGTCAGCGTCCTCACCGTCCTGCACC AGGACTGGCTGAATGGCAAGGAGTACAAGTGCAAGGTCTCCAACAAAGC CCTCCCAGCCCCCATCGAGAAAACCATCTCCAAAGCCAAAGGGCAGCCC CGAGAACCACAGGTGTACACCCTGCCCCCATCCCGGGATGAGCTGACCA AGAACCAGGTCAGCCTGACCTGCCTGGTCAAAGGCTTCTATCCCAGCGA CATCGCCGTGGAGTGGGAGAGCAATGGGCAGCCGGAGAACAACTACAAG ACCACGCCTCCCGTGCTGGACTCCGACGGCTCCTTCTTCCTCTACAGCA AGCTCACCGTGGACAAGAGCAGGTGGCAGCAGGGGAACGTCTTCTCATG CTCCGTGATGCATGAGGCTCTGCACAACCACTACACGCAGAAGAGCCTC TCCCTGTCTCCGGGTAAA |
| --- | --- | --- |
| SEQ. ID NO: 90 | 601 Lambda Light chain (nt) | TCCTATGTGCTGACTCAGCCAACCCTCAGCGTCTGGGACCCCCGGGCAGA GCGTCACCATCTCTTGTTCTGGAAGCACCTCCAACATCGGAAGTCATTA TGTGGTCTGGTACCAGCAGCTCCCAGGAACGGCCCCCAGACTCCTCATC TATAGGAATCATCAGCGGCCCTCAGGGGTCCCTGACCGACTCTCTGGCT CCAAGTCTGGCACCTCAGCCTCCTGGCCATCGGTGGGCTCCGGTCCGA GGATGAGGCTGATTATTACTGTGCAGTGTGGGATGACACCCTGAGTGGC TGGGTGTTCGGCGGAGGGACCAAGCTGACCGTCCTAGGTCAGCCCAAGG CTGCCCCCTCGGTCACTCTGTTCCCGCCCTCCTCTGAGGAGCTTCAAGC CAACAAGGCCACACTGGTGTGTCTCATAAGTGACTTCTACCCGGGAGCC GTGACAGTGGCCTGGAAGGCAGATAGCAGCCCCGTCAAGGCGGGAGTGG AGACCACCACACCCTCCAAACAAAGCAACAACAAGTACGCGGCCAGCAG CTATCTGAGCCTGACGCCTGAGCAGTGGAAGTCCCACAGAAGCTACAGC |

TABLE 16-continued

| | | |
|---|---|---|
| | | TGCCAGGTCACGCATGAAGGGAGCACCGTGGAGAAGACAGTGGCCCCTA<br>CAGAATGTTCA |
| SEQ.<br>ID<br>NO:<br>91 | 601<br>IgG-<br>heavy<br>chain<br>(aa) | QVQLVQSGAEVKKPGSSVKVSCKASGGTFSSYAMSWVRQAPGQGLEWMG<br>GIIPIFGTVNYAQKFQGRVTMTRDTSTSTVYMELSSLRSDDTAVYYCAR<br>RRGAKFDYWGQGTLVTVSSASTKGPSVFPLAPSSKSTSGGTAALGCLVK<br>DYFPEPVTVSWNSGALTSGVHTFPAVLQSSGLYSLSSVVTVPSSSLGTQ<br>TYICNVNHKPSNTKVDKKVEPKSCDKTHTCPPCPAPELLGGPSVFLFPP<br>KPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQP<br>REPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSL<br>SLSPGK |
| SEQ.<br>ID<br>NO:<br>92 | 601<br>Lambda<br>Light-<br>chain<br>(aa) | SYVLTQQPSASGTPGQSVTISCSGSTSNIGSHYVVWYQQLPGTAPRLLI<br>YRNHQRPSGVPDRLSGSKSGTSASLAIGGLRSEDEADYYCAVWDDTLSG<br>WVFGGGTKLTVLGQPKAAPSVTLFPPSSEELQANKATLVCLISDFYPGA<br>VTVAWKADSSPVKAGVETTTPSKQSNNKYAASSYLSLTPEQWKSHRSYS<br>CQVTHEGSTVEKTVAPTECS |

TABLE 17

| | | |
|---|---|---|
| SEQ.<br>ID<br>NO:<br>93 | 603<br>IgG1<br>heavy<br>chain<br>(nt) | CAGGTCCAGCTTGTACAGTCTGGGGCTGAGGTGAAGAAGCCTGGGTCCT<br>CGGTGAAGGTCTCCTGCAAGGCTTCTGGAGGCACCTTCAGCAGTATGC<br>TATGAGCTGGGTGCGACAGGCCCCTGGGCAAGGGCTTGAGTGGATGGGA<br>GGGATCATCCCTATCTTTGGTACAGTAAACTACGCACAGAAGTTCCAGG<br>GCAGAGTCACCATGACCAGGGACACGTCCACGAGCACAGTCTACATGGA<br>GCTGAGCAGCCTGAGATCTGATGACACGGCCGTGTATTACTGTGCGAGA<br>CGGCGCGGCGCTAAATTTGACTACTGGGGCCAAGGGACCCTGGTCACCG<br>TCTCCTCAGCCTCCACCAAGGGCCCATCGGTCTTCCCCCTGGCACCCTC<br>CTCCAAGAGCACCTCTGGGGGCACAGCGGCCCTGGGCTGCCTGGTCAAG<br>GACTACTTCCCCGAACCGGTGACGGTGTCGTGGAACTCAGGCGCCCTGA<br>CCAGCGGCGTGCACACCTTCCCGGCTGTCCTACAGTCCTCAGGACTCTA<br>CTCCCTCAGCAGCGTGGTGACCGTGCCCTCCAGCAGCTTGGGCACCCAG<br>ACCTACATCTGCAACGTGAATCACAAGCCCAGCAACACCAAGGTGGACA<br>AGAAAGTTGAGCCCAAATCTTGTGACAAAACTCACACATGCCCACCGTG<br>CCCAGCACCTGAACTCCTGGGGGGACCGTCAGTCTTCCTCTTCCCCCCA<br>AAACCCAAGGACACCCTCATGATCTCCCGGACCCCTGAGGTCACATGCG<br>TGGTGGTGGACGTGAGCCACGAAGACCCTGAGGTCAAGTTCAACTGGTA<br>CGTGGACGGCGTGGAGGTGCATAATGCCAAGACAAAGCCGCGGGAGGAG<br>CAGTACAACAGCACGTACCGTGTGGTCAGCGTCCTCACCGTCCTGCACC<br>AGGACTGGCTGAATGGCAAGGAGTACAAGTGCAAGGTCTCCAACAAAGC<br>CCTCCCAGCCCCCATCGAGAAAACCATCTCCAAAGCCAAAGGGCAGCCC<br>CGAGAACCACAGGTGTACACCCTGCCCCCATCCCGGGATGAGCTGACCA<br>AGAACCAGGTCAGCCTGACCTGCCTGGTCAAAGGCTTCTATCCCAGCGA<br>CATCGCCGTGGAGTGGGAGAGCAATGGGCAGCCGGAGAACAACTACAAG<br>ACCACGCCTCCCGTGCTGGACTCCGACGGCTCCTTCTTCCTCTACAGCA<br>AGCTCACCGTGGACAAGAGCAGGTGGCAGCAGGGGAACGTCTTCTCATG<br>CTCCGTGATGCATGAGGCTCTGCACAACCACTACACGCAGAAGAGCCTC<br>TCCCTGTCTCCGGGTAAA |
| SEQ.<br>ID<br>NO:<br>94 | 603<br>Lambda<br>Light<br>chain<br>(nt) | TCCTATGTGCTGACTCAGCCACCCTCAGCGTCTGGGACCCCCGGGCAGA<br>GCGTCACCATCTCTTGTTCTGGAAGCACCTCCAACATCGGAAGTCATTA<br>TGTGGTCTGGTACCAGCAGCTCCCAGGAACGGCCCCCAGACTCCTCATC<br>TATAGGAATCATCAGCGGCCCTCAGGGGTCCCTGACCGACTCTCTGGCT<br>CCAAGTCTGGCACCTCAGCCTCCCTGGCCATCGGTGGGCTCCGGTCCGA<br>GGATGAGGCTGATTATTACTGTGCAGTGTGGGATGACACCCTGAGTGGC<br>TGGGTGTTCGGCGGAGGGACCAAGCTGACCGTCCTAGGTCAGCCCAAGG<br>CTGCCCCCTCGGTCACTCTGTTCCCGCCCTCCTCTGAGGAGCTTCAAGC<br>CAACAAGGCCACACTGGTGTGTCTCATAAGTGACTTCTACCCGGGAGCC<br>GTGACAGTGGCCTGGAAGGCAGATAGCAGCCCCGTCAAGGCGGGAGTGG<br>AGACCACCACACCCTCCAAACAAAGCAACAACAAGTACGCGGCCAGCAG<br>CTATCTGAGCCTGACGCCTGAGCAGTGGAAGTCCCACAGAAGCTACAGC<br>TGCCAGGTCACGCATGAAGGGAGCACCGTGGAGAAGACAGTGGCCCCTA<br>CAGAATGTTCA |
| SEQ.<br>ID<br>NO:<br>95 | 603<br>IgG-<br>heavy<br>chain<br>(aa) | QVQLVQSGAEVKKPGSSVKVSCKASGGTFSSYAMSWVRQAPGQGLEWMG<br>GIIPIFGTVNYAQKFQGRVTMTRDTSTSTVYMELSSLRSDDTAVYYCAR<br>RRGAKFDYWGQGTLVTVSSASTKGPSVFPLAPSSKSTSGGTAALGCLVK<br>DYFPEPVTVSWNSGALTSGVHTFPAVLQSSGLYSLSSVVTVPSSSLGTQ<br>TYICNVNHKPSNTKVDKKVEPKSCDKTHTCPPCPAPELLGGPSVFLFPP<br>KPKDTLMISRTPEVTCVVVDVSHEDPEVKFNWYVDGVEVHNAKTKPREE |

TABLE 17-continued

| | | |
|---|---|---|
| | | QYNSTYRVVSVLTVLHQDWLNGKEYKCKVSNKALPAPIEKTISKAKGQP<br>REPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSL<br>SLSPGK |
| SEQ.<br>ID<br>NO:<br>96 | 603<br>Lambda<br>Light-<br>chain<br>(aa) | SYVLTQPPSASGTPGQSVTISCSGSTSNIGSHYVVWYQQLPGTAPRLLI<br>YRNHQRPSGVPDRLSGSKSGTSASLAIGGLRSEDEADYYCAVWDDTLSG<br>WVFGGGTKLTVLGQPKAAPSVTLFPPSSEELQANKATLVCLISDFYPGA<br>VTVAWKADSSPVKAGVETTTPSKQSNNKYAASSYLSLTPEQWKSHRSYS<br>CQVTHEGSTVEKTVAPTECS |

TABLE 18

| | | |
|---|---|---|
| SEQ.<br>ID<br>NO:<br>97 | 803<br>IgG1<br>heavy<br>chain<br>(nt) | CAGGTCCAGCTTGTACAGTCTGGGGCTGAGGTGAAGAAGCCTGGGTCCT<br>CGGTGAAGGTCTCCTGCAAGGCTTCTGGAGGCACCTTCAGCAGCTATGC<br>TATCAGCTGGGTGCGACAGGCCCCTGGACAAGGGCTTGAGTGGATGGGA<br>GGGATCATCCCTATCTTTGGTACAGCAAACTACGCACAGAAGTTCCAGG<br>GCAGAGTCACCATGACCAGGGACACGTCCACGAGCACAGTCTACATGGA<br>GCTGAGCAGCCTGAGATCTGAGGACACGGCCGTGTATTACTGTGCGAGA<br>CGGCGCGGCGCTAAATTTGACTACTGGGGCCAAGGGACCCTGGTCACCG<br>TCTCCTCAGCCTCCACCAAGGGCCCATCGGTCTTCCCCCTGGCACCCTC<br>CTCCAAGAGCACCTCTGGGGGCACAGCGGCCCTGGGCTGCCTGGTCAAG<br>GACTACTTCCCCGAACCGGTGACGGTGTCGTGGAACTCAGGCGCCCTGA<br>CCAGCGGCGTGCACACCTTCCCGGCTGTCCTACAGTCCTCAGGACTCTA<br>CTCCCTCAGCAGCGTGGTGACCGTGCCCTCCAGCAGCTTGGGCACCCAG<br>ACCTACATCTGCAACGTGAATCACAAGCCCAGCAACACCAAGGTGGACA<br>AGAAAGTTGAGCCCAAATCTTGTGACAAAACTCACACATGCCCACCGTG<br>CCCAGCACCTGAACTCCTGGGGGGACCGTCAGTCTTCCTCTTCCCCCCA<br>AAACCCAAGGACACCCTCATGATCTCCCGGACCCCTGAGGTCACATGCG<br>TGGTGGTGGACGTGAGCCACGAAGACCCTGAGGTCAAGTTCAACTGGTA<br>CGTGGACGGCGTGGAGGTGCATAATGCCAAGACAAAGCCGCGGGAGGAG<br>CAGTACAACAGCACGTACCGTGTGGTCAGCGTCCTCACCGTCCTGCACC<br>AGGACTGGCTGAATGGCAAGGAGTACAAGTGCAAGGTCTCCAACAAAGC<br>CCTCCCAGCCCCCATCGAGAAAACCATCTCCAAAGCCAAAGGGCAGCCC<br>CGAGAACCACAGGTGTACACCCTGCCCCCATCCCGGGATGAGCTGACCA<br>AGAACCAGGTCAGCCTGACCTGCCTGGTCAAAGGCTTCTATCCCAGCGA<br>CATCGCCGTGGAGTGGGAGAGCAATGGGCAGCCGGAGAACAACTACAAG<br>ACCACGCCTCCCGTGCTGGACTCCGACGGCTCCTTCTTCCTCTACAGCA<br>AGCTCACCGTGGACAAGAGCAGGTGGCAGCAGGGGAACGTCTTCTCATG<br>CTCCGTGATGCATGAGGCTCTGCACAACCACTACACGCAGAAGAGCCTC<br>TCCCTGTCTCCGGGTAAA |
| SEQ.<br>ID<br>NO:<br>98 | 803<br>Lambda<br>Light<br>chain<br>(nt) | TCCTATGTGCTGACTCAGCCACCCTCAGCGTCTGGGACCCCCGGGCAGA<br>GCGTCACCATCTCTTGTTCTGGAAGCACCTCCAACATCGGAAGTCATTA<br>TGTGGTCTGGTACCAGCAGCTCCCAGGAACGGCCCCCAGACTCCTCATC<br>TATAGGAATCATCAGCGGCCCTCAGGGGTCCCTGACCGACTCTCTGGCT<br>CCAAGTCTGGCACCTCAGCCTCCTGGCCATCGGTGGGCTCCGGTCCGA<br>GGATGAGGCTGATTATTACTGTGCAGTGTGGGATGACACCCTGAGTGGC<br>TGGGTGTTCGGCGGAGGGACCAAGCTGACCGTCCTAGGTCAGCCCAAGG<br>CTGCCCCCTCGGTCACTCTGTTCCCGCCCTCCTCTGAGGAGCTTCAAGC<br>CAACAAGGCCACACTGGTGTGTCTCATAAGTGACTTCTACCCGGGAGCC<br>GTGACAGTGGCCTGGAAGGCAGATAGCAGCCCCGTCAAGGCGGGAGTGG<br>AGACCACCACACCCTCCAAACAAAGCAACAACAAGTACGCGGCCAGCAG<br>CTATCTGAGCCTGACGCCTGAGCAGTGGAAGTCCACAGAAGCTACAGC<br>TGCCAGGTCACGCATGAAGGGAGCACCGTGGAGAAGACAGTGGCCCCTA<br>CAGAATGTTCA |
| SEQ.<br>ID<br>NO:<br>99 | 803<br>IgG-<br>heavy<br>chain<br>(aa) | QVQLVQSGAEVKKPGSSVKVSCKASGGTFSSYAISWVRQAPGQGLEWMG<br>GIIPIFGTANYAQKFQGRVTMTRDTSTSTVYMELSSLRSEDTAVYYCAR<br>RRGAKFDYWGQGTLVTVSSASTKGPSVFPLAPSSKSTSGGTAALGCLVK<br>DYFPEPVTVSWNSGALTSGVHTFPAVLQSSGLYSLSSVVTVPSSSLGTQ<br>TYICNVNHKPSNTKVDKKVEPKSCDKTHTCPPCPAPELLGGPSVFLFPP<br>KPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQP<br>REPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSL<br>SLSPGK |
| SEQ.<br>ID<br>NO:<br>100 | 803<br>Lambda<br>Light-<br>chain<br>(aa) | SYVLTQPPSASGTPGQSVTISCSGSTSNIGSHYVVWYQQLPGTAPRLLI<br>YRNHQRPSGVPDRLSGSKSGTSASLAIGGLRSEDEADYYCAVWDDTLSG<br>WVFGGGTKLTVLGQPKAAPSVTLFPPSSEELQANKATLVCLISDFYPGA<br>VTVAWKADSSPVKAGVETTTPSKQSNNKYAASSYLSLTPEQWKSHRSYS<br>CQVTHEGSTVEKTVAPTECS |

TABLE 19

Calculated IC50 values, derived from TARC-mediated Ca-Flux inhibition.

|  | 208 | 306 | 308 | 406 | 501 | 503 | 601 | 603 | 803 | KM3060 var |
|---|---|---|---|---|---|---|---|---|---|---|
| IC50 (nM) | 0.0019 | 0.0012 | 0.003 | 0.001 | 0.001 | 0.0012 | 0.003 | 0.002 | 0.01 | ~172.5 |
| $R^2$ | 0.98 | 0.98 | 0.99 | 0.96 | 0.94 | 0.93 | 0.97 | 0.99 | 0.99 | 0.43 |

TABLE 20

Determined $IC_{50}$ values from ligand-interfering binding experiments of anti-CCR4 IgGs using labelled ligands.

| $IC_{50}$ (nM) | 306 | 406 | 503 |
|---|---|---|---|
| MDC | 0.28 | 0.27 | 0.11 |
| $R^2$ | 0.98 | 0.99 | 0.97 |
| TARC | 0.51 | 0.94 | 0.87 |
| $R^2$ | 0.96 | 0.97 | 0.95 |

TABLE 21

Overview of antagonistic properties of anti-CCR4 antibodies in ligand mediated Ca-Flux experiments.

|  | Inhibition of TARC | | Inhibition of MDC |
|---|---|---|---|
|  | $IC_{50}$ (pM) | $R^2$ | Blockage of signaling in % |
| 306 | 39 ± 0.4 | 0.95 | 74% |
| 406 | 28 ± 6 | 0.97 | 74% |
| 503 | 13 ± 3.5 | 0.96 | 64% |
| KW0761 | n.d. | n.d. | n.d. |

*n.d. = not determined

TABLE 22

Overview of determined $IC_{50}$ values and remaining migration in % from inhibition of ligand-induced migration (CCL17/TARC and CCL22/MDC) by anti-CCR4 antibodies.

|  | Inhibition of CCL17/TARC | | Inhibition of CCL22/MDC |
|---|---|---|---|
| Sample | $IC_{50}$ (pM) | $R^2$ | Blockage of migration in % |
| 306 | 158 | 0.97 | 50% |
| 406 | 178 | 0.98 | 49% |
| 503 | 39 | 0.99 | 39% |
| KW0761 | n.d. | n.d. | n.d. |

*n.d. = not determined

TABLE 23

Overview of determined $IC_{50}$ values from inhibition of CCL17/TARC-induced invasion by anti-CCR4 antibody 503 on 786-O cells.

|  | CCL17/TARC (125 nM) | CCL17/TARC (25 nM) |
|---|---|---|
| $IC_{50}$ (µg/ml) | 1.33 | 0.12 |
| $R^2$ | 0.97 | 0.77 |

TABLE 24

Overview of determined $EC_{50}$ values from ADCC experiments on haematological tumor cell lines CCRF-CEM and L-428.

|  | CCRF-CEM | | L-428 | |
|---|---|---|---|---|
| IgG | $EC_{50}$ (pM) | Max. Killing (%; nM IgG) | $EC_{50}$ (pM) | Max. Killing (%; nM IgG) |
| 306 | 114 | 118 (1.4) | 708 | 88 (7) |
| 406 | 99.9 | 121 (1.4) | 704 | 78 (7) |
| 503 | 5.3 | 108 (1.4) | 233 | 93 (7) |
| KW0761 | 315 | 69.8 (1.4) | 57 | 84 (7) |

TABLE 25

Scoring table from IHC experiments for renal cell cancer tumor microarrays (TMA) and relevant control tissues (placenta and normal kidney).

| Score | CCR4—503-IgG | CCR4—Ab1669-IgG | CCL17 | CCL22 |
|---|---|---|---|---|
| | Placenta control tissue | | | |
| 0 | 32/39 | 33/40 | 38/38 | 36/37 |
| 1 | 7/39 | 7/40 | 0/38 | 1/37 |
| 2 | 0/39 | 0/40 | 0/38 | 0/37 |
| | Kidney control tissue | | | |
| 0 | 0/2 | 1/3 | 2/3 | 0/2 |
| 1 | 2/2 | 2/3 | 1/3 | 0/2 |
| 2 | 0/2 | 0/3 | 0/3 | 2/2 |
| | Renal cell cancer tissue | | | |
| 0 | 21/174 | 19/175 | 128/169 | 37/171 |
| 1 | 83/174 | 92/175 | 39/169 | 99/171 |
| 2 | 70/174 | 64/175 | 2/169 | 35/171 |

REFERENCES

The following references, to the extent that they provide exemplary procedural or other details supplementary to those set forth herein, are specifically incorporated herein by reference.

Altschul, Madden, Schaffer, Zhang, Zhang, Miller, Lipman, "Gapped BLAST and PSI-BLAST: a new generation of protein database search programs", *Nucleic Acids Res.*, 25:3389-3402, 1997.

Arbabi-Ghahroudi, Desmyter, Wyns, Hamers, Muyldermans, "Selection and identification of single domain antibody fragments from camel heavy-chain antibodies", *FEBS Lett.*, 414:521-526, 1997.

Baatar, Olkhanud, Newton, Sumitom, Biragyn. CCR4 expressing T cell tumors can be specifically controlled via delivery of toxins to chemokine receptors. *J Immunol* 179: 1996-2004 (2007a)

Baatar, Olkhanud, Sumitomo, Taub, Gress, Biragyn. Human peripheral blood T regulatory cells (Tregs), functionally primed CCR4⁺ Tregs and unprimed CCR4⁻ Tregs, regulate effector T cells using FasL. *J Immunol* 178: 4891-900 (2007b)

Baeverle and Gires, BJC, 96: 417-423, 2007.

Baldari, Murray, Ghiara, Cesareni, Galeotti, "A Novel Leader Peptide Which Allows Efficient Secretion of a Fragment of Human Interleukin 1 Beta in *Saccharomyces Cerevisiae*", *EMBO J.*, 6:229-234, 1987

Bayry, Tchilian, Davies, Forbes, Draper, Kaveri, Hill, Kazatchkine, Beverley, Flower, Tough. In silico identified CCR4 antagonists target regulatory T cells and exert adjuvant activity in vaccination. *Proc Natl Acad Sci USA* 105: 10221-6 (2008)

Beckman, Weiner and Davis, "Antibody Constructs in Cancer Therapy", *Cancer,* 109(2):170-179, 2006.

Brinster, Chen, Trumbauer, Yagle, Palmiter, "Factors Affecting the Efficiency of Introducing Foreign DNA into Mice by Microinjecting Eggs", *Proc. Natl. Acad. Sci. USA,* 82(13):4438-4442, 1985.

Burdi, Chi, Mattia, Harrington, Shi, Chen, Jacutin-Porte, Bennett, Carson, Yin, Kansra, Gonzalo, Coyle, Jaffee, Ocain, Hodge, LaRosa, Harriman. Small molecule antagonists of the CC chemokine receptor 4 (CCR4). *Bioorg Med Chem Lett* 17: 3141-5 (2007)

Carillo and Lipton, "The Multiple Sequence Alignment Problem in Biology", *SIAM J. Applied Math.,* 48:1073, 1988.

Cullen, Gray, Wilson, Hayenga, Lamsa, Rey, Norton, Berka, "Controlled Expression and Secretion of Bovine Chymosin in *Aspergillus Nidulans*", *BioTechnology,* 5:369, 1987.

Church: Clinical advances in therapies targeting the interleukin-2 receptor. *QJM* 96: 91-102 (2003)

Chvatchko, Hoogewerf, Meyer, Alouani, Juillard, Buser, Conquet, Proudfoot, Wells, Power A key role for CC chemokine receptor 4 in lipopolysaccharide-induced endotoxic shock. *J Exp Med* 191: 1755-64 (2000)

Curiel: (2008) Regulatory T cells and treatment of cancer. *Curr Opin Immunol* 20: 241-6

Dannull, Su, Rizzieri, Yang, Coleman, Yancey, Zhang, Dahm, Chao, Gilboa, Vieweg Enhancement of vaccine-mediated antitumor immunity in cancer patients after depletion of regulatory T cells. *J Clin Invest* 115: 3623-33 (2005)

Davies, Bayry, Tchilian, Vani, Shaila, Forbes, Draper, Beverley, Tough, Flower. Toward the discovery of vaccine adjuvants: coupling in silico screening and in vitro analysis of antagonist binding to human and mouse CCR4 receptors. *PLoS One* 4: e8084 (2009)

Davies and Cohen, "Interactions of protein antigens with antibodies," *Proc Natl. Acad. Sci. U.S.A.* 93:7-12, 1996.

Davies, Padlan, Sheriff, "Antibody-antigen complexes," *Annu. Rev. Biochem.* 59:439-473, 1990.

Davies and Riechmann, "Antibody VH domains as small recognition units", *Biotechnology (NY)*, 13:475-479, 1995.

Devereux, Haeberli, Smithies, "A Comprehensive Set of Sequence Analysis Programs for the VAX", *Nucleic Acids Res.,* 12:387, 1984.

Di Paolo et al., "A recombinant immunotoxin derived from a humanized epithelial cell adhesion molecule-specific single-chain antibody fragment has potent and selective antitumor activity", Clin Cancer Res 9: 2837-48, 2003.

Frische, Meldal, Werdelin, Mouritsen, Jensen, Galli-Stampino, Bock, "Multiple Column Synthesis of a Library of T-Cell Stimulating Tn-Antigenic Glycopeptide Analogues for the Molecular Characterization of T-Cell-Glycan Specificity", *J. Pept. Sci.,* 2(4): 212-22, 1996.

Goeddel, "Gene Expression Technology: Methods in Enzymology 185, Academic Press, San Diego, Calif., 1990.

Graham: D6 and the atypical chemokine receptor family: novel regulators of immune and inflammatory processes. *Eur J Immunol* 39: 342-51 (2009)

Hamers-Casterman and Atarhouch, "Naturally Occurring antibodies Devoid of Light Chains", *Nature,* 363(6428): 446-448, 1993.

Hammer, Pursel, Rexroad, Wall, Bolt, Ebert, Palmiter, Brinster, "Production of Transgenic Rabbits, Sheep and Pigs by Microinjection", *Nature,* 315:680-683, 1985.

Henikoff and Henikoff, "Amino acid Substitution Matrices from Protein Blocks", *Proc. Natl. Acad. Sci. USA,* 89:10915-10919, 1992.

Hinnen, Hicks, Fink, "Transformation of Yeast", *Proc. Natl. Acad. Sci. USA,* 75:1929, 1978.

Holliger and Hudson, "Engineered Antibody Fragments and the Rise of Single Domains", *Nature Biotechnology,* 23(9): 1126-1136, 2005.

Holm, "Dali: a Network Tool for Protein Structure Comparison", *Trends in Biochemical Sciences,* 20:478-480, 1995.

Holm, "Protein Structure Comparison by Alignment of Distance Matrices", *J. Mol. Biol.,* 233:123-38, 1993

Holm, "Touring Protein Fold Space With Dali/FSSP", *Nucleic Acid Res.,* 26:316-9, 1998.

Hoogenboom, Lutgerink, Pelsers, Rousch, Coote, Van Neer, De Bruïne, Van Nieuwenhoven, Glatz, Arends. Selection-dominant and nonaccessible epitopes on cell-surface receptors revealed by cell-panning with a large phage antibody library. Eur. J. Biochem 260, 774-784 (1999)

Ishida, Ishii, Inagaki, Yano, Komatsu, Iida, Inagaki, Ueda. Specific recruitment of CC chemokine receptor 4-positive regulatory T cells in Hodgkin lymphoma fosters immune privilege. Cancer Research, 66:11, pages 5716-5722, 2006

Ito, Fukuda, Murata, Kimura, "Transformation of Intact Yeast Cells Treated with Alkali Cations", *J. Bacteriol.,* 153:163-168, 1983.

Kabat, Wu, Perry, Gottesman, Foeller, "Sequences of Proteins of Immunological Interest", 5*th Ed. Public Health Service, National Institutes of Health*, Bethesda, Md., 647-669, 1991.

Kawasaki, Takizawa, Yoneyama, Nakayama, Fujisawa, Izumizaki, Imai, Yoshie, Homma, Yamamoto, Matsushima. Intervention of thymus and activation-regulated chemokine attenuates the development of allergic airway inflammation and hyperresponsiveness in mice. *J Immunol* 166: 2055-62 (2001)

Kaufman, Murtha, Davies, "Translational Efficiency of Polycistronic Mrnas and Their Utilization to Express Heterologous Genes in Mammalian Cells", *EMBO J.,* 6:187-195, 1987.

Kipriyanov, Moldenhauer, Martin, Kupriyanova, Little. Two amino acid mutations in an anti-human CD3 single chain Fv antibody fragment that affect the yield on bacterial secretion but not the affinity. Protein Eng 10: 445-53 (1997)

Kiss, Fisher, Pesavento, Dai, Valero, Ovecka, Nolan, Phipps, Velappan, Chasteen, Martinez, Waldo, Pavlik, Bradbury, "Antibody binding loop insertions as diversity elements", *Nucleic Acids Research,* 34(19):e132, 2006.

Kurjan and Herskowitz, "Structure of a Yeast Pheromone Gene (MFα): a Putative α-Factor Precursor Contains Four Tandem Copies of mature α-Factor", *Cell,* 30:933-943, 1982.

Le Gall, Reusch, Little and Kipriyanov, "Effect of Linker Sequences Between the Antibody Variable Domains on the Formation, Stability and Biological Activity of a Bispecific Tandem Diabody", *Protein Engineering, Design & Selection,* 17(4):357-366, 2004.

Levings, Sangregorio, Sartirana, Moschin, Battaglia, Orban, Roncarolo. Human CD25+CD4+ T suppressor cell clones produce transforming growth factor beta, but not interleukin 10, and are distinct from type 1 T regulatory cells. *J Exp Med* 196: 1335-46 (2002)

Locati, Torre, Galliera, Bonecchi, Bodduluri, Vago, Vecchi, Mantovani. Silent chemoattractant receptors: D6 as a decoy and scavenger receptor for inflammatory CC chemokines. *Cytokine Growth Factor Rev* 16: 679-86 (2005)

Luckow and Summers, "High Level Expression of Nonfused Foreign Genes with *Autographa Californica* Nuclear Polyhedrosis Virus Expression Vectors", *Virology*, 170:31-39, 1989.

Mahnke, Schonfeld, Fondel, Ring, Karakhanova, Wiedemeyer, Bedke, Johnson, Storn, Schallenberg, Enk. Depletion of CD4+CD25+ human regulatory T cells in vivo: kinetics of Treg depletion and alterations in immune functions in vivo and in vitro. *Int J Cancer* 120: 2723-33 (2007)

Marhaba et al., "CD44 and EpCAM: cancer-initiating cell markers", Curr Mol Med 8: 784-804, 2008.

Merrifield, "Solid Phase Peptide Synthesis 1. Synthesis of a Tetrapeptide", *J. Am. Chem. Assoc.*, 85:2149-2154, 1964.

Munz et al., "The carcinoma-associated antigen EpCAM upregulates c-myc and induces cell proliferation", Oncogene 23: 5748-58, 2004.

Myers and Miller, "Optical Alignments in Linear Space", *CABIOS*, 4:11-17, 1988.

Naundorf, Preithner, Mayer, Lippold, Wolf, Hanakam, Fichtner, Kufer, Raum, Riethmuller, Baeuerle, Dreier. In vitro and in vivo activity of MT201, a fully human monoclonal antibody for pancarcinoma treatment. *Int J Cancer* 100: 101-10 (2002)

Needleman and Wunsch, "A General Method Applicable to the Search For Similarities in the Amino Acid Sequence of Two Proteins", *J. Mol. Biol.*, 48:443, 1970.

Neuberger and Milstein, "Somatic hypermutation," *Curr. Opin. Immunol.*, 7:248-254, 1995.

Nicaise, Valerio-Lepiniec, Minard, Desmadril, "Affinity transfer by CDR grafting on a nonimmunoglobulin scaffold", *Protein Sci.*, 13: 1882-1891, 2004.

Niwa, Shoji-Hosaka, Sakurada, Shinkawa, Uchida, Nakamura, Matsushima, Ueda, Hanai, Shitara. Defucosylated chimeric anti-CC chemokine receptor 4 IgG1 with enhanced antibody-dependent cellular cytotoxicity shows potent therapeutic activity to T-cell leukemia and lymphoma. *Cancer Res* 64: 2127-33 (2004)

Norderhaug, Olafsen, Michaelsen, Sandlie. Versatile vectors for transient and stable expression of recombinant antibody molecules in mammalian cells. *J Immunol Methods* 204: 77-87 (1997)

O'Brien et al., "A human colon cancer cell capable of initiating tumour growth in immunodeficient mice", Nature 445: 106-10, 2007.

Olsen, Duvic, Frankel, Kim, Martin, Vonderheid, Jegasothy, Wood, Gordon, Heald, Oseroff, Pinter-Brown, Bowen, Kuzel, Fivenson, Foss, Glode, Molina, Knobler, Stewar, Cooper, Stevens, Craig, Reuben, Bacha, Nichols. Pivotal phase III trial of two dose levels of denileukin diftitox for the treatment of cutaneous T-cell lymphoma. *J Clin Oncol* 19: 376-88 (2001)

Palmiter and Brinster, "Transgenic Mice", *Cell*, 41:343-345, 1985.

Palmiter, Norstedt, Gelinas, Hammer, Brinster, "Metallothionein-Human GH Fusion Genes Stimulate Growth of Mice", *Science*, 222:809-814, 1983.

Panina-Bordignon, Papi, Mariani, Di Lucia, Casoni, Bellettato, Buonsanti, Miotto, Mapp, Villa, Arrigoni, Fabbri, Sinigaglia. The C-C chemokine receptors CCR4 and CCR8 identify airway T cells of allergen-challenged atopic asthmatics. *J Clin Invest* 107: 1357-64 (2001)

Pearson and Lipman, "Improved tools for biological sequence analysis", *Proc. Natl. Acad. Sci. USA,* 85:2444-2448, 1988.

Pearson, "Rapid and sensitive sequence comparison with FASTP and FASTA", *Methods in Enzymology,* 183:63-98, 1990.

Perros, Hoogsteden, Coyle, Lambrecht, Hammad. Blockade of CCR4 in a humanized model of asthma reveals a critical role for DC-derived CCL17 and CCL22 in attracting Th2 cells and inducing airway inflammation. *Allergy* 64: 995-1002 (2009)

Prang, Preithner, Brischwein, Göster, Wöppel, Müller, Steiger, Peters, Baeuerle, da Silva, "Cellular and complement-dependent cytotoxicity of Ep-CAM-specific monoclonal antibody MT201 against breast cancer cell lines", Br J Cancer, 92(2):342-349, 2005.

Purandare, Wan, Somerville, Burke, Vaccaro, Yang, McIntyre, Poss. Core exploration in optimization of chemokine receptor CCR4 antagonists. *Bioorg Med Chem Lett* 17: 679-82 (2007)

Qiu, Wang, Cai, Wang, Yue, "Small antibody mimetics comprising two complementarity-determining regions and a framework region for tumor targeting|, *Nature Biotechnology*, 25(8): 921-929, 2007.

Reff and Heard, "A Review of Modifications to Recombinant Antibodies: Attempt to Increase Efficacy in Oncology Applications", *Critical Reviews in Oncology Hematology*, 40:25-35, 2001.

Reiter, Ulrich Brinkmann, Lee and Pastan, "Engineering Antibody Fv Fragments for Cancer Detection and Therapy: Disulfide-Stabilized Fv Fragments", *Nature Biotechnology*, 14:1239-1245, 1996.

Ruter, Barnett, Krycze, Brumlik, Daniel, Coukos, Zou, Curiel. Altering regulatory T cell function in cancer immunotherapy: a novel means to boost the efficacy of cancer vaccines. *Front Biosci* 14: 1761-70 (2009)

Schodin, Kranz. Binding affinity and inhibitory properties of a single-chain anti-T cell receptor antibody. *J Biol Chem* 268: 25722-7 (1993)

Schultz, Tanner, Hofmann, Emini, Condra, Jones, Kieff, Ellis, "Expression and Secretion in Yeast of a 400-Kda Envelope Glycoprotein Derived from Epstein-Barr Virus", *Gene,* 54:113-123, 1987.

Seed, "an LFA-3 Cdna Encodes a Phospholipid-Linked Membrane Protein Homologous to its Receptor CD2", *Nature,* 329:840, 1987.

Sinkar, White, Gordon, "Molecular Biology of Ri-Plasmid a Review", *J. Biosci (Bangalore)*, 11:47-58, 1987.

Smith and Waterman, "Comparison of Biosequences", *Adv. Appl. Math.,* 2:482, 1981.

Smith, Summers, Fraser, "Production of Human Beta Interferon in Insect Cells Infected With Baculovirus Expression Vector", *Mol. Cell Biol.,* 3:2156-2165, 1983.

Spizzo et al., "High Ep-CAM expression is associated with poor prognosis in node-positive breast cancer", Breast Cancer Res Treat 86: 207-13, 2004.

Spizzo et al., "Overexpression of epithelial cell adhesion molecule (Ep-CAM) is an independent prognostic marker for reduced survival of patients with epithelial ovarian cancer", Gynecol Oncol 103: 483-8, 2006.

Sui, Bai, St Clair Tallarico, Xu, Marasco. Identification of CD4 and transferrin receptor antibodies by CXCR4 antibody-guided Pathfinder selection. Eur. J. Biochem 270, 4497-4506 (2003)

Thompson, Higgins, Gibson, "CLUSTAL W: Improving the sensitivity of progressive multiple sequence alignment through sequence weighting, position-specific gap penalties and weight matrix choice", Nucleic Acids Res., 22:4673-4680, 1994.

van den Beucken, Neer, Sablon, Desmet, Celis, Hoogenboom, Hufton, "Building novel binding ligands to B7.1 and B7.2 based on human antibody single variable light chain domains", J. Mol. Biol., 310:591-601, 2001.

Varga et al., "Overexpression of epithelial cell adhesion molecule antigen in gallbladder carcinoma is an independent marker for poor survival", Clin Cancer Res 10: 3131-6, 2004.

Wagner, Milstein, Neuberger, "Codon bias targets mutation," Nature, 376:732, 1995.

Ward, Güssow, Griffiths, Jones, Winter, "Binding Activities of a Repertoire of Single Immunoglobulin Variable Domains Secreted from Escherichia Coli", Nature, 341 (6242):544-546, 1989.

Went et al., "Frequent high-level expression of the immunotherapeutic target Ep-CAM in colon, stomach, prostate and lung cancers", Br J Cancer 94: 128-35, 2006.

Yang, Huang, Huang, Pardoll. Persistent Toll-like receptor signals are required for reversal of regulatory T cell-mediated CD8 tolerance. Nat Immunol 5: 508-15 (2004)

Yokoyama, Ishikawa, Igarashi, Kawano, Masuda, Hamaguchi, Yamasaki, Koganemaru, Hattori, Miyazaki, Ogino, Matsumoto, Takeuchi, Ohta. (2009) Potent and orally bioavailable CCR4 antagonists: Synthesis and structure-activity relationship study of 2-aminoquinazolines. Bioorg Med Chem 17: 64-73 (2009)

Yokoyama, Ishikawa, Igarashi, Kawano, Masuda, Hattori, Miyazaki, Ogino, Orita, Matsumoto, Takeuchi, Ohta M. Potent CCR4 antagonists: synthesis, evaluation, and docking study of 2,4-diaminoquinazolines. Bioorg Med Chem 16: 7968-74 (2008)

Young, MacKenzie, Narang, Oomen and Baenziger, "Thermal Stabilization of a Single-Chain Fv Antibody Fragment by Introduction of a Disulphide Bond", FEBS Letters, 16396(377):135-139, 1995.

Zambryski, Herrera-Estreila, DeBlock, Van Montagu, Schell "Genetic Engineering, Principles and Methods", Hollaender and Setlow (eds.), Vol. VI, pp. 253-278, Plenum Press, New York, 1984.

Zapata, Ridgway, Mordenti, Osaka, Wong, Bennett, Carter, "Engineering Linear $F(Ab')_2$ Fragments For Efficient Production in Escherichia Coli and Enhanced Antiproliferative Activity", Protein Eng., 8(10):1057-1062, 1995.

Zhang, Gildersleeve, Yang, Xu, Loo, Uryu, Wong, Schultz, "A New Strategy for the Synthesis of Glycoproteins", Science, 303(5656): 371-373, 2004.

The invention claimed is:

1. An antibody which binds to human CC chemokine receptor 4 (CCR4) and which is capable of inhibiting the binding of macrophage-derived chemokine (MDC) and/or thymus and activation regulated chemokine (TARC) to CCR4, and which comprises at least one heavy chain variable region that comprises three CDRs and at least one light chain variable region that comprises three CDRs, wherein said heavy chain variable region comprises
(i) a variable heavy (VH) CDR1 that has the amino acid sequence of SEQ ID NO: 1,
(ii) a variable heavy (VH) CDR2 that has the amino acid sequence of SEQ ID NO: 2, and
(iii) a variable heavy (VH) CDR3 that has the amino acid sequence of SEQ ID NO: 20;
and wherein said light chain variable region of said antibody comprises:
(iv) a variable light (VL) CDR1 that has the amino acid sequence of SEQ ID NO: 22;
(v) a VL CDR2 that has the amino acid sequence of SEQ ID NO: 5; and
(vi) a VL CDR3 that has the amino acid sequence of SEQ ID NO: 24.

2. An antibody which binds to human CC chemokine receptor 4 (CCR4) and which is capable of inhibiting the binding of macrophage-derived chemokine (MDC) and/or thymus and activation regulated chemokine (TARC) to CCR4 wherein said antibody has a VH domain having the sequence of SEQ ID NO: 39 and/or a VL domain having the sequence of SEQ ID NO: 40.

3. An antibody according to claim 1, wherein said antibody is a fully human antibody.

4. The antibody according to claim 1, wherein said antibody is an IgG antibody.

5. The antibody according to claim 1, wherein said antibody has a glycosylation pattern which is beneficial for therapeutic application of the antibodies.

6. The antibody according to claim 1, wherein at least 10% of the total complex N-glycoside-linked sugar chains bound to the Fc region of said antibody are sugar chains in which fucose is not bound to N-acetylglucosamine in the reducing end in the sugar chain.

7. The antibody according to claim 1, wherein said antibody is an antigen binding fragment of an antibody.

8. The antibody according to claim 1, wherein said antibody is an antigen binding fragment of an antibody selected from a Fab', Fab, F(ab')$_2$, single domain antibody, TandAbs dimer, Fv, scFv, dsFv, ds-scFv, Fd, linear antibody, minibody, diabody, bispecific antibody fragment, bibody, tribody, sc-diabody, kappa(lamda) body, BiTE, DVD-Ig, SIP, SMIP or DART.

9. The antibody claim 1, wherein said antibody is attached to a therapeutic or diagnostic agent.

10. The antibody claim 1, wherein said antibody is attached to a therapeutic or diagnostic agent selected from a radiotherapeutic agent, chemotherapeutic agent, anti-angiogenic agent, apoptosis-inducing agent, anti-tubulin drug, anti-cellular or cytotoxic agent, steroid, cytokine antagonist, cytokine expression inhibitor, chemokine antagonist, chemokine expression inhibitor, anti-inflammatory corticosteroid or NSAIDs, coagulant or anti-viral agent.

11. A pharmaceutical composition comprising an antibody according to claim 1 and a pharmacologically acceptable excipient, diluent or carrier.

12. A pharmaceutical composition comprising an antibody according to claim 1 and a pharmacologically acceptable excipient, diluent or carrier, further comprising at least a second therapeutic agent.

13. The antibody according to claim 1, wherein said antibody is an IgG$_1$ antibody.

* * * * *

SEQUENCE LISTING

```
<160> NUMBER OF SEQ ID NOS: 133

<210> SEQ ID NO 1
<211> LENGTH: 5
<212> TYPE: PRT
<213> ORGANISM: Homo sapiens

<400> SEQUENCE: 1

Ser Tyr Ala Met Ser
1               5

<210> SEQ ID NO 2
<211> LENGTH: 17
<212> TYPE: PRT
<213> ORGANISM: Homo sapiens

<400> SEQUENCE: 2

Gly Ile Ile Pro Ile Phe Gly Thr Val Asn Tyr Ala Gln Lys Phe Gln
1               5                   10                  15

Gly

<210> SEQ ID NO 3
<211> LENGTH: 8
<212> TYPE: PRT
<213> ORGANISM: Homo sapiens

<400> SEQUENCE: 3

Arg Gly Gly Ser Tyr Phe Asp Tyr
1               5

<210> SEQ ID NO 4
<211> LENGTH: 13
<212> TYPE: PRT
<213> ORGANISM: Homo sapiens
```

<400> SEQUENCE: 4

Ser Gly Ser Thr Ser Asn Ile Gly Ser His Tyr Val Phe
1               5                   10

<210> SEQ ID NO 5
<211> LENGTH: 7
<212> TYPE: PRT
<213> ORGANISM: Homo sapiens

<400> SEQUENCE: 5

Arg Asn His Gln Arg Pro Ser
1               5

<210> SEQ ID NO 6
<211> LENGTH: 11
<212> TYPE: PRT
<213> ORGANISM: Homo sapiens

<400> SEQUENCE: 6

Ala Val Trp Asp Ala Lys Tyr Arg Gly Trp Val
1               5                   10

<210> SEQ ID NO 7
<211> LENGTH: 30
<212> TYPE: PRT
<213> ORGANISM: Homo sapiens

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser
            20                  25                  30

<210> SEQ ID NO 8
<211> LENGTH: 14
<212> TYPE: PRT
<213> ORGANISM: Homo sapiens

<400> SEQUENCE: 8

Trp Val Arg Gln Ala Pro Gly Gln Gly Leu Glu Trp Met Gly
1               5                   10

<210> SEQ ID NO 9
<211> LENGTH: 32
<212> TYPE: PRT
<213> ORGANISM: Homo sapiens

<400> SEQUENCE: 9

Arg Val Thr Met Thr Arg Asp Thr Ser Thr Ser Thr Val Tyr Met Glu
1               5                   10                  15

Leu Ser Ser Leu Arg Ser Asp Asp Thr Ala Val Tyr Tyr Cys Ala Arg
            20                  25                  30

<210> SEQ ID NO 10
<211> LENGTH: 11
<212> TYPE: PRT
<213> ORGANISM: Homo sapiens

<400> SEQUENCE: 10

Trp Gly Gln Gly Thr Leu Val Thr Val Ser Ser
1               5                   10

<210> SEQ ID NO 11

```
<211> LENGTH: 21
<212> TYPE: PRT
<213> ORGANISM: Homo sapiens

<400> SEQUENCE: 11

Lys Leu Ser Gly Ser Ala Ser Ala Pro Lys Leu Glu Glu Gly Glu Phe
1               5                   10                  15

Ser Glu Ala Arg Val
            20

<210> SEQ ID NO 12
<211> LENGTH: 22
<212> TYPE: PRT
<213> ORGANISM: Homo sapiens

<400> SEQUENCE: 12

Ser Tyr Val Leu Thr Gln Pro Pro Ser Ala Ser Gly Thr Pro Gly Gln
1               5                   10                  15

Ser Val Thr Ile Ser Cys
            20

<210> SEQ ID NO 13
<211> LENGTH: 15
<212> TYPE: PRT
<213> ORGANISM: Homo sapiens

<400> SEQUENCE: 13

Trp Tyr Gln Gln Leu Pro Gly Thr Ala Pro Arg Leu Leu Ile Tyr
1               5                   10                  15

<210> SEQ ID NO 14
<211> LENGTH: 32
<212> TYPE: PRT
<213> ORGANISM: Homo sapiens

<400> SEQUENCE: 14

Gly Val Pro Asp Arg Leu Ser Gly Ser Lys Ser Gly Thr Ser Ala Ser
1               5                   10                  15

Leu Ala Ile Ser Gly Leu Arg Ser Glu Asp Glu Ala Asp Tyr Tyr Cys
            20                  25                  30

<210> SEQ ID NO 15
<211> LENGTH: 10
<212> TYPE: PRT
<213> ORGANISM: Homo sapiens

<400> SEQUENCE: 15

Phe Gly Gly Gly Thr Lys Leu Thr Val Leu
1               5                   10

<210> SEQ ID NO 16
<211> LENGTH: 32
<212> TYPE: PRT
<213> ORGANISM: Homo sapiens

<400> SEQUENCE: 16

Arg Val Thr Met Thr Arg Asp Thr Ser Thr Ser Thr Val Tyr Met Glu
1               5                   10                  15

Leu Ser Ser Leu Arg Pro Asp Asp Thr Ala Val Tyr Tyr Cys Ala Arg
            20                  25                  30

<210> SEQ ID NO 17
<211> LENGTH: 13
```

```
<212> TYPE: PRT
<213> ORGANISM: Homo sapiens

<400> SEQUENCE: 17

Ser Gly Ser Thr Ser Asn Ile Gly Ser His Tyr Val Ser
1               5                   10

<210> SEQ ID NO 18
<211> LENGTH: 32
<212> TYPE: PRT
<213> ORGANISM: Homo sapiens

<400> SEQUENCE: 18

Arg Val Thr Met Thr Arg Asp Thr Ser Thr Ser Thr Val Tyr Met Glu
1               5                   10                  15

Leu Ser Ser Leu Arg Pro Asp Asp Thr Ala Val Tyr Tyr Cys Ala Arg
            20                  25                  30

<210> SEQ ID NO 19
<211> LENGTH: 30
<212> TYPE: PRT
<213> ORGANISM: Homo sapiens

<400> SEQUENCE: 19

Gln Val Gln Leu Val Gln Ser Gly Ala Glu Val Lys Lys Pro Gly Ser
1               5                   10                  15

Ser Val Lys Val Ser Cys Lys Ala Ser Glu Gly Thr Phe Ser
            20                  25                  30

<210> SEQ ID NO 20
<211> LENGTH: 8
<212> TYPE: PRT
<213> ORGANISM: Homo sapiens

<400> SEQUENCE: 20

Arg Arg Gly Ala Lys Phe Asp Tyr
1               5

<210> SEQ ID NO 21
<211> LENGTH: 22
<212> TYPE: PRT
<213> ORGANISM: Homo sapiens

<400> SEQUENCE: 21

Ser Tyr Val Leu Thr Gln Gln Pro Ser Ala Ser Gly Thr Pro Gly Gln
1               5                   10                  15

Ser Val Thr Ile Ser Cys
            20

<210> SEQ ID NO 22
<211> LENGTH: 13
<212> TYPE: PRT
<213> ORGANISM: Homo sapiens

<400> SEQUENCE: 22

Ser Gly Ser Thr Ser Asn Ile Gly Ser His Tyr Val Val
1               5                   10

<210> SEQ ID NO 23
<211> LENGTH: 32
<212> TYPE: PRT
<213> ORGANISM: Homo sapiens

<400> SEQUENCE: 23
```

```
Gly Val Pro Asp Arg Leu Ser Gly Ser Lys Ser Gly Thr Ser Ala Ser
1               5                   10                  15

Leu Ala Ile Gly Gly Leu Arg Ser Glu Asp Glu Ala Asp Tyr Tyr Cys
            20                  25                  30
```

<210> SEQ ID NO 24
<211> LENGTH: 11
<212> TYPE: PRT
<213> ORGANISM: Homo sapiens

<400> SEQUENCE: 24

```
Ala Val Trp Asp Asp Thr Leu Ser Gly Trp Val
1               5                   10
```

<210> SEQ ID NO 25
<211> LENGTH: 22
<212> TYPE: PRT
<213> ORGANISM: Homo sapiens

<400> SEQUENCE: 25

```
Ser Tyr Val Leu Thr Gln Pro Pro Ser Ala Ser Gly Thr Pro Gly Gln
1               5                   10                  15

Ser Val Thr Ile Ser Cys
            20
```

<210> SEQ ID NO 26
<211> LENGTH: 5
<212> TYPE: PRT
<213> ORGANISM: Homo sapiens

<400> SEQUENCE: 26

```
Ser Tyr Ala Ile Ser
1               5
```

<210> SEQ ID NO 27
<211> LENGTH: 17
<212> TYPE: PRT
<213> ORGANISM: Homo sapiens

<400> SEQUENCE: 27

```
Gly Ile Ile Pro Ile Phe Gly Thr Ala Asn Tyr Ala Gln Lys Phe Gln
1               5                   10                  15

Gly
```

<210> SEQ ID NO 28
<211> LENGTH: 32
<212> TYPE: PRT
<213> ORGANISM: Homo sapiens

<400> SEQUENCE: 28

```
Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30
```

<210> SEQ ID NO 29
<211> LENGTH: 117
<212> TYPE: PRT
<213> ORGANISM: Homo sapiens

<400> SEQUENCE: 29

```
Gln Val Gln Leu Val Gln Ser Gly Ala Glu Val Lys Lys Pro Gly Ser
```

```
                1               5                  10                 15
Ser Val Lys Val Ser Cys Lys Ala Ser Gly Gly Thr Phe Ser Ser Tyr
                20                 25                 30

Ala Met Ser Trp Val Arg Gln Ala Pro Gly Gln Gly Leu Glu Trp Met
                35                 40                 45

Gly Gly Ile Ile Pro Ile Phe Gly Thr Val Asn Tyr Ala Gln Lys Phe
                50                 55                 60

Gln Gly Arg Val Thr Met Thr Arg Asp Thr Ser Thr Ser Thr Val Tyr
 65                 70                 75                 80

Met Glu Leu Ser Ser Leu Arg Ser Asp Asp Thr Ala Val Tyr Tyr Cys
                85                 90                 95

Ala Arg Arg Gly Gly Ser Tyr Phe Asp Tyr Trp Gly Gln Gly Thr Leu
                100                105                110

Val Thr Val Ser Ser
                115
```

<210> SEQ ID NO 30
<211> LENGTH: 110
<212> TYPE: PRT
<213> ORGANISM: Homo sapiens

<400> SEQUENCE: 30

```
Ser Tyr Val Leu Thr Gln Pro Pro Ser Ala Ser Gly Thr Pro Gly Gln
 1               5                  10                 15

Ser Val Thr Ile Ser Cys Ser Gly Ser Thr Ser Asn Ile Gly Ser His
                20                 25                 30

Tyr Val Phe Trp Tyr Gln Gln Leu Pro Gly Thr Ala Pro Arg Leu Leu
                35                 40                 45

Ile Tyr Arg Asn His Gln Arg Pro Ser Gly Val Pro Asp Arg Leu Ser
                50                 55                 60

Gly Ser Lys Ser Gly Thr Ser Ala Ser Leu Ala Ile Ser Gly Leu Arg
 65                 70                 75                 80

Ser Glu Asp Glu Ala Asp Tyr Tyr Cys Ala Val Trp Asp Ala Lys Tyr
                85                 90                 95

Arg Gly Trp Val Phe Gly Gly Gly Thr Lys Leu Thr Val Leu
                100                105                110
```

<210> SEQ ID NO 31
<211> LENGTH: 117
<212> TYPE: PRT
<213> ORGANISM: Homo sapiens

<400> SEQUENCE: 31

```
Gln Val Gln Leu Val Gln Ser Gly Ala Glu Val Lys Lys Pro Gly Ser
 1               5                  10                 15

Ser Val Lys Val Ser Cys Lys Ala Ser Gly Gly Thr Phe Ser Ser Tyr
                20                 25                 30

Ala Met Ser Trp Val Arg Gln Ala Pro Gly Gln Gly Leu Glu Trp Met
                35                 40                 45

Gly Gly Ile Ile Pro Ile Phe Gly Thr Val Asn Tyr Ala Gln Lys Phe
                50                 55                 60

Gln Gly Arg Val Thr Met Thr Arg Asp Thr Ser Thr Ser Thr Val Tyr
 65                 70                 75                 80

Met Glu Leu Ser Ser Leu Arg Pro Asp Asp Thr Ala Val Tyr Tyr Cys
                85                 90                 95

Ala Arg Arg Gly Gly Ser Tyr Phe Asp Tyr Trp Gly Gln Gly Thr Leu
```

```
                   100                 105                 110

Val Thr Val Ser Ser
        115

<210> SEQ ID NO 32
<211> LENGTH: 110
<212> TYPE: PRT
<213> ORGANISM: Homo sapiens

<400> SEQUENCE: 32

Ser Tyr Val Leu Thr Gln Pro Pro Ser Ala Ser Gly Thr Pro Gly Gln
1               5                   10                  15

Ser Val Thr Ile Ser Cys Ser Gly Ser Thr Ser Asn Ile Gly Ser His
            20                  25                  30

Tyr Val Ser Trp Tyr Gln Gln Leu Pro Gly Thr Ala Pro Arg Leu Leu
        35                  40                  45

Ile Tyr Arg Asn His Gln Arg Pro Ser Gly Val Pro Asp Arg Leu Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Val Trp Asp Ala Lys Tyr
                85                  90                  95

Arg Gly Trp Val Phe Gly Gly Gly Thr Lys Leu Thr Val Leu
            100                 105                 110

<210> SEQ ID NO 33
<211> LENGTH: 117
<212> TYPE: PRT
<213> ORGANISM: Homo sapiens

<400> SEQUENCE: 33

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Met Ser Trp Val Arg Gln Ala Pro Gly Gln Gly Leu Glu Trp Met
        35                  40                  45

Gly Gly Ile Ile Pro Ile Phe Gly Thr Val Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Pro Asp Asp Thr Ala Val Tyr Tyr Cys
                85                  90                  95

Ala Arg Arg Gly Gly Ser Tyr Phe Asp Tyr Trp Gly Gln Gly Thr Leu
            100                 105                 110

Val Thr Val Ser Ser
        115

<210> SEQ ID NO 34
<211> LENGTH: 110
<212> TYPE: PRT
<213> ORGANISM: Homo sapiens

<400> SEQUENCE: 34

Ser Tyr Val Leu Thr Gln Pro Pro Ser Ala Ser Gly Thr Pro Gly Gln
1               5                   10                  15

Ser Val Thr Ile Ser Cys Ser Gly Ser Thr Ser Asn Ile Gly Ser His
            20                  25                  30
```

```
Tyr Val Phe Trp Tyr Gln Gln Leu Pro Gly Thr Ala Pro Arg Leu Leu
            35                  40                  45

Ile Tyr Arg Asn His Gln Arg Pro Ser Gly Val Pro Asp Arg Leu Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Val Trp Asp Ala Lys Tyr
                85                  90                  95

Arg Gly Trp Val Phe Gly Gly Gly Thr Lys Leu Thr Val Leu
                100                 105                 110

<210> SEQ ID NO 35
<211> LENGTH: 117
<212> TYPE: PRT
<213> ORGANISM: Homo sapiens

<400> SEQUENCE: 35

Gln Val Gln Leu Val Gln Ser Gly Ala Glu Val Lys Lys Pro Gly Ser
1               5                   10                  15

Ser Val Lys Val Ser Cys Lys Ala Ser Glu Gly Thr Phe Ser Ser Tyr
                20                  25                  30

Ala Met Ser Trp Val Arg Gln Ala Pro Gly Gln Gly Leu Glu Trp Met
            35                  40                  45

Gly Gly Ile Ile Pro Ile Phe Gly Thr Val Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Asp Asp Thr Ala Val Tyr Tyr Cys
                85                  90                  95

Ala Arg Arg Gly Gly Ser Tyr Phe Asp Tyr Trp Gly Gln Gly Thr Leu
                100                 105                 110

Val Thr Val Ser Ser
            115

<210> SEQ ID NO 36
<211> LENGTH: 110
<212> TYPE: PRT
<213> ORGANISM: Homo sapiens

<400> SEQUENCE: 36

Ser Tyr Val Leu Thr Gln Pro Pro Ser Ala Ser Gly Thr Pro Gly Gln
1               5                   10                  15

Ser Val Thr Ile Ser Cys Ser Gly Ser Thr Ser Asn Ile Gly Ser His
                20                  25                  30

Tyr Val Ser Trp Tyr Gln Gln Leu Pro Gly Thr Ala Pro Arg Leu Leu
            35                  40                  45

Ile Tyr Arg Asn His Gln Arg Pro Ser Gly Val Pro Asp Arg Leu Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Val Trp Asp Ala Lys Tyr
                85                  90                  95

Arg Gly Trp Val Phe Gly Gly Gly Thr Lys Leu Thr Val Leu
                100                 105                 110

<210> SEQ ID NO 37
```

<211> LENGTH: 117
<212> TYPE: PRT
<213> ORGANISM: Homo sapiens

<400> SEQUENCE: 37

```
Gln Val Gln Leu Val Gln Ser Gly Ala Glu Val Lys Lys Pro Gly Ser
1               5                   10                  15

Ser Val Lys Val Ser Cys Lys Ala Ser Glu Gly Thr Phe Ser Ser Tyr
            20                  25                  30

Ala Met Ser Trp Val Arg Gln Ala Pro Gly Gln Gly Leu Glu Trp Met
        35                  40                  45

Gly Gly Ile Ile Pro Ile Phe Gly Thr Val Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Asp Asp Thr Ala Val Tyr Tyr Cys
                85                  90                  95

Ala Arg Arg Arg Gly Ala Lys Phe Asp Tyr Trp Gly Gln Gly Thr Leu
            100                 105                 110

Val Thr Val Ser Ser
        115
```

<210> SEQ ID NO 38
<211> LENGTH: 110
<212> TYPE: PRT
<213> ORGANISM: Homo sapiens

<400> SEQUENCE: 38

```
Ser Tyr Val Leu Thr Gln Gln Pro Ser Ala Ser Gly Thr Pro Gly Gln
1               5                   10                  15

Ser Val Thr Ile Ser Cys Ser Gly Ser Thr Ser Asn Ile Gly Ser His
            20                  25                  30

Tyr Val Val Trp Tyr Gln Gln Leu Pro Gly Thr Ala Pro Arg Leu Leu
        35                  40                  45

Ile Tyr Arg Asn His Gln Arg Pro Ser Gly Val Pro Asp Arg Leu Ser
    50                  55                  60

Gly Ser Lys Ser Gly Thr Ser Ala Ser Leu Ala Ile Gly Gly Leu Arg
65                  70                  75                  80

Ser Glu Asp Glu Ala Asp Tyr Tyr Cys Ala Val Trp Asp Asp Thr Leu
                85                  90                  95

Ser Gly Trp Val Phe Gly Gly Gly Thr Lys Leu Thr Val Leu
            100                 105                 110
```

<210> SEQ ID NO 39
<211> LENGTH: 117
<212> TYPE: PRT
<213> ORGANISM: Homo sapiens

<400> SEQUENCE: 39

```
Gln Val Gln Leu Val Gln Ser Gly Ala Glu Val Lys Lys Pro Gly Ser
1               5                   10                  15

Ser Val Lys Val Ser Cys Lys Ala Ser Glu Gly Thr Phe Ser Ser Tyr
            20                  25                  30

Ala Met Ser Trp Val Arg Gln Ala Pro Gly Gln Gly Leu Glu Trp Met
        35                  40                  45

Gly Gly Ile Ile Pro Ile Phe Gly Thr Val Asn Tyr Ala Gln Lys Phe
    50                  55                  60
```

```
Gln Gly Arg Val Thr Met Thr Arg Asp Thr Ser Thr Ser Thr Val Tyr
 65                  70                  75                  80

Met Glu Leu Ser Ser Leu Arg Ser Asp Asp Thr Ala Val Tyr Tyr Cys
                 85                  90                  95

Ala Arg Arg Arg Gly Ala Lys Phe Asp Tyr Trp Gly Gln Gly Thr Leu
            100                 105                 110

Val Thr Val Ser Ser
        115

<210> SEQ ID NO 40
<211> LENGTH: 110
<212> TYPE: PRT
<213> ORGANISM: Homo sapiens

<400> SEQUENCE: 40

Ser Tyr Val Leu Thr Gln Pro Pro Ser Ala Ser Gly Thr Pro Gly Gln
 1               5                  10                  15

Ser Val Thr Ile Ser Cys Ser Gly Ser Thr Ser Asn Ile Gly Ser His
             20                  25                  30

Tyr Val Val Trp Tyr Gln Gln Leu Pro Gly Thr Ala Pro Arg Leu Leu
         35                  40                  45

Ile Tyr Arg Asn His Gln Arg Pro Ser Gly Val Pro Asp Arg Leu Ser
 50                  55                  60

Gly Ser Lys Ser Gly Thr Ser Ala Ser Leu Ala Ile Gly Gly Leu Arg
 65                  70                  75                  80

Ser Glu Asp Glu Ala Asp Tyr Tyr Cys Ala Val Trp Asp Asp Thr Leu
                 85                  90                  95

Ser Gly Trp Val Phe Gly Gly Gly Thr Lys Leu Thr Val Leu
            100                 105                 110

<210> SEQ ID NO 41
<211> LENGTH: 117
<212> TYPE: PRT
<213> ORGANISM: Homo sapiens

<400> SEQUENCE: 41

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
             20                  25                  30

Ala Met Ser Trp Val Arg Gln Ala Pro Gly Gln Gly Leu Glu Trp Met
         35                  40                  45

Gly Gly Ile Ile Pro Ile Phe Gly Thr Val Asn Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Asp Asp Thr Ala Val Tyr Tyr Cys
                 85                  90                  95

Ala Arg Arg Arg Gly Ala Lys Phe Asp Tyr Trp Gly Gln Gly Thr Leu
            100                 105                 110

Val Thr Val Ser Ser
        115

<210> SEQ ID NO 42
<211> LENGTH: 109
<212> TYPE: PRT
<213> ORGANISM: Homo sapiens
```

```
<400> SEQUENCE: 42

Ser Tyr Val Leu Thr Gln Pro Ser Ala Ser Gly Thr Pro Gly Gln
1               5                   10                  15

Ser Val Thr Ile Ser Cys Ser Gly Ser Thr Ser Asn Ile Gly Ser His
            20                  25                  30

Tyr Val Val Trp Tyr Gln Gln Leu Pro Gly Thr Ala Pro Arg Leu Leu
        35                  40                  45

Ile Tyr Arg Asn His Gln Arg Pro Ser Gly Val Pro Asp Arg Leu Ser
    50                  55                  60

Gly Ser Lys Ser Gly Thr Ser Ala Ser Leu Ala Ile Gly Gly Leu Arg
65                  70                  75                  80

Ser Glu Asp Glu Ala Asp Tyr Tyr Cys Ala Val Trp Asp Asp Thr Leu
                85                  90                  95

Ser Gly Trp Val Phe Gly Gly Gly Thr Lys Leu Thr Val
            100                 105

<210> SEQ ID NO 43
<211> LENGTH: 117
<212> TYPE: PRT
<213> ORGANISM: Homo sapiens

<400> SEQUENCE: 43

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Met Ser Trp Val Arg Gln Ala Pro Gly Gln Gly Leu Glu Trp Met
        35                  40                  45

Gly Gly Ile Ile Pro Ile Phe Gly Thr Val Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Asp Asp Thr Ala Val Tyr Tyr Cys
                85                  90                  95

Ala Arg Arg Arg Gly Ala Lys Phe Asp Tyr Trp Gly Gln Gly Thr Leu
            100                 105                 110

Val Thr Val Ser Ser
        115

<210> SEQ ID NO 44
<211> LENGTH: 110
<212> TYPE: PRT
<213> ORGANISM: Homo sapiens

<400> SEQUENCE: 44

Ser Tyr Val Leu Thr Gln Pro Ser Ala Ser Gly Thr Pro Gly Gln
1               5                   10                  15

Ser Val Thr Ile Ser Cys Ser Gly Ser Thr Ser Asn Ile Gly Ser His
            20                  25                  30

Tyr Val Val Trp Tyr Gln Gln Leu Pro Gly Thr Ala Pro Arg Leu Leu
        35                  40                  45

Ile Tyr Arg Asn His Gln Arg Pro Ser Gly Val Pro Asp Arg Leu Ser
    50                  55                  60

Gly Ser Lys Ser Gly Thr Ser Ala Ser Leu Ala Ile Gly Gly Leu Arg
65                  70                  75                  80

Ser Glu Asp Glu Ala Asp Tyr Tyr Cys Ala Val Trp Asp Asp Thr Leu
```

```
                    85                  90                  95

Ser Gly Trp Val Phe Gly Gly Gly Thr Lys Leu Thr Val Leu
                100                 105                 110

<210> SEQ ID NO 45
<211> LENGTH: 117
<212> TYPE: PRT
<213> ORGANISM: Homo sapiens

<400> SEQUENCE: 45

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Arg Gly Ala Lys Phe Asp Tyr Trp Gly Gln Gly Thr Leu
                100                 105                 110

Val Thr Val Ser Ser
            115

<210> SEQ ID NO 46
<211> LENGTH: 110
<212> TYPE: PRT
<213> ORGANISM: Homo sapiens

<400> SEQUENCE: 46

Ser Tyr Val Leu Thr Gln Pro Pro Ser Ala Ser Gly Thr Pro Gly Gln
1               5                   10                  15

Ser Val Thr Ile Ser Cys Ser Gly Ser Thr Ser Asn Ile Gly Ser His
                20                  25                  30

Tyr Val Val Trp Tyr Gln Gln Leu Pro Gly Thr Ala Pro Arg Leu Leu
            35                  40                  45

Ile Tyr Arg Asn His Gln Arg Pro Ser Gly Val Pro Asp Arg Leu Ser
        50                  55                  60

Gly Ser Lys Ser Gly Thr Ser Ala Ser Leu Ala Ile Gly Gly Leu Arg
65                  70                  75                  80

Ser Glu Asp Glu Ala Asp Tyr Tyr Cys Ala Val Trp Asp Asp Thr Leu
                85                  90                  95

Ser Gly Trp Val Phe Gly Gly Gly Thr Lys Leu Thr Val Leu
                100                 105                 110

<210> SEQ ID NO 47
<211> LENGTH: 248
<212> TYPE: PRT
<213> ORGANISM: Homo sapiens

<400> SEQUENCE: 47

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30
```

Ala Met Ser Trp Val Arg Gln Ala Pro Gly Gln Gly Leu Glu Trp Met
            35                  40                  45

Gly Gly Ile Ile Pro Ile Phe Gly Thr Val Asn Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Asp Asp Thr Ala Val Tyr Tyr Cys
                85                  90                  95

Ala Arg Arg Gly Gly Ser Tyr Phe Asp Tyr Trp Gly Gln Gly Thr Leu
                100                 105                 110

Val Thr Val Ser Ser Lys Leu Ser Gly Ser Ala Ser Ala Pro Lys Leu
            115                 120                 125

Glu Glu Gly Glu Phe Ser Glu Ala Arg Val Ser Tyr Val Leu Thr Gln
130                 135                 140

Pro Pro Ser Ala Ser Gly Thr Pro Gly Gln Ser Val Thr Ile Ser Cys
145                 150                 155                 160

Ser Gly Ser Thr Ser Asn Ile Gly Ser His Tyr Val Phe Trp Tyr Gln
                165                 170                 175

Gln Leu Pro Gly Thr Ala Pro Arg Leu Leu Ile Tyr Arg Asn His Gln
                180                 185                 190

Arg Pro Ser Gly Val Pro Asp Arg Leu Ser Gly Ser Lys Ser Gly Thr
            195                 200                 205

Ser Ala Ser Leu Ala Ile Ser Gly Leu Arg Ser Glu Asp Glu Ala Asp
210                 215                 220

Tyr Tyr Cys Ala Val Trp Asp Ala Lys Tyr Arg Gly Trp Val Phe Gly
225                 230                 235                 240

Gly Gly Thr Lys Leu Thr Val Leu
                245

<210> SEQ ID NO 48
<211> LENGTH: 248
<212> TYPE: PRT
<213> ORGANISM: Homo sapiens

<400> SEQUENCE: 48

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Met Ser Trp Val Arg Gln Ala Pro Gly Gln Gly Leu Glu Trp Met
            35                  40                  45

Gly Gly Ile Ile Pro Ile Phe Gly Thr Val Asn Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Pro Asp Asp Thr Ala Val Tyr Tyr Cys
                85                  90                  95

Ala Arg Arg Gly Gly Ser Tyr Phe Asp Tyr Trp Gly Gln Gly Thr Leu
                100                 105                 110

Val Thr Val Ser Ser Lys Leu Ser Gly Ser Ala Ser Ala Pro Lys Leu
            115                 120                 125

Glu Glu Gly Glu Phe Ser Glu Ala Arg Val Ser Tyr Val Leu Thr Gln
130                 135                 140

Pro Pro Ser Ala Ser Gly Thr Pro Gly Gln Ser Val Thr Ile Ser Cys

```
                   145                 150                 155                 160
        Ser Gly Ser Thr Ser Asn Ile Gly Ser His Tyr Val Ser Trp Tyr Gln
                        165                 170                 175

Gln Leu Pro Gly Thr Ala Pro Arg Leu Leu Ile Tyr Arg Asn His Gln
                        180                 185                 190

Arg Pro Ser Gly Val Pro Asp Arg Leu Ser Gly Ser Lys Ser Gly Thr
                        195                 200                 205

Ser Ala Ser Leu Ala Ile Ser Gly Leu Arg Ser Glu Asp Glu Ala Asp
                        210                 215                 220

Tyr Tyr Cys Ala Val Trp Asp Ala Lys Tyr Arg Gly Trp Val Phe Gly
        225                 230                 235                 240

Gly Gly Thr Lys Leu Thr Val Leu
                        245

<210> SEQ ID NO 49
<211> LENGTH: 248
<212> TYPE: PRT
<213> ORGANISM: Homo sapiens

<400> SEQUENCE: 49

Gln Val Gln Leu Val Gln Ser Gly Ala Glu Val Lys Lys Pro Gly Ser
        1               5                   10                  15

Ser Val Lys Val Ser Cys Lys Ala Ser Gly Gly Thr Phe Ser Ser Tyr
                        20                  25                  30

Ala Met Ser Trp Val Arg Gln Ala Pro Gly Gln Gly Leu Glu Trp Met
                        35                  40                  45

Gly Gly Ile Ile Pro Ile Phe Gly Thr Val Asn Tyr Ala Gln Lys Phe
                50                  55                  60

Gln Gly Arg Val Thr Met Thr Arg Asp Thr Ser Thr Ser Thr Val Tyr
        65                  70                  75                  80

Met Glu Leu Ser Ser Leu Arg Pro Asp Thr Ala Val Tyr Tyr Cys
                        85                  90                  95

Ala Arg Arg Gly Gly Ser Tyr Phe Asp Tyr Trp Gly Gln Gly Thr Leu
                        100                 105                 110

Val Thr Val Ser Ser Lys Leu Ser Gly Ser Ala Ser Ala Pro Lys Leu
                        115                 120                 125

Glu Glu Gly Glu Phe Ser Glu Ala Arg Val Ser Tyr Val Leu Thr Gln
                        130                 135                 140

Pro Pro Ser Ala Ser Gly Thr Pro Gly Gln Ser Val Thr Ile Ser Cys
        145                 150                 155                 160

Ser Gly Ser Thr Ser Asn Ile Gly Ser His Tyr Val Phe Trp Tyr Gln
                        165                 170                 175

Gln Leu Pro Gly Thr Ala Pro Arg Leu Leu Ile Tyr Arg Asn His Gln
                        180                 185                 190

Arg Pro Ser Gly Val Pro Asp Arg Leu Ser Gly Ser Lys Ser Gly Thr
                        195                 200                 205

Ser Ala Ser Leu Ala Ile Ser Gly Leu Arg Ser Glu Asp Glu Ala Asp
                        210                 215                 220

Tyr Tyr Cys Ala Val Trp Asp Ala Lys Tyr Arg Gly Trp Val Phe Gly
        225                 230                 235                 240

Gly Gly Thr Lys Leu Thr Val Leu
                        245

<210> SEQ ID NO 50
<211> LENGTH: 248
```

```
<212> TYPE: PRT
<213> ORGANISM: Homo sapiens

<400> SEQUENCE: 50

Gln Val Gln Leu Val Gln Ser Gly Ala Glu Val Lys Lys Pro Gly Ser
1               5                   10                  15

Ser Val Lys Val Ser Cys Lys Ala Ser Glu Gly Thr Phe Ser Ser Tyr
            20                  25                  30

Ala Met Ser Trp Val Arg Gln Ala Pro Gly Gln Gly Leu Glu Trp Met
        35                  40                  45

Gly Gly Ile Ile Pro Ile Phe Gly Thr Val Asn Tyr Ala Gln Lys Phe
    50                  55                  60

Gln Gly Arg Val Thr Met Thr Arg Asp Thr Ser Ser Thr Val Tyr
65                  70                  75                  80

Met Glu Leu Ser Ser Leu Arg Ser Asp Asp Thr Ala Val Tyr Tyr Cys
                85                  90                  95

Ala Arg Arg Gly Gly Ser Tyr Phe Asp Tyr Trp Gly Gln Gly Thr Leu
            100                 105                 110

Val Thr Val Ser Ser Lys Leu Ser Gly Ser Ala Ser Ala Pro Lys Leu
        115                 120                 125

Glu Glu Gly Glu Phe Ser Glu Ala Arg Val Ser Tyr Val Leu Thr Gln
    130                 135                 140

Pro Pro Ser Ala Ser Gly Thr Pro Gly Gln Ser Val Thr Ile Ser Cys
145                 150                 155                 160

Ser Gly Ser Thr Ser Asn Ile Gly Ser His Tyr Val Ser Trp Tyr Gln
                165                 170                 175

Gln Leu Pro Gly Thr Ala Pro Arg Leu Leu Ile Tyr Arg Asn His Gln
            180                 185                 190

Arg Pro Ser Gly Val Pro Asp Arg Leu Ser Gly Ser Lys Ser Gly Thr
        195                 200                 205

Ser Ala Ser Leu Ala Ile Ser Gly Leu Arg Ser Glu Asp Glu Ala Asp
    210                 215                 220

Tyr Tyr Cys Ala Val Trp Asp Ala Lys Tyr Arg Gly Trp Val Phe Gly
225                 230                 235                 240

Gly Gly Thr Lys Leu Thr Val Leu
                245

<210> SEQ ID NO 51
<211> LENGTH: 248
<212> TYPE: PRT
<213> ORGANISM: Homo sapiens

<400> SEQUENCE: 51

Gln Val Gln Leu Val Gln Ser Gly Ala Glu Val Lys Lys Pro Gly Ser
1               5                   10                  15

Ser Val Lys Val Ser Cys Lys Ala Ser Glu Gly Thr Phe Ser Ser Tyr
            20                  25                  30

Ala Met Ser Trp Val Arg Gln Ala Pro Gly Gln Gly Leu Glu Trp Met
        35                  40                  45

Gly Gly Ile Ile Pro Ile Phe Gly Thr Val Asn Tyr Ala Gln Lys Phe
    50                  55                  60

Gln Gly Arg Val Thr Met Thr Arg Asp Thr Ser Ser Thr Val Tyr
65                  70                  75                  80

Met Glu Leu Ser Ser Leu Arg Ser Asp Asp Thr Ala Val Tyr Tyr Cys
                85                  90                  95
```

```
Ala Arg Arg Arg Gly Ala Lys Phe Asp Tyr Trp Gly Gln Gly Thr Leu
            100                 105                 110

Val Thr Val Ser Ser Lys Leu Ser Gly Ser Ala Ser Ala Pro Lys Leu
        115                 120                 125

Glu Glu Gly Glu Phe Ser Glu Ala Arg Val Ser Tyr Val Leu Thr Gln
    130                 135                 140

Gln Pro Ser Ala Ser Gly Thr Pro Gly Gln Ser Val Thr Ile Ser Cys
145                 150                 155                 160

Ser Gly Ser Thr Ser Asn Ile Gly Ser His Tyr Val Val Trp Tyr Gln
                165                 170                 175

Gln Leu Pro Gly Thr Ala Pro Arg Leu Leu Ile Tyr Arg Asn His Gln
            180                 185                 190

Arg Pro Ser Gly Val Pro Asp Arg Leu Ser Gly Ser Lys Ser Gly Thr
        195                 200                 205

Ser Ala Ser Leu Ala Ile Gly Gly Leu Arg Ser Glu Asp Glu Ala Asp
    210                 215                 220

Tyr Tyr Cys Ala Val Trp Asp Asp Thr Leu Ser Gly Trp Val Phe Gly
225                 230                 235                 240

Gly Gly Thr Lys Leu Thr Val Leu
                245

<210> SEQ ID NO 52
<211> LENGTH: 248
<212> TYPE: PRT
<213> ORGANISM: Homo sapiens

<400> SEQUENCE: 52

Gln Val Gln Leu Val Gln Ser Gly Ala Glu Val Lys Lys Pro Gly Ser
1               5                   10                  15

Ser Val Lys Val Ser Cys Lys Ala Ser Glu Gly Thr Phe Ser Ser Tyr
            20                  25                  30

Ala Met Ser Trp Val Arg Gln Ala Pro Gly Gln Gly Leu Glu Trp Met
        35                  40                  45

Gly Gly Ile Ile Pro Ile Phe Gly Thr Val Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Asp Asp Thr Ala Val Tyr Tyr Cys
                85                  90                  95

Ala Arg Arg Arg Gly Ala Lys Phe Asp Tyr Trp Gly Gln Gly Thr Leu
            100                 105                 110

Val Thr Val Ser Ser Lys Leu Ser Gly Ser Ala Ser Ala Pro Lys Leu
        115                 120                 125

Glu Glu Gly Glu Phe Ser Glu Ala Arg Val Ser Tyr Val Leu Thr Gln
    130                 135                 140

Pro Pro Ser Ala Ser Gly Thr Pro Gly Gln Ser Val Thr Ile Ser Cys
145                 150                 155                 160

Ser Gly Ser Thr Ser Asn Ile Gly Ser His Tyr Val Val Trp Tyr Gln
                165                 170                 175

Gln Leu Pro Gly Thr Ala Pro Arg Leu Leu Ile Tyr Arg Asn His Gln
            180                 185                 190

Arg Pro Ser Gly Val Pro Asp Arg Leu Ser Gly Ser Lys Ser Gly Thr
        195                 200                 205

Ser Ala Ser Leu Ala Ile Gly Gly Leu Arg Ser Glu Asp Glu Ala Asp
    210                 215                 220
```

```
Tyr Tyr Cys Ala Val Trp Asp Asp Thr Leu Ser Gly Trp Val Phe Gly
225                 230                 235                 240

Gly Gly Thr Lys Leu Thr Val Leu
                245
```

<210> SEQ ID NO 53
<211> LENGTH: 247
<212> TYPE: PRT
<213> ORGANISM: Homo sapiens

<400> SEQUENCE: 53

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Met Ser Trp Val Arg Gln Ala Pro Gly Gln Gly Leu Glu Trp Met
        35                  40                  45

Gly Gly Ile Ile Pro Ile Phe Gly Thr Val Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Asp Asp Thr Ala Val Tyr Tyr Cys
                85                  90                  95

Ala Arg Arg Gly Ala Lys Phe Asp Tyr Trp Gly Gln Gly Thr Leu
            100                 105                 110

Val Thr Val Ser Ser Lys Leu Ser Gly Ser Ala Ser Ala Pro Lys Leu
        115                 120                 125

Glu Glu Gly Glu Phe Ser Glu Ala Arg Val Ser Tyr Val Leu Thr Gln
    130                 135                 140

Gln Pro Ser Ala Ser Gly Thr Pro Gly Gln Ser Val Thr Ile Ser Cys
145                 150                 155                 160

Ser Gly Ser Thr Ser Asn Ile Gly Ser His Tyr Val Val Trp Tyr Gln
                165                 170                 175

Gln Leu Pro Gly Thr Ala Pro Arg Leu Leu Ile Tyr Arg Asn His Gln
            180                 185                 190

Arg Pro Ser Gly Val Pro Asp Arg Leu Ser Gly Ser Lys Ser Gly Thr
        195                 200                 205

Ser Ala Ser Leu Ala Ile Gly Gly Leu Arg Ser Glu Asp Glu Ala Asp
    210                 215                 220

Tyr Tyr Cys Ala Val Trp Asp Asp Thr Leu Ser Gly Trp Val Phe Gly
225                 230                 235                 240

Gly Gly Thr Lys Leu Thr Val
                245
```

<210> SEQ ID NO 54
<211> LENGTH: 248
<212> TYPE: PRT
<213> ORGANISM: Homo sapiens

<400> SEQUENCE: 54

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Met Ser Trp Val Arg Gln Ala Pro Gly Gln Gly Leu Glu Trp Met
        35                  40                  45
```

Gly Gly Ile Ile Pro Ile Phe Gly Thr Val Asn Tyr Ala Gln Lys Phe
            50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Asp Asp Thr Ala Val Tyr Tyr Cys
                85                  90                  95

Ala Arg Arg Arg Gly Ala Lys Phe Asp Tyr Trp Gly Gln Gly Thr Leu
                100                 105                 110

Val Thr Val Ser Ser Lys Leu Ser Gly Ser Ala Ser Ala Pro Lys Leu
            115                 120                 125

Glu Glu Gly Glu Phe Ser Glu Ala Arg Val Ser Tyr Val Leu Thr Gln
        130                 135                 140

Pro Pro Ser Ala Ser Gly Thr Pro Gly Gln Ser Val Thr Ile Ser Cys
145                 150                 155                 160

Ser Gly Ser Thr Ser Asn Ile Gly Ser His Tyr Val Val Trp Tyr Gln
                165                 170                 175

Gln Leu Pro Gly Thr Ala Pro Arg Leu Leu Ile Tyr Arg Asn His Gln
            180                 185                 190

Arg Pro Ser Gly Val Pro Asp Arg Leu Ser Gly Ser Lys Ser Gly Thr
        195                 200                 205

Ser Ala Ser Leu Ala Ile Gly Gly Leu Arg Ser Glu Asp Glu Ala Asp
    210                 215                 220

Tyr Tyr Cys Ala Val Trp Asp Asp Thr Leu Ser Gly Trp Val Phe Gly
225                 230                 235                 240

Gly Gly Thr Lys Leu Thr Val Leu
                245

<210> SEQ ID NO 55
<211> LENGTH: 248
<212> TYPE: PRT
<213> ORGANISM: Homo sapiens

<400> SEQUENCE: 55

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Arg Gly Ala Lys Phe Asp Tyr Trp Gly Gln Gly Thr Leu
                100                 105                 110

Val Thr Val Ser Ser Lys Leu Ser Gly Ser Ala Ser Ala Pro Lys Leu
            115                 120                 125

Glu Glu Gly Glu Phe Ser Glu Ala Arg Val Ser Tyr Val Leu Thr Gln
        130                 135                 140

Pro Pro Ser Ala Ser Gly Thr Pro Gly Gln Ser Val Thr Ile Ser Cys
145                 150                 155                 160

Ser Gly Ser Thr Ser Asn Ile Gly Ser His Tyr Val Val Trp Tyr Gln 165                 170                 175
Gln Leu Pro Gly Thr Ala Pro Arg Leu Leu Ile Tyr Arg Asn His Gln
                180                 185                 190

Arg Pro Ser Gly Val Pro Asp Arg Leu Ser Gly Ser Lys Ser Gly Thr
            195                 200                 205

Ser Ala Ser Leu Ala Ile Gly Gly Leu Arg Ser Glu Asp Glu Ala Asp
        210                 215                 220

Tyr Tyr Cys Ala Val Trp Asp Asp Thr Leu Ser Gly Trp Val Phe Gly
225                 230                 235                 240

Gly Gly Thr Lys Leu Thr Val Leu
                245

<210> SEQ ID NO 56
<211> LENGTH: 744
<212> TYPE: DNA
<213> ORGANISM: Homo sapiens

<400> SEQUENCE: 56
caggtccagc ttgtacagtc tggggctgag gtgaagaagc ctgggtcctc ggtgaaggtc        60
tcctgcaagg cttctggagg caccttcagc agctatgcta tgagctgggt gcgacaggcc       120
cctgggcaag ggcttgagtg gatgggaggg atcatcccta tctttggtac agtaaactac       180
gcacagaagt tccagggcag agtcaccatg accaggaca cgtccacgag cacagtctac        240
atggagctga gcagcctgag atctgatgac acggccgtgt attactgtgc gagacgcggt       300
gggagctact ttgactactg gggccaaggg accctggtca ccgtctcctc aaagctttca       360
gggagtgcat ccgccccaaa acttgaagaa ggtgaatttt cagaagcacg cgtatcctat       420
gtgctgactc agccaccctc agcgtctggg accccgggc agagcgtcac catctcttgt       480
tctggaagca cctccaacat cggaagtcat tatgtgttct ggtaccagca gctcccagga       540 acggcccca gactcctcat ctataggaat catcagcggc cctcagggt ccctgaccga        600 ctctctggct ccaagtctgg cacctcagcc tccctggcca tcagtgggct ccggtccgag       660
gatgaggctg attattactg tgcagtgtgg gatgcgaaat acaggggttg ggtgttcggc       720
ggagggacca agctgaccgt ccta                                              744

<210> SEQ ID NO 57
<211> LENGTH: 744
<212> TYPE: DNA
<213> ORGANISM: Homo sapiens

<400> SEQUENCE: 57
caggtccagc ttgtacagtc tggggctgag gtgaagaagc ctgggtcctc ggtgaaggtc        60
tcctgcaagg cttctggagg caccttcagc agctatgcta tgagctgggt gcgacaggcc       120
cctgggcaag ggcttgagtg gatgggaggg atcatcccta tctttggtac agtaaactac       180
gcacagaagt tccagggcag agtcaccatg accaggaca cgtccacgag cacagtctac        240
atggagctga gcagcctgag acctgatgac acggccgtgt attactgtgc gagacgcggt       300
gggagctact ttgactactg gggccaaggg accctggtca ccgtctcctc aaagctttca       360
gggagtgcat ccgccccaaa acttgaagaa ggtgaatttt cagaagcacg cgtatcctat       420
gtgctgactc agccaccctc agcgtctggg accccgggc agagcgtcac catctcttgt       480
tctggaagca cctccaacat cggaagtcat tatgtgtcct ggtaccagca gctcccagga       540 acggcccca gactcctcat ctataggaat catcagcggc cctcagggt ccctgaccga        600

```
ctctctggct ccaagtctgg cacctcagcc tccctggcca tcagtgggct ccggtccgag    660
gatgaggctg attattactg tgcagtgtgg gatgcgaaat acaggggttg ggtgttcggc    720
ggagggacca agctgaccgt ccta                                           744
```

<210> SEQ ID NO 58
<211> LENGTH: 744
<212> TYPE: DNA
<213> ORGANISM: Homo sapiens

<400> SEQUENCE: 58

```
caggtccagc ttgtacagtc tggggctgag gtgaagaagc ctgggtcctc ggtgaaggtc     60
tcctgcaagg cttctggagg caccttcagc agctatgcta tgagctgggt gcgacaggcc    120
cctgggcaag gcttgagtg gatgggaggg atcatccta tctttggtac agtaaactac    180
gcacagaagt tccagggcag agtcaccatg accagggaca cgtccacgag cacagtctac    240
atggagctga gcagcctgag acctgatgac acggccgtgt attactgtgc gagacgcggt    300
gggagctact ttgactactg gggccaaggg accctggtca ccgtctcctc aaagctttca    360
gggagtgcat ccgccccaaa acttgaagaa ggtgaatttt cagaagcacg cgtatcctat    420
gtgctgactc agccaccctc agcgtctggg accccgggc agagcgtcac catctcttgt    480
tctggaagca cctccaacat cggaagtcat tatgtgttct ggtaccagca gctcccagga    540
acggccccca gactcctcat ctataggaat catcagcggc cctcagggt ccctgaccga    600 ctctctggct ccaagtctgg cacctcagcc tccctggcca tcagtgggct ccggtccgag    660
gatgaggctg attattactg tgcagtgtgg gatgcgaaat acaggggttg ggtgttcggc    720
ggagggacca agctgaccgt ccta                                           744
```

<210> SEQ ID NO 59
<211> LENGTH: 744
<212> TYPE: DNA
<213> ORGANISM: Homo sapiens

<400> SEQUENCE: 59

```
caggtccagc ttgtacagtc tggggctgag gtgaagaagc ctgggtcctc ggtgaaggtc     60
tcctgcaagg cttctgaagg caccttcagc agctatgcta tgagctgggt gcgacaggcc    120
cctgggcaag gcttgagtg gatgggaggg atcatccta tctttggtac agtaaactac    180
gcacagaagt tccagggcag agtcaccatg accagggaca cgtccacgag cacagtctac    240
atggagctga gcagcctgag atctgatgac acggccgtgt attactgtgc gagacgcggt    300
gggagctact ttgactactg gggccaaggg accctggtca ccgtctcctc aaagctttca    360
gggagtgcat ccgccccaaa acttgaagaa ggtgaatttt cagaagcacg cgtatcctat    420
gtgctgactc agccaccctc agcgtctggg accccgggc agagcgtcac catctcttgt    480
tctggaagca cctccaacat cggaagtcat tatgtgtcct ggtaccagca gctcccagga    540
acggccccca gactcctcat ctataggaat catcagcggc cctcagggt ccctgaccga    600 ctctctggct ccaagtctgg cacctcagcc tccctggcca tcagtgggct ccggtccgag    660
gatgaggctg attattactg tgcagtgtgg gatgcgaaat acaggggttg ggtgttcggc    720
ggagggacca agctgaccgt ccta                                           744
```

<210> SEQ ID NO 60
<211> LENGTH: 744
<212> TYPE: DNA
<213> ORGANISM: Homo sapiens

<400> SEQUENCE: 60

```
caggtccagc ttgtacagtc tggggctgag gtgaagaagc ctgggtcctc ggtgaaggtc    60
tcctgcaagg cttctgaagg caccttcagc agctatgcta tgagctgggt gcgacaggcc   120
cctgggcaag ggcttgagtg gatgggaggg atcatcccta tctttggtac agtaaactac   180
gcacagaagt tccagggcag agtcaccatg accagggaca cgtccacgag cacagtctac   240
atggagctga gcagcctgag atctgatgac acggccgtgt attactgtgc gagacggcgc   300
ggcgctaaat ttgactactg ggccaaggg accctggtca ccgtctcctc aaagcttttca   360
gggagtgcat ccgccccaaa acttgaagaa ggtgaatttt cagaagcacg cgtatcctat   420
gtgctgactc agcaaccctc agcgtctggg accccgggc agagcgtcac catctcttgt    480
tctggaagca cctccaacat cggaagtcat tatgtggtct ggtaccagca gctcccagga   540
acggccccca gactcctcat ctataggaat catcagcggc cctcaggggt ccctgaccga   600
ctctctggct ccaagtctgg cacctcagcc tccctggcca tcggtgggct ccggtccgag   660
gatgaggctg attattactg tgcagtgtgg gatgacaccc tgagtggctg ggtgttcggc   720
ggagggacca agctgaccgt ccta                                          744
```

<210> SEQ ID NO 61
<211> LENGTH: 744
<212> TYPE: DNA
<213> ORGANISM: Homo sapiens

<400> SEQUENCE: 61

```
caggtccagc ttgtacagtc tggggctgag gtgaagaagc ctgggtcctc ggtgaaggtc    60
tcctgcaagg cttctgaagg caccttcagc agctatgcta tgagctgggt gcgacaggcc   120
cctgggcaag ggcttgagtg gatgggaggg atcatcccta tctttggtac agtaaactac   180
gcacagaagt tccagggcag agtcaccatg accagggaca cgtccacgag cacagtctac   240
atggagctga gcagcctgag atctgatgac acggccgtgt attactgtgc gagacggcgc   300
ggcgctaaat ttgactactg ggccaaggg accctggtca ccgtctcctc aaagcttttca   360
gggagtgcat ccgccccaaa acttgaagaa ggtgaatttt cagaagcacg cgtatcctat   420
gtgctgactc agccaccctc agcgtctggg accccgggc agagcgtcac catctcttgt    480
tctggaagca cctccaacat cggaagtcat tatgtggtct ggtaccagca gctcccagga   540
acggccccca gactcctcat ctataggaat catcagcggc cctcaggggt ccctgaccga   600
ctctctggct ccaagtctgg cacctcagcc tccctggcca tcggtgggct ccggtccgag   660
gatgaggctg attattactg tgcagtgtgg gatgacaccc tgagtggctg ggtgttcggc   720
ggagggacca agctgaccgt ccta                                          744
```

<210> SEQ ID NO 62
<211> LENGTH: 744
<212> TYPE: DNA
<213> ORGANISM: Homo sapiens

<400> SEQUENCE: 62

```
caggtccagc ttgtacagtc tggggctgag gtgaagaagc ctgggtcctc ggtgaaggtc    60
tcctgcaagg cttctggagg caccttcagc agctatgcta tgagctgggt gcgacaggcc   120
cctgggcaag ggcttgagtg gatgggaggg atcatcccta tctttggtac agtaaactac   180
gcacagaagt tccagggcag agtcaccatg accagggaca cgtccacgag cacagtctac   240
```

```
atggagctga gcagcctgag atctgatgac acggccgtgt attactgtgc gagacggcgc    300
ggcgctaaat ttgactactg gggccaaggg accctggtca ccgtctcctc aaagctttca    360
gggagtgcat ccgccccaaa acttgaagaa ggtgaatttt cagaagcacg cgtatcctat    420
gtgctgactc agcaaccctc agcgtctggg accccgggc agagcgtcac catctcttgt     480
tctggaagca cctccaacat cggaagtcat tatgtggtct ggtaccagca gctcccagga    540
acggccccca gactcctcat ctataggaat catcagcggc cctcaggggt ccctgaccga    600
ctctctggct ccaagtctgg cacctcagcc tccctggcca tcggtgggct ccggtccgag    660
gatgaggctg attattactg tgcagtgtgg gatgacaccc tgagtggctg ggtgttcggc    720
ggagggacca agctgaccgt ccta                                           744
```

<210> SEQ ID NO 63
<211> LENGTH: 744
<212> TYPE: DNA
<213> ORGANISM: Homo sapiens

<400> SEQUENCE: 63

```
caggtccagc ttgtacagtc tggggctgag gtgaagaagc ctgggtcctc ggtgaaggtc     60
tcctgcaagg cttctggagg caccttcagc agctatgcta tgagctgggt gcgacaggcc    120
cctgggcaag gcttgagtg gatgggaggg atcatcccta tctttggtac agtaaactac     180
gcacagaagt tccagggcag agtcaccatg accaggaca cgtccacgag cacagtctac      240
atggagctga gcagcctgag atctgatgac acggccgtgt attactgtgc gagacggcgc    300
ggcgctaaat ttgactactg gggccaaggg accctggtca ccgtctcctc aaagctttca    360
gggagtgcat ccgccccaaa acttgaagaa ggtgaatttt cagaagcacg cgtatcctat    420
gtgctgactc agccaccctc agcgtctggg accccgggc agagcgtcac catctcttgt     480
tctggaagca cctccaacat cggaagtcat tatgtggtct ggtaccagca gctcccagga    540
acggccccca gactcctcat ctataggaat catcagcggc cctcaggggt ccctgaccga    600
ctctctggct ccaagtctgg cacctcagcc tccctggcca tcggtgggct ccggtccgag    660
gatgaggctg attattactg tgcagtgtgg gatgacaccc tgagtggctg ggtgttcggc    720
ggagggacca agctgaccgt ccta                                           744
```

<210> SEQ ID NO 64
<211> LENGTH: 744
<212> TYPE: DNA
<213> ORGANISM: Homo sapiens

<400> SEQUENCE: 64

```
caggtccagc ttgtacagtc tggggctgag gtgaagaagc ctgggtcctc ggtgaaggtc     60
tcctgcaagg cttctggagg caccttcagc agctatgcta tcagctgggt gcgacaggcc    120
cctggacaag gcttgagtg gatgggaggg atcatcccta tctttggtac agcaaactac     180
gcacagaagt tccagggcag agtcaccatg accaggaca cgtccacgag cacagtctac      240
atggagctga gcagcctgag atctgaggac acggccgtgt attactgtgc gagacggcgc    300
ggcgctaaat ttgactactg gggccaaggg accctggtca ccgtctcctc aaagctttca    360
gggagtgcat ccgccccaaa acttgaagaa ggtgaatttt cagaagcacg cgtatcctat    420
gtgctgactc agccaccctc agcgtctggg accccgggc agagcgtcac catctcttgt     480
tctggaagca cctccaacat cggaagtcat tatgtggtct ggtaccagca gctcccagga    540
acggccccca gactcctcat ctataggaat catcagcggc cctcaggggt ccctgaccga    600
```

```
ctctctggct ccaagtctgg cacctcagcc tccctggcca tcggtgggct ccggtccgag      660
gatgaggctg attattactg tgcagtgtgg gatgacaccc tgagtggctg ggtgttcggc      720
ggagggacca agctgaccgt ccta                                             744
```

<210> SEQ ID NO 65
<211> LENGTH: 1341
<212> TYPE: DNA
<213> ORGANISM: Homo sapiens

<400> SEQUENCE: 65

```
caggtccagc ttgtacagtc tggggctgag gtgaagaagc ctgggtcctc ggtgaaggtc       60
tcctgcaagg cttctggagg cacctcagc agctatgcta tgagctgggt gcgacaggcc      120
cctgggcaag gcttgagtg gatgggaggg atcatcccta tctttggtac agtaaactac      180
gcacagaagt tccagggcag agtcaccatg accagggaca cgtccacgag cacagtctac      240
atggagctga gcagcctgag atctgatgac acggccgtgt attactgtgc gagacgcggt      300
gggagctact ttgactactg gggccaaggg accctggtca ccgtctcctc agcctccacc      360
aagggcccat cggtcttccc cctggcaccc tcctccaaga gcacctctgg gggcacagcg      420
gccctgggct gcctggtcaa ggactacttc cccgaaccgg tgacggtgtc gtggaactca      480
ggcgccctga ccagcggcgt gcacaccttc ccggctgtcc tacagtcctc aggactctac      540
tccctcagca gcgtggtgac cgtgccctcc agcagcttgg gcacccagac ctacatctgc      600
aacgtgaatc acaagcccag caacaccaag gtggacaaga agttgagcc caaatcttgt      660 gacaaaactc acacatgccc accgtgccca gcacctgaac tcctgggggg accgtcagtc      720
ttcctcttcc ccccaaaacc caaggacacc ctcatgatct cccggacccc tgaggtcaca      780
tgcgtggtgg tggacgtgag ccacgaagac cctgaggtca agttcaactg gtacgtggac      840
ggcgtggagg tgcataatgc caagacaaag ccgcgggagg agcagtacaa cagcacgtac      900
cgtgtggtca gcgtcctcac cgtcctgcac caggactggc tgaatggcaa ggagtacaag      960
tgcaaggtct ccaacaaagc cctcccagcc cccatcgaga aaaccatctc caaagccaaa     1020
gggcagcccc gagaaccaca ggtgtacacc ctgcccccat cccgggatga gctgaccaag     1080
aaccaggtca gcctgacctg cctggtcaaa ggcttctatc ccagcgacat cgccgtggag     1140
tgggagagca atgggcagcc ggagaacaac tacaagacca cgcctcccgt gctggactcc     1200
gacggctcct tcttcctcta cagcaagctc accgtggaca gagcaggtg gcagcagggg     1260 aacgtcttct catgctccgt gatgcatgag gctctgcaca accactacac gcagaagagc     1320
ctctccctgt ctccgggtaa a                                              1341
```

<210> SEQ ID NO 66
<211> LENGTH: 648
<212> TYPE: DNA
<213> ORGANISM: Homo sapiens

<400> SEQUENCE: 66

```
tcctatgtgc tgactcagcc accctcagcg tctgggaccc ccgggcagag cgtcaccatc       60
tcttgttctg gaagcaccctc caacatcgga agtcattatg tgttctggta ccagcagctc     120
ccaggaacgg ccccccagact cctcatctat aggaatcatc agcggccctc agggtgtccct    180 gaccgactct ctggctccaa gtctggcacc tcagcctccc tggccatcag tgggctccgg     240
tccgaggatg aggctgatta ttactgtgca gtgtgggatg cgaaatacag ggttgggtg      300
```

```
ttcggcggag ggaccaagct gaccgtccta ggtcagccca aggctgcccc ctcggtcact    360
ctgttcccgc cctcctctga ggagcttcaa gccaacaagg ccacactggt gtgtctcata    420
agtgacttct acccgggagc cgtgacagtg gcctggaagg cagatagcag ccccgtcaag    480
gcgggagtgg agaccaccac accctccaaa caaagcaaca acaagtacgc ggccagcagc    540
tatctgagcc tgacgcctga gcagtggaag tcccacagaa gctacagctg ccaggtcacg    600
catgaaggga gcaccgtgga agacagtgtg cccctacag aatgttca                  648
```

<210> SEQ ID NO 67
<211> LENGTH: 447
<212> TYPE: PRT
<213> ORGANISM: Homo sapiens

<400> SEQUENCE: 67

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Met Ser Trp Val Arg Gln Ala Pro Gly Gln Gly Leu Glu Trp Met
        35                  40                  45

Gly Gly Ile Ile Pro Ile Phe Gly Thr Val Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Asp Asp Thr Ala Val Tyr Tyr Cys
                85                  90                  95

Ala Arg Arg Gly Gly Ser Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 68
<211> LENGTH: 216
<212> TYPE: PRT
<213> ORGANISM: Homo sapiens

<400> SEQUENCE: 68

Ser Tyr Val Leu Thr Gln Pro Pro Ser Ala Ser Gly Thr Pro Gly Gln
1               5                   10                  15

Ser Val Thr Ile Ser Cys Ser Gly Ser Thr Ser Asn Ile Gly Ser His
            20                  25                  30

Tyr Val Phe Trp Tyr Gln Gln Leu Pro Gly Thr Ala Pro Arg Leu Leu
        35                  40                  45

Ile Tyr Arg Asn His Gln Arg Pro Ser Gly Val Pro Asp Arg Leu Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Val Trp Asp Ala Lys Tyr
                85                  90                  95

Arg Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 69
<211> LENGTH: 1341
<212> TYPE: DNA

<213> ORGANISM: Homo sapiens

<400> SEQUENCE: 69

```
caggtccagc ttgtacagtc tggggctgag gtgaagaagc ctgggtcctc ggtgaaggtc      60
tcctgcaagg cttctggagg caccttcagc agctatgcta tgagctgggt gcgacaggcc     120
cctgggcaag ggcttgagtg gatgggaggg atcatcccta tctttggtac agtaaactac     180
gcacagaagt tccagggcag agtcaccatg accagggaca cgtccacgag cacagtctac     240
atggagctga gcagcctgag acctgatgac acggccgtgt attactgtgc gagacgcggt     300
gggagctact ttgactactg gggccaaggg accctggtca ccgtctcctc agcctccacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt      660
gacaaaactc acacatgccc accgtgccca gcacctgaac tcctgggggg accgtcagtc     720
ttcctcttcc cccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
gggcagcccc gagaaccaca ggtgtacacc ctgccccat cccgggatga gctgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca gagcaggtg gcagcagggg    1260
aacgtcttct catgctccgt gatgcatgag gctctgcaca accactacac gcagaagagc    1320
ctctcccctgt ctccgggtaa a                                              1341
```

<210> SEQ ID NO 70
<211> LENGTH: 648
<212> TYPE: DNA
<213> ORGANISM: Homo sapiens

<400> SEQUENCE: 70

```
tcctatgtgc tgactcagcc accctcagcg tctgggaccc ccgggcagag cgtcaccatc      60
tcttgttctg gaagcacctc caacatcgga agtcattatg tgtcctggta ccagcagctc     120
ccaggaacgg cccccagact cctcatctat aggaatcatc agcggccctc aggggtccct     180
gaccgactct ctggctccaa gtctggcacc tcagcctccc tggccatcag tgggctccgg     240
tccgaggatg aggctgatta ttactgtgca gtgtgggatc gaaatacag gggttgggtg     300
ttcggcggag ggaccaagct gaccgtccta ggtcagccca aggctgcccc ctcggtcact     360
ctgttcccgc cctcctctga ggagcttcaa gccaacaagg ccacactggt gtgtctcata     420
agtgacttct acccgggagc cgtgacagtg gcctggaagg cagatagcag ccccgtcaag     480
gcgggagtgg agaccaccac accctccaaa caaagcaaca acaagtacgc ggccagcagc     540
tatctgagcc tgacgcctga gcagtggaag tcccacagaa gctacagctg ccaggtcacg     600
catgaaggga gcaccgtgga agacagtgt gccctacag aatgttca                    648
```

<210> SEQ ID NO 71
<211> LENGTH: 447
<212> TYPE: PRT
<213> ORGANISM: Homo sapiens

<400> SEQUENCE: 71

```
Gln Val Gln Leu Val Gln Ser Gly Ala Glu Val Lys Pro Gly Ser
1               5                   10                  15

Ser Val Lys Val Ser Cys Lys Ala Ser Gly Gly Thr Phe Ser Ser Tyr
            20                  25                  30

Ala Met Ser Trp Val Arg Gln Ala Pro Gly Gln Gly Leu Glu Trp Met
        35                  40                  45

Gly Gly Ile Ile Pro Ile Phe Gly Thr Val Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Pro Asp Thr Ala Val Tyr Tyr Cys
                85                  90                  95

Ala Arg Arg Gly Gly Ser Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
```

Gly Gln Pro Glu Asn Asn Tyr Lys Thr Thr Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys
    435                 440                 445

<210> SEQ ID NO 72
<211> LENGTH: 216
<212> TYPE: PRT
<213> ORGANISM: Homo sapiens

<400> SEQUENCE: 72

Ser Tyr Val Leu Thr Gln Pro Pro Ser Ala Ser Gly Thr Pro Gly Gln
1               5                   10                  15

Ser Val Thr Ile Ser Cys Ser Gly Ser Thr Ser Asn Ile Gly Ser His
            20                  25                  30

Tyr Val Ser Trp Tyr Gln Gln Leu Pro Gly Thr Ala Pro Arg Leu Leu
        35                  40                  45

Ile Tyr Arg Asn His Gln Arg Pro Ser Gly Val Pro Asp Arg Leu Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Val Trp Asp Ala Lys Tyr
                85                  90                  95

Arg Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 73
<211> LENGTH: 1341
<212> TYPE: DNA
<213> ORGANISM: Homo sapiens

<400> SEQUENCE: 73
caggtccagc ttgtacagtc tggggctgag gtgaagaagc ctgggtcctc ggtgaaggtc      60
tcctgcaagg cttctggagg caccttcagc agctatgcta tgagctgggt gcgacaggcc     120
cctgggcaag gcttgagtg gatgggaggg atcatcccta tctttggtac agtaaactac     180
gcacagaagt tccagggcag agtcaccatg accagggaca cgtccacgag cacagtctac     240

```
atggagctga gcagcctgag acctgatgac acggccgtgt attactgtgc gagacgcggt      300
gggagctact ttgactactg gggccaaggg accctggtca ccgtctcctc agcctccacc      360
aagggcccat cggtcttccc cctggcaccc tcctccaaga gcacctctgg gggcacagcg      420
gccctgggct gcctggtcaa ggactacttc cccgaaccgg tgacggtgtc gtggaactca      480
ggcgccctga ccagcggcgt gcacaccttc ccggctgtcc tacagtcctc aggactctac      540
tccctcagca gcgtggtgac cgtgccctcc agcagcttgg gcacccagac ctacatctgc      600
aacgtgaatc acaagcccag caacaccaag gtggacaaga agttgagcc caaatcttgt       660 gacaaaactc acacatgccc accgtgccca gcacctgaac tcctggggg accgtcagtc       720 ttcctcttcc ccccaaaacc caaggacacc ctcatgatct cccggacccc tgaggtcaca      780
tgcgtggtgg tggacgtgag ccacgaagac cctgaggtca agttcaactg gtacgtggac      840
ggcgtggagg tgcataatgc caagacaaag ccgcgggagg agcagtacaa cagcacgtac      900
cgtgtggtca gcgtcctcac cgtcctgcac caggactggc tgaatggcaa ggagtacaag      960
tgcaaggtct ccaacaaagc cctcccagcc cccatcgaga aaaccatctc caaagccaaa     1020
gggcagcccc gagaaccaca ggtgtacacc ctgcccccat cccgggatga gctgaccaag     1080
aaccaggtca gcctgacctg cctggtcaaa ggcttctatc ccagcgacat cgccgtggag     1140
tgggagagca atgggcagcc ggagaacaac tacaagacca cgcctcccgt gctggactcc     1200
gacggctcct tcttcctcta cagcaagctc accgtggaca agagcaggtg gcagcagggg     1260
aacgtcttct catgctccgt gatgcatgag gctctgcaca accactacac gcagaagagc     1320
ctctccctgt ctccgggtaa a                                               1341
```

<210> SEQ ID NO 74
<211> LENGTH: 648
<212> TYPE: DNA
<213> ORGANISM: Homo sapiens

<400> SEQUENCE: 74

```
tcctatgtgc tgactcagcc accctcagcg tctgggaccc ccgggcagag cgtcaccatc       60
tcttgttctg gaagcacctc caacatcgga agtcattatg tgttctggta ccagcagctc      120
ccaggaacgg cccccagact cctcatctat aggaatcatc agcggccctc aggggtccct      180
gaccgactct ctggctccaa gtctggcacc tcagcctccc tggccatcag tgggctccgg      240
tccgaggatg aggctgatta ttactgtgca gtgtgggatg cgaaatacag gggttgggtg      300
ttcggcggag ggaccaagct gaccgtccta ggtcagccca aggctgcccc ctcggtcact      360
ctgttcccgc cctcctctga ggagcttcaa gccaacaagg ccacactggt gtgtctcata      420
agtgacttct acccgggagc cgtgacagtg gcctggaagg cagatagcag ccccgtcaag      480
gcgggagtgg agaccaccac acccctccaaa caaagcaaca caagtacgc ggccagcagc     540 tatctgagcc tgacgcctga gcagtggaag tcccacagaa gctacagctg ccaggtcacg      600
catgaaggga gcaccgtgga aagacagtg gccctacag aatgttca                    648
```

<210> SEQ ID NO 75
<211> LENGTH: 447
<212> TYPE: PRT
<213> ORGANISM: Homo sapiens

<400> SEQUENCE: 75

Gln Val Gln Leu Val Gln Ser Gly Ala Glu Val Lys Lys Pro Gly Ser
1               5                   10                  15

```
Ser Val Lys Val Ser Cys Lys Ala Ser Gly Gly Thr Phe Ser Ser Tyr
            20                  25                  30

Ala Met Ser Trp Val Arg Gln Ala Pro Gly Gln Gly Leu Glu Trp Met
            35                  40                  45

Gly Gly Ile Ile Pro Ile Phe Gly Thr Val Asn Tyr Ala Gln Lys Phe
 50                      55                  60

Gln Gly Arg Val Thr Met Thr Arg Asp Thr Ser Thr Ser Thr Val Tyr
 65                  70                  75                  80

Met Glu Leu Ser Ser Leu Arg Pro Asp Asp Thr Ala Val Tyr Tyr Cys
                85                  90                  95

Ala Arg Arg Gly Gly Ser Tyr Phe Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
            210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430
```

His Asn His Tyr Thr Gln Lys Ser Leu Ser Leu Ser Pro Gly Lys
            435                 440                 445

<210> SEQ ID NO 76
<211> LENGTH: 216
<212> TYPE: PRT
<213> ORGANISM: Homo sapiens

<400> SEQUENCE: 76

Ser Tyr Val Leu Thr Gln Pro Pro Ser Ala Ser Gly Thr Pro Gly Gln
1               5                   10                  15

Ser Val Thr Ile Ser Cys Ser Gly Ser Thr Ser Asn Ile Gly Ser His
            20                  25                  30

Tyr Val Phe Trp Tyr Gln Gln Leu Pro Gly Thr Ala Pro Arg Leu Leu
        35                  40                  45

Ile Tyr Arg Asn His Gln Arg Pro Ser Gly Val Pro Asp Arg Leu Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Val Trp Asp Ala Lys Tyr
                85                  90                  95

Arg Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 77
<211> LENGTH: 1341
<212> TYPE: DNA
<213> ORGANISM: Homo sapiens

<400> SEQUENCE: 77
caggtccagc ttgtacagtc tggggctgag gtgaagaagc ctgggtcctc ggtgaaggtc     60
tcctgcaagg cttctgaagg caccttcagc agctatgcta tgagctgggt gcgacaggcc    120
cctgggcaag gcttgagtg gatgggaggg atcatcccta tctttggtac agtaaaactac    180 gcacagaagt tccagggcag agtcaccatg accagggaca cgtccacgag cacagtctac    240
atggagctga gcagcctgag atctgatgac acggccgtgt attactgtgc gagacgcggt    300
gggagctact ttgactactg gggccaaggg accctggtca ccgtctcctc agcctccacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540

-continued

```
tccctcagca gcgtggtgac cgtgccctcc agcagcttgg gcacccagac ctacatctgc        600
aacgtgaatc acaagcccag caacaccaag gtggacaaga agttgagcc caaatcttgt         660
gacaaaactc acacatgccc accgtgccca gcacctgaac tcctgggggg accgtcagtc        720
ttcctcttcc ccccaaaacc caaggacacc ctcatgatct cccggacccc tgaggtcaca        780
tgcgtggtgg tggacgtgag ccacgaagac cctgaggtca agttcaactg gtacgtggac        840
ggcgtggagg tgcataatgc caagacaaag ccgcgggagg agcagtacaa cagcacgtac        900
cgtgtggtca gcgtcctcac cgtcctgcac caggactggc tgaatggcaa ggagtacaag        960
tgcaaggtct ccaacaaagc cctcccagcc cccatcgaga aaccatctc caaagccaaa        1020
gggcagcccc gagaaccaca ggtgtacacc ctgcccccat cccgggatga gctgaccaag       1080
aaccaggtca gcctgacctg cctggtcaaa ggcttctatc ccagcgacat cgccgtggag       1140
tgggagagca atgggcagcc ggagaacaac tacaagacca cgcctcccgt gctggactcc       1200
gacggctcct tcttcctcta cagcaagctc accgtggaca agagcaggtg gcagcagggg       1260
aacgtcttct catgctccgt gatgcatgag gctctgcaca accactacac gcagaagagc       1320
ctctccctgt ctccgggtaa a                                                 1341
```

<210> SEQ ID NO 78
<211> LENGTH: 648
<212> TYPE: DNA
<213> ORGANISM: Homo sapiens

<400> SEQUENCE: 78

```
tcctatgtgc tgactcagcc accctcagcg tctgggaccc ccgggcagag cgtcaccatc         60
tcttgttctg gaagcacctc caacatcgga agtcattatg tgtcctggta ccagcagctc        120
ccaggaacgg cccccagact cctcatctat aggaatcatc agcggccctc aggggtccct        180
gaccgactct ctggctccaa gtctggcacc tcagcctccc tggccatcag tgggctccgg        240
tccgaggatg aggctgatta ttactgtgca gtgtgggatg cgaaatacag ggttggggtg        300
ttcggcggag ggaccaagct gaccgtccta ggtcagccca aggctgcccc ctcggtcact        360
ctgttcccgc cctcctctga ggagcttcaa gccaacaagg ccacactggt gtgtctcata        420
agtgacttct acccgggagc cgtgacagtg gcctggaagg cagatagcag ccccgtcaag        480
gcggagtgg agaccaccac acctccaaa caaagcaaca caagtacgc ggccagcagc           540
tatctgagcc tgacgcctga gcagtggaag tcccacagaa gctacagctg ccaggtcacg        600
catgaaggga gcaccgtgga gaagacagtg gcccctacag aatgttca                    648
```

<210> SEQ ID NO 79
<211> LENGTH: 447
<212> TYPE: PRT
<213> ORGANISM: Homo sapiens

<400> SEQUENCE: 79

```
Gln Val Gln Leu Val Gln Ser Gly Ala Glu Val Lys Lys Pro Gly Ser
1               5                   10                  15

Ser Val Lys Val Ser Cys Lys Ala Ser Glu Gly Thr Phe Ser Ser Tyr
            20                  25                  30

Ala Met Ser Trp Val Arg Gln Ala Pro Gly Gln Gly Leu Glu Trp Met
        35                  40                  45

Gly Gly Ile Ile Pro Ile Phe Gly Thr Val Asn Tyr Ala Gln Lys Phe
    50                  55                  60

Gln Gly Arg Val Thr Met Thr Arg Asp Thr Ser Thr Ser Thr Val Tyr
```

```
                65                  70                  75                  80
        Met Glu Leu Ser Ser Leu Arg Ser Asp Asp Thr Ala Val Tyr Tyr Cys
                        85                  90                  95

Ala Arg Arg Gly Gly Ser Tyr Phe Asp Tyr Trp Gly Gln Gly Thr Leu
                        100                 105                 110

Val Thr Val Ser Ser Ala Ser Thr Lys Gly Pro Ser Val Phe Pro Leu
                        115                 120                 125

Ala Pro Ser Ser Lys Ser Thr Ser Gly Gly Thr Ala Ala Leu Gly Cys
                130                 135                 140

Leu Val Lys Asp Tyr Phe Pro Glu Pro Val Thr Val Ser Trp Asn Ser
        145                 150                 155                 160

Gly Ala Leu Thr Ser Gly Val His Thr Phe Pro Ala Val Leu Gln Ser
                        165                 170                 175

Ser Gly Leu Tyr Ser Leu Ser Ser Val Val Thr Val Pro Ser Ser Ser
                        180                 185                 190

Leu Gly Thr Gln Thr Tyr Ile Cys Asn Val Asn His Lys Pro Ser Asn
                        195                 200                 205

Thr Lys Val Asp Lys Lys Val Glu Pro Lys Ser Cys Asp Lys Thr His
                210                 215                 220

Thr Cys Pro Pro Cys Pro Ala Pro Glu Leu Leu Gly Gly Pro Ser Val
        225                 230                 235                 240

Phe Leu Phe Pro Pro Lys Pro Lys Asp Thr Leu Met Ile Ser Arg Thr
                        245                 250                 255

Pro Glu Val Thr Cys Val Val Val Asp Val Ser His Glu Asp Pro Glu
                        260                 265                 270

Val Lys Phe Asn Trp Tyr Val Asp Gly Val Glu Val His Asn Ala Lys
                        275                 280                 285

Thr Lys Pro Arg Glu Glu Gln Tyr Asn Ser Thr Tyr Arg Val Val Ser
                290                 295                 300

Val Leu Thr Val Leu His Gln Asp Trp Leu Asn Gly Lys Glu Tyr Lys
        305                 310                 315                 320

Cys Lys Val Ser Asn Lys Ala Leu Pro Ala Pro Ile Glu Lys Thr Ile
                        325                 330                 335

Ser Lys Ala Lys Gly Gln Pro Arg Glu Pro Gln Val Tyr Thr Leu Pro
                        340                 345                 350

Pro Ser Arg Asp Glu Leu Thr Lys Asn Gln Val Ser Leu Thr Cys Leu
                        355                 360                 365

Val Lys Gly Phe Tyr Pro Ser Asp Ile Ala Val Glu Trp Glu Ser Asn
                370                 375                 380

Gly Gln Pro Glu Asn Asn Tyr Lys Thr Thr Pro Pro Val Leu Asp Ser
        385                 390                 395                 400

Asp Gly Ser Phe Phe Leu Tyr Ser Lys Leu Thr Val Asp Lys Ser Arg
                        405                 410                 415

Trp Gln Gln Gly Asn Val Phe Ser Cys Ser Val Met His Glu Ala Leu
                        420                 425                 430

His Asn His Tyr Thr Gln Lys Ser Leu Ser Leu Ser Pro Gly Lys
                        435                 440                 445

<210> SEQ ID NO 80
<211> LENGTH: 216
<212> TYPE: PRT
<213> ORGANISM: Homo sapiens

<400> SEQUENCE: 80
```

```
Ser Tyr Val Leu Thr Gln Pro Pro Ser Ala Ser Gly Thr Pro Gly Gln
  1               5                  10                 15

Ser Val Thr Ile Ser Cys Ser Gly Ser Thr Ser Asn Ile Gly Ser His
             20                  25                  30

Tyr Val Ser Trp Tyr Gln Gln Leu Pro Gly Thr Ala Pro Arg Leu Leu
         35                  40                  45

Ile Tyr Arg Asn His Gln Arg Pro Ser Gly Val Pro Asp Arg Leu Ser
     50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Val Trp Asp Ala Lys Tyr
                 85                  90                  95

Arg Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 81
<211> LENGTH: 1341
<212> TYPE: DNA
<213> ORGANISM: Homo sapiens

<400> SEQUENCE: 81
caggtccagc ttgtacagtc tggggctgag gtgaagaagc ctgggtcctc ggtgaaggtc      60
tcctgcaagg cttctgaagg caccttcagc agctatgcta tgagctgggt gcgacaggcc    120
cctgggcaag ggcttgagtg gatgggaggg atcatcccta tctttggtac agtaaactac    180
gcacagaagt tccagggcag agtcaccatg accagggaca cgtccacgag cacagtctac    240
atggagctga gcagcctgag atctgatgac acggccgtgt attactgtgc gagacggcgc    300
ggcgctaaat tgactactg ggccaagggg accctggtca ccgtctcctc agcctccacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagccc aaatcttgt     660 gacaaaactc acacatgccc accgtgccca gcacctgaac tcctgggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
```

```
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
gggcagcccc gagaaccaca ggtgtacacc ctgcccccat cccgggatga gctgaccaag   1080
aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta cagcaagctc accgtggaca gagcaggtg gcagcagggg   1260 aacgtcttct catgctccgt gatgcatgag gctctgcaca accactacac gcagaagagc   1320 ctctcccctgt ctccgggtaa a                                            1341

<210> SEQ ID NO 82
<211> LENGTH: 648
<212> TYPE: DNA
<213> ORGANISM: Homo sapiens

<400> SEQUENCE: 82
tcctatgtgc tgactcagca accctcagcg tctgggaccc ccgggcagag cgtcaccatc      60
tcttgttctg gaagcacctc caacatcgga agtcattatg tggtctggta ccagcagctc     120
ccaggaacgg cccccagact cctcatctat aggaatcatc agcggccctc agggtccct     180 gaccgactct ctggctccaa gtctggcacc tcagcctccc tggccatcgg tgggctccgg     240
tccgaggatg aggctgatta ttactgtgca gtgtgggatg acaccctgag tggctgggtg     300
ttcggcggag ggaccaagct gaccgtccta ggtcagccca aggctgcccc ctcggtcact     360
ctgttcccgc cctcctctga ggagcttcaa gccaacaagg ccacactggt gtgtctcata     420
agtgacttct acccgggagc cgtgacagtg gcctggaagg cagatagcag ccccgtcaag     480
gcgggagtgg agaccaccac accctccaaa caaagcaaca caagtacgc ggccagcagc     540 tatctgagcc tgacgcctga cagtggaag tcccacagaa gctacagctg ccaggtcacg     600
catgaaggga gcaccgtgga aagacagtg gcccctacag aatgttca                  648

<210> SEQ ID NO 83
<211> LENGTH: 447
<212> TYPE: PRT
<213> ORGANISM: Homo sapiens

<400> SEQUENCE: 83

Gln Val Gln Leu Val Gln Ser Gly Ala Glu Val Lys Lys Pro Gly Ser
1               5                   10                  15

Ser Val Lys Val Ser Cys Lys Ala Ser Glu Gly Thr Phe Ser Ser Tyr
            20                  25                  30

Ala Met Ser Trp Val Arg Gln Ala Pro Gly Gln Gly Leu Glu Trp Met
        35                  40                  45

Gly Gly Ile Ile Pro Ile Phe Gly Thr Val Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Asp Asp Thr Ala Val Tyr Tyr Cys
                85                  90                  95

Ala Arg Arg Arg Gly Ala Lys Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125
```

```
Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 84
<211> LENGTH: 216
<212> TYPE: PRT
<213> ORGANISM: Homo sapiens

<400> SEQUENCE: 84

Ser Tyr Val Leu Thr Gln Gln Pro Ser Ala Ser Gly Thr Pro Gly Gln
1               5                   10                  15

Ser Val Thr Ile Ser Cys Ser Gly Ser Thr Ser Asn Ile Gly Ser His
            20                  25                  30

Tyr Val Val Trp Tyr Gln Gln Leu Pro Gly Thr Ala Pro Arg Leu Leu
        35                  40                  45

Ile Tyr Arg Asn His Gln Arg Pro Ser Gly Val Pro Asp Arg Leu Ser
    50                  55                  60
```

```
Gly Ser Lys Ser Gly Thr Ser Ala Ser Leu Ala Ile Gly Gly Leu Arg
 65                  70                  75                  80

Ser Glu Asp Glu Ala Asp Tyr Tyr Cys Ala Val Trp Asp Asp Thr Leu
             85                   90                  95

Ser Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
            165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
    210                 215

<210> SEQ ID NO 85
<211> LENGTH: 1341
<212> TYPE: DNA
<213> ORGANISM: Homo sapiens

<400> SEQUENCE: 85
caggtccagc ttgtacagtc tggggctgag gtgaagaagc ctgggtcctc ggtgaaggtc      60
tcctgcaagg cttctgaagg caccttcagc agctatgcta tgagctgggt gcgacaggcc     120
cctgggcaag gcttgagtg gatgggaggg atcatcccta tctttggtac agtaaaactac     180 gcacagaagt tccagggcag agtcaccatg accaggaca cgtccacgag cacagtctac     240
atggagctga gcagcctgag atctgatgac acggccgtgt attactgtgc gagacggcgc     300
ggcgctaaat ttgactactg gggccaaggg accctggtca ccgtctcctc agcctccacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt     660 gacaaaactc acacatgccc accgtgccca gcacctgaac tcctgggggg accgtcagtc     720
ttcctcttcc ccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
gggcagcccc gagaaccaca ggtgtacacc ctgcccccat cccgggatga gctgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
```

```
gacggctcct tcttcctcta cagcaagctc accgtggaca agagcaggtg gcagcagggg   1260
aacgtcttct catgctccgt gatgcatgag gctctgcaca accactacac gcagaagagc   1320
ctctccctgt ctccgggtaa a                                             1341
```

```
<210> SEQ ID NO 86
<211> LENGTH: 648
<212> TYPE: DNA
<213> ORGANISM: Homo sapiens

<400> SEQUENCE: 86
tcctatgtgc tgactcagcc accctcagcg tctgggaccc ccgggcagag cgtcaccatc    60
tcttgttctg gaagcacctc caacatcgga agtcattatg tggtctggta ccagcagctc   120
ccaggaacgg cccccagact cctcatctat aggaatcatc agcggccctc aggggtccct   180
gaccgactct ctggctccaa gtctggcacc tcagcctccc tggccatcgg tgggctccgg   240
tccgaggatg aggctgatta ttactgtgca gtgtgggatg acaccctgag tggctgggtg   300
ttcggcggag ggaccaagct gaccgtccta ggtcagccca aggctgcccc ctcggtcact   360
ctgttcccgc cctcctctga ggagcttcaa gccaacaagg ccacactggt gtgtctcata   420
agtgacttct acccgggagc cgtgacagtg gcctggaagg cagatagcag ccccgtcaag   480
gcgggagtgg agaccaccac accctccaaa caaagcaaca acaagtacgc ggccagcagc   540
tatctgagcc tgacgcctga gcagtggaag tcccacagaa gctacagctg ccaggtcacg   600
catgaaggga gcaccgtgga agacagtg gcccctacag aatgttca                  648
```

```
<210> SEQ ID NO 87
<211> LENGTH: 447
<212> TYPE: PRT
<213> ORGANISM: Homo sapiens

<400> SEQUENCE: 87

Gln Val Gln Leu Val Gln Ser Gly Ala Glu Val Lys Lys Pro Gly Ser
1               5                   10                  15

Ser Val Lys Val Ser Cys Lys Ala Ser Glu Gly Thr Phe Ser Ser Tyr
            20                  25                  30

Ala Met Ser Trp Val Arg Gln Ala Pro Gly Gln Gly Leu Glu Trp Met
        35                  40                  45

Gly Gly Ile Ile Pro Ile Phe Gly Thr Val Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Asp Asp Thr Ala Val Tyr Tyr Cys
                85                  90                  95

Ala Arg Arg Arg Gly Ala Lys Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190
```

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

```
<210> SEQ ID NO 88
<211> LENGTH: 216
<212> TYPE: PRT
<213> ORGANISM: Homo sapiens

<400> SEQUENCE: 88
```

Ser Tyr Val Leu Thr Gln Pro Pro Ser Ala Ser Gly Thr Pro Gly Gln
1               5                   10                  15

Ser Val Thr Ile Ser Cys Ser Gly Ser Thr Ser Asn Ile Gly Ser His
            20                  25                  30

Tyr Val Val Trp Tyr Gln Gln Leu Pro Gly Thr Ala Pro Arg Leu Leu
        35                  40                  45

Ile Tyr Arg Asn His Gln Arg Pro Ser Gly Val Pro Asp Arg Leu Ser
    50                  55                  60

Gly Ser Lys Ser Gly Thr Ser Ala Ser Leu Ala Ile Gly Gly Leu Arg
65                  70                  75                  80

Ser Glu Asp Glu Ala Asp Tyr Tyr Cys Ala Val Trp Asp Asp Thr Leu
                85                  90                  95

Ser Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu

| | 115 | | | | 120 | | | | 125 | | |
|---|---|---|---|---|---|---|---|---|---|---|---|

Leu Gln Ala Asn Lys Ala Thr Leu Val Cys Leu Ile Ser Asp Phe Tyr
                130                    135                    140

Pro Gly Ala Val Thr Val Ala Trp Lys Ala Asp Ser Ser Pro Val Lys
145                  150                    155                    160

Ala Gly Val Glu Thr Thr Thr Pro Ser Lys Gln Ser Asn Asn Lys Tyr
                165                    170                    175

Ala Ala Ser Ser Tyr Leu Ser Leu Thr Pro Glu Gln Trp Lys Ser His
                  180                    185                    190

Arg Ser Tyr Ser Cys Gln Val Thr His Glu Gly Ser Thr Val Glu Lys
              195                    200                    205

Thr Val Ala Pro Thr Glu Cys Ser
210                  215

<210> SEQ ID NO 89
<211> LENGTH: 1341
<212> TYPE: DNA
<213> ORGANISM: Homo sapiens

<400> SEQUENCE: 89

| | |
|---|---|
| caggtccagc ttgtacagtc tggggctgag gtgaagaagc ctgggtcctc ggtgaaggtc | 60 |
| tcctgcaagg cttctggagg caccttcagc agctatgcta tgagctgggt gcgacaggcc | 120 |
| cctgggcaag gcttgagtg gatgggaggg atcatcccta tctttggtac agtaaactac | 180 |
| gcacagaagt tccagggcag agtcaccatg accagggaca cgtccacgag cacagtctac | 240 |
| atggagctga gcagcctgag atctgatgac acggccgtgt attactgtgc gagacggcgc | 300 |
| ggcgctaaat ttgactactg gggccaaggg accctggtca ccgtctcctc agcctccacc | 360 |
| aagggcccat cggtcttccc cctggcaccc tcctccaaga gcacctctgg gggcacagcg | 420 |
| gccctgggct gcctggtcaa ggactacttc cccgaaccgg tgacggtgtc gtggaactca | 480 |
| ggcgccctga ccagcggcgt gcacaccttc ccggctgtcc tacagtcctc aggactctac | 540 |
| tccctcagca gcgtggtgac cgtgccctcc agcagcttgg gcacccagac ctacatctgc | 600 |
| aacgtgaatc acaagcccag caacaccaag gtggacaaga agttgagcc caaatcttgt | 660 |
| gacaaaactc acacatgccc accgtgccca gcacctgaac tcctgggggg accgtcagtc | 720 |
| ttcctcttcc ccccaaaacc caaggacacc ctcatgatct cccggacccc tgaggtcaca | 780 |
| tgcgtggtgg tggacgtgag ccacgaagac cctgaggtca agttcaactg gtacgtggac | 840 |
| ggcgtggagg tgcataatgc caagacaaag ccgcgggagg agcagtacaa cagcacgtac | 900 |
| cgtgtggtca gcgtcctcac cgtcctgcac caggactggc tgaatggcaa ggagtacaag | 960 |
| tgcaaggtct ccaacaaagc cctcccagcc ccatcgaga aaaccatctc caaagccaaa | 1020 |
| gggcagcccc gagaaccaca ggtgtacacc ctgcccccat cccgggatga gctgaccaag | 1080 |
| aaccaggtca gcctgacctg cctggtcaaa ggcttctatc ccagcgacat cgccgtggag | 1140 |
| tgggagagca atgggcagcc ggagaacaac tacaagacca cgcctcccgt gctggactcc | 1200 |
| gacggctcct tcttcctcta cagcaagctc accgtggaca gagcaggtg gcagcagggg | 1260 |
| aacgtcttct catgctccgt gatgcatgag gctctgcaca accactacac gcagaagagc | 1320 |
| ctctccctgt ctccgggtaa a | 1341 |

<210> SEQ ID NO 90
<211> LENGTH: 648
<212> TYPE: DNA
<213> ORGANISM: Homo sapiens

<400> SEQUENCE: 90

```
tcctatgtgc tgactcagca accctcagcg tctgggaccc ccgggcagag cgtcaccatc    60
tcttgttctg gaagcacctc aacatcgga agtcattatg tggtctggta ccagcagctc   120
ccaggaacgg cccccagact cctcatctat aggaatcatc agcggccctc aggggtccct   180
gaccgactct ctggctccaa gtctggcacc tcagcctccc tggccatcgg tgggctccgg   240
tccgaggatg aggctgatta ttactgtgca gtgtgggatg acaccctgag tggctgggtg   300
ttcggcggag ggaccaagct gaccgtccta ggtcagccca aggctgcccc ctcggtcact   360
ctgttcccgc cctcctctga ggagcttcaa gccaacaagg ccacactggt gtgtctcata   420
agtgacttct acccgggagc cgtgacagtg gcctggaagg cagatagcag ccccgtcaag   480
gcggagtgg agaccaccac accctccaaa caaagcaaca acaagtacgc ggccagcagc   540
tatctgagcc tgacgcctga gcagtggaag tcccacagaa gctacagctg ccaggtcacg   600
catgaaggga gcaccgtgga aagacagtg gcccctacag aatgttca                648
```

<210> SEQ ID NO 91
<211> LENGTH: 447
<212> TYPE: PRT
<213> ORGANISM: Homo sapiens

<400> SEQUENCE: 91

```
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Met Ser Trp Val Arg Gln Ala Pro Gly Gln Gly Leu Glu Trp Met
        35                  40                  45
Gly Gly Ile Ile Pro Ile Phe Gly Thr Val Asn Tyr Ala Gln Lys Phe
    50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Asp Asp Thr Ala Val Tyr Tyr Cys
                85                  90                  95
Ala Arg Arg Arg Gly Ala Lys Phe Asp Tyr Trp Gly Gln Gly Thr Leu
            100                 105                 110
Val Thr Val Ser Ser Ala Ser Thr Lys Gly Pro Ser Val Phe Pro Leu
        115                 120                 125
Ala Pro Ser Ser Lys Ser Thr Ser Gly Gly Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Lys Val Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
```

```
                        245                 250                 255
Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 92
<211> LENGTH: 216
<212> TYPE: PRT
<213> ORGANISM: Homo sapiens

<400> SEQUENCE: 92

Ser Tyr Val Leu Thr Gln Gln Pro Ser Ala Ser Gly Thr Pro Gly Gln
1               5                   10                  15

Ser Val Thr Ile Ser Cys Ser Gly Ser Thr Ser Asn Ile Gly Ser His
            20                  25                  30

Tyr Val Val Trp Tyr Gln Gln Leu Pro Gly Thr Ala Pro Arg Leu Leu
        35                  40                  45

Ile Tyr Arg Asn His Gln Arg Pro Ser Gly Val Pro Asp Arg Leu Ser
    50                  55                  60

Gly Ser Lys Ser Gly Thr Ser Ala Ser Leu Ala Ile Gly Gly Leu Arg
65                  70                  75                  80

Ser Glu Asp Glu Ala Asp Tyr Tyr Cys Ala Val Trp Asp Asp Thr Leu
                85                  90                  95

Ser Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175
```

```
Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 93
<211> LENGTH: 1341
<212> TYPE: DNA
<213> ORGANISM: Homo sapiens

<400> SEQUENCE: 93
caggtccagc ttgtacagtc tggggctgag gtgaagaagc ctgggtcctc ggtgaaggtc      60
tcctgcaagg cttctggagg cacctt cagc agctatgcta tgagctgggt gcgacaggcc     120
cctgggcaag ggcttgagtg gatgggaggg atcatcccta tctttggtac agtaaactac     180
gcacagaagt tccagggcag agtcaccatg accaggga ca cgtccacgag cacagtctac     240
atggagctga gcagcctgag atctgatgac acggccgtgt attactgtgc gagacggcgc     300
ggcgctaaat ttgactactg ggccaaggg a accctggtca ccgtctcctc agcctccacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagccc aaatcttgt      660 gacaaaactc acacatgccc accgtgccca gcacctgaac tcctgggggg accgtcagtc     720
ttcctcttcc ccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
gggcagcccc gagaaccaca ggtgtacacc ctgcccccat cccgggatga gctgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca agagcaggtg gcagcagggg    1260
aacgtcttct catgctccgt gatgcatgag gctctgcaca accactacac gcagaagagc    1320 ctctcccctgt ctccgggtaa a                                              1341

<210> SEQ ID NO 94
<211> LENGTH: 648
<212> TYPE: DNA
<213> ORGANISM: Homo sapiens

<400> SEQUENCE: 94
tcctatgtgc tgactcagcc accctcagcg tctgggaccc ccgggcagag cgtcaccatc      60
tcttgttctg gaagcaccct caacatcgga agtcattatg tggtctggta ccagcagctc     120
ccaggaacgg ccccccagact cctcatctat aggaatcatc agcggccctc agggg tccct    180 gaccgactct ctggctccaa gtctggcacc tcagcctccc tggccatcgg tgggctccgg     240
```

-continued

```
tccgaggatg aggctgatta ttactgtgca gtgtgggatg acaccctgag tggctgggtg      300
ttcggcggag ggaccaagct gaccgtccta ggtcagccca aggctgcccc ctcggtcact      360
ctgttcccgc cctcctctga ggagcttcaa gccaacaagg ccacactggt gtgtctcata      420
agtgacttct acccgggagc cgtgacagtg gcctggaagg cagatagcag ccccgtcaag      480
gcgggagtgg agaccaccac accctccaaa caaagcaaca caagtacgcg gccagcagc      540 tatctgagcc tgacgcctga gcagtggaag tcccacagaa gctacagctg ccaggtcacg      600
catgaaggga gcaccgtgga gaagacagtg gcccctacag aatgttca                  648
```

<210> SEQ ID NO 95
<211> LENGTH: 447
<212> TYPE: PRT
<213> ORGANISM: Homo sapiens

<400> SEQUENCE: 95

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Met Ser Trp Val Arg Gln Ala Pro Gly Gln Gly Leu Glu Trp Met
        35                  40                  45

Gly Gly Ile Ile Pro Ile Phe Gly Thr Val Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Asp Asp Thr Ala Val Tyr Tyr Cys
                85                  90                  95

Ala Arg Arg Arg Gly Ala Lys Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300
```

```
Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 96
<211> LENGTH: 216
<212> TYPE: PRT
<213> ORGANISM: Homo sapiens

<400> SEQUENCE: 96

Ser Tyr Val Leu Thr Gln Pro Pro Ser Ala Ser Gly Thr Pro Gly Gln
1               5                   10                  15

Ser Val Thr Ile Ser Cys Ser Gly Ser Thr Ser Asn Ile Gly Ser His
            20                  25                  30

Tyr Val Val Trp Tyr Gln Gln Leu Pro Gly Thr Ala Pro Arg Leu Leu
        35                  40                  45

Ile Tyr Arg Asn His Gln Arg Pro Ser Gly Val Pro Asp Arg Leu Ser
    50                  55                  60

Gly Ser Lys Ser Gly Thr Ser Ala Ser Leu Ala Ile Gly Gly Leu Arg
65                  70                  75                  80

Ser Glu Asp Glu Ala Asp Tyr Tyr Cys Ala Val Trp Asp Asp Thr Leu
                85                  90                  95

Ser Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 97
```

<211> LENGTH: 1341
<212> TYPE: DNA
<213> ORGANISM: Homo sapiens

<400> SEQUENCE: 97

```
caggtccagc ttgtacagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcaccatg accagggaca cgtccacgag cacagtctac     240
atggagctga gcagcctgag atctgaggac acggccgtgt attactgtgc gagacggcgc     300
ggcgctaaat ttgactactg gggccaaggg accctggtca ccgtctcctc agcctccacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt      660
gacaaaactc acacatgccc accgtgccca gcacctgaac tcctgggggg accgtcagtc     720
ttcctcttcc ccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
gggcagcccc gagaaccaca ggtgtacacc ctgcccccat cccgggatga gctgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca agagcaggtg gcagcagggg    1260
aacgtcttct catgctccgt gatgcatgag gctctgcaca accactacac gcagaagagc    1320
ctctccctgt ctccgggtaa a                                              1341
```

<210> SEQ ID NO 98
<211> LENGTH: 648
<212> TYPE: DNA
<213> ORGANISM: Homo sapiens

<400> SEQUENCE: 98

```
tcctatgtgc tgactcagcc accctcagcg tctgggaccc ccgggcagag cgtcaccatc      60
tcttgttctg gaagcacctc caacatcgga agtcattatg tggtctggta ccagcagctc     120
ccaggaacgg cccccagact cctcatctat aggaatcatc agcggccctc agggatccct     180
gaccgactct ctggctccaa gtctggcacc tcagcctccc tggccatcgg tgggctccgg     240
tccgaggatg aggctgatta ttactgtgca gtgtgggatg acaccctgag tggctgggtg     300
ttcggcggag ggaccaagct gaccgtccta ggtcagccca aggctgcccc ctcggtcact     360
ctgttcccgc cctcctctga ggagcttcaa gccaacaagg ccacactggt gtgtctcata     420
agtgacttct acccgggagc cgtgacagtg gcctggaagg cagatagcag ccccgtcaag     480
gcgggagtgg agaccaccac acccctccaaa caaagcaaca caagtacgc ggccagcagc     540
tatctgagcc tgacgcctga gcagtggaag tcccacagaa gctacagctg ccaggtcacg     600
```
catgaaggga gcaccgtgga gaagacagtg gcccctacag aatgttca        648

<210> SEQ ID NO 99
<211> LENGTH: 447
<212> TYPE: PRT
<213> ORGANISM: Homo sapiens

<400> SEQUENCE: 99

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Gly Ala Lys Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 100
<211> LENGTH: 216
<212> TYPE: PRT
<213> ORGANISM: Homo sapiens

<400> SEQUENCE: 100

Ser Tyr Val Leu Thr Gln Pro Pro Ser Ala Ser Gly Thr Pro Gly Gln
1               5                   10                  15

Ser Val Thr Ile Ser Cys Ser Gly Ser Thr Ser Asn Ile Gly Ser His
            20                  25                  30

Tyr Val Val Trp Tyr Gln Gln Leu Pro Gly Thr Ala Pro Arg Leu Leu
        35                  40                  45

Ile Tyr Arg Asn His Gln Arg Pro Ser Gly Val Pro Asp Arg Leu Ser
    50                  55                  60

Gly Ser Lys Ser Gly Thr Ser Ala Ser Leu Ala Ile Gly Gly Leu Arg
65                  70                  75                  80

Ser Glu Asp Glu Ala Asp Tyr Tyr Cys Ala Val Trp Asp Asp Thr Leu
                85                  90                  95

Ser Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 101
<211> LENGTH: 351
<212> TYPE: DNA
<213> ORGANISM: Homo sapiens

<400> SEQUENCE: 101
caggtccagc ttgtacagtc tggggctgag gtgaagaagc ctgggtcctc ggtgaaggtc    60
tcctgcaagg cttctggagg caccttcagc agctatgcta tgagctgggt gcgacaggcc   120
cctgggcaag ggcttgagtg gatgggaggg atcatcccta tctttggtac agtaaactac   180

```
gcacagaagt tccagggcag agtcaccatg accagggaca cgtccacgag cacagtctac    240
atggagctga gcagcctgag atctgatgac acggccgtgt attactgtgc gagacgcggt    300
gggagctact ttgactactg gggccaaggg accctggtca ccgtctcctc a             351

<210> SEQ ID NO 102
<211> LENGTH: 330
<212> TYPE: DNA
<213> ORGANISM: Homo sapiens

<400> SEQUENCE: 102
tcctatgtgc tgactcagcc accctcagcg tctgggaccc ccgggcagag cgtcaccatc     60
tcttgttctg gaagcacctc caacatcgga agtcattatg tgttctggta ccagcagctc    120
ccaggaacgg cccccagact cctcatctat aggaatcatc agcggccctc agggtccct     180 gaccgactct ctggctccaa gtctggcacc tcagcctccc tggccatcag tgggctccgg    240
tccgaggatg aggctgatta ttactgtgca gtgtgggatg cgaaatacag ggttgggtg     300 ttcggcggag ggaccaagct gaccgtccta                                     330

<210> SEQ ID NO 103
<211> LENGTH: 351
<212> TYPE: DNA
<213> ORGANISM: Homo sapiens

<400> SEQUENCE: 103
caggtccagc ttgtacagtc tggggctgag gtgaagaagc ctgggtcctc ggtgaaggtc     60
tcctgcaagg cttctggagg caccttcagc agctatgcta tgagctgggt gcgacaggcc    120
cctgggcaag gcttgagtg gatgggaggg atcatcccta tctttggtac agtaaactac    180
gcacagaagt ccagggcag agtcaccatg accagggaca cgtccacgag cacagtctac     240
atggagctga gcagcctgag acctgatgac acggccgtgt attactgtgc gagacgcggt    300
gggagctact ttgactactg gggccaaggg accctggtca ccgtctcctc a             351

<210> SEQ ID NO 104
<211> LENGTH: 330
<212> TYPE: DNA
<213> ORGANISM: Homo sapiens

<400> SEQUENCE: 104
tcctatgtgc tgactcagcc accctcagcg tctgggaccc ccgggcagag cgtcaccatc     60
tcttgttctg gaagcacctc caacatcgga agtcattatg tgtcctggta ccagcagctc    120
ccaggaacgg cccccagact cctcatctat aggaatcatc agcggccctc agggtccct     180 gaccgactct ctggctccaa gtctggcacc tcagcctccc tggccatcag tgggctccgg    240
tccgaggatg aggctgatta ttactgtgca gtgtgggatg cgaaatacag ggttgggtg     300 ttcggcggag ggaccaagct gaccgtccta                                     330

<210> SEQ ID NO 105
<211> LENGTH: 351
<212> TYPE: DNA
<213> ORGANISM: Homo sapiens

<400> SEQUENCE: 105
caggtccagc ttgtacagtc tggggctgag gtgaagaagc ctgggtcctc ggtgaaggtc     60
tcctgcaagg cttctggagg caccttcagc agctatgcta tgagctgggt gcgacaggcc    120
```

| | |
|---|---|
| cctgggcaag ggcttgagtg gatgggaggg atcatccota tctttggtac agtaaactac | 180 |
| gcacagaagt tccagggcag agtcaccatg accagggaca cgtccacgag cacagtctac | 240 |
| atggagctga gcagcctgag acctgatgac acggccgtgt attactgtgc gagacgcggt | 300 |
| gggagctact tgactactg gggccaaggg accctggtca ccgtctcctc a | 351 |

<210> SEQ ID NO 106
<211> LENGTH: 330
<212> TYPE: DNA
<213> ORGANISM: Homo sapiens

<400> SEQUENCE: 106

| | |
|---|---|
| tcctatgtgc tgactcagcc accctcagcg tctgggaccc ccgggcagag cgtcaccatc | 60 |
| tcttgttctg gaagcacctc caacatcgga agtcattatg tgttctggta ccagcagctc | 120 |
| ccaggaacgg cccccagact cctcatctat aggaatcatc agcggccctc agggatccct | 180 |
| gaccgactct ctggctccaa gtctggcacc tcagcctccc tggccatcag tgggctccgg | 240 |
| tccgaggatg aggctgatta ttactgtgca gtgtgggatg cgaaatacag gggttgggtg | 300 |
| ttcggcggag ggaccaagct gaccgtccta | 330 |

<210> SEQ ID NO 107
<211> LENGTH: 351
<212> TYPE: DNA
<213> ORGANISM: Homo sapiens

<400> SEQUENCE: 107

| | |
|---|---|
| caggtccagc ttgtacagtc tggggctgag gtgaagaagc ctgggtcctc ggtgaaggtc | 60 |
| tcctgcaagg cttctgaagg caccttcagc agctatgcta tgagctgggt gcgacaggcc | 120 |
| cctgggcaag ggcttgagtg gatgggaggg atcatcccta tctttggtac agtaaactac | 180 |
| gcacagaagt tccagggcag agtcaccatg accagggaca cgtccacgag cacagtctac | 240 |
| atggagctga gcagcctgag atctgatgac acggccgtgt attactgtgc gagacgcggt | 300 |
| gggagctact tgactactg gggccaaggg accctggtca ccgtctcctc a | 351 |

<210> SEQ ID NO 108
<211> LENGTH: 330
<212> TYPE: DNA
<213> ORGANISM: Homo sapiens

<400> SEQUENCE: 108

| | |
|---|---|
| tcctatgtgc tgactcagcc accctcagcg tctgggaccc ccgggcagag cgtcaccatc | 60 |
| tcttgttctg gaagcacctc caacatcgga agtcattatg tgtcctggta ccagcagctc | 120 |
| ccaggaacgg cccccagact cctcatctat aggaatcatc agcggccctc agggatccct | 180 |
| gaccgactct ctggctccaa gtctggcacc tcagcctccc tggccatcag tgggctccgg | 240 |
| tccgaggatg aggctgatta ttactgtgca gtgtgggatg cgaaatacag gggttgggtg | 300 |
| ttcggcggag ggaccaagct gaccgtccta | 330 |

<210> SEQ ID NO 109
<211> LENGTH: 351
<212> TYPE: DNA
<213> ORGANISM: Homo sapiens

<400> SEQUENCE: 109

| | |
|---|---|
| caggtccagc ttgtacagtc tggggctgag gtgaagaagc ctgggtcctc ggtgaaggtc | 60 |
| tcctgcaagg cttctgaagg caccttcagc agctatgcta tgagctgggt gcgacaggcc | 120 | cctgggcaag ggcttgagtg gatgggaggg atcatccta tctttggtac agtaaactac      180 gcacagaagt tccagggcag agtcaccatg accagggaca cgtccacgag cacagtctac      240 atggagctga gcagcctgag atctgatgac acggccgtgt attactgtgc gagacggcgc      300 ggcgctaaat ttgactactg gggccaaggg accctggtca ccgtctcctc a               351

<210> SEQ ID NO 110
<211> LENGTH: 330
<212> TYPE: DNA
<213> ORGANISM: Homo sapiens

<400> SEQUENCE: 110
tcctatgtgc tgactcagca accctcagcg tctgggaccc ccgggcagag cgtcaccatc      60
tcttgttctg gaagcacctc caacatcgga agtcattatg tggtctggta ccagcagctc     120
ccaggaacgg cccccagact cctcatctat aggaatcatc agcggccctc agggtccct      180 gaccgactct ctggctccaa gtctggcacc tcagcctccc tggccatcgg tgggctccgg     240
tccgaggatg aggctgatta ttactgtgca gtgtgggatg acaccctgag tggctgggtg     300
ttcggcggag ggaccaagct gaccgtccta                                       330

<210> SEQ ID NO 111
<211> LENGTH: 351
<212> TYPE: DNA
<213> ORGANISM: Homo sapiens

<400> SEQUENCE: 111
caggtccagc ttgtacagtc tggggctgag gtgaagaagc ctgggtcctc ggtgaaggtc      60
tcctgcaagg cttctgaagg caccttcagc agctatgcta tgagctgggt gcgacaggcc     120
cctgggcaag ggcttgagtg gatgggaggg atcatccta tctttggtac agtaaactac      180
gcacagaagt tccagggcag agtcaccatg accagggaca cgtccacgag cacagtctac     240
atggagctga gcagcctgag atctgatgac acggccgtgt attactgtgc gagacggcgc     300
ggcgctaaat ttgactactg gggccaaggg accctggtca ccgtctcctc a               351

<210> SEQ ID NO 112
<211> LENGTH: 330
<212> TYPE: DNA
<213> ORGANISM: Homo sapiens

<400> SEQUENCE: 112
tcctatgtgc tgactcagcc accctcagcg tctgggaccc ccgggcagag cgtcaccatc      60
tcttgttctg gaagcacctc caacatcgga agtcattatg tggtctggta ccagcagctc     120
ccaggaacgg cccccagact cctcatctat aggaatcatc agcggccctc agggtccct      180 gaccgactct ctggctccaa gtctggcacc tcagcctccc tggccatcgg tgggctccgg     240
tccgaggatg aggctgatta ttactgtgca gtgtgggatg acaccctgag tggctgggtg     300
ttcggcggag ggaccaagct gaccgtccta                                       330

<210> SEQ ID NO 113
<211> LENGTH: 351
<212> TYPE: DNA
<213> ORGANISM: Homo sapiens

<400> SEQUENCE: 113
caggtccagc ttgtacagtc tggggctgag gtgaagaagc ctgggtcctc ggtgaaggtc      60

```
tcctgcaagg cttctggagg caccttcagc agctatgcta tgagctgggt gcgacaggcc    120
cctgggcaag ggcttgagtg gatgggaggg atcatccct a tctttggtac agtaaactac   180
gcacagaagt tccagggcag agtcaccatg accagggaca cgtccacgag cacagtctac    240
atggagctga gcagcctgag atctgatgac acggccgtgt attactgtgc gagacggcgc    300
ggcgctaaat ttgactactg gggccaaggg accctggtca ccgtctcctc a             351
```

```
<210> SEQ ID NO 114
<211> LENGTH: 330
<212> TYPE: DNA
<213> ORGANISM: Homo sapiens

<400> SEQUENCE: 114
```

```
tcctatgtgc tgactcagca accctcagcg tctgggaccc ccgggcagag cgtcaccatc    60
tcttgttctg gaagcacctc caacatcgga agtcattatg tggtctggta ccagcagctc    120
ccaggaacgg cccccagact cctcatctat aggaatcatc agcggccctc agggtccct     180 gaccgactct ctggctccaa gtctggcacc tcagcctccc tggccatcgg tgggctccgg    240
tccgaggatg aggctgatta ttactgtgca gtgtgggatg acaccctgag tggctgggtg    300
ttcggcggag ggaccaagct gaccgtccta                                      330
```

```
<210> SEQ ID NO 115
<211> LENGTH: 351
<212> TYPE: DNA
<213> ORGANISM: Homo sapiens

<400> SEQUENCE: 115
```

```
caggtccagc ttgtacagtc tggggctgag gtgaagaagc ctgggtcctc ggtgaaggtc    60
tcctgcaagg cttctggagg caccttcagc agctatgcta tgagctgggt gcgacaggcc    120
cctgggcaag ggcttgagtg gatgggaggg atcatcccta tctttggtac agtaaactac    180
gcacagaagt tccagggcag agtcaccatg accagggaca cgtccacgag cacagtctac    240
atggagctga gcagcctgag atctgatgac acggccgtgt attactgtgc gagacggcgc    300
ggcgctaaat ttgactactg gggccaaggg accctggtca ccgtctcctc a              351
```

```
<210> SEQ ID NO 116
<211> LENGTH: 330
<212> TYPE: DNA
<213> ORGANISM: Homo sapiens

<400> SEQUENCE: 116
```

```
tcctatgtgc tgactcagcc accctcagcg tctgggaccc ccgggcagag cgtcaccatc    60
tcttgttctg gaagcacctc caacatcgga agtcattatg tggtctggta ccagcagctc    120
ccaggaacgg cccccagact cctcatctat aggaatcatc agcggccctc agggtccct     180 gaccgactct ctggctccaa gtctggcacc tcagcctccc tggccatcgg tgggctccgg    240
tccgaggatg aggctgatta ttactgtgca gtgtgggatg acaccctgag tggctgggtg    300
ttcggcggag ggaccaagct gaccgtccta                                      330
```

```
<210> SEQ ID NO 117
<211> LENGTH: 351
<212> TYPE: DNA
<213> ORGANISM: Homo sapiens

<400> SEQUENCE: 117
```

```
caggtccagc ttgtacagtc tggggctgag gtgaagaagc ctgggtcctc ggtgaaggtc    60
```

```
tcctgcaagg cttctggagg caccttcagc agctatgcta tcagctgggt gcgacaggcc    120
cctggacaag ggcttgagtg gatgggaggg atcatccta tctttggtac agcaaactac    180
gcacagaagt tccagggcag agtcaccatg accagggaca cgtccacgag cacagtctac    240
atggagctga gcagcctgag atctgaggac acggccgtgt attactgtgc gagcggcgc     300 ggcgctaaat tgactactg gggccaaggg accctggtca ccgtctcctc a              351
```

<210> SEQ ID NO 118
<211> LENGTH: 330
<212> TYPE: DNA
<213> ORGANISM: Homo sapiens

<400> SEQUENCE: 118

```
tcctatgtgc tgactcagcc accctcagcg tctgggaccc ccgggcagag cgtcaccatc     60
tcttgttctg gaagcacctc caacatcgga agtcattatg tggtctggta ccagcagctc    120
ccaggaacgg cccccagact cctcatctat aggaatcatc agcggccctc aggggtccct    180
gaccgactct ctggctccaa gtctggcacc tcagcctccc tggccatcgg tgggctccgg    240
tccgaggatg aggctgatta ttactgtgca gtgtgggatg acaccctgag tggctgggtg    300
ttcggcggag ggaccaagct gaccgtccta                                     330
```

<210> SEQ ID NO 119
<211> LENGTH: 5
<212> TYPE: PRT
<213> ORGANISM: artificial sequence
<220> FEATURE:
<223> OTHER INFORMATION: consensus sequence
<220> FEATURE:
<221> NAME/KEY: misc_feature
<222> LOCATION: (4)..(4)
<223> OTHER INFORMATION: Xaa can be any naturally occurring amino acid

<400> SEQUENCE: 119

Ser Tyr Ala Xaa Ser
1               5

<210> SEQ ID NO 120
<211> LENGTH: 5
<212> TYPE: PRT
<213> ORGANISM: artificial sequence
<220> FEATURE:
<223> OTHER INFORMATION: consensus sequence
<220> FEATURE:
<221> NAME/KEY: MISC_FEATURE
<222> LOCATION: (4)..(4)
<223> OTHER INFORMATION: Xaa can be M or I

<400> SEQUENCE: 120

Ser Tyr Ala Xaa Ser
1               5

<210> SEQ ID NO 121
<211> LENGTH: 17
<212> TYPE: PRT
<213> ORGANISM: artificial sequence
<220> FEATURE:
<223> OTHER INFORMATION: consensus sequence
<220> FEATURE:
<221> NAME/KEY: VARIANT
<222> LOCATION: (1)..(17)
<223> OTHER INFORMATION: X= any amino acid

<400> SEQUENCE: 121

```
Gly Ile Ile Pro Ile Phe Gly Thr Xaa Asn Tyr Ala Gln Lys Phe Gln
 1               5                  10                  15

Gly

<210> SEQ ID NO 122
<211> LENGTH: 17
<212> TYPE: PRT
<213> ORGANISM: artificial sequence
<220> FEATURE:
<223> OTHER INFORMATION: consensus sequence
<220> FEATURE:
<221> NAME/KEY: VARIANT
<222> LOCATION: (1)..(17)
<223> OTHER INFORMATION: X = V, I or A

<400> SEQUENCE: 122

Gly Ile Ile Pro Ile Phe Gly Thr Xaa Asn Tyr Ala Gln Lys Phe Gln
 1               5                  10                  15

Gly

<210> SEQ ID NO 123
<211> LENGTH: 8
<212> TYPE: PRT
<213> ORGANISM: artificial sequence
<220> FEATURE:
<223> OTHER INFORMATION: consensus sequence
<220> FEATURE:
<221> NAME/KEY: VARIANT
<222> LOCATION: (1)..(8)
<223> OTHER INFORMATION: each X may independently be any amino acid

<400> SEQUENCE: 123

Arg Xaa Gly Xaa Xaa Phe Asp Tyr
 1               5

<210> SEQ ID NO 124
<211> LENGTH: 8
<212> TYPE: PRT
<213> ORGANISM: artificial sequence
<220> FEATURE:
<223> OTHER INFORMATION: consensus sequence
<220> FEATURE:
<221> NAME/KEY: VARIANT
<222> LOCATION: (2)..(2)
<223> OTHER INFORMATION: X=R or G
<220> FEATURE:
<221> NAME/KEY: VARIANT
<222> LOCATION: (4)..(4)
<223> OTHER INFORMATION: X=S or A
<220> FEATURE:
<221> NAME/KEY: VARIANT
<222> LOCATION: (5)..(5)
<223> OTHER INFORMATION: X= Y or K

<400> SEQUENCE: 124

Arg Xaa Gly Xaa Xaa Phe Asp Tyr
 1               5

<210> SEQ ID NO 125
<211> LENGTH: 13
<212> TYPE: PRT
<213> ORGANISM: artificial sequence
<220> FEATURE:
<223> OTHER INFORMATION: consensus sequence
<220> FEATURE:
<221> NAME/KEY: VARIANT
<222> LOCATION: (1)..(13)
<223> OTHER INFORMATION: X = any amino acid

<400> SEQUENCE: 125
```

```
Ser Gly Ser Thr Ser Asn Ile Gly Ser His Tyr Val Xaa
1               5                   10

<210> SEQ ID NO 126
<211> LENGTH: 13
<212> TYPE: PRT
<213> ORGANISM: artificial sequence
<220> FEATURE:
<223> OTHER INFORMATION: consensus sequence
<220> FEATURE:
<221> NAME/KEY: VARIANT
<222> LOCATION: (1)..(13)
<223> OTHER INFORMATION: X = F, S or Y

<400> SEQUENCE: 126

Ser Gly Ser Thr Ser Asn Ile Gly Ser His Tyr Val Xaa
1               5                   10

<210> SEQ ID NO 127
<211> LENGTH: 11
<212> TYPE: PRT
<213> ORGANISM: artificial sequence
<220> FEATURE:
<223> OTHER INFORMATION: consensus sequence
<220> FEATURE:
<221> NAME/KEY: VARIANT
<222> LOCATION: (1)..(11)
<223> OTHER INFORMATION: each X may independently be any amino acid

<400> SEQUENCE: 127

Ala Val Trp Asp Xaa Xaa Xaa Xaa Gly Trp Val
1               5                   10

<210> SEQ ID NO 128
<211> LENGTH: 11
<212> TYPE: PRT
<213> ORGANISM: artificial sequence
<220> FEATURE:
<223> OTHER INFORMATION: consensus sequence
<220> FEATURE:
<221> NAME/KEY: VARIANT
<222> LOCATION: (5)..(5)
<223> OTHER INFORMATION: X= A or D
<220> FEATURE:
<221> NAME/KEY: VARIANT
<222> LOCATION: (6)..(6)
<223> OTHER INFORMATION: X= K or T
<220> FEATURE:
<221> NAME/KEY: VARIANT
<222> LOCATION: (7)..(7)
<223> OTHER INFORMATION: X= Y or L
<220> FEATURE:
<221> NAME/KEY: VARIANT
<222> LOCATION: (8)..(8)
<223> OTHER INFORMATION: X= R or S

<400> SEQUENCE: 128

Ala Val Trp Asp Xaa Xaa Xaa Xaa Gly Trp Val
1               5                   10

<210> SEQ ID NO 129
<211> LENGTH: 22
<212> TYPE: PRT
<213> ORGANISM: artificial sequence
<220> FEATURE:
<223> OTHER INFORMATION: homologue
<220> FEATURE:
<221> NAME/KEY: VARIANT
<222> LOCATION: (1)..(22)
<223> OTHER INFORMATION: Each X may independently be any amino acid
```

<400> SEQUENCE: 129

Xaa Xaa Val Leu Thr Gln Pro Pro Ser Ala Ser Gly Thr Pro Gly Gln
1               5                   10                  15

Ser Val Thr Ile Ser Cys
            20

<210> SEQ ID NO 130
<211> LENGTH: 22
<212> TYPE: PRT
<213> ORGANISM: artificial sequence
<220> FEATURE:
<223> OTHER INFORMATION: homologue
<220> FEATURE:
<221> NAME/KEY: VARIANT
<222> LOCATION: (1)..(2)
<223> OTHER INFORMATION: X at position 1 = Q and/or X at position 2 = S

<400> SEQUENCE: 130

Xaa Xaa Val Leu Thr Gln Pro Pro Ser Ala Ser Gly Thr Pro Gly Gln
1               5                   10                  15

Ser Val Thr Ile Ser Cys
            20

<210> SEQ ID NO 131
<211> LENGTH: 22
<212> TYPE: PRT
<213> ORGANISM: artificial sequence
<220> FEATURE:
<223> OTHER INFORMATION: homologue
<220> FEATURE:
<221> NAME/KEY: VARIANT
<222> LOCATION: (1)..(22)
<223> OTHER INFORMATION: Each X may be any amino acid

<400> SEQUENCE: 131

Xaa Xaa Val Leu Thr Gln Gln Pro Ser Ala Ser Gly Thr Pro Gly Gln
1               5                   10                  15

Ser Val Thr Ile Ser Cys
            20

<210> SEQ ID NO 132
<211> LENGTH: 22
<212> TYPE: PRT
<213> ORGANISM: artificial sequence
<220> FEATURE:
<223> OTHER INFORMATION: homologue
<220> FEATURE:
<221> NAME/KEY: VARIANT
<222> LOCATION: (1)..(2)
<223> OTHER INFORMATION: X at position 1 = Q and/or X at position 2 = S

<400> SEQUENCE: 132

Xaa Xaa Val Leu Thr Gln Gln Pro Ser Ala Ser Gly Thr Pro Gly Gln
1               5                   10                  15

Ser Val Thr Ile Ser Cys
            20

<210> SEQ ID NO 133
<211> LENGTH: 330
<212> TYPE: DNA
<213> ORGANISM: Homo sapiens

<400> SEQUENCE: 133
caaagcgtgc tgactcagcc accctcagcg tctgggaccc ccgggcagag cgtcaccatc      60
tcttgttctg gaagcaccct caacatcgga agtcattatg tggtctggta ccagcagctc     120

```
ccaggaacgg cccccagact cctcatctat aggaatcatc agcggccctc aggggtccct    180
gaccgactct ctggctccaa gtctggcacc tcagcctccc tggccatcgg tgggctccgg    240
tccgaggatg aggctgatta ttactgtgca gtgtgggatg acaccctgag tggctgggtg    300
ttcggcggag ggaccaagct gaccgtccta                                     330
```